US012649930B2

(12) United States Patent
Barney et al.

(10) Patent No.: US 12,649,930 B2
(45) Date of Patent: Jun. 9, 2026

(54) COMPOSITIONS, DEVICES, AND METHODS FOR TREATING FABRY DISEASE

(71) Applicant: SIGILON THERAPEUTICS, INC., Cambridge, MA (US)

(72) Inventors: Lauren Emily Barney, Cambridge, MA (US); Michael Beauregard, Boston, MA (US); Guillaume Carmona, Cambridge, MA (US); Francisco Caballero Gonzalez, Brookline, MA (US); Richard Heidebrecht, Somerville, MA (US); Erika Ellen Johnston, Cambridge, MA (US); Robert James Miller, East Bridgewater, MA (US); Owen O'Connor, Raynham, MA (US); Matthias Alexander Oberli, Cambridge, MA (US); David Peritt, Skokie, IL (US); Jared A. Sewell, Somerville, MA (US); Devyn McKinley Smith, Barrington, RI (US); Omid Veiseh, Bellaire, TX (US); Jeffrey Charles Way, Cambridge, MA (US); Paul Kevin Wotton, Boston, MA (US); Zoe Yin, Boston, MA (US); Elina Makino, Winchester, MA (US); Brian Richard Fluharty, Boston, MA (US); Marianthi Papakosta, Cambridge, MA (US)

(73) Assignee: SIGILON THERAPEUTICS, INC., Cambridge, MA (US)

( * ) Notice: Subject to any disclaimer, the term of this patent is extended or adjusted under 35 U.S.C. 154(b) by 1195 days.

(21) Appl. No.: 17/598,176

(22) PCT Filed: Mar. 27, 2020

(86) PCT No.: PCT/US2020/025485
§ 371 (c)(1),
(2) Date: Sep. 24, 2021

(87) PCT Pub. No.: WO2020/198685
PCT Pub. Date: Oct. 1, 2020

(65) Prior Publication Data

US 2022/0267794 A1 Aug. 25, 2022

Related U.S. Application Data

(60) Provisional application No. 62/907,380, filed on Sep. 27, 2019, provisional application No. 62/824,969, filed on Mar. 27, 2019.

(51) Int. Cl.

| | |
|---|---|
| ***C12N 15/85*** | (2006.01) |
| ***A61K 9/50*** | (2006.01) |
| ***A61K 38/47*** | (2006.01) |
| ***A61K 47/22*** | (2006.01) |
| ***C08L 5/04*** | (2006.01) |

(52) U.S. Cl.
CPC ............ *C12N 15/85* (2013.01); *A61K 9/5036* (2013.01); *A61K 38/47* (2013.01); *A61K 47/22* (2013.01); *C08L 5/04* (2013.01)

(58) Field of Classification Search
CPC ............ C07K 2319/02; C07K 2319/00; C07K 14/71; A61K 38/47; A61L 27/20; A61L 27/3813; A61P 3/00; C12N 15/85; C12N 2510/00; C12N 2800/22; C12Y 302/01022
USPC ........................................................ 435/320.1
See application file for complete search history.

(56) References Cited

U.S. PATENT DOCUMENTS

| | | | |
|---|---|---|---|
| 4,784,950 | A | 11/1988 | Hagen et al. |
| 6,361,771 | B1 | 3/2002 | Tao et al. |
| 6,533,819 | B1 | 3/2003 | Urry et al. |
| 6,924,365 | B1 * | 8/2005 | Miller et al. |
| 8,741,340 | B2 | 6/2014 | Kusk et al. |
| 9,121,037 | B2 | 9/2015 | Kusk et al. |
| 9,422,373 | B2 | 8/2016 | Vegas et al. |
| 9,447,168 | B2 | 9/2016 | Nathwani et al. |
| 9,555,007 | B2 | 1/2017 | Ma et al. |
| 9,867,781 | B2 | 1/2018 | Anderson et al. |
| 9,925,219 | B2 | 3/2018 | Kauper et al. |
| 10,172,791 | B2 | 1/2019 | Ma et al. |
| 10,278,922 | B2 | 5/2019 | Anderson et al. |
| 10,285,949 | B2 | 5/2019 | Vegas et al. |
| 10,292,936 | B2 | 5/2019 | Vegas et al. |
| 10,426,735 | B2 | 10/2019 | Vegas et al. |
| 2008/0076174 | A1 | 3/2008 | Selden et al. |
| 2013/0259924 | A1 | 10/2013 | Bancel et al. |

(Continued)

FOREIGN PATENT DOCUMENTS

| | | | |
|---|---|---|---|
| CN | 101351230 | A | 1/2009 |
| CN | 104072478 | A | 10/2014 |

(Continued)

OTHER PUBLICATIONS

International Search Report and Written Opinion for Application No. PCT/US2018/053191 mailed Mar. 5, 2019.
Sieving et al., "Ciliary neurotrophic factor (CNTF) for human retinal degeneration: Phase I trial of CNTF delivered by encapsulated cell intraocular implants" Proceedings of the National Academy of Sciences, 2006, vol. 103, No. 10, pp. 3896-3901.
Shintani et al., "Review and update: Current treatment trends for patients with retinitis pigmentosa" Optometry, 2009, vol. 80, No. 7, pp. 384-401.

(Continued)

*Primary Examiner* — Tekchand Saidha
*Assistant Examiner* — Mohammad Y Meah
(74) *Attorney, Agent, or Firm* — Quarles & Brady, LLP

(57) ABSTRACT

Described herein are RPE cells engineered to secrete a GLA protein, as well as compositions, pharmaceutical preparations, and implantable devices comprising the engineered RPE cells, and methods of making and using the same for treating Fabry disease.

18 Claims, 24 Drawing Sheets

Specification includes a Sequence Listing.

(56) References Cited

U.S. PATENT DOCUMENTS

| | | | |
|---|---|---|---|
| 2014/0010861 | A1 | 1/2014 | Bancel et al. |
| 2014/0017212 | A1 | 1/2014 | Rebar |
| 2014/0271843 | A1 | 9/2014 | Ma et al. |
| 2014/0350089 | A1 | 11/2014 | Selden et al. |
| 2016/0030359 | A1 | 2/2016 | Ma et al. |
| 2016/0030360 | A1 | 2/2016 | Vegas et al. |
| 2016/0207978 | A1 | 7/2016 | Kelly |
| 2017/0260516 | A1 | 9/2017 | Tan et al. |
| 2018/0318612 | A1 | 11/2018 | Tzahor et al. |
| 2019/0000932 | A1 | 1/2019 | Martini et al. |

FOREIGN PATENT DOCUMENTS

| | | | |
|---|---|---|---|
| JP | 2004-532234 | A | 10/2004 |
| JP | 5725475 | B2 | 5/2015 |
| JP | 2016-516020 | A | 6/2016 |
| JP | 2016-517879 | A | 6/2016 |
| JP | 2017-524768 | A | 8/2017 |
| RU | 2542967 | C2 | 2/2015 |
| WO | 2008/021388 | A1 | 2/2008 |
| WO | 2008/036308 | A2 | 3/2008 |
| WO | 2010/005533 | A2 | 1/2010 |
| WO | 2012/112982 | A2 | 8/2012 |
| WO | 2012/167223 | A1 | 12/2012 |
| WO | 2014/147386 | A1 | 9/2014 |
| WO | 2014/153126 | A1 | 9/2014 |
| WO | 2015/143418 | A2 | 9/2015 |
| WO | 2016/019391 | A1 | 2/2016 |
| WO | 2016/187225 | A1 | 11/2016 |
| WO | 2017/018086 | A1 | 2/2017 |
| WO | 2017/072498 | A1 | 5/2017 |
| WO | 2017/075630 | A1 | 5/2017 |
| WO | 2017/075631 | A1 | 5/2017 |
| WO | 2017/136358 | A1 | 8/2017 |
| WO | 2017/201328 | A1 | 11/2017 |
| WO | 2018/067615 | A1 | 4/2018 |
| WO | 2018/075328 | A1 | 4/2018 |
| WO | 2018/075736 | A1 | 4/2018 |
| WO | 2018/185468 | A1 | 10/2018 |
| WO | 2018/206168 | A1 | 11/2018 |
| WO | 2018/213886 | A1 | 11/2018 |
| WO | 2019/067766 | A1 | 4/2019 |
| WO | 2019/195056 | A1 | 10/2019 |

OTHER PUBLICATIONS

Wikstrom et al., "Alginate-based microencapsulation of retinal pigment epithelial cell line for cell therapy" Biomaterials, 2008, vol. 29, pp. 869-876.

Carvalho et al., "'Click Chemistry' synthesis of a library of 1,2,3-triazole-substituted galactose derivatives and their evaluation against Trypanosoma cruzi and its cell surface trans-sialidase," Bioorganic & Medicinal Chemistry, vol. 18, No. 7, pp. 2412-2427, (2010).

Corbel et al., "Identification of potential cellular targets of aloisine A by affinity chromatography," Bioorganic & Medicinal Chemistry, vol. 17, No. 15, pp. 5572-5582, (2009).

Struthers et al., "'Click-to-Chelate': Design and Incorporation of Triazole-containing Metal-chelating Systems into Biomolecules of Diagnostic and Therapeutic Interest," Chemistry—A European Journal, vol. 14, No. 20, pp. 6173-6183, (2008).

International Search Report and Written Opinion for PCT/US2017/055001 mailed Nov. 27, 2017.

Arunrungvichian et al., "Selectivity optimization of substituted 1,2,3-Triazoles as a7 nicotinic acetylcholine receptor agonists" ACS Chemical Neuroscience, vol. 6, No. 8, 2015, pp. 1317-1330.

RN:1545351-08-3, Database Registry [Online], Retrieved from STN, Feb. 16, 2014.

Panda et al., "A nucleus-imaging probe that selectively stabilizes a minor conformation of c-MYC G-quadruplex and Down-regulates c-MYC Transcription in Human Cancer Cells" Scienctific Reports, 2015, vol. 5, pp. 1-16.

Bochenek et al., "Alginate encapsulation as long-term immune protection of allogeneic pancreatic islet cells transplanted into the omental bursa of macaques" Nature Biomedical Engineering, 2018, vol. 2, No. 11, pp. 810-821.

Vegas et al., "Long-term glycemic control using polymer-encapsulated human stem cell-derived beta cells in immune-competent mice" Nature Medicine, 2016, vol. 22, No. 3, pp. 306-311.

Vegas et al., "Combinatorial hydrogel library enables identification of materials that mitigate the foreign body response in primates" Nature Biotechnology, 2016, vol. 34, No. 3, pp. 345-352.

International Search Report and Written Opinion for Application No. PCT/US2019/024385 mailed Aug. 7, 2019.

Bremond et al., "Formation of liquid-core capsules having a thin hydrogel membrane: liquid pearls" Soft Matter, 2010, vol. 6, No. 11, pp. 2484-2488.

Veiseh et al., "Size- and shape-dependent foreign body immune response to materials implanted in rodents and non-human primates" Nature Materials, 2015, vol. 14, pp. 643-652.

Lee et al., "Size and shape of calcium alginate beads produced by extrusion dripping" Chemical Engineering and Technology, 2013, vol. 36, No. 10, pp. 1627-1642.

International Search Report and Written Opinion for Application No. PCT/US2019/020248 mailed Jun. 26, 2019.

International Search Report and Written Opinion for Application No. PCT/US2019/020405 mailed Jul. 15, 2019.

International Search Report and Written Opinion for Application No. PCT/US2019/024371 mailed Aug. 14, 2019.

Llacua et al., "Extracellular matrix molecules and their potential contribution to the function of transplanted pancreatic islets" Diabetologia, 2018, vol. 61, pp. 1261-1272.

Llacua et al., "Laminin and collagen IV inclusion in immunoisolating microcapsules reduces cytokine-mediated cell death in human pancreatic islets" Journal of Tissue Engineering and Regenerative Medicine, 2017, 25 pages.

Orive et al., "Engineering a clinically translatable bioartificial pancreas to treat type I diabetes" Trends in Biotechnology, 2018, 12 pages.

Llacua et al., "Extracellular matrix components supporting human islet function in alginate-based immunoprotective microcapsules for treatment of diabetes" Journal of Biomedical Materials Research Part A, 2018, 10 pages.

Bochenek et al., "Alginate encapsulation as long-term immune protection of allogeneic pancreatic islet cells transplanted into the omental bursa of macaques" Nature Biomedical Engineering, vol. 2, No. 11, pp. 810-821, 2018.

Belhaj, "Enhancements in alginate microencapsulation technology & impacts on cell therapy development", Disseration, Jan. 2018 (109 pages).

Weber et al., "Multifunctional pancreatic islet encapsulation barriers achieved via multilayer PEG hydrogels", Cell Transplantation, vol. 16, No. 10, pp. 1049-1057, 2007.

Jeon et al., "Biodegradable, photocrosslinked alginate hydrogels with independently tailorable physical properties and cell adhesivity", Tissue Engineering, vol. 16, No. 9, pp. 2915-2925, 2010.

International Search Report and Written Opinion for Application No. PCT/US2019/053637 mailed Feb. 14, 2020.

International Search Report and Written Opinion for Application No. PCT/2020/025511 mailed Aug. 28, 2020.

Barron et al., "Targeted genetic modification of cell lines for recombinant protein production" Cytotechnology, 2007, vol. 53, pp. 65-73.

Carmona et al., "Correcting rare blood disorders using coagulation factors produced in vivo by shielded living therapeutics" Blood, 2019, vol. 134, 3 pages.

International Search Report and Written Opinion for Application No. PCT/2020/02585 mailed Aug. 28, 2020.

Fluharty B. et al.: "SIG-007: Novel 1-15 encapsulated non-viral cell-based therapy for Fabry—Poster Presentation #073—Thursday, Feb. 11", 17th Annual World Symposium, Feb. 11, 2021.

* cited by examiner

FIG. 1A (SEQ ID NO:1)

```
MQLRNPELHL GCALALRFLA LVSWDIPGAR ALDNGLARTP TMGWLHWERF 50
MCNLDCQEEP DSCISEKLFM EMAELMVSEG WKDAGYEYLC IDDCWMAPQR 100
DSEGRLQADP QRFPHGIRQL ANYVHSKGLK LGIYADVGNK TCAGFPGSFG 150
YYDIDAQTFA DWGVDLLKFD GCYCDSLENL ADGYKHMSLA LNRTGRSIVY 200
SCEWPLYMWP FQKPNYTEIR QYCNHWRNFA DIDDSWKSIK SILDWTSFNQ 250
ERIVDVAGPG GWNDPDMLVI GNFGLSWNQQ VTQMALWAIM AAPLFMSNDL 300
RHISPQAKAL LQDKDVIAIN QDPLGKQGYQ LRQGDNFEVW ERPLSGLAWA 350
VAMINRQEIG GPRSYTIAVA SLGKGVACNP ACFITQLLPV KRKLGFYEWT 400
SRLRSHINPT GTVLLQLENT MQMSLKDLL                        429
```

FIG. 1B (SEQ ID NO:2)

```
ATGCAGCTGA GGAACCCAGA ACTACATCTG GGCTGCGCGC TTGCGCTTCG 50
CTTCCTGGCC CTCGTTTCCT GGGACATCCC TGGGGCTAGA GCACTGGACA 100
ATGGATTGGC AAGGACGCCT ACCATGGGCT GGCTGCACTG GGAGCGCTTC 150
ATGTGCAACC TTGACTGCCA GGAAGAGCCA GATTCCTGCA TCAGTGAGAA 200
GCTCTTCATG GAGATGGCAG AGCTCATGGT CTCAGAAGGC TGGAAGGATG 250
CAGGTTATGA GTACCTCTGC ATTGATGACT GTTGGATGGC TCCCCAAAGA 300
GATTCAGAAG GCAGACTTCA GGCAGACCCT CAGCGCTTTC CTCATGGGAT 350
TCGCCAGCTA GCTAATTATG TTCACAGCAA AGGACTGAAG CTAGGGATTT 400
ATGCAGATGT TGGAAATAAA ACCTGCGCAG GCTTCCCTGG GAGTTTTGGA 450
TACTACGACA TTGATGCCCA GACCTTTGCT GACTGGGGAG TAGATCTGCT 500
AAAATTTGAT GGTTGTTACT GTGACAGTTT GGAAAATTTG GCAGATGGTT 550
ATAAGCACAT GTCCTTGGCC CTGAATAGGA CTGGCAGAAG CATTGTGTAC 600
TCCTGTGAGT GGCCTCTTTA TATGTGGCCC TTTCAAAAGC CCAATTATAC 650
AGAAATCCGA CAGTACTGCA ATCACTGGCG AAATTTTGCT GACATTGATG 700
ATTCCTGGAA AAGTATAAAG AGTATCTTGG ACTGGACATC TTTTAACCAG 750
GAGAGAATTG TTGATGTTGC TGGACCAGGG GGTTGGAATG ACCCAGATAT 800
GTTAGTGATT GGCAACTTTG GCCTCAGCTG GAATCAGCAA GTAACTCAGA 850
TGGCCCTCTG GGCTATCATG GCTGCTCCTT TATTCATGTC TAATGACCTC 900
CGACACATCA GCCCTCAAGC CAAAGCTCTC CTTCAGGATA AGGACGTAAT 950
TGCCATCAAT CAGGACCCCT TGGGCAAGCA AGGGTACCAG CTTAGACAGG 1000
GAGACAACTT TGAAGTGTGG GAACGACCTC TCTCAGGCTT AGCCTGGGCT 1050
GTAGCTATGA TAAACCGGCA GGAGATTGGT GGACCTCGCT CTTATACCAT 1100
CGCAGTTGCT TCCCTGGGTA AAGGAGTGGC CTGTAATCCT GCCTGCTTCA 1150
TCACACAGCT CCTCCCTGTG AAAAGGAAGC TAGGGTTCTA TGAATGGACT 1200
TCAAGGTTAA GAAGTCACAT AAATCCCACA GGCACTGTTT TGCTTCAGCT 1250
AGAAAATACA ATGCAGATGT CATTAAAAGA CTTACTTTAA            1290
```

FIG. 2 (SEQ ID NO:3)

```
ATGCAGCTGA GAAACCCCGA ACTGCACCTG GGATGTGCCC TGGCTCTGAG 50
ATTTCTGGCC CTGGTGTCTT GGGACATCCC TGGCGCTAGA GCCCTGGATA 100
ATGGCCTGGC CAGAACACCT ACAATGGGCT GGCTGCACTG GGAGAGATTC 150
ATGTGCAACC TGGACTGCCA AGAGGAACCC GACAGCTGCA TCAGCGAGAA 200
GCTGTTCATG GAAATGGCCG AGCTGATGGT GTCCGAAGGC TGGAAGGATG 250
CCGGCTACGA GTACCTGTGC ATCGACGACT GTTGGATGGC CCCTCAGAGA 300
GACTCTGAGG GCAGACTGCA GGCCGATCCT CAGAGATTTC CCCACGGCAT 350
TAGACAGCTG GCCAACTACG TGCACAGCAA GGGCCTGAAG CTGGGCATCT 400
ATGCCGACGT GGGCAACAAG ACCTGTGCCG GCTTTCCTGG CAGCTTCGGC 450
TACTACGATA TCGACGCCCA GACCTTCGCC GATTGGGGAG TCGATCTGCT 500
GAAGTTCGAC GGCTGCTACT GCGACAGCCT GGAAAATCTG GCCGACGGCT 550
ACAAGCACAT GTCACTGGCC CTGAATCGGA CCGGCAGATC CATCGTGTAC 600
AGCTGCGAGT GGCCCCTGTA CATGTGGCCC TTCCAGAAGC CTAACTACAC 650
CGAGATCAGA CAGTACTGCA ACCACTGGCG GAACTTCGCC GACATCGACG 700
ATAGCTGGAA GTCCATCAAG AGCATCCTGG ACTGGACCAG CTTCAATCAA 750
GAGCGGATCG TGGACGTGGC AGGACCTGGC GGATGGAACG ATCCTGACAT 800
GCTGGTCATC GGCAACTTCG GCCTGAGCTG GAACCAGCAA GTGACCCAGA 850
TGGCCCTGTG GGCCATTATG GCCGCTCCTC TGTTCATGAG CAACGACCTG 900
AGACACATCA GCCCTCAGGC CAAGGCTCTG CTGCAGGACA AGGATGTGAT 950
CGCTATCAAC CAGGATCCTC TGGGCAAGCA GGGCTACCAG CTGAGACAGG 1000
GCGACAATTT CGAAGTGTGG GAAAGACCCC TGAGCGGACT GGCTTGGGCC 1050
GTCGCCATGA TCAACAGACA AGAGATCGGC GGACCCCGGT CCTACACAAT 1100
TGCCGTGGCT TCTCTCGGCA AAGGCGTGGC CTGTAATCCC GCCTGCTTTA 1150
TCACACAGCT GCTGCCCGTG AAGAGAAAGC TGGGCTTTTA CGAGTGGACC 1200
AGCAGACTGC GGAGCCACAT CAATCCTACC GGCACAGTGC TGCTGCAGCT 1250
GGAAAACACC ATGCAGATGA GCCTGAAGGA CCTGCTGTAA            1290
```

FIG. 3 (SEQ ID NO:4)

```
ATGCAGCTGC GCAACCCCGA GCTGCACCTG GGCTGCGCCC TGGCCCTGCG 50
CTTCCTGGCC CTGGTGAGCT GGGACATCCC CGGCGCCCGC GCCCTGGACA 100
ACGGCCTGGC CCGCACCCCC ACCATGGGCT GGCTGCACTG GGAGCGCTTC 150
ATGTGCAACC TGGACTGCCA GGAGGAGCCC GACAGCTGCA TCAGCGAGAA 200
GCTGTTCATG GAGATGGCCG AGCTGATGGT GAGCGAGGGC TGGAAGGACG 250
CCGGCTACGA GTACCTGTGC ATCGACGACT GCTGGATGGC CCCCCAGCGC 300
GACAGCGAGG GCCGCCTGCA GGCCGACCCC CAGCGCTTCC CCCACGGCAT 350
CCGCCAGCTG GCCAACTACG TGCACAGCAA GGGCCTGAAG CTGGGCATCT 400
ACGCCGACGT GGGCAACAAG ACCTGCGCCG GCTTCCCCGG CAGCTTCGGC 450
TACTACGACA TCGACGCCCA GACCTTCGCC GACTGGGGCG TGGACCTGCT 500
GAAGTTCGAC GGCTGCTACT GCGACAGCCT GGAGAACCTG GCCGACGGCT 550
ACAAGCACAT GAGCCTGGCC CTGAACCGCA CCGGCCGCAG CATCGTGTAC 600
AGCTGCGAGT GGCCCCTGTA CATGTGGCCC TTCCAGAAGC CCAACTACAC 650
CGAGATCCGC CAGTACTGCA ACCACTGGCG CAACTTCGCC GACATCGACG 700
ACAGCTGGAA GAGCATCAAG AGCATCCTGG ACTGGACCAG CTTCAACCAG 750
GAGCGCATCG TGGACGTGGC CGGCCCCGGC GGCTGGAACG ACCCCGACAT 800
GCTGGTGATC GGCAACTTCG GCCTGAGCTG GAACCAGCAG GTGACCCAGA 850
TGGCCCTGTG GGCCATCATG GCCGCCCCCC TGTTCATGAG CAACGACCTG 900
CGCCACATCA GCCCCCAGGC CAAGGCCCTG CTGCAGGACA AGGACGTGAT 950
CGCCATCAAC CAGGACCCCC TGGGCAAGCA GGGCTACCAG CTGCGCCAGG 1000
GCGACAACTT CGAGGTGTGG GAGCGCCCCC TGAGCGGCCT GGCCTGGGCC 1050
GTGGCCATGA TCAACCGCCA GGAGATCGGC GGCCCCCGCA GCTACACCAT 1100
CGCCGTGGCC AGCCTGGGCA AGGGCGTGGC CTGCAACCCC GCCTGCTTCA 1150
TCACCCAGCT GCTGCCCGTG AAGCGCAAGC TGGGCTTCTA CGAGTGGACC 1200
AGCCGCCTGC GCAGCCACAT CAACCCCACC GGCACCGTGC TGCTGCAGCT 1250
GGAGAACACC ATGCAGATGA GCCTGAAGGA CCTGCTGTAA            1290
```

FIG. 4A (SEQ ID NO:5)

```
MGWRAAGALL LALLLHGRLL ALDNGLARTP TMGWLHWERF MCNLDCQEEP  50
DSCISEKLFM EMAELMVSEG WKDAGYEYLC IDDCWMAPQR DSEGRLQADP 100
QRFPHGIRQL ANYVHSKGLK LGIYADVGNK TCAGFPGSFG YYDIDAQTFA 150
DWGVDLLKFD GCYCDSLENL ADGYKHMSLA LNRTGRSIVY SCEWPLYMWP 200
FQKPNYTEIR QYCNHWRNFA DIDDSWKSIK SILDWTSFNQ ERIVDVAGPG 250
GWNDPDMLVI GNFGLSWNQQ VTQMALWAIM AAPLFMSNDL RHISPQAKAL 300
LQDKDVIAIN QDPLGKQGYQ LRQGDNFEVW ERPLSGLAWA VAMINRQEIG 350
GPRSYTIAVA SLGKGVACNP ACFITQLLPV KRKLGFYEWT SRLRSHINPT 400
GTVLLQLENT MQMSLKDLL                                   419
```

FIG. 4B (SEQ ID NO:6)

```
ATGGGCTGGC GAGCTGCTGG TGCACTTCTG CTGGCTCTGC TGCTTCATGG 50
CAGACTGCTT GCTCTGGACA ACGGCCTGGC CCGCACCCCC ACCATGGGCT 100
GGCTGCACTG GGAGCGCTTC ATGTGCAACC TGGACTGCCA GGAGGAGCCC 150
GACAGCTGCA TCAGCGAGAA GCTGTTCATG GAGATGGCCG AGCTGATGGT 200
GAGCGAGGGC TGGAAGGACG CCGGCTACGA GTACCTGTGC ATCGACGACT 250
GCTGGATGGC CCCCCAGCGC GACAGCGAGG GCCGCCTGCA GGCCGACCCC 300
CAGCGCTTCC CCCACGGCAT CCGCCAGCTG GCCAACTACG TGCACAGCAA 350
GGGCCTGAAG CTGGGCATCT ACGCCGACGT GGGCAACAAG ACCTGCGCCG 400
GCTTCCCCGG CAGCTTCGGC TACTACGACA TCGACGCCCA GACCTTCGCC 450
GACTGGGGCG TGGACCTGCT GAAGTTCGAC GGCTGCTACT GCGACAGCCT 500
GGAGAACCTG GCCGACGGCT ACAAGCACAT GAGCCTGGCC CTGAACCGCA 550
CCGGCCGCAG CATCGTGTAC AGCTGCGAGT GGCCCCTGTA CATGTGGCCC 600
TTCCAGAAGC CCAACTACAC CGAGATCCGC CAGTACTGCA ACCACTGGCG 650
CAACTTCGCC GACATCGACG ACAGCTGGAA GAGCATCAAG AGCATCCTGG 700
ACTGGACCAG CTTCAACCAG GAGCGCATCG TGGACGTGGC CGGCCCCGGC 750
GGCTGGAACG ACCCCGACAT GCTGGTGATC GGCAACTTCG GCCTGAGCTG 800
GAACCAGCAG GTGACCCAGA TGGCCCTGTG GGCCATCATG GCCGCCCCCC 850
TGTTCATGAG CAACGACCTG CGCCACATCA GCCCCCAGGC CAAGGCCCTG 900
CTGCAGGACA AGGACGTGAT CGCCATCAAC CAGGACCCCC TGGGCAAGCA 950
GGGCTACCAG CTGCGCCAGG GCGACAACTT CGAGGTGTGG GAGCGCCCCC 1000
TGAGCGGCCT GGCCTGGGCC GTGGCCATGA TCAACCGCCA GGAGATCGGC 1050
GGCCCCCGCA GCTACACCAT CGCCGTGGCC AGCCTGGGCA AGGGCGTGGC 1100
CTGCAACCCC GCCTGCTTCA TCACCCAGCT GCTGCCCGTG AAGCGCAAGC 1150
TGGGCTTCTA CGAGTGGACC AGCCGCCTGC GCAGCCACAT CAACCCCACC 1200
GGCACCGTGC TGCTGCAGCT GGAGAACACC ATGCAGATGA GCCTGAAGGA 1250
CCTGCTGTAA                                            1260
```

FIG. 5A (SEQ ID NO:7)

MGWRAAGALL LALLLHGRLL ALDNGLARTP TMGWLHWERF MCNLDCQEEP 50
DSCISEKLFM EMAELMVSEG WKDAGYEYLC IDDCWMAPQR DSEGRLQADP 100
QRFPHGIRQL ANYVHSKGLK LGIYADVGNK TCAGFPGSFG YYDIDAQTFA 150
DWGVDLLKFD GCYCDSLENL ADGYKHMSLA LNRTGRSIVY SCEWPLYMWP 200
FQKPNYTEIR QYCNHWRNFA DIDDSWKSIK SILDWTSFNQ ERIVDVAGPG 250
GWNDPDMLVI GNFGLSWNQQ VTQMALWAIM AAPLFMSNDL RHISPQAKAL 300
LQDKDVIAIN QDPLGKQGYQ LRQGDNFEVW ERPLSGLAWA VAMINRQEIG 350
GPRSYTIAVA SLGKGVACNP ACFITQLLPV KRKLGFYEWT SRLRSHINPT 400
GTVLLQLENT MQMSLKDLL*G GSS*RTVAAPS VFIFPPSDEQ LKSGTASVVC 450
LLNNFYPREA KVQWKVDNAL QSGNSQESVT EQDSKDSTYS LSSTLTLSKA 500
DYEKHKVYAC EVTHQGLSSP VTKSFNRGEC 530

FIG. 5B (SEQ ID NO:8)

MGWRAAGALL LALLLHGRLL AASTKGPSVF PLAPSSKSTS GGTAALGCLV 50
KDYFPEPVTV SWNSGALTSG VHTFPAVLQS SGLYSLSSVV TVPSSSLGTQ 100
TYICNVNHKP SNTKVDKKVE PKSCDKTHTC PPCPAPELLG GPSVFLFPPK 150
PKDTLMISRT PEVTCVVVDV SHEDPEVKFN WYVDGVEVHN AKTKPREEQY 200
NSTYRVVSVL TVLHQDWLNG KEYKCKVSNK ALPAPIEKTI SKAKGQPREP 250
QVYTLPPSRD ELTKNQVSLT CLVKGFYPSD IAVEWESNGQ PENNYKTTPP 300
VLDSDGSFFL YSKLTVDKSR WQQGNVFSCS VMHEALHNHY TQKSLSLSPG 350
K 351

FIG. 5C (SEQ ID NO:9)

ATGGGCTGGC GAGCTGCTGG TGCACTTCTG CTGGCTCTGC TGCTTCATGG 50
CAGACTGCTT GCTCTGGACA ACGGCCTGGC CCGCACCCCC ACCATGGGCT 100
GGCTGCACTG GGAGCGCTTC ATGTGCAACC TGGACTGCCA GGAGGAGCCC 150
GACAGCTGCA TCAGCGAGAA GCTGTTCATG GAGATGGCCG AGCTGATGGT 200
GAGCGAGGGC TGGAAGGACG CCGGCTACGA GTACCTGTGC ATCGACGACT 250
GCTGGATGGC CCCCCAGCGC GACAGCGAGG GCCGCCTGCA GGCCGACCCC 300
CAGCGCTTCC CCCACGGCAT CCGCCAGCTG GCCAACTACG TGCACAGCAA 350
GGGCCTGAAG CTGGGCATCT ACGCCGACGT GGGCAACAAG ACCTGCGCCG 400
GCTTCCCCGG CAGCTTCGGC TACTACGACA TCGACGCCCA GACCTTCGCC 450
GACTGGGGCG TGGACCTGCT GAAGTTCGAC GGCTGCTACT GCGACAGCCT 500
GGAGAACCTG GCCGACGGCT ACAAGCACAT GAGCCTGGCC CTGAACCGCA 550
CCGGCCGCAG CATCGTGTAC AGCTGCGAGT GGCCCCTGTA CATGTGGCCC 600
TTCCAGAAGC CCAACTACAC CGAGATCCGC CAGTACTGCA ACCACTGGCG 650
CAACTTCGCC GACATCGACG ACAGCTGGAA GAGCATCAAG AGCATCCTGG 700
ACTGGACCAG CTTCAACCAG GAGCGCATCG TGGACGTGGC CGGCCCCGGC 750
GGCTGGAACG ACCCCGACAT GCTGGTGATC GGCAACTTCG GCCTGAGCTG 800
GAACCAGCAG GTGACCCAGA TGGCCCTGTG GGCCATCATG GCCGCCCCCC 850
TGTTCATGAG CAACGACCTG CGCCACATCA GCCCCCAGGC CAAGGCCCTG 900
CTGCAGGACA AGGACGTGAT CGCCATCAAC CAGGACCCCC TGGGCAAGCA 950
GGGCTACCAG CTGCGCCAGG GCGACAACTT CGAGGTGTGG GAGCGCCCCC 1000
TGAGCGGCCT GGCCTGGGCC GTGGCCATGA TCAACCGCCA GGAGATCGGC 1050
GGCCCCCGCA GCTACACCAT CGCCGTGGCC AGCCTGGGCA AGGGCGTGGC 1100
CTGCAACCCC GCCTGCTTCA TCACCCAGCT GCTGCCCGTG AAGCGCAAGC 1150
TGGGCTTCTA CGAGTGGACC AGCCGCCTGC GCAGCCACAT CAACCCCACC 1200
GGCACCGTGC TGCTGCAGCT GGAGAACACC ATGCAGATGA GCCTGAAGGA 1250
CCTGCTGGGC GGCAGCAGCC GCACCGTGGC CGCCCCCAGC GTGTTCATCT 1300
TCCCCCCCAG CGACGAGCAG CTGAAGAGCG GCACCGCCAG CGTGGTGTGC 1350
CTGCTGAACA ACTTCTACCC CCGCGAGGCC AAGGTGCAGT GGAAGGTGGA 1400
CAACGCCCTG CAGAGCGGCA ACAGCCAGGA GAGCGTGACC GAGCAGGACA 1450
GCAAGGACAG CACCTACAGC CTGAGCAGCA CCCTGACCCT GAGCAAGGCC 1500
GACTACGAGA AGCACAAGGT GTACGCCTGC GAGGTGACCC ACCAGGGCCT 1550
GAGCAGCCCC GTGACCAAGA GCTTCAACCG CGGCGAGTGC TAA 1593

FIG. 5D (SEQ ID NO:10)

```
ATGGGCTGGC GAGCTGCTGG TGCACTTCTG CTGGCTCTGC TGCTTCATGG 50
CAGACTGCTT GCTGCCAGCA CCAAGGGCCC CAGCGTGTTC CCCCTGGCCC 100
CCAGCAGCAA GAGCACCAGC GGCGGCACCG CCGCCCTGGG CTGCCTGGTG 150
AAGGACTACT TCCCCGAGCC CGTGACCGTG AGCTGGAACA GCGGCGCCCT 200
GACCAGCGGC GTGCACACCT TCCCCGCCGT GCTGCAGAGC AGCGGCCTGT 250
ACAGCCTGAG CAGCGTGGTG ACCGTGCCCA GCAGCAGCCT GGGCACCCAG 300
ACCTACATCT GCAACGTGAA CCACAAGCCC AGCAACACCA AGGTGGACAA 350
GAAGGTGGAG CCCAAGAGCT GCGACAAGAC CCACACCTGC CCCCCCTGCC 400
CCGCCCCCGA GCTGCTGGGC GGCCCCAGCG TGTTCCTGTT CCCCCCCAAG 450
CCCAAGGACA CCCTGATGAT CAGCCGCACC CCCGAGGTGA CCTGCGTGGT 500
GGTGGACGTG AGCCACGAGG ACCCCGAGGT GAAGTTCAAC TGGTACGTGG 550
ACGGCGTGGA GGTGCACAAC GCCAAGACCA AGCCCCGCGA GGAGCAGTAC 600
AACAGCACCT ACCGCGTGGT GAGCGTGCTG ACCGTGCTGC ACCAGGACTG 650
GCTGAACGGC AAGGAGTACA AGTGCAAGGT GAGCAACAAG GCCCTGCCCG 700
CCCCCATCGA GAAGACCATC AGCAAGGCCA AGGGCCAGCC CCGCGAGCCC 750
CAGGTGTACA CCCTGCCCCC CAGCCGCGAC GAGCTGACCA AGAACCAGGT 800
GAGCCTGACC TGCCTGGTGA AGGGCTTCTA CCCCAGCGAC ATCGCCGTGG 850
AGTGGGAGAG CAACGGCCAG CCCGAGAACA ACTACAAGAC CACCCCCCCC 900
GTGCTGGACA GCGACGGCAG CTTCTTCCTG TACAGCAAGC TGACCGTGGA 950
CAAGAGCCGC TGGCAGCAGG GCAACGTGTT CAGCTGCAGC GTGATGCACG 1000
AGGCCCTGCA CAACCACTAC ACCCAGAAGA GCCTGAGCCT GAGCCCCGGC 1050
AAGTAA                                                1056
```

FIG. 6A (SEQ ID NO:11)

MGWRAAGALL LALLLHGRLL ALDNGLARTP TMGWLHWERF MCNLDCQEEP 50
DSCISEKLFM EMAELMVSEG WKDAGYEYLC IDDCWMAPQR DSEGRLQADP 100
QRFPHGIRQL ANYVHSKGLK LGIYADVGNK TCAGFPGSFG YYDIDAQTFA 150
DWGVDLLKFD GCYCDSLENL ADGYKHMSLA LNRTGRSIVY SCEWPLYMWP 200
FQKPNYTEIR QYCNHWRNFA DIDDSWKSIK SILDWTSFNQ ERIVDVAGPG 250
GWNDPDMLVI GNFGLSWNQQ VTQMALWAIM AAPLFMSNDL RHISPQAKAL 300
LQDKDVIAIN QDPLGKQGYQ LRQGDNFEVW ERPLSGLAWA VAMINRQEIG 350
GPRSYTIAVA SLGKGVACNP ACFITQLLPV KRKLGFYEWT SRLRSHINPT 400
GTVLLQLENT MQMSLKDLL*G GSS*EVQLQAS GGGLVQAGGS LRLSCAASGF 450
KITHYTMGWF RQAPGKEREF VSRITWGGDN TFYSNSVKGR FTISRDNAKN 500
TVYLQMNSLK PEDTADYYCA AGSTSTATPL RVDYWGKGTQ VTVSSEPKSS 550
DKTHTCPPCP APELLGGPSV FLFPPKPKDT LMISRTPEVT CVVVDVSHED 600
PEVKFNWYVD GVEVHNAKTK PREEQYNSTY RVVSVLTVLH QDWLNGKEYK 650
CKVSNKALPA PIEKTISKAK GQPREPQVYT LPPSRDELTK NQVSLTCLVK 700
GFYPSDIAVE WESNGQPENN YKTTPPVLDS DGSFFLYSKL TVDKSRWQQG 750
NVFSCSVMHE ALHNHYTQKS LSLSPGK 777

FIG. 6B (SEQ ID NO:12)

ATGGGCTGGC GAGCTGCTGG TGCACTTCTG CTGGCTCTGC TGCTTCATGG 50
CAGACTGCTT GCTCTGGACA ACGGCCTGGC CCGCACCCCC ACCATGGGCT 100
GGCTGCACTG GGAGCGCTTC ATGTGCAACC TGGACTGCCA GGAGGAGCCC 150
GACAGCTGCA TCAGCGAGAA GCTGTTCATG GAGATGGCCG AGCTGATGGT 200
GAGCGAGGGC TGGAAGGACG CCGGCTACGA GTACCTGTGC ATCGACGACT 250
GCTGGATGGC CCCCCAGCGC GACAGCGAGG GCCGCCTGCA GGCCGACCCC 300
CAGCGCTTCC CCCACGGCAT CCGCCAGCTG GCCAACTACG TGCACAGCAA 350
GGGCCTGAAG CTGGGCATCT ACGCCGACGT GGGCAACAAG ACCTGCGCCG 400
GCTTCCCCGG CAGCTTCGGC TACTACGACA TCGACGCCCA GACCTTCGCC 450
GACTGGGGCG TGGACCTGCT GAAGTTCGAC GGCTGCTACT GCGACAGCCT 500
GGAGAACCTG GCCGACGGCT ACAAGCACAT GAGCCTGGCC CTGAACCGCA 550
CCGGCCGCAG CATCGTGTAC AGCTGCGAGT GGCCCCTGTA CATGTGGCCC 600
TTCCAGAAGC CCAACTACAC CGAGATCCGC CAGTACTGCA ACCACTGGCG 650
CAACTTCGCC GACATCGACG ACAGCTGGAA GAGCATCAAG AGCATCCTGG 700
ACTGGACCAG CTTCAACCAG GAGCGCATCG TGGACGTGGC CGGCCCCGGC 750
GGCTGGAACG ACCCCGACAT GCTGGTGATC GGCAACTTCG GCCTGAGCTG 800
GAACCAGCAG GTGACCCAGA TGGCCCTGTG GGCCATCATG GCCGCCCCCC 850
TGTTCATGAG CAACGACCTG CGCCACATCA GCCCCCAGGC CAAGGCCCTG 900
CTGCAGGACA AGGACGTGAT CGCCATCAAC CAGGACCCCC TGGGCAAGCA 950
GGGCTACCAG CTGCGCCAGG GCGACAACTT CGAGGTGTGG GAGCGCCCCC 1000
TGAGCGGCCT GGCCTGGGCC GTGGCCATGA TCAACCGCCA GGAGATCGGC 1050
GGCCCCCGCA GCTACACCAT CGCCGTGGCC AGCCTGGGCA AGGGCGTGGC 1100
CTGCAACCCC GCCTGCTTCA TCACCCAGCT GCTGCCCGTG AAGCGCAAGC 1150
TGGGCTTCTA CGAGTGGACC AGCCGCCTGC GCAGCCACAT CAACCCCACC 1200
GGCACCGTGC TGCTGCAGCT GGAGAACACC ATGCAGATGA GCCTGAAGGA 1250
CCTGCTG*GGC GGCAGCAG*CG AGGTGCAGCT GCAGGCCAGC GGCGGCGGCC 1300
TGGTGCAGGC CGGCGGCAGC CTGCGCCTGA GCTGCGCCGC CAGCGGCTTC 1350
AAGATCACCC ACTACACCAT GGGCTGGTTC CGCCAGGCCC CCGGCAAGGA 1400
GCGCGAGTTC GTGAGCCGCA TCACCTGGGG CGGCGACAAC ACCTTCTACA 1450
GCAACAGCGT GAAGGGCCGC TTCACCATCA GCCGCGACAA CGCCAAGAAC 1500

FIG. 6B continued (SEQ ID NO:12)

```
ACCGTGTACC TGCAGATGAA CAGCCTGAAG CCCGAGGACA CCGCCGACTA 1550
CTACTGCGCC GCCGGCAGCA CCAGCACCGC CACCCCCCTG CGCGTGGACT 1600
ACTGGGGCAA GGGCACCCAG GTGACCGTGA GCAGCGAGCC CAAGAGCAGC 1650
GACAAGACCC ACACCTGCCC CCCCTGCCCC GCCCCCGAGC TGCTGGGCGG 1700
CCCCAGCGTG TTCCTGTTCC CCCCCAAGCC CAAGGACACC CTGATGATCA 1750
GCCGCACCCC CGAGGTGACC TGCGTGGTGG TGGACGTGAG CCACGAGGAC 1800
CCCGAGGTGA AGTTCAACTG GTACGTGGAC GGCGTGGAGG TGCACAACGC 1850
CAAGACCAAG CCCCGCGAGG AGCAGTACAA CAGCACCTAC CGCGTGGTGA 1900
GCGTGCTGAC CGTGCTGCAC CAGGACTGGC TGAACGGCAA GGAGTACAAG 1950
TGCAAGGTGA GCAACAAGGC CCTGCCCGCC CCCATCGAGA AGACCATCAG 2000
CAAGGCCAAG GGCCAGCCCC GCGAGCCCCA GGTGTACACC CTGCCCCCCA 2050
GCCGCGACGA GCTGACCAAG AACCAGGTGA GCCTGACCTG CCTGGTGAAG 2100
GGCTTCTACC CCAGCGACAT CGCCGTGGAG TGGGAGAGCA ACGGCCAGCC 2150
CGAGAACAAC TACAAGACCA CCCCCCCCGT GCTGGACAGC GACGGCAGCT 2200
TCTTCCTGTA CAGCAAGCTG ACCGTGGACA AGAGCCGCTG GCAGCAGGGC 2250
AACGTGTTCA GCTGCAGCGT GATGCACGAG GCCCTGCACA ACCACTACAC 2300
CCAGAAGAGC CTGAGCCTGA GCCCCGGCAA GTAA 2334
```

FIG. 7A (SEQ ID NO:13)

MGWRAAGALL LALLLHGRLL ALDNGLARTP TMGWLHWERF MCNLDCQEEP 50
DSCISEKLFM EMAELMVSEG WKDAGYEYLC IDDCWMAPQR DSEGRLQADP 100
QRFPHGIRQL ANYVHSKGLK LGIYADVGNK TCAGFPGSFG YYDIDAQTFA 150
DWGVDLLKFD GCYCDSLENL ADGYKHMSLA LNRTGRSIVY SCEWPLYMWP 200
FQKPNYTEIR QYCNHWRNFA DIDDSWKSIK SILDWTSFNQ ERIVDVAGPG 250
GWNDPDMLVI GNFGLSWNQQ VTQMALWAIM AAPLFMSNDL RHISPQAKAL 300
LQDKDVIAIN QDPLGKQGYQ LRQGDNFEVW ERPLSGLAWA VAMINRQEIG 350
GPRSYTIAVA SLGKGVACNP ACFITQLLPV KRKLGFYEWT SRLRSHINPT 400
GTVLLQLENT MQMSLKDLL*G GSS*EPKSSDK THTCPPCPAP ELLGGPSVFL 450
FPPKPKDTLM ISRTPEVTCV VVDVSHEDPE VKFNWYVDGV EVHNAKTKPR 500
EEQYNSTYRV VSVLTVLHQD WLNGKEYKCK VSNKALPAPI EKTISKAKGQ 550
PREPQVYTLP PSRDELTKNQ VSLTCLVKGF YPSDIAVEWE SNGQPENNYK 600
TTPPVLDSDG SFFLYSKLTV DKSRWQQGNV FSCSVMHEAL HNHYTQKSLS 650
LSPGK 655

FIG. 7B (SEQ ID NO:14)

ATGGGCTGGC GAGCTGCTGG TGCACTTCTG CTGGCTCTGC TGCTTCATGG 50
CAGACTGCTT GCTCTGGACA ACGGCCTGGC CCGCACCCCC ACCATGGGCT 100
GGCTGCACTG GGAGCGCTTC ATGTGCAACC TGGACTGCCA GGAGGAGCCC 150
GACAGCTGCA TCAGCGAGAA GCTGTTCATG GAGATGGCCG AGCTGATGGT 200
GAGCGAGGGC TGGAAGGACG CCGGCTACGA GTACCTGTGC ATCGACGACT 250
GCTGGATGGC CCCCCAGCGC GACAGCGAGG GCCGCCTGCA GGCCGACCCC 300
CAGCGCTTCC CCCACGGCAT CCGCCAGCTG GCCAACTACG TGCACAGCAA 350
GGGCCTGAAG CTGGGCATCT ACGCCGACGT GGGCAACAAG ACCTGCGCCG 400
GCTTCCCCGG CAGCTTCGGC TACTACGACA TCGACGCCCA GACCTTCGCC 450
GACTGGGGCG TGGACCTGCT GAAGTTCGAC GGCTGCTACT GCGACAGCCT 500
GGAGAACCTG GCCGACGGCT ACAAGCACAT GAGCCTGGCC CTGAACCGCA 550
CCGGCCGCAG CATCGTGTAC AGCTGCGAGT GGCCCCTGTA CATGTGGCCC 600
TTCCAGAAGC CCAACTACAC CGAGATCCGC CAGTACTGCA ACCACTGGCG 650
CAACTTCGCC GACATCGACG ACAGCTGGAA GAGCATCAAG AGCATCCTGG 700
ACTGGACCAG CTTCAACCAG GAGCGCATCG TGGACGTGGC CGGCCCCGGC 750
GGCTGGAACG ACCCCGACAT GCTGGTGATC GGCAACTTCG GCCTGAGCTG 800
GAACCAGCAG GTGACCCAGA TGGCCCTGTG GGCCATCATG GCCGCCCCCC 850
TGTTCATGAG CAACGACCTG CGCCACATCA GCCCCCAGGC CAAGGCCCTG 900
CTGCAGGACA AGGACGTGAT CGCCATCAAC CAGGACCCCC TGGGCAAGCA 950
GGGCTACCAG CTGCGCCAGG GCGACAACTT CGAGGTGTGG GAGCGCCCCC 1000
TGAGCGGCCT GGCCTGGGCC GTGGCCATGA TCAACCGCCA GGAGATCGGC 1050
GGCCCCCGCA GCTACACCAT CGCCGTGGCC AGCCTGGGCA AGGGCGTGGC 1100
CTGCAACCCC GCCTGCTTCA TCACCCAGCT GCTGCCCGTG AAGCGCAAGC 1150
TGGGCTTCTA CGAGTGGACC AGCCGCCTGC GCAGCCACAT CAACCCCACC 1200
GGCACCGTGC TGCTGCAGCT GGAGAACACC ATGCAGATGA GCCTGAAGGA 1250
CCTGCTG*GGC GGCAGCAGC*G AGCCCAAGAG CAGCGACAAG ACCCACACCT 1300
GCCCCCCCTG CCCCGCCCCC GAGCTGCTGG GCGGCCCCAG CGTGTTCCTG 1350
TTCCCCCCCA AGCCCAAGGA CACCCTGATG ATCAGCCGCA CCCCCGAGGT 1400
GACCTGCGTG GTGGTGGACG TGAGCCACGA GGACCCCGAG GTGAAGTTCA 1450
ACTGGTACGT GGACGGCGTG GAGGTGCACA ACGCCAAGAC CAAGCCCCGC 1500

FIG. 7B continued (SEQ ID NO:14)

GAGGAGCAGT ACAACAGCAC CTACCGCGTG GTGAGCGTGC TGACCGTGCT 1550
GCACCAGGAC TGGCTGAACG GCAAGGAGTA CAAGTGCAAG GTGAGCAACA 1600
AGGCCCTGCC CGCCCCCATC GAGAAGACCA TCAGCAAGGC CAAGGGCCAG 1650
CCCCGCGAGC CCCAGGTGTA CACCCTGCCC CCCAGCCGCG ACGAGCTGAC 1700
CAAGAACCAG GTGAGCCTGA CCTGCCTGGT GAAGGGCTTC TACCCCAGCG 1750
ACATCGCCGT GGAGTGGGAG AGCAACGGCC AGCCCGAGAA CAACTACAAG 1800
ACCACCCCCC CCGTGCTGGA CAGCGACGGC AGCTTCTTCC TGTACAGCAA 1850
GCTGACCGTG GACAAGAGCC GCTGGCAGCA GGGCAACGTG TTCAGCTGCA 1900
GCGTGATGCA CGAGGCCCTG CACAACCACT ACACCCAGAA GAGCCTGAGC 1950
CTGAGCCCCG GCAAGTAA 1968

FIG. 8B (SEQ ID NO:17)

1 TTAACCCTAG AAAGATAGTC TGCGTAAAAT TGACGCATGC ATTCTTGAAA TATTGCTCTC TCTTTCTAAA TAGCGCGAAT

81 CCGTCGCTGT GCATTTAGGA CATCTCAGTC GCCGCTTGGA GCTCCCGTGA GGCGTGCTTG TCAATGCGGT AAGTGTCACT

161 GATTTTGAAC TATAACGACC GCGTGAGTCA AAATGACGCA TGATTATCTT TTACGTGACT TTTAAGATTT AACTCATACG

241 ATAATTATAT TGTTATTTCA TGTTCTACTT ACGTGATAAC TTATTATATA TATATTTTCT TGTTATAGAT ATCATCAACT

321 TTGTATAGAA AAGTTGCTCG ACATTGATTA TTGACTAGTT ATTAATAGTA ATCAATTACG GGGTCATTAG TTCATAGCCC

401 ATATATGGAG TTCCGCGTTA CATAACTTAC GGTAAATGGC CCGCCTGGCT GACCGCCCAA CGACCCCCGC CCATTGACGT

481 CAATAATGAC GTATGTTCCC ATAGTAACGC CAATAGGGAC TTTCCATTGA CGTCAATGGG TGGAGTATTT ACGGTAAACT

561 GCCCACTTGG CAGTACATCA AGTGTATCAT ATGCCAAGTA CGCCCCCTAT TGACGTCAAT GACGGTAAAT GGCCCGCCTG

641 GCATTATGCC CAGTACATGA CCTTATGGGA CTTTCCTACT TGGCAGTACA TCTACGTATT AGTCATCGCT ATTACCATGG

721 TCGAGGTGAG CCCCACGTTC TGCTTCACTC TCCCCATCTC CCCCCCCTCC CCACCCCCAA TTTTGTATTT ATTTATTTTT

801 TAATTATTTT GTGCAGCGAT GGGGGCGGGG GGGGGGGGGG GGCGCGCGCC AGGCGGGGCG GGGCGGGGCG AGGGGCGGGG

881 CGGGGCGAGG CGGAGAGGTG CGGCGGCAGC CAATCAGAGC GGCGCGCTCC GAAAGTTTCC TTTTATGGCG AGGCGGCGGC

961 GGCGGCGGCC CTATAAAAAG CGAAGCGCGC GGCGGGCGGG AGTCGCTGCG CGCTGCCTTC GCCCCGTGCC CCGCTCCGCC

1041 GCCGCCTCGC GCCGCCCGCC CCGGCTCTGA CTGACCGCGT TACTCCCACA GGTGAGCGGG CGGGACGGCC CTTCTCCTCC

1121 GGGCTGTAAT TAGCGCTTGG TTTAATGACG GCTTGTTTCT TTTCTGTGGC TGCGTGAAAG CCTTGAGGGG CTCCGGGAGG

1201 GCCCTTTGTG CGGGGGGAGC GGCTCGGGGG GTGCGTGCGT GTGTGTGTGC GTGGGGAGCG CCGCGTGCGG CTCCGCGCTG

1281 CCCGGCGGCT GTGAGCGCTG CGGGCGCGGC GCGGGGCTTT GTGCGCTCCG CAGTGTGCGC GAGGGGAGCG CGGCCGGGGG

1361 CGGTGCCCCG CGGTGCGGGG GGGGCTGCGA GGGGAACAAA GGCTGCGTGC GGGGTGTGTG CGTGGGGGGG TGAGCAGGGG

1441 GTGTGGGCGC GTCGGTCGGG CTGCAACCCC CCCTGCACCC CCCTCCCCGA GTTGCTGAGC ACGGCCCGGC TTCGGGTGCG

1521 GGGCTCCGTA CGGGGCGTGG CGCGGGGCTC GCCGTGCCGG GCGGGGGGTG GCGGCAGGTG GGGGTGCCGG GCGGGGCGGG

1601 GCCGCCTCGG GCCGGGGAGG GCTCGGGGGA GGGGCGCGGC GGCCCCCGGA GCGCCGGCGG CTGTCGAGGC GCGGCGAGCC

1681 GCAGCCATTG CCTTTTATGG TAATCGTGCG AGAGGGCGCA GGGACTTCCT TTGTCCCAAA TCTGTGCGGA GCCGAAATCT

1761 GGGAGGCGCC GCCGCACCCC CTCTAGCGGG CGCGGGGCGA AGCGGTGCGG CGCCGGCAGG AAGGAAATGG GCGGGGAGGG

1841 CCTTCGTGCG TCGCCGCGCC GCCGTCCCCT TCTCCCTCTC CAGCCTCGGG GCTGTCCGCG GGGGGACGGC TGCCTTCGGG

1921 GGGGACGGGG CAGGGCGGGG TTCGGCTTCT GGCGTGTGAC CGGCGGCTCT AGAGCCTCTG CTAACCATGT TCATGCCTTC

2001 TTCTTTTTCC TACAGCTCCT GGGCAACGTG CTGGTTATTG TGCTGTCTCA TCATTTTGGC AAAGAATTGC AAGTTTGTAC

2081 AAAAAAGCAG GCTGCCACCG AATTCGCGGC CGCTAAACCC AGCTTTCTTG TACAAAGTGG CAACTTTATT ATACATAGTT

2161 GATCCTCAGG TGCAGGCTGC CTATCAGAAG GTGGTGGCTG GTGTGGCCAA TGCCCTGGCT CACAAATACC ACTGAGATCT

2241 TTTTCCCTCT GCCAAAAATT ATGGGGACAT CATGAAGCCC CTTGAGCATC TGACTTCTGG CTAATAAAGG AAATTTATTT

2321 TCATTGCAAT AGTGTGTTGG AATTTTTTGT GTCTCTCACT CGGAAGGACA TATGGGAGGG CAAATCATTT AAAACATCAG

2401 AATGAGTATT TGGTTTAGAG TTTGGCAACA TATGCCCATA TGCTGGCTGC CATGAACAAA GGTTGGCTAT AAAGAGGTCA

2481 TCAGTATATG AAACAGCCCC CTGCTGTCCA TTCCTTATTC CATAGAAAAG CCTTGACTTG AGGTTAGATT TTTTTTATAT

2561 TTTGTTTTGT GTTATTTTTT TCTTTAACAT CCCTAAAATT TTCCTTACAT GTTTTACTAG CCAGATTTTT CCTCCTCTCC

2641 TGACTACTCC CAGTCATAGC TGTCCCTCTT CTCTTATGGA GATCCCTCGA CCTGCAGCCC AAGCTTGGAT CCCTCGAGTT

2721 AATTAACGAG AGCATAATAT TGATATGTGC CAAAGTTGTT TCTGACTGAC TAATAAGTAT AATTTGTTTC TATTATGTAT

2801 AGGTTAAGCT AATTACTTAT TTTATAATAC AACATGACTG TTTTTAAAGT ACAAAATAAG TTTATTTTTG TAAAAGAGAG

2881 AATGTTTAAA AGTTTTGTTA CTTTATAGAA GAAATTTTGA GTTTTTGTTT TTTTTTAATA AATAAATAAA CATAAATAAA

2961 TTGTTTGTTG AATTTATTAT TAGTATGTAA GTGTAAATAT AATAAAACTT AATATCTATT CAAATTAATA AATAAACCTC

3041 GATATACAGA CCGATAAAAC ACATGCGTCA ATTTTACGCA TGATTATCTT TAACGTACGT CACAATATGA TTATCTTTCT

3121 AGGGTTAAAT AATAGTTTCT AATTTTTTTA TTATTCAGCC TGCTGTCGTG AATACCGAGC TCCAATTCGC CCTATAGTGA

3201 GTCGTATTAC AATTCACTGG CCGTCGTTTT ACAACGTCGT GACTGGGAAA ACCCTGGCGT TACCCAACTT AATCGCCTTG

3281 CAGCACATCC CCCTTTCGCC AGCTGGCGTA ATAGCGAAGA GGCCCGCACC GATCGCCCTT CCCAACAGTT GCGCAGCCTG

3361 AATGGCGAAT GGGACGCGCC CTGTAGCGGC GCATTAAGCG CGGCGGGTGT GGTGGTTACG CGCAGCGTGA CCGCTACACT

3441 TGCCAGCGCC CTAGCGCCCG CTCCTTTCGC TTTCTTCCCT TCCTTTCTCG CCACGTTCGC CGGCTTTCCC CGTCAAGCTC

3521 TAAATCGGGG GCTCCCTTTA GGGTTCCGAT TTAGTGCTTT ACGGCACCTC GACCCCAAAA AACTTGATTA GGGTGATGGT

FIG. 8B continued (SEQ ID NO:17)

3601 TCACGTAGTG GGCCATCGCC CTGATAGACG GTTTTTCGCC CTTTGACGTT GGAGTCCACG TTCTTTAATA GTGGACTCTT
3681 GTTCCAAACT GGAACAACAC TCAACCCTAT CTCGGTCTAT TCTTTTGATT TATAAGGGAT TTTGCCGATT TCGGCCTATT
3761 GGTTAAAAAA TGAGCTGATT TAACAAAAAT TTAACGCGAA TTTTAACAAA ATATTAACGC TTACAATTTA GGTGGCACTT
3841 TTCGGGGAAA TGTGCGCGGA ACCCCTATTT GTTTATTTTT CTAAATACAT TCAAATATGT ATCCGCTCAT GAGACAATAA
3921 CCCTGATAAA TGCTTCAATA ATATTGAAAA AGGAAGAGTA TGAGTATTCA ACATTTCCGT GTCGCCCTTA TTCCCTTTTT
4001 TGCGGCATTT TGCCTTCCTG TTTTTGCTCA CCCAGAAACG CTGGTGAAAG TAAAAGATGC TGAAGATCAG TTGGGTGCAC
4081 GAGTGGGTTA CATCGAACTG GATCTCAACA GCGGTAAGAT CCTTGAGAGT TTTCGCCCCG AAGAACGTTT TCCAATGATG
4161 AGCACTTTTA AAGTTCTGCT ATGTGGCGCG GTATTATCCC GTATTGACGC CGGGCAAGAG CAACTCGGTC GCCGCATACA
4241 CTATTCTCAG AATGACTTGG TTGAGTACTC ACCAGTCACA GAAAAGCATC TTACGGATGG CATGACAGTA AGAGAATTAT
4321 GCAGTGCTGC CATAACCATG AGTGATAACA CTGCGGCCAA CTTACTTCTG ACAACGATCG GAGGACCGAA GGAGCTAACC
4401 GCTTTTTTGC ACAACATGGG GGATCATGTA ACTCGCCTTG ATCGTTGGGA ACCGGAGCTG AATGAAGCCA TACCAAACGA
4481 CGAGCGTGAC ACCACGATGC CTGTAGCAAT GGCAACAACG TTGCGCAAAC TATTAACTGG CGAACTACTT ACTCTAGCTT
4561 CCCGGCAACA ATTAATAGAC TGGATGGAGG CGGATAAAGT TGCAGGACCA CTTCTGCGCT CGGCCCTTCC GGCTGGCTGG
4641 TTTATTGCTG ATAAATCTGG AGCCGGTGAG CGTGGGTCTC GCGGTATCAT TGCAGCACTG GGGCCAGATG GTAAGCCCTC
4721 CCGTATCGTA GTTATCTACA CGACGGGGAG TCAGGCAACT ATGGATGAAC GAAATAGACA GATCGCTGAG ATAGGTGCCT
4801 CACTGATTAA GCATTGGTAA CTGTCAGACC AAGTTTACTC ATATATACTT TAGATTGATT TAAAACTTCA TTTTTAATTT
4881 AAAAGGATCT AGGTGAAGAT CCTTTTTGAT AATCTCATGA CCAAAATCCC TTAACGTGAG TTTTCGTTCC ACTGAGCGTC
4961 AGACCCCGTA GAAAAGATCA AAGGATCTTC TTGAGATCCT TTTTTTCTGC GCGTAATCTG CTGCTTGCAA ACAAAAAAAC
5041 CACCGCTACC AGCGGTGGTT TGTTTGCCGG ATCAAGAGCT ACCAACTCTT TTTCCGAAGG TAACTGGCTT CAGCAGAGCG
5121 CAGATACCAA ATACTGTTCT TCTAGTGTAG CCGTAGTTAG GCCACCACTT CAAGAACTCT GTAGCACCGC CTACATACCT
5201 CGCTCTGCTA ATCCTGTTAC CAGTGGCTGC TGCCAGTGGC GATAAGTCGT GTCTTACCGG GTTGGACTCA AGACGATAGT
5281 TACCGGATAA GGCGCAGCGG TCGGGCTGAA CGGGGGGTTC GTGCACACAG CCCAGCTTGG AGCGAACGAC CTACACCGAA
5361 CTGAGATACC TACAGCGTGA GCTATGAGAA AGCGCCACGC TTCCCGAAGA GAGAAAGGCG GACAGGTATC CGGTAAGCGG
5441 CAGGGTCGGA ACAGGAGAGC GCACGAGGGA GCTTCCAGGG GGAAACGCCT GGTATCTTTA TAGTCCTGTC GGGTTTCGCC
5521 ACCTCTGACT TGAGCGTCGA TTTTTGTGAT GCTCGTCAGG GGGGCGGAGC CTATGGAAAA ACGCCAGCAA CGCGGCCTTT
5601 TTACGGTTCC TGGCCTTTTG CTGGCCTTTT GCTCACATGT TCTTTCCTGC GTTATCCCCT GATTCTGTGG ATAACCGTAT
5681 TACCGCCTTT GAGTGAGCTG ATACCGCTCG CCGCAGCCGA ACGACCGAGC GCAGCGAGTC AGTGAGCGAG GAAGCGGAAG
5761 AGCGCCCAAT ACGCAAACCG CCTCTCCCCG CGCGTTGGCC GATTCATTAA TGCAGCTGGC ACGACAGGTT TCCCGACTGG
5841 AAAGCGGGCA GTGAGCGCAA CGCAATTAAT GTGAGTTAGC TCACTCATTA GGCACCCCAG GCTTTACACT TTATGCTTCC
5921 GGCTCGTATG TTGTGTGGAA TTGTGAGCGG ATAACAATTT CACACAGGAA ACAGCTATGA CCATGATTAC GCCAAGCTCG
6001 AAATTAACCC TCACTAAAGG GAACAAAAGC TGGTACCTCG CGCGACTTGG TTTGCCATTC TTTAGCGCGC GTCGCGTCAC
6081 ACAGCTTGGC CACAATGTGG TTTTTGTCAA ACGAAGATTC TATGACGTGT TTAAAGTTTA GGTCGAGTAA AGCGCAAATC
6161 TTTT

SEQUENCE LISTING

```
<160> NUMBER OF SEQ ID NOS: 51

<210> SEQ ID NO 1
<211> LENGTH: 429
<212> TYPE: PRT
<213> ORGANISM: Homo sapiens

<400> SEQUENCE: 1

Met Gln Leu Arg Asn Pro Glu Leu His Leu Gly Cys Ala Leu Ala Leu
1               5                   10                  15
```

-continued

```
Arg Phe Leu Ala Leu Val Ser Trp Asp Ile Pro Gly Ala Arg Ala Leu
            20                  25                  30

Asp Asn Gly Leu Ala Arg Thr Pro Thr Met Gly Trp Leu His Trp Glu
        35                  40                  45

Arg Phe Met Cys Asn Leu Asp Cys Gln Glu Glu Pro Asp Ser Cys Ile
    50                  55                  60

Ser Glu Lys Leu Phe Met Glu Met Ala Glu Leu Met Val Ser Glu Gly
65                  70                  75                  80

Trp Lys Asp Ala Gly Tyr Glu Tyr Leu Cys Ile Asp Asp Cys Trp Met
                85                  90                  95

Ala Pro Gln Arg Asp Ser Glu Gly Arg Leu Gln Ala Asp Pro Gln Arg
            100                 105                 110

Phe Pro His Gly Ile Arg Gln Leu Ala Asn Tyr Val His Ser Lys Gly
        115                 120                 125

Leu Lys Leu Gly Ile Tyr Ala Asp Val Gly Asn Lys Thr Cys Ala Gly
    130                 135                 140

Phe Pro Gly Ser Phe Gly Tyr Tyr Asp Ile Asp Ala Gln Thr Phe Ala
145                 150                 155                 160

Asp Trp Gly Val Asp Leu Leu Lys Phe Asp Gly Cys Tyr Cys Asp Ser
                165                 170                 175

Leu Glu Asn Leu Ala Asp Gly Tyr Lys His Met Ser Leu Ala Leu Asn
            180                 185                 190

Arg Thr Gly Arg Ser Ile Val Tyr Ser Cys Glu Trp Pro Leu Tyr Met
        195                 200                 205

Trp Pro Phe Gln Lys Pro Asn Tyr Thr Glu Ile Arg Gln Tyr Cys Asn
    210                 215                 220

His Trp Arg Asn Phe Ala Asp Ile Asp Asp Ser Trp Lys Ser Ile Lys
225                 230                 235                 240

Ser Ile Leu Asp Trp Thr Ser Phe Asn Gln Glu Arg Ile Val Asp Val
                245                 250                 255

Ala Gly Pro Gly Gly Trp Asn Asp Pro Asp Met Leu Val Ile Gly Asn
            260                 265                 270

Phe Gly Leu Ser Trp Asn Gln Gln Val Thr Gln Met Ala Leu Trp Ala
        275                 280                 285

Ile Met Ala Ala Pro Leu Phe Met Ser Asn Asp Leu Arg His Ile Ser
    290                 295                 300

Pro Gln Ala Lys Ala Leu Leu Gln Asp Lys Asp Val Ile Ala Ile Asn
305                 310                 315                 320

Gln Asp Pro Leu Gly Lys Gln Gly Tyr Gln Leu Arg Gln Gly Asp Asn
                325                 330                 335

Phe Glu Val Trp Glu Arg Pro Leu Ser Gly Leu Ala Trp Ala Val Ala
            340                 345                 350

Met Ile Asn Arg Gln Glu Ile Gly Gly Pro Arg Ser Tyr Thr Ile Ala
        355                 360                 365

Val Ala Ser Leu Gly Lys Gly Val Ala Cys Asn Pro Ala Cys Phe Ile
    370                 375                 380

Thr Gln Leu Leu Pro Val Lys Arg Lys Leu Gly Phe Tyr Glu Trp Thr
385                 390                 395                 400

Ser Arg Leu Arg Ser His Ile Asn Pro Thr Gly Thr Val Leu Leu Gln
                405                 410                 415

Leu Glu Asn Thr Met Gln Met Ser Leu Lys Asp Leu Leu
            420                 425
```

<210> SEQ ID NO 2
<211> LENGTH: 1290
<212> TYPE: DNA
<213> ORGANISM: Homo sapiens

<400> SEQUENCE: 2

```
atgcagctga ggaacccaga actacatctg ggctgcgcgc ttgcgcttcg cttcctggcc     60

ctcgtttcct gggacatccc tggggctaga gcactggaca atggattggc aaggacgcct    120

accatgggct ggctgcactg ggagcgcttc atgtgcaacc ttgactgcca ggaagagcca    180

gattcctgca tcagtgagaa gctcttcatg gagatggcag agctcatggt ctcagaaggc    240

tggaaggatg caggttatga gtacctctgc attgatgact gttggatggc tccccaaaga    300

gattcagaag gcagacttca ggcagaccct cagcgctttc ctcatgggat tcgccagcta    360

gctaattatg ttcacagcaa aggactgaag ctagggattt atgcagatgt tggaaataaa    420

acctgcgcag gcttccctgg gagttttgga tactacgaca ttgatgccca gacctttgct    480

gactggggag tagatctgct aaaatttgat ggttgttact gtgacagttt ggaaaatttg    540

gcagatggtt ataagcacat gtccttggcc ctgaatagga ctggcagaag cattgtgtac    600

tcctgtgagt ggcctcttta tatgtggccc tttcaaaagc ccaattatac agaaatccga    660

cagtactgca atcactggcg aaattttgct gacattgatg attcctggaa aagtataaag    720

agtatcttgg actggacatc ttttaaccag gagagaattg ttgatgttgc tggaccaggg    780

ggttggaatg acccagatat gttagtgatt ggcaactttg gcctcagctg gaatcagcaa    840

gtaactcaga tggccctctg ggctatcatg gctgctcctt tattcatgtc taatgacctc    900

cgacacatca gccctcaagc caaagctctc cttcaggata aggacgtaat tgccatcaat    960

caggacccct tgggcaagca agggtaccag cttagacagg gagacaactt tgaagtgtgg   1020

gaacgacctc tctcaggctt agcctgggct gtagctatga taaaccggca ggagattggt   1080

ggacctcgct cttataccat cgcagttgct tccctgggta aaggagtggc ctgtaatcct   1140

gcctgcttca tcacacagct cctccctgtg aaaaggaagc tagggttcta tgaatggact   1200

tcaaggttaa gaagtcacat aaatcccaca ggcactgttt tgcttcagct agaaaataca   1260

atgcagatgt cattaaaaga cttactttaa                                    1290
```

<210> SEQ ID NO 3
<211> LENGTH: 1290
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 3

```
atgcagctga gaaaccccga actgcacctg ggatgtgccc tggctctgag atttctggcc     60

ctggtgtctt gggacatccc tggcgctaga gccctggata atggcctggc cagaacacct    120

acaatgggct ggctgcactg ggagagattc atgtgcaacc tggactgcca agaggaaccc    180

gacagctgca tcagcgagaa gctgttcatg gaaatggccg agctgatggt gtccgaaggc    240

tggaaggatg ccggctacga gtacctgtgc atcgacgact gttggatggc ccctcagaga    300

gactctgagg gcagactgca ggccgatcct cagagatttc cccacggcat tagacagctg    360

gccaactacg tgcacagcaa gggcctgaag ctgggcatct atgccgacgt gggcaacaag    420

acctgtgccg gctttcctgg cagcttcggc tactacgata tcgacgccca gaccttcgcc    480

gattggggag tcgatctgct gaagttcgac ggctgctact gcgacagcct ggaaaatctg    540
```

```
gccgacggct acaagcacat gtcactggcc ctgaatcgga ccggcagatc catcgtgtac    600
agctgcgagt ggcccctgta catgtggccc ttccagaagc ctaactacac cgagatcaga    660
cagtactgca accactggcg gaacttcgcc gacatcgacg atagctggaa gtccatcaag    720
agcatcctgg actggaccag cttcaatcaa gagcggatcg tggacgtggc aggacctggc    780
ggatggaacg atcctgacat gctggtcatc ggcaacttcg gcctgagctg gaaccagcaa    840
gtgacccaga tggccctgtg ggccattatg gccgctcctc tgttcatgag caacgacctg    900
agacacatca gccctcaggc caaggctctg ctgcaggaca aggatgtgat cgctatcaac    960
caggatcctc tgggcaagca gggctaccag ctgagacagg gcgacaattt cgaagtgtgg   1020
gaaagacccc tgagcggact ggcttgggcc gtcgccatga tcaacagaca agagatcggc   1080
ggaccccggt cctacacaat tgccgtggct tctctcggca aaggcgtggc ctgtaatccc   1140
gcctgcttta tcacacagct gctgcccgtg aagagaaagc tgggctttta cgagtggacc   1200
agcagactgc ggagccacat caatcctacc ggcacagtgc tgctgcagct ggaaaacacc   1260
atgcagatga gcctgaagga cctgctgtaa                                    1290
```

<210> SEQ ID NO 4
<211> LENGTH: 1290
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 4

```
atgcagctgc gcaaccccga gctgcacctg ggctgcgccc tggccctgcg cttcctggcc     60
ctggtgagct gggacatccc cggcgcccgc gccctggaca acggcctggc ccgcaccccc    120
accatgggct ggctgcactg ggagcgcttc atgtgcaacc tggactgcca ggaggagccc    180
gacagctgca tcagcgagaa gctgttcatg gagatggccg agctgatggt gagcgagggc    240
tggaaggacg ccggctacga gtacctgtgc atcgacgact gctggatggc cccccagcgc    300
gacagcgagg gccgcctgca ggccgacccc cagcgcttcc cccacggcat ccgccagctg    360
gccaactacg tgcacagcaa gggcctgaag ctgggcatct acgccgacgt gggcaacaag    420
acctgcgccg gcttccccgg cagcttcggc tactacgaca tcgacgccca gaccttcgcc    480
gactggggcg tggacctgct gaagttcgac ggctgctact gcgacagcct ggagaacctg    540
gccgacggct acaagcacat gagcctggcc ctgaaccgca ccggccgcag catcgtgtac    600
agctgcgagt ggcccctgta catgtggccc ttccagaagc ccaactacac cgagatccgc    660
cagtactgca accactggcg caacttcgcc gacatcgacg acagctggaa gagcatcaag    720
agcatcctgg actggaccag cttcaaccag gagcgcatcg tggacgtggc cggccccggc    780
ggctggaacg accccgacat gctggtgatc ggcaacttcg gcctgagctg gaaccagcag    840
gtgacccaga tggccctgtg ggccatcatg gccgcccccc tgttcatgag caacgacctg    900
cgccacatca gcccccaggc caaggccctg ctgcaggaca aggacgtgat cgccatcaac    960
caggaccccc tgggcaagca gggctaccag ctgcgccagg gcgacaactt cgaggtgtgg   1020
gagcgccccc tgagcggcct ggcctgggcc gtggccatga tcaaccgcca ggagatcggc   1080
ggcccccgca gctacaccat cgccgtggcc agcctgggca agggcgtggc ctgcaacccc   1140
gcctgcttca tcacccagct gctgcccgtg aagcgcaagc tgggcttcta cgagtggacc   1200
agccgcctgc gcagccacat caaccccacc ggcaccgtgc tgctgcagct ggagaacacc   1260
```

```
atgcagatga gcctgaagga cctgctgtaa                                    1290


<210> SEQ ID NO 5
<211> LENGTH: 419
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Gly Trp Arg Ala Ala Gly Ala Leu Leu Leu Ala Leu Leu Leu His
1               5                   10                  15

Gly Arg Leu Leu Ala Leu Asp Asn Gly Leu Ala Arg Thr Pro Thr Met
            20                  25                  30

Gly Trp Leu His Trp Glu Arg Phe Met Cys Asn Leu Asp Cys Gln Glu
        35                  40                  45

Glu Pro Asp Ser Cys Ile Ser Glu Lys Leu Phe Met Glu Met Ala Glu
    50                  55                  60

Leu Met Val Ser Glu Gly Trp Lys Asp Ala Gly Tyr Glu Tyr Leu Cys
65                  70                  75                  80

Ile Asp Asp Cys Trp Met Ala Pro Gln Arg Asp Ser Glu Gly Arg Leu
                85                  90                  95

Gln Ala Asp Pro Gln Arg Phe Pro His Gly Ile Arg Gln Leu Ala Asn
            100                 105                 110

Tyr Val His Ser Lys Gly Leu Lys Leu Gly Ile Tyr Ala Asp Val Gly
        115                 120                 125

Asn Lys Thr Cys Ala Gly Phe Pro Gly Ser Phe Gly Tyr Tyr Asp Ile
    130                 135                 140

Asp Ala Gln Thr Phe Ala Asp Trp Gly Val Asp Leu Leu Lys Phe Asp
145                 150                 155                 160

Gly Cys Tyr Cys Asp Ser Leu Glu Asn Leu Ala Asp Gly Tyr Lys His
                165                 170                 175

Met Ser Leu Ala Leu Asn Arg Thr Gly Arg Ser Ile Val Tyr Ser Cys
            180                 185                 190

Glu Trp Pro Leu Tyr Met Trp Pro Phe Gln Lys Pro Asn Tyr Thr Glu
        195                 200                 205

Ile Arg Gln Tyr Cys Asn His Trp Arg Asn Phe Ala Asp Ile Asp Asp
    210                 215                 220

Ser Trp Lys Ser Ile Lys Ser Ile Leu Asp Trp Thr Ser Phe Asn Gln
225                 230                 235                 240

Glu Arg Ile Val Asp Val Ala Gly Pro Gly Gly Trp Asn Asp Pro Asp
                245                 250                 255

Met Leu Val Ile Gly Asn Phe Gly Leu Ser Trp Asn Gln Gln Val Thr
            260                 265                 270

Gln Met Ala Leu Trp Ala Ile Met Ala Ala Pro Leu Phe Met Ser Asn
        275                 280                 285

Asp Leu Arg His Ile Ser Pro Gln Ala Lys Ala Leu Leu Gln Asp Lys
    290                 295                 300

Asp Val Ile Ala Ile Asn Gln Asp Pro Leu Gly Lys Gln Gly Tyr Gln
305                 310                 315                 320

Leu Arg Gln Gly Asp Asn Phe Glu Val Trp Glu Arg Pro Leu Ser Gly
                325                 330                 335

Leu Ala Trp Ala Val Ala Met Ile Asn Arg Gln Glu Ile Gly Gly Pro
            340                 345                 350
```

-continued

```
Arg Ser Tyr Thr Ile Ala Val Ala Ser Leu Gly Lys Gly Val Ala Cys
        355                 360                 365

Asn Pro Ala Cys Phe Ile Thr Gln Leu Leu Pro Val Lys Arg Lys Leu
    370                 375                 380

Gly Phe Tyr Glu Trp Thr Ser Arg Leu Arg Ser His Ile Asn Pro Thr
385                 390                 395                 400

Gly Thr Val Leu Leu Gln Leu Glu Asn Thr Met Gln Met Ser Leu Lys
                405                 410                 415

Asp Leu Leu
```

<210> SEQ ID NO 6
<211> LENGTH: 1260
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 6

```
atgggctggc gagctgctgg tgcacttctg ctggctctgc tgcttcatgg cagactgctt     60

gctctggaca acggcctggc ccgcaccccc accatgggct ggctgcactg ggagcgcttc    120

atgtgcaacc tggactgcca ggaggagccc gacagctgca tcagcgagaa gctgttcatg    180

gagatggccg agctgatggt gagcgagggc tggaaggacg ccggctacga gtacctgtgc    240

atcgacgact gctggatggc cccccagcgc gacagcgagg gccgcctgca ggccgacccc    300

cagcgcttcc cccacggcat ccgccagctg gccaactacg tgcacagcaa gggcctgaag    360

ctgggcatct acgccgacgt gggcaacaag acctgcgccg gcttccccgg cagcttcggc    420

tactacgaca tcgacgccca gaccttcgcc gactggggcg tggacctgct gaagttcgac    480

ggctgctact gcgacagcct ggagaacctg gccgacggct acaagcacat gagcctggcc    540

ctgaaccgca ccggccgcag catcgtgtac agctgcgagt ggcccctgta catgtggccc    600

ttccagaagc ccaactacac cgagatccgc cagtactgca accactggcg caacttcgcc    660

gacatcgacg acagctggaa gagcatcaag agcatcctgg actggaccag cttcaaccag    720

gagcgcatcg tggacgtggc cggccccggc ggctggaacg accccgacat gctggtgatc    780

ggcaacttcg gcctgagctg gaaccagcag gtgacccaga tggccctgtg ggccatcatg    840

gccgcccccc tgttcatgag caacgacctg cgccacatca gcccccaggc caaggccctg    900

ctgcaggaca aggacgtgat cgccatcaac caggaccccc tgggcaagca gggctaccag    960

ctgcgccagg gcgacaactt cgaggtgtgg gagcgccccc tgagcggcct ggcctgggcc   1020

gtggccatga tcaaccgcca ggagatcggc ggcccccgca gctacaccat cgccgtggcc   1080

agcctgggca agggcgtggc ctgcaacccc gcctgcttca tcacccagct gctgcccgtg   1140

aagcgcaagc tgggcttcta cgagtggacc agccgcctgc gcagccacat caaccccacc   1200

ggcaccgtgc tgctgcagct ggagaacacc atgcagatga gcctgaagga cctgctgtaa   1260
```

<210> SEQ ID NO 7
<211> LENGTH: 530
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 7

-continued

```
Met Gly Trp Arg Ala Ala Gly Ala Leu Leu Leu Ala Leu Leu Leu His
1               5                   10                  15

Gly Arg Leu Leu Ala Leu Asp Asn Gly Leu Ala Arg Thr Pro Thr Met
            20                  25                  30

Gly Trp Leu His Trp Glu Arg Phe Met Cys Asn Leu Asp Cys Gln Glu
        35                  40                  45

Glu Pro Asp Ser Cys Ile Ser Glu Lys Leu Phe Met Glu Met Ala Glu
    50                  55                  60

Leu Met Val Ser Glu Gly Trp Lys Asp Ala Gly Tyr Glu Tyr Leu Cys
65                  70                  75                  80

Ile Asp Asp Cys Trp Met Ala Pro Gln Arg Asp Ser Glu Gly Arg Leu
                85                  90                  95

Gln Ala Asp Pro Gln Arg Phe Pro His Gly Ile Arg Gln Leu Ala Asn
            100                 105                 110

Tyr Val His Ser Lys Gly Leu Lys Leu Gly Ile Tyr Ala Asp Val Gly
        115                 120                 125

Asn Lys Thr Cys Ala Gly Phe Pro Gly Ser Phe Gly Tyr Tyr Asp Ile
    130                 135                 140

Asp Ala Gln Thr Phe Ala Asp Trp Gly Val Asp Leu Leu Lys Phe Asp
145                 150                 155                 160

Gly Cys Tyr Cys Asp Ser Leu Glu Asn Leu Ala Asp Gly Tyr Lys His
                165                 170                 175

Met Ser Leu Ala Leu Asn Arg Thr Gly Arg Ser Ile Val Tyr Ser Cys
            180                 185                 190

Glu Trp Pro Leu Tyr Met Trp Pro Phe Gln Lys Pro Asn Tyr Thr Glu
        195                 200                 205

Ile Arg Gln Tyr Cys Asn His Trp Arg Asn Phe Ala Asp Ile Asp Asp
    210                 215                 220

Ser Trp Lys Ser Ile Lys Ser Ile Leu Asp Trp Thr Ser Phe Asn Gln
225                 230                 235                 240

Glu Arg Ile Val Asp Val Ala Gly Pro Gly Gly Trp Asn Asp Pro Asp
                245                 250                 255

Met Leu Val Ile Gly Asn Phe Gly Leu Ser Trp Asn Gln Gln Val Thr
            260                 265                 270

Gln Met Ala Leu Trp Ala Ile Met Ala Ala Pro Leu Phe Met Ser Asn
        275                 280                 285

Asp Leu Arg His Ile Ser Pro Gln Ala Lys Ala Leu Leu Gln Asp Lys
    290                 295                 300

Asp Val Ile Ala Ile Asn Gln Asp Pro Leu Gly Lys Gln Gly Tyr Gln
305                 310                 315                 320

Leu Arg Gln Gly Asp Asn Phe Glu Val Trp Glu Arg Pro Leu Ser Gly
                325                 330                 335

Leu Ala Trp Ala Val Ala Met Ile Asn Arg Gln Glu Ile Gly Gly Pro
            340                 345                 350

Arg Ser Tyr Thr Ile Ala Val Ala Ser Leu Gly Lys Gly Val Ala Cys
        355                 360                 365

Asn Pro Ala Cys Phe Ile Thr Gln Leu Leu Pro Val Lys Arg Lys Leu
    370                 375                 380

Gly Phe Tyr Glu Trp Thr Ser Arg Leu Arg Ser His Ile Asn Pro Thr
385                 390                 395                 400

Gly Thr Val Leu Leu Gln Leu Glu Asn Thr Met Gln Met Ser Leu Lys
                405                 410                 415

Asp Leu Leu Gly Gly Ser Ser Arg Thr Val Ala Ala Pro Ser Val Phe
```

```
            420                 425                 430

Ile Phe Pro Pro Ser Asp Glu Gln Leu Lys Ser Gly Thr Ala Ser Val
        435                 440                 445

Val Cys Leu Leu Asn Asn Phe Tyr Pro Arg Glu Ala Lys Val Gln Trp
    450                 455                 460

Lys Val Asp Asn Ala Leu Gln Ser Gly Asn Ser Gln Glu Ser Val Thr
465                 470                 475                 480

Glu Gln Asp Ser Lys Asp Ser Thr Tyr Ser Leu Ser Ser Thr Leu Thr
                485                 490                 495

Leu Ser Lys Ala Asp Tyr Glu Lys His Lys Val Tyr Ala Cys Glu Val
            500                 505                 510

Thr His Gln Gly Leu Ser Ser Pro Val Thr Lys Ser Phe Asn Arg Gly
        515                 520                 525

Glu Cys
    530


<210> SEQ ID NO 8
<211> LENGTH: 351
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Gly Trp Arg Ala Ala Gly Ala Leu Leu Leu Ala Leu Leu Leu His
1               5                   10                  15

Gly Arg Leu Leu Ala Ala Ser Thr Lys Gly Pro Ser Val Phe Pro Leu
            20                  25                  30

Ala Pro Ser Ser Lys Ser Thr Ser Gly Gly Thr Ala Ala Leu Gly Cys
        35                  40                  45

Leu Val Lys Asp Tyr Phe Pro Glu Pro Val Thr Val Ser Trp Asn Ser
    50                  55                  60

Gly Ala Leu Thr Ser Gly Val His Thr Phe Pro Ala Val Leu Gln Ser
65                  70                  75                  80

Ser Gly Leu Tyr Ser Leu Ser Ser Val Val Thr Val Pro Ser Ser Ser
                85                  90                  95

Leu Gly Thr Gln Thr Tyr Ile Cys Asn Val Asn His Lys Pro Ser Asn
            100                 105                 110

Thr Lys Val Asp Lys Lys Val Glu Pro Lys Ser Cys Asp Lys Thr His
        115                 120                 125

Thr Cys Pro Pro Cys Pro Ala Pro Glu Leu Leu Gly Gly Pro Ser Val
    130                 135                 140

Phe Leu Phe Pro Pro Lys Pro Lys Asp Thr Leu Met Ile Ser Arg Thr
145                 150                 155                 160

Pro Glu Val Thr Cys Val Val Val Asp Val Ser His Glu Asp Pro Glu
                165                 170                 175

Val Lys Phe Asn Trp Tyr Val Asp Gly Val Glu Val His Asn Ala Lys
            180                 185                 190

Thr Lys Pro Arg Glu Glu Gln Tyr Asn Ser Thr Tyr Arg Val Val Ser
        195                 200                 205

Val Leu Thr Val Leu His Gln Asp Trp Leu Asn Gly Lys Glu Tyr Lys
    210                 215                 220

Cys Lys Val Ser Asn Lys Ala Leu Pro Ala Pro Ile Glu Lys Thr Ile
225                 230                 235                 240
```

-continued

```
Ser Lys Ala Lys Gly Gln Pro Arg Glu Pro Gln Val Tyr Thr Leu Pro
                245                 250                 255

Pro Ser Arg Asp Glu Leu Thr Lys Asn Gln Val Ser Leu Thr Cys Leu
            260                 265                 270

Val Lys Gly Phe Tyr Pro Ser Asp Ile Ala Val Glu Trp Glu Ser Asn
        275                 280                 285

Gly Gln Pro Glu Asn Asn Tyr Lys Thr Thr Pro Pro Val Leu Asp Ser
    290                 295                 300

Asp Gly Ser Phe Phe Leu Tyr Ser Lys Leu Thr Val Asp Lys Ser Arg
305                 310                 315                 320

Trp Gln Gln Gly Asn Val Phe Ser Cys Ser Val Met His Glu Ala Leu
                325                 330                 335

His Asn His Tyr Thr Gln Lys Ser Leu Ser Leu Ser Pro Gly Lys
            340                 345                 350


<210> SEQ ID NO 9
<211> LENGTH: 1593
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9

atgggctggc gagctgctgg tgcacttctg ctggctctgc tgcttcatgg cagactgctt     60

gctctggaca acggcctggc ccgcaccccc accatgggct ggctgcactg ggagcgcttc    120

atgtgcaacc tggactgcca ggaggagccc gacagctgca tcagcgagaa gctgttcatg    180

gagatggccg agctgatggt gagcgagggc tggaaggacg ccggctacga gtacctgtgc    240

atcgacgact gctggatggc cccccagcgc gacagcgagg gccgcctgca ggccgacccc    300

cagcgcttcc cccacggcat ccgccagctg gccaactacg tgcacagcaa gggcctgaag    360

ctgggcatct acgccgacgt gggcaacaag acctgcgccg gcttccccgg cagcttcggc    420

tactacgaca tcgacgccca gaccttcgcc gactggggcg tggacctgct gaagttcgac    480

ggctgctact gcgacagcct ggagaacctg gccgacggct acaagcacat gagcctggcc    540

ctgaaccgca ccggccgcag catcgtgtac agctgcgagt ggcccctgta catgtggccc    600

ttccagaagc ccaactacac cgagatccgc cagtactgca accactggcg caacttcgcc    660

gacatcgacg acagctggaa gagcatcaag agcatcctgg actggaccag cttcaaccag    720

gagcgcatcg tggacgtggc cggccccggc ggctggaacg accccgacat gctggtgatc    780

ggcaacttcg gcctgagctg gaaccagcag gtgacccaga tggccctgtg ggccatcatg    840

gccgcccccc tgttcatgag caacgacctg cgccacatca gcccccaggc caaggccctg    900

ctgcaggaca aggacgtgat cgccatcaac caggaccccc tgggcaagca gggctaccag    960

ctgcgccagg gcgacaactt cgaggtgtgg gagcgccccc tgagcggcct ggcctgggcc   1020

gtggccatga tcaaccgcca ggagatcggc ggcccccgca gctacaccat cgccgtggcc   1080

agcctgggca agggcgtggc ctgcaacccc gcctgcttca tcacccagct gctgcccgtg   1140

aagcgcaagc tgggcttcta cgagtggacc agccgcctgc gcagccacat caaccccacc   1200

ggcaccgtgc tgctgcagct ggagaacacc atgcagatga gcctgaagga cctgctgggc   1260

ggcagcagcc gcaccgtggc cgcccccagc gtgttcatct tcccccccag cgacgagcag   1320

ctgaagagcg gcaccgccag cgtggtgtgc ctgctgaaca acttctaccc ccgcgaggcc   1380

aaggtgcagt ggaaggtgga caacgccctg cagagcggca acagccagga gagcgtgacc   1440
```

gagcaggaca gcaaggacag cacctacagc ctgagcagca ccctgaccct gagcaaggcc 1500
gactacgaga agcacaaggt gtacgcctgc gaggtgaccc accagggcct gagcagcccc 1560
gtgaccaaga gcttcaaccg cggcgagtgc taa 1593

<210> SEQ ID NO 10
<211> LENGTH: 1056
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 10
atgggctggc gagctgctgg tgcacttctg ctggctctgc tgcttcatgg cagactgctt 60
gctgccagca ccaagggccc cagcgtgttc cccctggccc ccagcagcaa gagcaccagc 120
ggcggcaccg ccgccctggg ctgcctggtg aaggactact tccccgagcc cgtgaccgtg 180
agctggaaca gcggcgccct gaccagcggc gtgcacacct tccccgccgt gctgcagagc 240
agcggcctgt acagcctgag cagcgtggtg accgtgccca gcagcagcct gggcacccag 300
acctacatct gcaacgtgaa ccacaagccc agcaacacca aggtggacaa gaaggtggag 360
cccaagagct gcgacaagac ccacacctgc ccccccctgcc ccgcccccga gctgctgggc 420
ggccccagcg tgttcctgtt ccccccccaag cccaaggaca ccctgatgat cagccgcacc 480
cccgaggtga cctgcgtggt ggtggacgtg agccacgagg accccgaggt gaagttcaac 540
tggtacgtgg acggcgtgga ggtgcacaac gccaagacca agccccgcga ggagcagtac 600
aacagcacct accgcgtggt gagcgtgctg accgtgctgc accaggactg gctgaacggc 660
aaggagtaca agtgcaaggt gagcaacaag gccctgcccg cccccatcga gaagaccatc 720
agcaaggcca agggccagcc ccgcgagccc caggtgtaca ccctgccccc cagccgcgac 780
gagctgacca agaaccaggt gagcctgacc tgcctggtga agggcttcta ccccagcgac 840
atcgccgtgg agtgggagag caacggccag cccgagaaca actacaagac caccccccccc 900 gtgctggaca gcgacggcag cttcttcctg tacagcaagc tgaccgtgga caagagccgc 960
tggcagcagg gcaacgtgtt cagctgcagc gtgatgcacg aggccctgca caaccactac 1020
acccagaaga gcctgagcct gagccccggc aagtaa 1056

<210> SEQ ID NO 11
<211> LENGTH: 777
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 11

Met Gly Trp Arg Ala Ala Gly Ala Leu Leu Leu Ala Leu Leu Leu His
1 5 10 15

Gly Arg Leu Leu Ala Leu Asp Asn Gly Leu Ala Arg Thr Pro Thr Met
20 25 30

Gly Trp Leu His Trp Glu Arg Phe Met Cys Asn Leu Asp Cys Gln Glu
35 40 45

Glu Pro Asp Ser Cys Ile Ser Glu Lys Leu Phe Met Glu Met Ala Glu
50 55 60

Leu Met Val Ser Glu Gly Trp Lys Asp Ala Gly Tyr Glu Tyr Leu Cys
65 70 75 80

-continued

```
Ile Asp Asp Cys Trp Met Ala Pro Gln Arg Asp Ser Glu Gly Arg Leu
                85                  90                  95

Gln Ala Asp Pro Gln Arg Phe Pro His Gly Ile Arg Gln Leu Ala Asn
            100                 105                 110

Tyr Val His Ser Lys Gly Leu Lys Leu Gly Ile Tyr Ala Asp Val Gly
        115                 120                 125

Asn Lys Thr Cys Ala Gly Phe Pro Gly Ser Phe Gly Tyr Tyr Asp Ile
    130                 135                 140

Asp Ala Gln Thr Phe Ala Asp Trp Gly Val Asp Leu Leu Lys Phe Asp
145                 150                 155                 160

Gly Cys Tyr Cys Asp Ser Leu Glu Asn Leu Ala Asp Gly Tyr Lys His
                165                 170                 175

Met Ser Leu Ala Leu Asn Arg Thr Gly Arg Ser Ile Val Tyr Ser Cys
            180                 185                 190

Glu Trp Pro Leu Tyr Met Trp Pro Phe Gln Lys Pro Asn Tyr Thr Glu
        195                 200                 205

Ile Arg Gln Tyr Cys Asn His Trp Arg Asn Phe Ala Asp Ile Asp Asp
    210                 215                 220

Ser Trp Lys Ser Ile Lys Ser Ile Leu Asp Trp Thr Ser Phe Asn Gln
225                 230                 235                 240

Glu Arg Ile Val Asp Val Ala Gly Pro Gly Gly Trp Asn Asp Pro Asp
                245                 250                 255

Met Leu Val Ile Gly Asn Phe Gly Leu Ser Trp Asn Gln Gln Val Thr
            260                 265                 270

Gln Met Ala Leu Trp Ala Ile Met Ala Ala Pro Leu Phe Met Ser Asn
        275                 280                 285

Asp Leu Arg His Ile Ser Pro Gln Ala Lys Ala Leu Leu Gln Asp Lys
    290                 295                 300

Asp Val Ile Ala Ile Asn Gln Asp Pro Leu Gly Lys Gln Gly Tyr Gln
305                 310                 315                 320

Leu Arg Gln Gly Asp Asn Phe Glu Val Trp Glu Arg Pro Leu Ser Gly
                325                 330                 335

Leu Ala Trp Ala Val Ala Met Ile Asn Arg Gln Glu Ile Gly Gly Pro
            340                 345                 350

Arg Ser Tyr Thr Ile Ala Val Ala Ser Leu Gly Lys Gly Val Ala Cys
        355                 360                 365

Asn Pro Ala Cys Phe Ile Thr Gln Leu Leu Pro Val Lys Arg Lys Leu
    370                 375                 380

Gly Phe Tyr Glu Trp Thr Ser Arg Leu Arg Ser His Ile Asn Pro Thr
385                 390                 395                 400

Gly Thr Val Leu Leu Gln Leu Glu Asn Thr Met Gln Met Ser Leu Lys
                405                 410                 415

Asp Leu Leu Gly Gly Ser Ser Glu Val Gln Leu Gln Ala Ser Gly Gly
            420                 425                 430

Gly Leu Val Gln Ala Gly Gly Ser Leu Arg Leu Ser Cys Ala Ala Ser
        435                 440                 445

Gly Phe Lys Ile Thr His Tyr Thr Met Gly Trp Phe Arg Gln Ala Pro
    450                 455                 460

Gly Lys Glu Arg Glu Phe Val Ser Arg Ile Thr Trp Gly Gly Asp Asn
465                 470                 475                 480

Thr Phe Tyr Ser Asn Ser Val Lys Gly Arg Phe Thr Ile Ser Arg Asp
                485                 490                 495
```

-continued

```
Asn Ala Lys Asn Thr Val Tyr Leu Gln Met Asn Ser Leu Lys Pro Glu
            500                 505                 510

Asp Thr Ala Asp Tyr Tyr Cys Ala Ala Gly Ser Thr Ser Thr Ala Thr
        515                 520                 525

Pro Leu Arg Val Asp Tyr Trp Gly Lys Gly Thr Gln Val Thr Val Ser
    530                 535                 540

Ser Glu Pro Lys Ser Ser Asp Lys Thr His Thr Cys Pro Pro Cys Pro
545                 550                 555                 560

Ala Pro Glu Leu Leu Gly Gly Pro Ser Val Phe Leu Phe Pro Pro Lys
                565                 570                 575

Pro Lys Asp Thr Leu Met Ile Ser Arg Thr Pro Glu Val Thr Cys Val
            580                 585                 590

Val Val Asp Val Ser His Glu Asp Pro Glu Val Lys Phe Asn Trp Tyr
        595                 600                 605

Val Asp Gly Val Glu Val His Asn Ala Lys Thr Lys Pro Arg Glu Glu
    610                 615                 620

Gln Tyr Asn Ser Thr Tyr Arg Val Val Ser Val Leu Thr Val Leu His
625                 630                 635                 640

Gln Asp Trp Leu Asn Gly Lys Glu Tyr Lys Cys Lys Val Ser Asn Lys
                645                 650                 655

Ala Leu Pro Ala Pro Ile Glu Lys Thr Ile Ser Lys Ala Lys Gly Gln
            660                 665                 670

Pro Arg Glu Pro Gln Val Tyr Thr Leu Pro Pro Ser Arg Asp Glu Leu
        675                 680                 685

Thr Lys Asn Gln Val Ser Leu Thr Cys Leu Val Lys Gly Phe Tyr Pro
    690                 695                 700

Ser Asp Ile Ala Val Glu Trp Glu Ser Asn Gly Gln Pro Glu Asn Asn
705                 710                 715                 720

Tyr Lys Thr Thr Pro Pro Val Leu Asp Ser Asp Gly Ser Phe Phe Leu
                725                 730                 735

Tyr Ser Lys Leu Thr Val Asp Lys Ser Arg Trp Gln Gln Gly Asn Val
            740                 745                 750

Phe Ser Cys Ser Val Met His Glu Ala Leu His Asn His Tyr Thr Gln
        755                 760                 765

Lys Ser Leu Ser Leu Ser Pro Gly Lys
    770                 775
```

```
<210> SEQ ID NO 12
<211> LENGTH: 2334
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12

atgggctggc gagctgctgg tgcacttctg ctggctctgc tgcttcatgg cagactgctt      60

gctctggaca acggcctggc ccgcaccccc accatgggct ggctgcactg ggagcgcttc     120

atgtgcaacc tggactgcca ggaggagccc gacagctgca tcagcgagaa gctgttcatg     180

gagatggccg agctgatggt gagcgagggc tggaaggacg ccggctacga gtacctgtgc     240

atcgacgact gctggatggc cccccagcgc gacagcgagg gccgcctgca ggccgacccc     300

cagcgcttcc cccacggcat ccgccagctg gccaactacg tgcacagcaa gggcctgaag     360

ctgggcatct acgccgacgt gggcaacaag acctgcgccg gcttccccgg cagcttcggc     420
```

-continued

```
tactacgaca tcgacgccca gaccttcgcc gactggggcg tggacctgct gaagttcgac    480

ggctgctact gcgacagcct ggagaacctg gccgacggct acaagcacat gagcctggcc    540

ctgaaccgca ccggccgcag catcgtgtac agctgcgagt ggcccctgta catgtggccc    600

ttccagaagc ccaactacac cgagatccgc cagtactgca accactggcg caacttcgcc    660

gacatcgacg acagctggaa gagcatcaag agcatcctgg actggaccag cttcaaccag    720

gagcgcatcg tggacgtggc cggccccggc ggctggaacg accccgacat gctggtgatc    780

ggcaacttcg gcctgagctg gaaccagcag gtgacccaga tggccctgtg ggccatcatg    840

gccgcccccc tgttcatgag caacgacctg cgccacatca gcccccaggc caaggccctg    900

ctgcaggaca aggacgtgat cgccatcaac caggaccccc tgggcaagca gggctaccag    960

ctgcgccagg gcgacaactt cgaggtgtgg gagcgccccc tgagcggcct ggcctgggcc   1020

gtggccatga tcaaccgcca ggagatcggc ggcccccgca gctacaccat cgccgtggcc   1080

agcctgggca agggcgtggc ctgcaacccc gcctgcttca tcacccagct gctgcccgtg   1140

aagcgcaagc tgggcttcta cgagtggacc agccgcctgc gcagccacat caaccccacc   1200

ggcaccgtgc tgctgcagct ggagaacacc atgcagatga gcctgaagga cctgctgggc   1260

ggcagcagcg aggtgcagct gcaggccagc ggcggcggcc tggtgcaggc cggcggcagc   1320

ctgcgcctga gctgcgccgc cagcggcttc aagatcaccc actacaccat gggctggttc   1380

cgccaggccc ccggcaagga gcgcgagttc gtgagccgca tcacctgggg cggcgacaac   1440

accttctaca gcaacagcgt gaagggccgc ttcaccatca gccgcgacaa cgccaagaac   1500

accgtgtacc tgcagatgaa cagcctgaag cccgaggaca ccgccgacta ctactgcgcc   1560

gccggcagca ccagcaccgc caccccccctg cgcgtggact actggggcaa gggcacccag   1620

gtgaccgtga gcagcgagcc caagagcagc gacaagaccc acacctgccc cccctgcccc   1680

gcccccgagc tgctgggcgg ccccagcgtg ttcctgttcc cccccaagcc caaggacacc   1740

ctgatgatca gccgcacccc cgaggtgacc tgcgtggtgg tggacgtgag ccacgaggac   1800

cccgaggtga agttcaactg gtacgtggac ggcgtggagg tgcacaacgc caagaccaag   1860

ccccgcgagg agcagtacaa cagcacctac cgcgtggtga gcgtgctgac cgtgctgcac   1920

caggactggc tgaacggcaa ggagtacaag tgcaaggtga gcaacaaggc cctgcccgcc   1980

cccatcgaga agaccatcag caaggccaag ggccagcccc gcgagcccca ggtgtacacc   2040

ctgcccccca gccgcgacga gctgaccaag aaccaggtga gcctgacctg cctggtgaag   2100

ggcttctacc ccagcgacat cgccgtggag tgggagagca acggccagcc cgagaacaac   2160

tacaagacca cccccccccgt gctggacagc gacggcagct tcttcctgta cagcaagctg   2220

accgtggaca agagccgctg gcagcagggc aacgtgttca gctgcagcgt gatgcacgag   2280

gccctgcaca accactacac ccagaagagc ctgagcctga gccccggcaa gtaa         2334
```

<210> SEQ ID NO 13
<211> LENGTH: 655
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

```
Met Gly Trp Arg Ala Ala Gly Ala Leu Leu Leu Ala Leu Leu Leu His
1               5                   10                  15

Gly Arg Leu Leu Ala Leu Asp Asn Gly Leu Ala Arg Thr Pro Thr Met
```

-continued

```
            20                  25                  30

Gly Trp Leu His Trp Glu Arg Phe Met Cys Asn Leu Asp Cys Gln Glu
        35                  40                  45

Glu Pro Asp Ser Cys Ile Ser Glu Lys Leu Phe Met Glu Met Ala Glu
    50                  55                  60

Leu Met Val Ser Glu Gly Trp Lys Asp Ala Gly Tyr Glu Tyr Leu Cys
65                  70                  75                  80

Ile Asp Asp Cys Trp Met Ala Pro Gln Arg Asp Ser Glu Gly Arg Leu
                85                  90                  95

Gln Ala Asp Pro Gln Arg Phe Pro His Gly Ile Arg Gln Leu Ala Asn
            100                 105                 110

Tyr Val His Ser Lys Gly Leu Lys Leu Gly Ile Tyr Ala Asp Val Gly
        115                 120                 125

Asn Lys Thr Cys Ala Gly Phe Pro Gly Ser Phe Gly Tyr Tyr Asp Ile
    130                 135                 140

Asp Ala Gln Thr Phe Ala Asp Trp Gly Val Asp Leu Leu Lys Phe Asp
145                 150                 155                 160

Gly Cys Tyr Cys Asp Ser Leu Glu Asn Leu Ala Asp Gly Tyr Lys His
                165                 170                 175

Met Ser Leu Ala Leu Asn Arg Thr Gly Arg Ser Ile Val Tyr Ser Cys
            180                 185                 190

Glu Trp Pro Leu Tyr Met Trp Pro Phe Gln Lys Pro Asn Tyr Thr Glu
        195                 200                 205

Ile Arg Gln Tyr Cys Asn His Trp Arg Asn Phe Ala Asp Ile Asp Asp
    210                 215                 220

Ser Trp Lys Ser Ile Lys Ser Ile Leu Asp Trp Thr Ser Phe Asn Gln
225                 230                 235                 240

Glu Arg Ile Val Asp Val Ala Gly Pro Gly Gly Trp Asn Asp Pro Asp
                245                 250                 255

Met Leu Val Ile Gly Asn Phe Gly Leu Ser Trp Asn Gln Gln Val Thr
            260                 265                 270

Gln Met Ala Leu Trp Ala Ile Met Ala Ala Pro Leu Phe Met Ser Asn
        275                 280                 285

Asp Leu Arg His Ile Ser Pro Gln Ala Lys Ala Leu Leu Gln Asp Lys
    290                 295                 300

Asp Val Ile Ala Ile Asn Gln Asp Pro Leu Gly Lys Gln Gly Tyr Gln
305                 310                 315                 320

Leu Arg Gln Gly Asp Asn Phe Glu Val Trp Glu Arg Pro Leu Ser Gly
                325                 330                 335

Leu Ala Trp Ala Val Ala Met Ile Asn Arg Gln Glu Ile Gly Gly Pro
            340                 345                 350

Arg Ser Tyr Thr Ile Ala Val Ala Ser Leu Gly Lys Gly Val Ala Cys
        355                 360                 365

Asn Pro Ala Cys Phe Ile Thr Gln Leu Leu Pro Val Lys Arg Lys Leu
    370                 375                 380

Gly Phe Tyr Glu Trp Thr Ser Arg Leu Arg Ser His Ile Asn Pro Thr
385                 390                 395                 400

Gly Thr Val Leu Leu Gln Leu Glu Asn Thr Met Gln Met Ser Leu Lys
                405                 410                 415

Asp Leu Leu Gly Gly Ser Ser Glu Pro Lys Ser Ser Asp Lys Thr His
            420                 425                 430

Thr Cys Pro Pro Cys Pro Ala Pro Glu Leu Leu Gly Gly Pro Ser Val
        435                 440                 445
```

```
Phe Leu Phe Pro Pro Lys Pro Lys Asp Thr Leu Met Ile Ser Arg Thr
    450                 455                 460

Pro Glu Val Thr Cys Val Val Val Asp Val Ser His Glu Asp Pro Glu
465                 470                 475                 480

Val Lys Phe Asn Trp Tyr Val Asp Gly Val Glu Val His Asn Ala Lys
                485                 490                 495

Thr Lys Pro Arg Glu Glu Gln Tyr Asn Ser Thr Tyr Arg Val Val Ser
            500                 505                 510

Val Leu Thr Val Leu His Gln Asp Trp Leu Asn Gly Lys Glu Tyr Lys
        515                 520                 525

Cys Lys Val Ser Asn Lys Ala Leu Pro Ala Pro Ile Glu Lys Thr Ile
    530                 535                 540

Ser Lys Ala Lys Gly Gln Pro Arg Glu Pro Gln Val Tyr Thr Leu Pro
545                 550                 555                 560

Pro Ser Arg Asp Glu Leu Thr Lys Asn Gln Val Ser Leu Thr Cys Leu
                565                 570                 575

Val Lys Gly Phe Tyr Pro Ser Asp Ile Ala Val Glu Trp Glu Ser Asn
            580                 585                 590

Gly Gln Pro Glu Asn Asn Tyr Lys Thr Thr Pro Pro Val Leu Asp Ser
        595                 600                 605

Asp Gly Ser Phe Phe Leu Tyr Ser Lys Leu Thr Val Asp Lys Ser Arg
    610                 615                 620

Trp Gln Gln Gly Asn Val Phe Ser Cys Ser Val Met His Glu Ala Leu
625                 630                 635                 640

His Asn His Tyr Thr Gln Lys Ser Leu Ser Leu Ser Pro Gly Lys
                645                 650                 655
```

<210> SEQ ID NO 14
<211> LENGTH: 1968
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 14

```
atgggctggc gagctgctgg tgcacttctg ctggctctgc tgcttcatgg cagactgctt      60

gctctggaca acggcctggc ccgcaccccc accatgggct ggctgcactg ggagcgcttc     120

atgtgcaacc tggactgcca ggaggagccc gacagctgca tcagcgagaa gctgttcatg     180

gagatggccg agctgatggt gagcgagggc tggaaggacg ccggctacga gtacctgtgc     240

atcgacgact gctggatggc cccccagcgc gacagcgagg gccgcctgca ggccgacccc     300

cagcgcttcc cccacggcat ccgccagctg gccaactacg tgcacagcaa gggcctgaag     360

ctgggcatct acgccgacgt gggcaacaag acctgcgccg gcttccccgg cagcttcggc     420

tactacgaca tcgacgccca gaccttcgcc gactggggcg tggacctgct gaagttcgac     480

ggctgctact gcgacagcct ggagaacctg gccgacggct acaagcacat gagcctggcc     540

ctgaaccgca ccggccgcag catcgtgtac agctgcgagt ggcccctgta catgtggccc     600

ttccagaagc ccaactacac cgagatccgc cagtactgca accactggcg caacttcgcc     660

gacatcgacg acagctggaa gagcatcaag agcatcctgg actggaccag cttcaaccag     720

gagcgcatcg tggacgtggc cggccccggc ggctggaacg accccgacat gctggtgatc     780

ggcaacttcg gcctgagctg gaaccagcag gtgacccaga tggccctgtg ggccatcatg     840
```

-continued gccgcccccc tgttcatgag caacgacctg cgccacatca gcccccaggc caaggccctg 900
ctgcaggaca aggacgtgat cgccatcaac caggaccccc tgggcaagca gggctaccag 960
ctgcgccagg gcgacaactt cgaggtgtgg gagcgccccc tgagcggcct ggcctgggcc 1020
gtggccatga tcaaccgcca ggagatcggc ggcccccgca gctacaccat cgccgtggcc 1080
agcctgggca agggcgtggc ctgcaacccc gcctgcttca tcacccagct gctgcccgtg 1140
aagcgcaagc tgggcttcta cgagtggacc agccgcctgc gcagccacat caaccccacc 1200
ggcaccgtgc tgctgcagct ggagaacacc atgcagatga gcctgaagga cctgctgggc 1260
ggcagcagcg agcccaagag cagcgacaag acccacacct gccccccctg ccccgccccc 1320
gagctgctgg gcggccccag cgtgttcctg ttccccccca agcccaagga caccctgatg 1380
atcagccgca cccccgaggt gacctgcgtg gtggtggacg tgagccacga ggaccccgag 1440
gtgaagttca actggtacgt ggacggcgtg gaggtgcaca acgccaagac caagccccgc 1500
gaggagcagt acaacagcac ctaccgcgtg gtgagcgtgc tgaccgtgct gcaccaggac 1560
tggctgaacg gcaaggagta caagtgcaag gtgagcaaca aggccctgcc cgcccccatc 1620
gagaagacca tcagcaaggc caagggccag ccccgcgagc cccaggtgta caccctgccc 1680
cccagccgcg acgagctgac caagaaccag gtgagcctga cctgcctggt gaagggcttc 1740
taccccagcg acatcgccgt ggagtgggag agcaacggcc agcccgagaa caactacaag 1800
accacccccc ccgtgctgga cagcgacggc agcttcttcc tgtacagcaa gctgaccgtg 1860
gacaagagcc gctggcagca gggcaacgtg ttcagctgca gcgtgatgca cgaggccctg 1920
cacaaccact acacccagaa gagcctgagc ctgagccccg gcaagtaa 1968

<210> SEQ ID NO 15
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 15

Met Gly Trp Arg Ala Ala Gly Ala Leu Leu Leu Ala Leu Leu Leu His
1               5                   10                  15

Gly Arg Leu Leu Ala
            20

<210> SEQ ID NO 16
<211> LENGTH: 63
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 16
atgggctggc gagctgctgg tgcacttctg ctggctctgc tgcttcatgg cagactgctt 60
gct 63

<210> SEQ ID NO 17
<211> LENGTH: 6164
<212> TYPE: DNA
<213> ORGANISM: Artificial Sequence
<220> FEATURE:
<223> OTHER INFORMATION: Description of Artificial Sequence: Synthetic polynucleotide -continued

<400> SEQUENCE: 17
ttaaccctag aaagatagtc tgcgtaaaat tgacgcatgc attcttgaaa tattgctctc 60
tctttctaaa tagcgcgaat ccgtcgctgt gcatttagga catctcagtc gccgcttgga 120
gctcccgtga ggcgtgcttg tcaatgcggt aagtgtcact gattttgaac tataacgacc 180
gcgtgagtca aaatgacgca tgattatctt ttacgtgact tttaagattt aactcatacg 240
ataattatat tgttatttca tgttctactt acgtgataac ttattatata tatattttct 300
tgttatagat atcatcaact ttgtatagaa aagttgctcg acattgatta ttgactagtt 360
attaatagta atcaattacg gggtcattag ttcatagccc atatatggag ttccgcgtta 420
cataacttac ggtaaatggc ccgcctggct gaccgcccaa cgacccccgc ccattgacgt 480
caataatgac gtatgttccc atagtaacgc caatagggac tttccattga cgtcaatggg 540
tggagtattt acggtaaact gcccacttgg cagtacatca agtgtatcat atgccaagta 600
cgccccctat tgacgtcaat gacggtaaat ggcccgcctg gcattatgcc cagtacatga 660
ccttatggga ctttcctact tggcagtaca tctacgtatt agtcatcgct attaccatgg 720
tcgaggtgag ccccacgttc tgcttcactc tccccatctc ccccccctcc ccacccccaa 780
ttttgtattt atttattttt taattatttt gtgcagcgat gggggcgggg gggggggggg 840
ggcgcgcgcc aggcggggcg gggcggggcg aggggcgggg cggggcgagg cggagaggtg 900
cggcggcagc caatcagagc ggcgcgctcc gaaagtttcc ttttatggcg aggcggcggc 960
ggcggcggcc ctataaaaag cgaagcgcgc ggcgggcggg agtcgctgcg cgctgccttc 1020
gccccgtgcc ccgctccgcc gccgcctcgc gccgcccgcc ccggctctga ctgaccgcgt 1080
tactcccaca ggtgagcggg cgggacggcc cttctcctcc gggctgtaat tagcgcttgg 1140
tttaatgacg gcttgtttct tttctgtggc tgcgtgaaag ccttgagggg ctccgggagg 1200
gccctttgtg cggggggagc ggctcggggg gtgcgtgcgt gtgtgtgtgc gtggggagcg 1260
ccgcgtgcgg ctccgcgctg cccggcggct gtgagcgctg cgggcgcggc gcggggcttt 1320
gtgcgctccg cagtgtgcgc gaggggagcg cggccggggg cggtgccccg cggtgcgggg 1380
ggggctgcga ggggaacaaa ggctgcgtgc ggggtgtgtg cgtgggggg tgagcagggg 1440
gtgtgggcgc gtcggtcggg ctgcaacccc ccctgcaccc ccctccccga gttgctgagc 1500
acggcccggc ttcgggtgcg gggctccgta cggggcgtgg cgcggggctc gccgtgccgg 1560
gcggggggtg gcggcaggtg ggggtgccgg gcggggcggg gccgcctcgg gccggggagg 1620
gctcggggga ggggcgcggc ggcccccgga gcgccggcgg ctgtcgaggc gcggcgagcc 1680
gcagccattg ccttttatgg taatcgtgcg agagggcgca gggacttcct ttgtcccaaa 1740
tctgtgcgga gccgaaatct gggaggcgcc gccgcacccc ctctagcggg cgcggggcga 1800
agcggtgcgg cgccggcagg aaggaaatgg gcggggaggg ccttcgtgcg tcgccgcgcc 1860
gccgtcccct tctccctctc cagcctcggg gctgtccgcg gggggacggc tgccttcggg 1920
ggggacgggg cagggcgggg ttcggcttct ggcgtgtgac cggcggctct agagcctctg 1980
ctaaccatgt tcatgccttc ttcttttcc tacagctcct gggcaacgtg ctggttattg 2040
tgctgtctca tcattttggc aaagaattgc aagtttgtac aaaaaagcag gctgccaccg 2100
aattcgcggc cgctaaaccc agctttcttg tacaaagtgg caactttatt atacatagtt 2160
gatcctcagg tgcaggctgc ctatcagaag gtggtggctg gtgtggccaa tgccctggct 2220
cacaaatacc actgagatct tttccctct gccaaaaatt atggggacat catgaagccc 2280
cttgagcatc tgacttctgg ctaataaagg aaatttattt tcattgcaat agtgtgttgg 2340 aatttttgt gtctctcact cggaaggaca tatgggaggg caaatcattt aaaacatcag 2400
aatgagtatt tggtttagag tttggcaaca tatgcccata tgctggctgc catgaacaaa 2460
ggttggctat aaagaggtca tcagtatatg aaacagcccc ctgctgtcca ttccttattc 2520
catagaaaag ccttgacttg aggttagatt ttttttatat tttgttttgt gttatttttt 2580
tctttaacat ccctaaaatt ttccttacat gttttactag ccagattttt cctcctctcc 2640
tgactactcc cagtcatagc tgtccctctt ctcttatgga gatccctcga cctgcagccc 2700
aagcttggat ccctcgagtt aattaacgag agcataatat tgatatgtgc caaagttgtt 2760
tctgactgac taataagtat aatttgtttc tattatgtat aggttaagct aattacttat 2820
tttataatac aacatgactg tttttaaagt acaaaataag tttatttttg taaaagagag 2880
aatgtttaaa agttttgtta ctttatagaa gaaattttga gtttttgttt ttttttaata 2940
aataaataaa cataaataaa ttgtttgttg aatttattat tagtatgtaa gtgtaaatat 3000
aataaaactt aatatctatt caaattaata aataaacctc gatatacaga ccgataaaac 3060
acatgcgtca attttacgca tgattatctt taacgtacgt cacaatatga ttatctttct 3120
agggttaaat aatagtttct aatttttta ttattcagcc tgctgtcgtg aataccgagc 3180
tccaattcgc cctatagtga gtcgtattac aattcactgg ccgtcgtttt acaacgtcgt 3240
gactgggaaa accctggcgt tacccaactt aatcgccttg cagcacatcc ccctttcgcc 3300
agctggcgta atagcgaaga ggcccgcacc gatcgccctt cccaacagtt gcgcagcctg 3360
aatggcgaat gggacgcgcc ctgtagcggc gcattaagcg cggcgggtgt ggtggttacg 3420
cgcagcgtga ccgctacact tgccagcgcc ctagcgcccg ctcctttcgc tttcttccct 3480
tcctttctcg ccacgttcgc cggctttccc cgtcaagctc taaatcgggg gctcccttta 3540
gggttccgat ttagtgcttt acggcacctc gaccccaaaa aacttgatta gggtgatggt 3600
tcacgtagtg ggccatcgcc ctgatagacg gtttttcgcc ctttgacgtt ggagtccacg 3660
ttctttaata gtggactctt gttccaaact ggaacaacac tcaaccctat ctcggtctat 3720
tcttttgatt tataagggat tttgccgatt tcggcctatt ggttaaaaaa tgagctgatt 3780
taacaaaaat ttaacgcgaa ttttaacaaa atattaacgc ttacaattta ggtggcactt 3840
ttcggggaaa tgtgcgcgga acccctattt gtttattttt ctaaatacat tcaaatatgt 3900
atccgctcat gagacaataa ccctgataaa tgcttcaata atattgaaaa aggaagagta 3960
tgagtattca acatttccgt gtcgccctta ttcccttttt tgcggcattt tgccttcctg 4020
tttttgctca cccagaaacg ctggtgaaag taaaagatgc tgaagatcag ttgggtgcac 4080
gagtgggtta catcgaactg gatctcaaca gcggtaagat ccttgagagt tttcgccccg 4140
aagaacgttt tccaatgatg agcactttta aagttctgct atgtggcgcg gtattatccc 4200
gtattgacgc cgggcaagag caactcggtc gccgcataca ctattctcag aatgacttgg 4260
ttgagtactc accagtcaca gaaaagcatc ttacggatgg catgacagta agagaattat 4320
gcagtgctgc cataaccatg agtgataaca ctgcggccaa cttacttctg acaacgatcg 4380
gaggaccgaa ggagctaacc gcttttttgc acaacatggg ggatcatgta actcgccttg 4440
atcgttggga accggagctg aatgaagcca taccaaacga cgagcgtgac accacgatgc 4500
ctgtagcaat ggcaacaacg ttgcgcaaac tattaactgg cgaactactt actctagctt 4560
cccggcaaca attaatagac tggatggagg cggataaagt tgcaggacca cttctgcgct 4620
cggcccttcc ggctggctgg tttattgctg ataaatctgg agccggtgag cgtgggtctc 4680

-continued

```
gcggtatcat tgcagcactg gggccagatg gtaagccctc ccgtatcgta gttatctaca   4740

cgacggggag tcaggcaact atggatgaac gaaatagaca gatcgctgag ataggtgcct   4800

cactgattaa gcattggtaa ctgtcagacc aagtttactc atatatactt tagattgatt   4860

taaaacttca tttttaattt aaaaggatct aggtgaagat cctttttgat aatctcatga   4920

ccaaaatccc ttaacgtgag ttttcgttcc actgagcgtc agaccccgta gaaaagatca   4980

aaggatcttc ttgagatcct ttttttctgc gcgtaatctg ctgcttgcaa acaaaaaaac   5040

caccgctacc agcggtggtt tgtttgccgg atcaagagct accaactctt tttccgaagg   5100

taactggctt cagcagagcg cagataccaa atactgttct tctagtgtag ccgtagttag   5160

gccaccactt caagaactct gtagcaccgc ctacatacct cgctctgcta atcctgttac   5220

cagtggctgc tgccagtggc gataagtcgt gtcttaccgg gttggactca agacgatagt   5280

taccggataa ggcgcagcgg tcgggctgaa cggggggttc gtgcacacag cccagcttgg   5340

agcgaacgac ctacaccgaa ctgagatacc tacagcgtga gctatgagaa agcgccacgc   5400

ttcccgaaga gagaaaggcg gacaggtatc cggtaagcgg cagggtcgga acaggagagc   5460

gcacgaggga gcttccaggg ggaaacgcct ggtatcttta tagtcctgtc gggtttcgcc   5520

acctctgact tgagcgtcga tttttgtgat gctcgtcagg ggggcggagc ctatggaaaa   5580

acgccagcaa cgcggccttt ttacggttcc tggccttttg ctggcctttt gctcacatgt   5640

tctttcctgc gttatcccct gattctgtgg ataaccgtat taccgccttt gagtgagctg   5700

ataccgctcg ccgcagccga acgaccgagc gcagcgagtc agtgagcgag gaagcggaag   5760

agcgcccaat acgcaaaccg cctctccccg cgcgttggcc gattcattaa tgcagctggc   5820

acgacaggtt tcccgactgg aaagcgggca gtgagcgcaa cgcaattaat gtgagttagc   5880

tcactcatta ggcaccccag gctttacact ttatgcttcc ggctcgtatg ttgtgtggaa   5940

ttgtgagcgg ataacaattt cacacaggaa acagctatga ccatgattac gccaagctcg   6000

aaattaaccc tcactaaagg gaacaaaagc tggtacctcg cgcgacttgg tttgccattc   6060

tttagcgcgc gtcgcgtcac acagcttggc cacaatgtgg tttttgtcaa acgaagattc   6120

tatgacgtgt ttaaagttta ggtcgagtaa agcgcaaatc tttt                     6164
```

```
<210> SEQ ID NO 18
<211> LENGTH: 1733
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18
```

```
ctcgacattg attattgact agttattaat agtaatcaat tacggggtca ttagttcata     60

gcccatatat ggagttccgc gttacataac ttacggtaaa tggcccgcct ggctgaccgc    120

ccaacgaccc ccgcccattg acgtcaataa tgacgtatgt tcccatagta acgccaatag    180

ggactttcca ttgacgtcaa tgggtggagt atttacggta aactgcccac ttggcagtac    240

atcaagtgta tcatatgcca agtacgcccc ctattgacgt caatgacggt aaatggcccg    300

cctggcatta tgcccagtac atgaccttat gggactttcc tacttggcag tacatctacg    360

tattagtcat cgctattacc atggtcgagg tgagccccac gttctgcttc actctcccca    420

tctccccccc ctccccaccc ccaattttgt atttatttat tttttaatta ttttgtgcag    480

cgatgggggc gggggggggg ggggggcgcg cgccaggcgg ggcggggcgg ggcgaggggc    540
```

-continued

```
ggggcggggc gaggcggaga ggtgcggcgg cagccaatca gagcggcgcg ctccgaaagt    600

ttccttttat ggcgaggcgg cggcggcggc ggccctataa aaagcgaagc gcgcggcggg    660

cgggagtcgc tgcgcgctgc cttcgccccg tgccccgctc cgccgccgcc tcgcgccgcc    720

cgccccggct ctgactgacc gcgttactcc cacaggtgag cgggcgggac ggcccttctc    780

ctccgggctg taattagcgc ttggtttaat gacggcttgt ttcttttctg tggctgcgtg    840

aaagccttga ggggctccgg gagggccctt tgtgcggggg gagcggctcg gggggtgcgt    900

gcgtgtgtgt gtgcgtgggg agcgccgcgt gcggctccgc gctgcccggc ggctgtgagc    960

gctgcgggcg cggcgcgggg ctttgtgcgc tccgcagtgt gcgcgagggg agcgcggccg   1020

ggggcggtgc cccgcggtgc ggggggggct gcgaggggaa caaaggctgc gtgcggggtg   1080

tgtgcgtggg ggggtgagca gggggtgtgg gcgcgtcggt cgggctgcaa ccccccctgc   1140

accccctcc ccgagttgct gagcacggcc cggcttcggg tgcggggctc cgtacggggc   1200

gtggcgcggg gctcgccgtg ccgggcgggg ggtggcggca ggtgggggtg ccgggcgggg   1260

cggggccgcc tcgggccggg gagggctcgg gggaggggcg cggcggcccc cggagcgccg   1320

gcggctgtcg aggcgcggcg agccgcagcc attgcctttt atggtaatcg tgcgagaggg   1380

cgcagggact tcctttgtcc caaatctgtg cggagccgaa atctgggagg cgccgccgca   1440

ccccctctag cgggcgcggg gcgaagcggt gcggcgccgg caggaaggaa atgggcgggg   1500

agggccttcg tgcgtcgccg cgccgccgtc cccttctccc tctccagcct cggggctgtc   1560

cgcgggggga cggctgcctt cgggggggac ggggcagggc ggggttcggc ttctggcgtg   1620

tgaccggcgg ctctagagcc tctgctaacc atgttcatgc cttcttcttt ttcctacagc   1680

tcctgggcaa cgtgctggtt attgtgctgt ctcatcattt tggcaaagaa ttg          1733
```

```
<210> SEQ ID NO 19
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19

gccacc                                                                  6


<210> SEQ ID NO 20
<211> LENGTH: 522
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20

tcctcaggtg caggctgcct atcagaaggt ggtggctggt gtggccaatg ccctggctca     60

caaataccac tgagatcttt ttccctctgc caaaaattat ggggacatca tgaagcccct    120

tgagcatctg acttctggct aataaaggaa atttattttc attgcaatag tgtgttggaa    180

ttttttgtgt ctctcactcg gaaggacata tgggagggca aatcatttaa aacatcagaa    240

tgagtatttg gtttagagtt tggcaacata tgcccatatg ctggctgcca tgaacaaagg    300

ttggctataa agaggtcatc agtatatgaa acagccccct gctgtccatt ccttattcca    360

tagaaaagcc ttgacttgag gttagatttt ttttatattt tgttttgtgt tatttttttc    420

tttaacatcc ctaaaatttt ccttacatgt tttactagcc agatttttcc tcctctcctg    480
```

actactccca gtcatagctg tccctcttct cttatggaga tc 522

<210> SEQ ID NO 21
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 21

Ser Trp Glu Leu Tyr Tyr Pro Leu Arg Ala Asn Leu
1 5 10

<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 22

His Ala Val Asp Ile
1 5

<210> SEQ ID NO 23
<211> LENGTH: 4
<212> TYPE: PRT
<213> ORGANISM: Artificial Sequence
<220> FEATURE:
<223> OTHER INFORMATION: Description of Artificial Sequence: Synthetic peptide

<400> SEQUENCE: 23

Asp Gly Glu Ala
1

<210> SEQ ID NO 24
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 24

Phe Tyr Phe Asp Leu Arg
1 5

<210> SEQ ID NO 25
<211> LENGTH: 6
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (3)..(3)
<223> OTHER INFORMATION: 4-hydroxyproline

<400> SEQUENCE: 25

Gly Phe Pro Gly Glu Arg
1 5

<210> SEQ ID NO 26

<211> LENGTH: 37
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: MOD_RES
<222> LOCATION: (19)..(19)
<223> OTHER INFORMATION: 4-hydroxyproline

<400> SEQUENCE: 26

```
Pro Gly Pro Pro Gly Pro Pro Gly Pro Pro Gly Pro Pro Gly Pro Pro
1               5                   10                  15

Gly Phe Pro Gly Glu Arg Gly Pro Pro Gly Pro Pro Gly Pro Pro Gly
            20                  25                  30

Pro Pro Gly Pro Pro
        35
```

<210> SEQ ID NO 27
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 27

```
Val Ala Pro Gly
1
```

<210> SEQ ID NO 28
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 28

```
Arg Gly Asp
1
```

<210> SEQ ID NO 29
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 29

```
Gly Pro Arg
1
```

<210> SEQ ID NO 30
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 30

```
Lys Gln Ala Gly Asp Val
1               5
```

-continued

<210> SEQ ID NO 31
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 31

Pro His Ser Arg Asn
1 5

<210> SEQ ID NO 32
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 32

Pro His Ser Arg Asn Gly Gly Gly Gly Gly Gly Arg Gly Asp Ser
1 5 10 15

<210> SEQ ID NO 33
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 33

Arg Glu Asp Val
1

<210> SEQ ID NO 34
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 34

Ile Lys Val Ala Val
1 5

<210> SEQ ID NO 35
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 35

Ser Arg Ala Arg Lys Gln Ala Ala Ser Ile Lys Val Ala Val Ala Asp
1 5 10 15

Arg

<210> SEQ ID NO 36
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 36

Leu Arg Glu
1

<210> SEQ ID NO 37
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 37

Lys Gln Leu Arg Glu Gln
1 5

<210> SEQ ID NO 38
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 38

Tyr Ile Gly Ser Arg
1 5

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 39

Ser Val Val Tyr Gly Leu Arg
1 5

<210> SEQ ID NO 40
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 40

Ala Glu Ile Asp Gly Ile Glu Leu
1 5

<210> SEQ ID NO 41
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 41

Val Thr Cys Gly
1

<210> SEQ ID NO 42
<211> LENGTH: 5

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 42

Ser Val Thr Cys Gly
1 5

<210> SEQ ID NO 43
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 43

Gly Arg Gly Asp
1

<210> SEQ ID NO 44
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 44

Gly Arg Gly Asp Ser Pro
1 5

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 45

Gly Gly Arg Gly Asp Ser Pro
1 5

<210> SEQ ID NO 46
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 46

Gly Gly Gly Arg Gly Asp Ser Pro
1 5

<210> SEQ ID NO 47
<211> LENGTH: 4347
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 47
ttaaccctag aaagatagtc tgcgtaaaat tgacgcatgc attcttgaaa tattgctctc 60
tctttctaaa tagcgcgaat ccgtcgctgt gcatttagga catctcagtc gccgcttgga 120
gctcccgtga ggcgtgcttg tcaatgcggt aagtgtcact gattttgaac tataacgacc 180
gcgtgagtca aaatgacgca tgattatctt ttacgtgact tttaagattt aactcatacg 240
ataattatat tgttatttca tgttctactt acgtgataac ttattatata tatattttct 300
tgttatagat atcatcaact ttgtatagaa aagttgctcg acattgatta ttgactagtt 360
attaatagta atcaattacg gggtcattag ttcatagccc atatatggag ttccgcgtta 420
cataacttac ggtaaatggc ccgcctggct gaccgcccaa cgacccccgc ccattgacgt 480
caataatgac gtatgttccc atagtaacgc caatagggac tttccattga cgtcaatggg 540
tggagtattt acggtaaact gcccacttgg cagtacatca agtgtatcat atgccaagta 600
cgccccctat tgacgtcaat gacggtaaat ggcccgcctg gcattatgcc cagtacatga 660
ccttatggga ctttcctact tggcagtaca tctacgtatt agtcatcgct attaccatgg 720
tcgaggtgag ccccacgttc tgcttcactc tccccatctc ccccccctcc ccacccccaa 780
ttttgtattt atttattttt taattatttt gtgcagcgat gggggcgggg gggggggggg 840
ggcgcgcgcc aggcggggcg gggcggggcg aggggcgggg cggggcgagg cggagaggtg 900
cggcggcagc caatcagagc ggcgcgctcc gaaagtttcc ttttatggcg aggcggcggc 960
ggcggcggcc ctataaaaag cgaagcgcgc ggcgggcggg agtcgctgcg cgctgccttc 1020
gccccgtgcc ccgctccgcc gccgcctcgc gccgcccgcc ccggctctga ctgaccgcgt 1080
tactcccaca ggtgagcggg cgggacggcc cttctcctcc gggctgtaat tagcgcttgg 1140
tttaatgacg gcttgtttct tttctgtggc tgcgtgaaag ccttgagggg ctccgggagg 1200
gccctttgtg cggggggagc ggctcggggg gtgcgtgcgt gtgtgtgtgc gtggggagcg 1260
ccgcgtgcgg ctccgcgctg cccggcggct gtgagcgctg cgggcgcggc gcggggcttt 1320
gtgcgctccg cagtgtgcgc gaggggagcg cggccggggg cggtgccccg cggtgcgggg 1380
ggggctgcga ggggaacaaa ggctgcgtgc ggggtgtgtg cgtggggggg tgagcagggg 1440
gtgtgggcgc gtcggtcggg ctgcaacccc ccctgcaccc ccctccccga gttgctgagc 1500
acggcccggc ttcgggtgcg gggctccgta cggggcgtgg cgcggggctc gccgtgccgg 1560
gcgggggggtg gcggcaggtg ggggtgccgg gcggggcggg gccgcctcgg gccggggagg 1620
gctcggggga ggggcgcggc ggcccccgga gcgccggcgg ctgtcgaggc gcggcgagcc 1680
gcagccattg ccttttatgg taatcgtgcg agagggcgca gggacttcct ttgtcccaaa 1740
tctgtgcgga gccgaaatct gggaggcgcc gccgcacccc ctctagcggg cgcggggcga 1800
agcggtgcgg cgccggcagg aaggaaatgg gcggggaggg ccttcgtgcg tcgccgcgcc 1860
gccgtcccct tctccctctc cagcctcggg gctgtccgcg ggggacggc tgccttcggg 1920
ggggacgggg cagggcgggg ttcggcttct ggcgtgtgac cggcggctct agagcctctg 1980
ctaaccatgt tcatgccttc ttcttttttcc tacagctcct gggcaacgtg ctggttattg 2040
tgctgtctca tcattttggc aaagaattgc aagtttgtac aaaaaagcag gctgccacca 2100
tgggctggcg agctgctggt gcacttctgc tggctctgct gcttcatggc agactgcttg 2160
ctctggacaa cggcctggcc cgcacccccca ccatgggctg gctgcactgg gagcgcttca 2220
tgtgcaacct ggactgccag gaggagcccg acagctgcat cagcgagaag ctgttcatgg 2280
agatggccga gctgatggtg agcgagggct ggaaggacgc cggctacgag tacctgtgca 2340
tcgacgactg ctggatggcc ccccagcgcg acagcgaggg ccgcctgcag gccgaccccc 2400

-continued

```
agcgcttccc ccacggcatc cgccagctgg ccaactacgt gcacagcaag ggcctgaagc   2460
tgggcatcta cgccgacgtg ggcaacaaga cctgcgccgg cttccccggc agcttcggct   2520
actacgacat cgacgcccag accttcgccg actggggcgt ggacctgctg aagttcgacg   2580
gctgctactg cgacagcctg gagaacctgg ccgacggcta caagcacatg agcctggccc   2640
tgaaccgcac cggccgcagc atcgtgtaca gctgcgagtg gcccctgtac atgtggccct   2700
tccagaagcc caactacacc gagatccgcc agtactgcaa ccactggcgc aacttcgccg   2760
acatcgacga cagctggaag agcatcaaga gcatcctgga ctggaccagc ttcaaccagg   2820
agcgcatcgt ggacgtggcc ggccccggcg gctggaacga ccccgacatg ctggtgatcg   2880
gcaacttcgg cctgagctgg aaccagcagg tgacccagat ggccctgtgg gccatcatgg   2940
ccgcccccct gttcatgagc aacgacctgc gccacatcag cccccaggcc aaggccctgc   3000
tgcaggacaa ggacgtgatc gccatcaacc aggacccccct gggcaagcag ggctaccagc   3060
tgcgccaggg cgacaacttc gaggtgtggg agcgccccct gagcggcctg gcctgggccg   3120
tggccatgat caaccgccag gagatcggcg gcccccgcag ctacaccatc gccgtggcca   3180
gcctgggcaa gggcgtggcc tgcaaccccg cctgcttcat cacccagctg ctgcccgtga   3240
agcgcaagct gggcttctac gagtggacca gccgcctgcg cagccacatc aaccccaccg   3300
gcaccgtgct gctgcagctg gagaacacca tgcagatgag cctgaaggac ctgctgtaac   3360
aactttatta tacatagttg atcctcaggt gcaggctgcc tatcagaagg tggtggctgg   3420
tgtggccaat gccctggctc acaaatacca ctgagatctt tttccctctg ccaaaaatta   3480
tggggacatc atgaagcccc ttgagcatct gacttctggc taataaagga aatttatttt   3540
cattgcaata gtgtgttgga atttttttgtg tctctcactc ggaaggacat atgggagggc   3600
aaatcattta aaacatcaga atgagtattt ggtttagagt ttggcaacat atgcccatat   3660
gctggctgcc atgaacaaag gttggctata aagaggtcat cagtatatga aacagccccc   3720
tgctgtccat tccttattcc atagaaaagc cttgacttga ggttagattt tttttatatt   3780
ttgttttgtg ttattttttt ctttaacatc cctaaaattt tccttacatg ttttactagc   3840
cagatttttc ctcctctcct gactactccc agtcatagct gtccctcttc tcttatggag   3900
atccctcgac ctgcagccca agcttggatc cctcgagtta attaacgaga gcataatatt   3960
gatatgtgcc aaagttgttt ctgactgact aataagtata atttgtttct attatgtata   4020
ggttaagcta attacttatt ttataataca acatgactgt ttttaaagta caaaataagt   4080
ttatttttgt aaaagagaga atgtttaaaa gttttgttac tttatagaag aaattttgag   4140
tttttgtttt tttttaataa ataaataaac ataaataaat tgtttgttga atttattatt   4200
agtatgtaag tgtaaatata ataaaactta atatctattc aaattaataa ataaacctcg   4260
atatacagac cgataaaaca catgcgtcaa ttttacgcat gattatcttt aacgtacgtc   4320
acaatatgat tatctttcta gggttaa                                       4347
```

<210> SEQ ID NO 48
<211> LENGTH: 7383
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 48

```
ttaaccctag aaagatagtc tgcgtaaaat tgacgcatgc attcttgaaa tattgctctc     60
```

-continued

```
tctttctaaa tagcgcgaat ccgtcgctgt gcatttagga catctcagtc gccgcttgga    120
gctcccgtga ggcgtgcttg tcaatgcggt aagtgtcact gattttgaac tataacgacc    180
gcgtgagtca aaatgacgca tgattatctt ttacgtgact tttaagattt aactcatacg    240
ataattatat tgttatttca tgttctactt acgtgataac ttattatata tatattttct    300
tgttatagat atcatcaact ttgtatagaa aagttgctcg acattgatta ttgactagtt    360
attaatagta atcaattacg gggtcattag ttcatagccc atatatggag ttccgcgtta    420
cataacttac ggtaaatggc ccgcctggct gaccgcccaa cgacccccgc ccattgacgt    480
caataatgac gtatgttccc atagtaacgc caatagggac tttccattga cgtcaatggg    540
tggagtattt acggtaaact gcccacttgg cagtacatca agtgtatcat atgccaagta    600
cgccccctat tgacgtcaat gacggtaaat ggcccgcctg gcattatgcc cagtacatga    660
ccttatggga ctttcctact tggcagtaca tctacgtatt agtcatcgct attaccatgg    720
tcgaggtgag ccccacgttc tgcttcactc tccccatctc ccccccctcc ccacccccaa    780
ttttgtattt atttattttt taattatttt gtgcagcgat gggggcgggg gggggggggg    840
ggcgcgcgcc aggcggggcg gggcggggcg aggggcgggg cggggcgagg cggagaggtg    900
cggcggcagc caatcagagc ggcgcgctcc gaaagtttcc ttttatggcg aggcggcggc    960
ggcggcggcc ctataaaaag cgaagcgcgc ggcgggcggg agtcgctgcg cgctgccttc   1020
gccccgtgcc ccgctccgcc gccgcctcgc gccgcccgcc ccggctctga ctgaccgcgt   1080
tactcccaca ggtgagcggg cgggacggcc cttctcctcc gggctgtaat tagcgcttgg   1140
tttaatgacg gcttgtttct tttctgtggc tgcgtgaaag ccttgagggg ctccgggagg   1200
gccctttgtg cggggggagc ggctcggggg gtgcgtgcgt gtgtgtgtgc gtggggagcg   1260
ccgcgtgcgg ctccgcgctg cccggcggct gtgagcgctg cgggcgcggc gcggggcttt   1320
gtgcgctccg cagtgtgcgc gaggggagcg cggccggggg cggtgccccg cggtgcgggg   1380
ggggctgcga ggggaacaaa ggctgcgtgc ggggtgtgtg cgtggggggg tgagcagggg   1440
gtgtgggcgc gtcggtcggg ctgcaacccc ccctgcaccc ccctccccga gttgctgagc   1500
acggcccggc ttcgggtgcg gggctccgta cggggcgtgg cgcggggctc gccgtgccgg   1560
gcggggggtg gcggcaggtg gggggtgccgg gcggggcggg gccgcctcgg gccggggagg   1620
gctcggggga ggggcgcggc ggcccccgga gcgccggcgg ctgtcgaggc gcggcgagcc   1680
gcagccattg ccttttatgg taatcgtgcg agagggcgca gggacttcct ttgtcccaaa   1740
tctgtgcgga gccgaaatct gggaggcgcc gccgcacccc ctctagcggg cgcggggcga   1800
agcggtgcgg cgccggcagg aaggaaatgg gcggggaggg ccttcgtgcg tcgccgcgcc   1860
gccgtcccct tctccctctc cagcctcggg gctgtccgcg gggggacggc tgccttcggg   1920
ggggacgggg cagggcgggg ttcggcttct ggcgtgtgac cggcggctct agagcctctg   1980
ctaaccatgt tcatgccttc ttcttttcc tacagctcct gggcaacgtg ctggttattg   2040
tgctgtctca tcattttggc aaagaattgc aagtttgtac aaaaaagcag gctgccacca   2100
tgggctggcg agctgctggt gcacttctgc tggctctgct gcttcatggc agactgcttg   2160
ctctggacaa cggcctggcc cgcacccca ccatgggctg gctgcactgg gagcgcttca   2220
tgtgcaacct ggactgccag gaggagcccg acagctgcat cagcgagaag ctgttcatgg   2280
agatggccga gctgatggtg agcgagggct ggaaggacgc cggctacgag tacctgtgca   2340
tcgacgactg ctggatggcc ccccagcgcg acagcgaggg ccgcctgcag gccgaccccc   2400
agcgcttccc ccacggcatc cgccagctgg ccaactacgt gcacagcaag ggcctgaagc   2460
```

-continued

```
tgggcatcta cgccgacgtg ggcaacaaga cctgcgccgg cttccccggc agcttcggct   2520
actacgacat cgacgcccag accttcgccg actggggcgt ggacctgctg aagttcgacg   2580
gctgctactg cgacagcctg gagaacctgg ccgacggcta caagcacatg agcctggccc   2640
tgaaccgcac cggccgcagc atcgtgtaca gctgcgagtg gcccctgtac atgtggccct   2700
tccagaagcc caactacacc gagatccgcc agtactgcaa ccactggcgc aacttcgccg   2760
acatcgacga cagctggaag agcatcaaga gcatcctgga ctggaccagc ttcaaccagg   2820
agcgcatcgt ggacgtggcc ggccccggcg gctggaacga ccccgacatg ctggtgatcg   2880
gcaacttcgg cctgagctgg aaccagcagg tgacccagat ggccctgtgg gccatcatgg   2940
ccgccccct gttcatgagc aacgacctgc gccacatcag cccccaggcc aaggccctgc   3000
tgcaggacaa ggacgtgatc gccatcaacc aggaccccct gggcaagcag ggctaccagc   3060
tgcgccaggg cgacaacttc gaggtgtggg agcgccccct gagcggcctg gcctgggccg   3120
tggccatgat caaccgccag gagatcggcg gcccccgcag ctacaccatc gccgtggcca   3180
gcctgggcaa gggcgtggcc tgcaaccccg cctgcttcat cacccagctg ctgcccgtga   3240
agcgcaagct gggcttctac gagtggacca gccgcctgcg cagccacatc aaccccaccg   3300
gcaccgtgct gctgcagctg gagaacacca tgcagatgag cctgaaggac ctgctgtaac   3360
aactttatta tacatagttg atcctcaggt gcaggctgcc tatcagaagg tggtggctgg   3420
tgtggccaat gccctggctc acaaatacca ctgagatctt tttccctctg ccaaaaatta   3480
tggggacatc atgaagcccc ttgagcatct gacttctggc taataaagga aatttatttt   3540
cattgcaata gtgtgttgga atttttgtg tctctcactc ggaaggacat atgggagggc   3600
aaatcattta aaacatcaga atgagtattt ggtttagagt ttggcaacat atgcccatat   3660
gctggctgcc atgaacaaag gttggctata aagaggtcat cagtatatga aacagccccc   3720
tgctgtccat tccttattcc atagaaaagc cttgacttga ggttagattt tttttatatt   3780
ttgttttgtg ttattttttt ctttaacatc cctaaaattt tccttacatg ttttactagc   3840
cagatttttc ctcctctcct gactactccc agtcatagct gtccctcttc tcttatggag   3900
atccctcgac ctgcagccca agcttggatc cctcgagtta attaacgaga gcataatatt   3960
gatatgtgcc aaagttgttt ctgactgact aataagtata atttgtttct attatgtata   4020
ggttaagcta attacttatt ttataataca acatgactgt ttttaaagta caaaataagt   4080
ttattttttgt aaaagagaga atgtttaaaa gttttgttac tttatagaag aaattttgag   4140
tttttgtttt tttttaataa ataaataaac ataaataaat tgtttgttga atttattatt   4200
agtatgtaag tgtaaatata ataaaactta atatctattc aaattaataa ataaacctcg   4260
atatacagac cgataaaaca catgcgtcaa ttttacgcat gattatcttt aacgtacgtc   4320
acaatatgat tatctttcta gggttaaata atagtttcta atttttttat tattcagcct   4380
gctgtcgtga ataccgagct ccaattcgcc ctatagtgag tcgtattaca attcactggc   4440
cgtcgtttta caacgtcgtg actgggaaaa ccctggcgtt acccaactta atcgccttgc   4500
agcacatccc cctttcgcca gctggcgtaa tagcgaagag gcccgcaccg atcgcccttc   4560
ccaacagttg cgcagcctga atggcgaatg ggacgcgccc tgtagcggcg cattaagcgc   4620
ggcgggtgtg gtggttacgc gcagcgtgac cgctacactt gccagcgccc tagcgcccgc   4680
tcctttcgct ttcttccctt cctttctcgc cacgttcgcc ggctttcccc gtcaagctct   4740
aaatcggggg ctccctttag ggttccgatt tagtgcttta cggcacctcg accccaaaaa   4800
```

-continued

```
acttgattag ggtgatggtt cacgtagtgg gccatcgccc tgatagacgg tttttcgccc   4860
tttgacgttg gagtccacgt tctttaatag tggactcttg ttccaaactg gaacaacact   4920
caaccctatc tcggtctatt cttttgattt ataagggatt ttgccgattt cggcctattg   4980
gttaaaaaat gagctgattt aacaaaaatt taacgcgaat tttaacaaaa tattaacgct   5040
tacaatttag gtggcacttt tcggggaaat gtgcgcggaa cccctatttg tttatttttc   5100
taaatacatt caaatatgta tccgctcatg agacaataac cctgataaat gcttcaataa   5160
tattgaaaaa ggaagagtat gagtattcaa catttccgtg tcgcccttat tccctttttt   5220
gcggcatttt gccttcctgt ttttgctcac ccagaaacgc tggtgaaagt aaaagatgct   5280
gaagatcagt tgggtgcacg agtgggttac atcgaactgg atctcaacag cggtaagatc   5340
cttgagagtt ttcgccccga agaacgtttt ccaatgatga gcacttttaa agttctgcta   5400
tgtggcgcgg tattatcccg tattgacgcc gggcaagagc aactcggtcg ccgcatacac   5460
tattctcaga atgacttggt tgagtactca ccagtcacag aaaagcatct tacggatggc   5520
atgacagtaa gagaattatg cagtgctgcc ataaccatga gtgataacac tgcggccaac   5580
ttacttctga caacgatcgg aggaccgaag gagctaaccg cttttttgca caacatgggg   5640
gatcatgtaa ctcgccttga tcgttgggaa ccggagctga atgaagccat accaaacgac   5700
gagcgtgaca ccacgatgcc tgtagcaatg gcaacaacgt tgcgcaaact attaactggc   5760
gaactactta ctctagcttc ccggcaacaa ttaatagact ggatggaggc ggataaagtt   5820
gcaggaccac ttctgcgctc ggcccttccg gctggctggt ttattgctga taaatctgga   5880
gccggtgagc gtgggtctcg cggtatcatt gcagcactgg ggccagatgg taagccctcc   5940
cgtatcgtag ttatctacac gacggggagt caggcaacta tggatgaacg aaatagacag   6000
atcgctgaga taggtgcctc actgattaag cattggtaac tgtcagacca agtttactca   6060
tatatacttt agattgattt aaaacttcat ttttaattta aaaggatcta ggtgaagatc   6120
ctttttgata atctcatgac caaaatccct taacgtgagt tttcgttcca ctgagcgtca   6180
gaccccgtag aaaagatcaa aggatcttct tgagatcctt tttttctgcg cgtaatctgc   6240
tgcttgcaaa caaaaaaacc accgctacca gcggtggttt gtttgccgga tcaagagcta   6300
ccaactcttt ttccgaaggt aactggcttc agcagagcgc agataccaaa tactgttctt   6360
ctagtgtagc cgtagttagg ccaccacttc aagaactctg tagcaccgcc tacatacctc   6420
gctctgctaa tcctgttacc agtggctgct gccagtggcg ataagtcgtg tcttaccggg   6480
ttggactcaa gacgatagtt accggataag gcgcagcggt cgggctgaac ggggggttcg   6540
tgcacacagc ccagcttgga gcgaacgacc tacaccgaac tgagatacct acagcgtgag   6600
ctatgagaaa gcgccacgct tcccgaagag agaaaggcgg acaggtatcc ggtaagcggc   6660
agggtcggaa caggagagcg cacgagggag cttccagggg gaaacgcctg gtatctttat   6720
agtcctgtcg ggtttcgcca cctctgactt gagcgtcgat ttttgtgatg ctcgtcaggg   6780
gggcggagcc tatggaaaaa cgccagcaac gcggcctttt tacggttcct ggccttttgc   6840
tggccttttg ctcacatgtt ctttcctgcg ttatcccctg attctgtgga taaccgtatt   6900
accgcctttg agtgagctga taccgctcgc cgcagccgaa cgaccgagcg cagcgagtca   6960
gtgagcgagg aagcggaaga gcgcccaata cgcaaaccgc ctctccccgc gcgttggccg   7020
attcattaat gcagctggca cgacaggttt cccgactgga aagcgggcag tgagcgcaac   7080
gcaattaatg tgagttagct cactcattag gcaccccagg ctttacactt tatgcttccg   7140
gctcgtatgt tgtgtggaat tgtgagcgga taacaatttc acacaggaaa cagctatgac   7200
```

-continued

```
catgattacg ccaagctcga aattaaccct cactaaaggg aacaaaagct ggtacctcgc   7260

gcgacttggt ttgccattct ttagcgcgcg tcgcgtcaca cagcttggcc acaatgtggt   7320

ttttgtcaaa cgaagattct atgacgtgtt taaagtttag gtcgagtaaa gcgcaaatct   7380

ttt                                                                 7383


<210> SEQ ID NO 49
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Arg Gly Asp Ser Pro
1               5


<210> SEQ ID NO 50
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(3)
<223> OTHER INFORMATION: This region may encompass 1-3 residues

<400> SEQUENCE: 50

Gly Gly Gly Arg Gly Asp
1               5


<210> SEQ ID NO 51
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(3)
<223> OTHER INFORMATION: This region may encompass 1-3 residues

<400> SEQUENCE: 51

Gly Gly Gly Arg Gly Asp Ser Pro
1               5
```

COMPOSITIONS, DEVICES, AND METHODS FOR TREATING FABRY DISEASE

CLAIM OF PRIORITY

This application is a U.S. National Phase Application under 35 U.S.C. § 371 of International Application No. PCT/US2020/025485, filed Mar. 27, 2020, which claims priority to U.S. Provisional Application No. 62/824,969, filed Mar. 27, 2019, and U.S. Provisional Application No. 62/907,380, filed Sep. 27, 2019. The disclosure of each of the foregoing applications is incorporated herein by reference in its entirety.

SEQUENCE LISTING

The instant application contains a Sequence Listing which has been submitted electronically in ASCII format and is hereby incorporated by reference in its entirety. Said ASCII copy, created on Mar. 25, 2020, is named S2225-7028WO-_SL.txt and is 79,658 bytes in size.

BACKGROUND

Fabry disease is a rare, X-linked, lysosomal storage disorder caused by deficient activity of the enzyme alpha-galactosidase A (GLA or GALA), which leads to damaging accumulation of the glycosphingolipid globotriaosylceramide (Gb3) in various tissues and organs. The GLA gene encodes a homodimeric glycoprotein that hydrolyses the terminal alpha-galactosyl moieties from glycolipids and glycoproteins, and the predominant substrate is globotriaosylceramide (Gb3, ceramide trihexoside). More than 370 mutations in the GLA gene have been identified in people with Fabry disease, many of which are unique to single families. Mutations that eliminate GLA activity lead to the severe, classic form of Fabry disease, which typically begins in childhood. Milder, late-onset forms of Fabry disease are correlated with mutations that reduce, but do not eliminate, GLA activity.

Recombinantly-produced GLA protein has been approved for use in enzyme replacement therapy for Fabry disease. Gene therapy is being investigated as an alternative approach to deliver GLA enzyme to Fabry patients. However, ERT and gene therapy approaches to treating Fabry disease pose various manufacturing and efficacy challenges; thus, novel treatment modalities for Fabry disease are desirable.

SUMMARY

Described herein is a retinal pigment epithelial (RPE) cell that is engineered to express and secrete GLA, as well as compositions, pharmaceutical products, and medical devices comprising the engineered RPE cell, and methods of making and using the same. In some embodiments, the compositions, products and devices comprising the engineered RPE cell are configured to mitigate the foreign body response when administered to, e.g., placed inside, a mammalian subject.

In one aspect, the present disclosure features an isolated polynucleotide comprising a promoter operably linked to a precursor GLA coding sequence. In an embodiment, the promoter sequence consists essentially of a nucleotide sequence that is identical to, or substantially identical to, nucleotides 337-2069 of the sequence shown in FIG. 8B (referred to herein as SEQ ID NO:18). In an embodiment, the precursor GLA coding sequence encodes a GLA fusion protein. In an embodiment, the GLA fusion protein comprises a signal peptide from a secretory protein operably linked to the N-terminus of a mature human GLA amino acid sequence. In an embodiment, the precursor or mature GLA coding sequence is codon-optimized for expression in a mammalian cell. In an embodiment, the precursor GLA codon-optimized coding sequence is SEQ ID NO:3, SEQ ID NO:4 or SEQ ID NO:6. In an embodiment, the signal peptide is from HSPG2 (e.g., amino acids 1-21 of FIG. 4A). In an embodiment, the GLA fusion protein comprises a signal peptide (e.g., from human GLA or HSPG2) operably linked to the N-terminus of a mature human GLA amino acid sequence, and an amino acid sequence encoding a non-GLA polypeptide operably linked to the C-terminus of the GLA amino acid sequence. In an embodiment, the non-GLA polypeptide confers a beneficial property to the fusion protein, e.g., increases the amount of protein expressed and/or secreted, extends the half-life in vivo, or enhances the distribution or increases uptake of the fusion protein into tissues. In an embodiment, the isolated polynucleotide comprises SEQ ID NO:47. In an embodiment, the isolated polynucleotide is provided as an isolated double-stranded DNA molecule, and in an embodiment the DNA molecule comprises SEQ ID NO:48.

In another aspect, the present disclosure provides an engineered RPE cell comprising an exogenous nucleotide sequence, which comprises a promoter sequence operably linked to a precursor GLA coding sequence. In an embodiment, the exogenous nucleotide sequence comprises an extrachromosomal expression vector. In an embodiment, the exogenous nucleotide sequence is integrated into at least one location in the genome of the RPE cell, e.g., ARPE19 cell.

In yet another aspect, the present disclosure provides a device comprising at least one cell-containing compartment which comprises an engineered RPE cell described herein or a plurality of such cells. In some embodiments, the compositions, products and devices comprise a polymer composition encapsulating the engineered RPE cell(s). In an embodiment, the encapsulating polymer composition at least one cell binding-substance (CBS), e.g., a cell binding peptide, e.g., RGD (SEQ ID NO: 28) or RGDSP (SEQ ID NO:49). In an embodiment, the encapsulating polymer composition comprises an alginate covalently modified with GRGDSP (SEQ ID NO:44). In some embodiments, the device further comprises at least one means for mitigating the foreign body response (FBR) when the device is placed inside a subject. In an embodiment, the means for mitigating the FBR comprises an afibrotic compound, as defined herein, disposed on an exterior surface of the device and/or within a barrier compartment surrounding the cell-containing compartment. In an embodiment, the afibrotic compound is a compound of Formula (I):

(I)

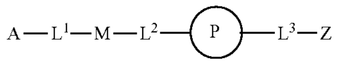

or a pharmaceutically acceptable salt thereof, wherein the variables A, $L^1$, M, $L^2$, P, $L^3$, and Z, as well as related subvariables, are defined herein. In some embodiments, the compound of Formula (I) or a pharmaceutically acceptable salt thereof (e.g., Formulas (I-a), (I-b), (I-c), (I-d), (I-e), (I-f), (II), (II-a), (III), (III-a), (III-b), (III-c), or (III-d)) is a compound described herein, including for example, one of the compounds shown in Table 3 herein. In an embodiment, the afibrotic compound is Compound 100, Compound 101 or Compound 102 shown in Table 3.

In one aspect, a device of the disclosure is a 2-compartment hydrogel capsule (e.g., a microcapsule (less than 1 mm in diameter) or a millicapsule (at least 1 mm in diameter)) in which a cell-containing compartment (e.g., the inner compartment) comprising a plurality of live engineered RPE cells (and optionally one or more cell binding substances) is surrounded by a barrier compartment comprising an afibrotic polymer (e.g., the outer compartment). In an embodiment, the afibrotic compound is a compound of Formula (I). In an embodiment, the hydrogel capsule is a spherical capsule.

In another aspect, the present disclosure features a preparation (e.g., a composition) comprising a plurality (at least any of 3, 6, 12, 25, 50 or more) of an RPE cell-containing device described herein. In some embodiments, the preparation is a pharmaceutically acceptable composition.

In another aspect, the present disclosure features a method of making or manufacturing a device comprising a plurality of RPE cells engineered to express and secrete GLA. In some embodiments, the method comprises providing the plurality of engineered RPE cells and disposing the plurality of RPE cells in an enclosing component, e.g., a cell-containing compartment of the device as described herein. In some embodiments, the enclosing component comprises a flexible polymer (e.g., PLA, PLG, PEG, CMC, or a polysaccharide, e.g., alginate). In some embodiments, the enclosing component comprises an inflexible polymer or metal housing. In some embodiments, the surface of the device is chemically modified, e.g., with a compound of Formula (I) as described herein.

In another aspect, the present disclosure features a method of evaluating an engineered RPE cell or a device described herein. In some embodiments, the method comprises providing the engineered RPE cell or device and evaluating a structural or functional parameter of the RPE cell or device. In some embodiments, the method comprises evaluating the engineered RPE cell or device for one or more of a) cell viability and b) amount of GLA produced. In some embodiments, the evaluation is performed at least 1, 5, 10, 20, 30, 60, 90 or 120 days after (i) formation of the device (or preparation of devices) or (ii) administration of the device (or preparation of devices) to a subject. In an embodiment, the evaluation further comprises assessing the amount of fibrosis and/or structural integrity of the device (or devices within a preparation) at least 30, 60, 90 or 120 days after administration to the subject. In some embodiments, the subject is a mammal (e.g., a mouse, a human).

In another aspect, the present disclosure features a method of treating a subject for Fabry Disease comprising administering to the subject a device or device preparation comprising an RPE cell engineered to express and secrete GLA, as described herein. In some embodiments, the administering step comprises placing into the subject a pharmaceutically acceptable preparation comprising a plurality of devices, each of which has the ability to produce GLA. In some embodiments, the device or device preparation is administered to, placed in, or provided to a site other than the central nervous system, brain, spinal column, eye, or retina. In some embodiments, the implantable element is administered to, placed in, or injected in the peritoneal cavity (e.g., the lesser sac), the omentum, or the subcutaneous fat of a subject. In an embodiment, the method further comprises measuring the amount or activity of GLA present in a tissue sample removed from the subject, e.g., in plasma separated from a blood sample, a liver biopsy. In an embodiment, the tissue sample is removed at 15, 30, 60 or 120 days. In some embodiments, the subject is a human.

The details of one or more embodiments of the disclosure are set forth herein. Other features, objects, and advantages of the disclosure will be apparent from the Detailed Description, the Figures, the Examples, and the Claims.

BRIEF DESCRIPTION OF THE DRAWINGS

FIG. 1 shows the amino acid sequence (FIG. 1A, SEQ ID NO: 1) and nucleotide coding sequence (FIG. 1B, SEQ ID NO:2) for a wild-type human precursor GLA protein expressed by an exemplary engineered human RPE cell, with underlining indicating the amino acid and coding sequences for the GLA signal peptide.

FIG. 2 shows an exemplary codon-optimized nucleotide sequence (SEQ ID NO:3) encoding the wild-type precursor human GLA protein shown in FIG. 1, with underlining indicating the coding sequence for the GLA signal peptide.

FIG. 3 shows another exemplary codon-optimized nucleotide sequence (SEQ ID NO:4) encoding the wild-type precursor human GLA protein shown in FIG. 1, with underlining indicating the coding sequence for the GLA signal peptide.

FIG. 4 shows the amino acid sequence (FIG. 4A, SEQ ID NO:5) and codon-optimized nucleotide coding sequence (FIG. 4B, SEQ ID NO:6) for a GLA fusion protein expressed by an exemplary engineered human RPE cell, in which the HSPG2 signal peptide is fused to the human wild-type mature GLA amino acid sequence, with underlining indicating the amino acid and coding sequences for the HSPG2 signal peptide (SEQ ID NO:15 and SEQ ID NO: 16, respectively).

FIG. 5 shows the amino acid and nucleotide coding sequences for an exemplary GLA-IgG fusion protein expressed by an exemplary engineered human RPE cell, with FIG. 5A (SEQ ID NO:7) showing the HSPG2 signal peptide (underlined) fused to the N-terminus of a human wild-type GLA mature amino acid sequence, which is fused to an amino acid sequence for the light chain constant region of an IgG (bold font) via a linker amino acid linker sequence (italics), FIG. 5B (SEQ ID NO:8) showing the HSPG2 signal peptide (underlined) fused to the amino acid sequence for the IgG1 heavy chain constant regions, and FIG. 5C (SEQ ID NO:9) and FIG. 5D (SEQ ID NO:10) showing the nucleotide coding sequences for the amino acid sequences in FIG. 5A and FIG. 5B, respectively, with the coding sequence for the HSPG2 signal peptide indicated by underlining, the linker coding sequence shown in italics and the IgG light chain coding sequence shown in bold font.

FIG. 6 shows amino acid and nucleotide coding sequences for an exemplary GLA-nanobody-Fc fusion protein expressed by an exemplary engineered human RPE cell, with FIG. 6A (SEQ ID NO:11) showing the HSPG2 signal peptide (underlined) fused to the N-terminus of a human wild-type GLA mature amino acid sequence, which is fused to the amino acid sequence for the FC5 nanobody (bold) and the Fc region of human IgG1 (bold, underlined) via a linker amino acid sequence (italics) and FIG. 6B (SEQ ID NO: 12) showing the nucleotide coding sequence for the amino acid sequence in FIG. 6A, with the coding sequence for the HSPG2 signal peptide indicated by underlining, the linker coding sequence shown in italics, and the coding sequence for the FC5 and IgG1 Fc regions shown in bold.

FIG. 7 shows amino acid and nucleotide coding sequences for an exemplary GLA-Fc fusion protein expressed by an exemplary engineered human RPE cell, with FIG. 7A (SEQ ID NO: 13) showing the HSPG2 signal peptide (underlined) fused to the N-terminus of a human wild-type GLA mature amino acid sequence, which is fused to the Fc region of human IgG1 (bold font) via a linker (italics) and FIG. 7B (SEQ ID NO:14) showing the nucleotide coding sequence for the amino acid sequence in FIG. 6A, with the coding sequence for the HSPG2 signal peptide indicated by underlining, the linker coding sequence shown in italics, and the coding sequence for the IgG1 Fc region shown in bold.

FIG. 9 discloses "GRGDSP" as SEQ ID NO: 44.

DETAILED DESCRIPTION

Figure 8A:
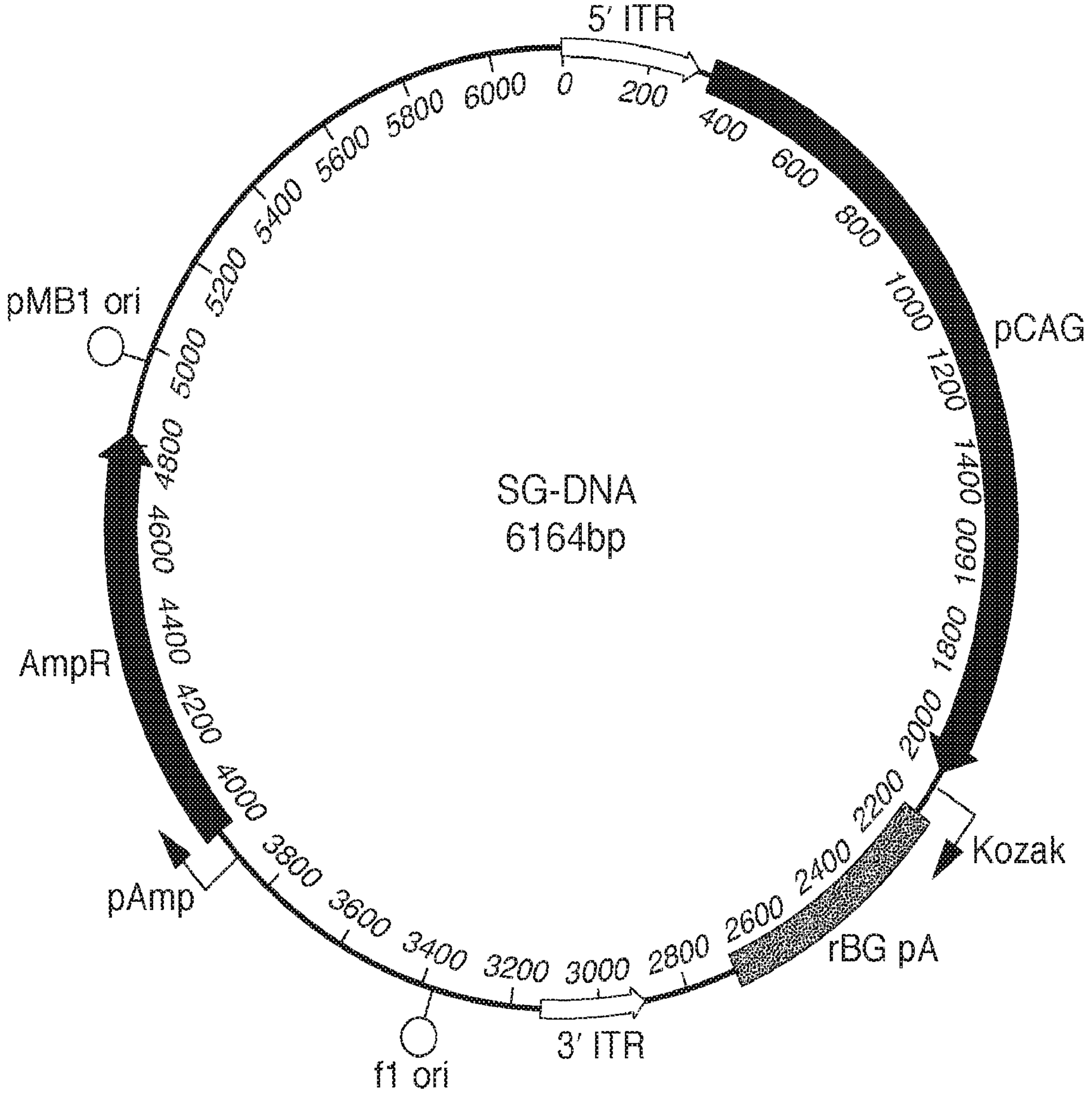
FIG. 8 illustrates an exemplary PiggyBac transposon expression vector useful for generating engineered RPE cells expressing a GLA protein described herein, with FIG. 8A showing a vector map and FIG. 8B showing the nucleotide sequence of the vector (SEQ ID NO: 17), with the promoter sequence underlined (SEQ ID NO: 18).

The present disclosure features retinal pigment epithelial (RPE) cells engineered to express and secrete GLA (e.g., GLA cell therapy), as well as compositions thereof, devices comprising such engineered RPE cells, and device preparations comprising the same. In some embodiments, the devices comprise a cell-containing compartment which includes a cell binding substance as well as the engineered RPE cells. In some embodiments, the devices are configured to mitigate the FBR when placed inside a subject, e.g., a human subject. In some embodiments, the engineered RPE cells, compositions, and devices are useful for the treatment of Fabry Disease.

Abbreviations and Definitions

Throughout the detailed description and examples of the disclosure the following abbreviations will be used.

CBP cell-binding peptide
CBPP cell-binding polypeptide
CBP-polymer polymer covalently modified with a CBP via a linker
CBS cell-binding substance
CM-Alg chemically modified alginate
CM-LMW-Alg chemically modified, low molecular weight alginate
CM-LMW-Alg-101 low molecular weight alginate, chemically modified with Compound 101 shown in Table 3
CM-HMW-Alg chemically modified, high molecular weight alginate
CM-HMW-Alg-101 high molecular weight alginate, chemically modified with Compound 101 shown in Table 3
CM-MMW-Alg chemically modified, medium molecular weight alginate
CM-MMW-Alg-101 medium molecular weight alginate, chemically modified with Compound 101 shown in Table 3
Gb3 or GL3 globotriaosylceramide
LysoGb3 or Lyso-Gb3 globotriaosylsphingosine
HMW-Alg high molecular weight alginate
MMW-Alg medium molecular weight alginate
RGD-alginate an alginate covalently modified with a peptide comprising the amino acid sequence RGD ("RGD" disclosed as SEQ ID NO: 28).
U-Alg unmodified alginate
U-HMW-Alg unmodified high molecular weight alginate
U-LMW-Alg unmodified low molecular weight alginate
U-MMW-Alg unmodified medium molecular weight alginate
70:30 CM-Alg:U-Alg 70:30 mixture (V:V) of a chemically modified alginate and an unmodified alginate, e.g., as described in the Examples below So that the disclosure may be more readily understood, certain technical and scientific terms used herein are specifically defined below. Unless specifically defined elsewhere in this document, all other technical and scientific terms used herein have the meaning commonly understood by one of ordinary skill in the art to which this disclosure belongs.

As used herein, including the appended claims, the singular forms of words such as "a," "an," and "the," include their corresponding plural references unless the context clearly dictates otherwise.

"About" or "approximately" when used herein to modify a numerically defined parameter (e.g., amount of GLA secreted by an RPE cell, a physical description of a device (e.g., hydrogel capsule) such as diameter, sphericity, number of cells encapsulated therein, the number of devices in a preparation), means that the recited numerical value is within an acceptable functional range for the defined parameter as determined by one of ordinary skill in the art, which will depend in part on how the numerical value is measured or determined, e.g., the limitations of the measurement system, including the acceptable error range for that measurement system. For example, "about" can mean a range of 20% above and below the recited numerical value. As a non-limiting example, a device defined as having a diameter of about 1.5 millimeters (mm) and encapsulating about 5 million (M) cells may have a diameter of 1.2 to 1.8 mm and may encapsulate 4 M to 6 M cells. As another non-limiting example, a preparation of about 100 devices (e.g., hydrogel capsules) includes preparations having 80 to 120 devices. In some embodiments, the term "about" means that the modified parameter may vary by as much as 15%, 10% or 5% above and below the stated numerical value for that parameter. Alternatively, particularly with respect to certain properties of the devices described herein, such as cell productivity, or density of the CBP or the afibrotic compound, the term "about" can mean within an order of magnitude above and below the recited value, e.g., within 5-fold, 4-fold, 3-fold, 2-fold or 1-fold.

"Acquire" or "acquiring" as used herein, refer to obtaining possession of a value, e.g., a numerical value, or image, or a physical entity (e.g., a sample), by "directly acquiring" or "indirectly acquiring" the value or physical entity. "Directly acquiring" means performing a process (e.g., performing an analytical method or protocol) to obtain the value or physical entity. "Indirectly acquiring" refers to receiving the value or physical entity from another party or source (e.g., a third-party laboratory that directly acquired the physical entity or value). Directly acquiring a value or physical entity includes performing a process that includes a physical change in a physical substance or the use of a machine or device. Examples of directly acquiring a value include obtaining a sample from a human subject. Directly acquiring a value includes performing a process that uses a machine or device, e.g., using a fluorescence microscope to acquire fluorescence microscopy data.

"Administer," "administering," or "administration," as used herein, refer to implanting, absorbing, ingesting, injecting, placing or otherwise introducing into a subject, an entity described herein (e.g., a device or a preparation of devices), or providing such an entity to a subject for administration.

"Afibrotic", as used herein, means a compound or material that mitigates the foreign body response (FBR). For example, the amount of FBR in a biological tissue that is induced by implant into that tissue of a device (e.g., a hydrogel capsule) comprising an afibrotic compound (e.g., a hydrogel capsule comprising a polymer covalently modified with a compound listed in Table 3) is lower than the FBR induced by implantation of an afibrotic-null reference device, i.e., a device that lacks any afibrotic compound, but is of substantially the same composition (e.g., same CBP-polymer, same cell type(s)) and structure (e.g., size, shape, no. of compartments). In an embodiment, the degree of the FBR is assessed by the immunological response in the tissue containing the implanted device (e.g., hydrogel capsule), which may include, for example, protein adsorption, macrophages, multinucleated foreign body giant cells, fibroblasts, and angiogenesis, using assays known in the art, e.g., as described in WO 2017/075630, or using one or more of the assays/methods described Vegas, A., et al., Nature Biotechnol (supra), (e.g., subcutaneous cathepsin measurement of implanted capsules, Masson's trichrome (MT), hematoxylin or eosin staining of tissue sections, quantification of collagen density, cellular staining and confocal microscopy for macrophages (CD68 or F4/80), myofibroblasts (alpha-muscle actin, SMA) or general cellular deposition, quantification of 79 RNA sequences of known inflammation factors and immune cell markers, or FACS analysis for macrophage and neutrophil cells on retrieved devices (e.g., capsules) after 14 days in the intraperitoneal space of a suitable test subject, e.g., an immunocompetent mouse. In an embodiment, the FBR is assessed by measuring the levels in the tissue containing the implant of one or more biomarkers of immune response, e.g., cathepsin, TNF-α, IL-13, IL-6, G-CSF, GM-CSF, IL-4, CCL2, or CCL4. In some embodiments, the FBR induced by a device of the invention (e.g., a hydrogel capsule comprising an afibrotic compound disposed on its outer surface), is at least about 80%, about 85%, about 90%, about 95%, about 99%, or about 100% lower than the FBR induced by an FBR-null reference device, e.g., a device that is substantially identical to the test or claimed device except for lacking the means for mitigating the FBR (e.g., a hydrogel capsule that does not comprise an afibrotic compound but is otherwise substantially identical to the claimed capsule. In some embodiments, the FBR (e.g., level of a biomarker(s)) is measured after about 30 minutes, about 1 hour, about 6 hours, about 12 hours, about 1 day, about 2 days, about 3 days, about 4 days, about 1 week, about 2 weeks, about 1 month, about 2 months, about 3 months, about 6 months, or longer.

"Alpha-galactosidase A", "α-Gal A" "alpha-D-galactosidase-A", alpha-galactoside galactohydrolase", "galactosidase alpha", and "GLA protein" may be used interchangeably herein and refer to a homodimeric protein comprising the mature amino acid sequence encoded by a wild-type mammalian GLA gene or an amino acid sequence with conservative substitutions thereof. In an embodiment, the conservatively substituted GLA protein has enzyme activity that is within 80-120%, 85-115%, 90-110% or 95-105% of the corresponding wild-type mammalian mature GLA protein, as measured by a GLA activity assay described herein. The wild-type human GLA gene encodes a 429-amino acid polypeptide, of which the N-terminal 31 amino acids constitute a signal peptide. The full DNA sequence of the wild-type human GLA gene, including introns and exons, is available in GenBank Accession No. X14448.1. The amino acid sequence for wild-type human precursor α-Gal A is available in GenBank Accession Nos. X14448.1 and U78027 and shown in FIG. 1 (SEQ ID NO: 1). In some embodiments, the term "GLA protein" (and any of the aforesaid synonyms) refers to a polypeptide comprising the wild-type mature amino acid sequence, and optionally preceded by the GLA signal peptide or by a signal peptide for a different secretory protein, e.g., a protein secreted by RPE cells, e.g., the signal peptide for HSPG2.

"Cell," as used herein, refers to an engineered cell or a cell that is not engineered. In an embodiment, a cell is an immortalized cell, or an engineered cell derived from an immortalized cell. In an embodiment, the cell is a live cell, e.g., is viable as measured by any technique described herein or known in the art.

"Cell-binding peptide (CBP)", as used herein, means a linear or cyclic peptide that comprises an amino acid sequence that is derived from the cell binding domain of a ligand for a cell-adhesion molecule (CAM) (e.g., that mediates cell-matrix junctions or cell-cell junctions). The CBP is less than 50, 40, 30, 25, 20, 15 or 10 amino acids in length. In an embodiment, the CBP is between 3 and 12 amino acids, 4 and 10 amino acids in length, or is 3, 4, 5, 6, 7, 8, 9 or 10 amino acids in length. The CBP amino acid sequence may be identical to the naturally-occurring binding domain sequence or may be a conservatively substituted variant thereof. In an embodiment, the CAM ligand is a mammalian protein. In an embodiment, the CAM ligand is a human protein selected from the group of proteins listed in Table 1 below. In an embodiment, the CBP comprises, consists essentially of, or consists of a cell binding sequence listed in Table 1 below or a conservatively substituted variant thereof. In an embodiment, the CBP is an RGD peptide, which means the peptide comprises the amino acid sequence RGD (SEQ ID NO: 28) and optionally comprises one or more additional amino acids located at one or both of the N-terminus and C-terminus. In an embodiment, the CBP is a cyclic peptide comprising RGD (SEQ ID NO: 28), e.g., one of the cyclic RGD peptides described in Vilaca, H. et al., *Tetrahedron* 70 (35):5420-5427 (2014). In an embodiment, the CBP is a linear peptide comprising RGD (SEQ ID NO: 28) and is less than 6 amino acids in length. In an embodiment, the CBP is a linear peptide that consists essentially of RGD (SEQ ID NO: 28) or RGDSP (SEQ ID NO: 49).

TABLE 1

Exemplary CAM Ligand Proteins and Cell Binding Sequences

| Protein | Cell Binding Sequence |
|---|---|
| E-cadherin | SWELYYPILRANIL (SEQ ID NO: 21) |
| N-cadherin | HAVDI (SEQ ID NO: 22) |
| Collagen I | DGEA (SEQ ID NO: 23) |
| Collagen IV | FYFDLR (SEQ ID NO: 24)<br>GFOGER (SEQ ID NO: 25)<br>P(GPP)$_5$GFOGER(GPP)$_5$ (SEQ ID NO: 26)<br>where O in SEQ ID NO: 25 and SEQ ID NO: 26 is 4-hydroxyproline |
| Elastin | VAPG (SEQ ID NO: 27) |
| Fibrinogen | RGD (SEQ ID NO: 28)<br>GPR (SEQ ID NO: 29) |
| Fibronectin | RGD (SEQ ID NO: 28)<br>KQAGDV (SEQ ID NO: 30)<br>PHSRN (SEQ ID NO: 31)<br>PHSRNGGGGGGRGDS (SEQ ID NO: 32)<br>REDV (SEQ ID NO: 33) |
| Laminin | IKVAV (SEQ ID NO: 34)<br>SRARKQAASIKVAVADR (SEQ ID NO: 35)<br>LRE (SEQ ID NO: 36)<br>KQLREQ (SEQ ID NO: 37)<br>YIGSR (SEQ ID NO: 38) |
| Nidogen-1 | RGD (SEQ ID NO: 28) |
| Osteopontin | SVVYGLR (SEQ ID NO: 39) |
| Tenascin C (TN-C) | AEIDGIEL (SEQ ID NO: 40) |
| Tenascin-R | RGD (SEQ ID NO: 28) |
| Tenascin-X | RGD (SEQ ID NO: 28) |
| Thrombospondin | VTCG (SEQ ID NO: 41)<br>SVTCG (SEQ ID NO: 42) |
| Vitronectin | RGD (SEQ ID NO: 28) |
| Von Willebrand Factor | RGD (SEQ ID NO: 28) |

"CBP-polymer", as used herein, means a polymer comprising at least one cell-binding peptide molecule covalently attached to the polymer via a linker. In an embodiment, the polymer in the CBP-polymer is not a peptide or a polypeptide. In an embodiment, the polymer in a CBP-polymer is a synthetic or naturally-occurring polysaccharide, e.g., an alginate, e.g., a sodium alginate. In an embodiment, the linker is an amino acid linker (i.e., consists essentially of a single amino acid, or a peptide of several identical or different amino acids), which is joined via a peptide bond to the N-terminus or C-terminus of the CBP. In an embodiment, the C-terminus of an amino acid linker is joined to the N-terminus of the CBP and the N-terminus of the amino acid linker is joined to at least one pendant carboxyl group in the polysaccharide via an amide bond. In an embodiment, the structure of the linker-CBP is expressed as $G_{(1-4)}$-CBP, meaning that the linker has one, two, three or four glycine residues. In an embodiment, one or more of the monosaccharide moieties in a CBP-polysaccharide, e.g., a CBP-alginate) is not modified with the CBP, e.g, the unmodified moiety has a free carboxyl group or lacks a modifiable pendant carboxyl group. In an embodiment, the number of polysaccharide moieties with a covalently attached CBP is less than any of the following values: 99%, 95%, 90%, 80%, 70%, 60%, 50%, 40% 30%, 20%, 10%, 5%, 1%.

In an embodiment, the density of CBP modification in the CBP-polymer is estimated by combustion analysis for percent nitrogen, e.g., as described in the Examples below. In an embodiment, the CBP-polymer is an RGD-polymer (e.g., an RGD-alginate), which is a polymer (e.g., an alginate) covalently modified with a linker-RGD molecule (e.g., a peptide consisting essentially of GRGD (SEQ ID NO:43) or GRGDSP (SEQ ID NO:44)) and the density of modification with the linker-RGD molecule is about 0.05% nitrogen (N) to 1.00% N, about 0.10% N to about 0.75% N, about 0.20% N to about 0.50% N, or about 0.30% N to about 0.40% N, as determined using an assay described herein. In an embodiment, the conjugation density of the linker-RGD modification in an RGD-alginate (e.g., a MMW alginate covalently modified with GRGDSP (SEQ ID NO: 44)) is 0.2 to 2.0, 0.2 to 1.5, 0.2 to 1.0, 0.3 to 0.7, 0.3 to 0.6, or 0.4 to 0.6 micromoles of the linker-RGD moiety per g of the RGD-polymer in solution (e.g., saline solution) with a viscosity of 80-120 cP, as determined by any assay that is capable of quantitating the amount of a peptide conjugated to a polymer, e.g., a quantitative peptide conjugation assay described herein. Unless otherwise explicitly stated or readily apparent from the context, a specifically recited numerical concentration, concentration range, density or density range for a CBP in a CBP-polymer refers to the concentration of conjugated CBP molecules in the CBP-polymer composition, i.e., it does not include any residual free (e.g., unconjugated) CBP that may be present in the CBP-polymer.

"Cell-binding polypeptide (CBPP)", as used herein, means a polypeptide of at least 50, at least 75, or at least 100 amino acids in length and comprising the amino acid sequence of a cell binding domain of a CAM ligand, or a conservatively substituted variant thereof. In an embodiment, the CAM ligand is a mammalian protein. In an embodiment, the CBPP amino acid comprises the naturally-occurring amino acid sequence of a full-length CAM ligand, e.g., one of the proteins listed in Table 1 below, or a conservatively substituted variant thereof.

"CBP-density", as used herein, refers to the concentration of a linker-CBP moiety in a CBP-polymer composition, e.g., an alginate modified with $G_{1-3}$RGD (SEQ ID NO: 50) or $G_{1-3}$RGDSP (SEQ ID NO: 51), unless otherwise explicitly stated herein.

"Cell-binding substance (CBS)", as used herein, means any chemical, biological or other type of substance (e.g., a small organic compound, a peptide, a polypeptide) that is capable of mimicking at least one activity of a ligand for a cell-adhesion molecule (CAM) or other cell-surface molecule that mediates cell-matrix junctions or cell-cell junctions or other receptor-mediated signaling. In an embodiment, when present in a polymer composition encapsulating live cells, the CBS is capable of forming a transient or permanent bond or contact with one or more of the cells. In an embodiment, the CBS facilitates interactions between two or more live cells encapsulated in the polymer composition. In an embodiment, the presence of a CBS in a polymer composition encapsulating a plurality of cells (e.g., live cells) is correlated with one or both of increased cell productivity (e.g., expression of a therapeutic agent) and increased cell viability when the encapsulated cells are implanted into a test subject, e.g., a mouse. In an embodiment, the CBS is physically attached to one or more polymer molecules in the polymer composition. In an embodiment, the CBS is a cell-binding peptide or cell-binding polypeptide, as defined herein.

"Conservatively modified variants" or conservative substitution", as used herein, refers to a variant of a reference peptide or polypeptide that is identical to the reference molecule, except for having one or more conservative amino acid substitutions in its amino acid sequence. In an embodiment, a conservatively modified variant consists of an amino acid sequence that is at least 70%, 80%, 85%, 90%, 95%, 97%, 98% or 99% identical to the reference amino acid sequence. A conservative amino acid substitution refers to substitution of an amino acid with an amino acid having similar characteristics (e.g., charge, side-chain size, hydrophobicity/hydrophilicity, backbone conformation and rigidity, etc.) and which has minimal impact on the biological activity of the resulting substituted peptide or polypeptide. Conservative substitution tables of functionally similar amino acids are well known in the art, and exemplary substitutions grouped by functional features are set forth in Table 2 below.

TABLE 2

Exemplary conservative amino acid substitution groups.

| Feature | Conservative Amino Group |
|---|---|
| Charge/Polarity | His, Arg, Lys |
| | Asp, Glu |
| | Cys, Thr, Ser, Gly, Asn, Gln, Tyr |
| | Ala, Pro, Met, Leu, Ile, Val, Phe, Trp |
| Hydrophobicity | Asp, Glu, Asn, Gln, Arg, Lys |
| | Cys, Ser, Thr, Pro, Gly, His, Tyr |
| | Ala, Met, Ile Leu, Val, Phe, Trp |
| Structural/Surface Exposure | Asp, Glu, Asn, Aln, His, Arg, Lys |
| | Cys, Ser, Tyr, Pro, Ala, Gly, Trp, Tyr |
| | Met, Ile, Leu, Val, Phe |
| Secondary Structure Propensity | Ala, Glu, Aln, His, Lys, Met, Leu, Arg |
| | Cys, Thr, Ile, Val, Phe, Tyr, Trp |
| | Ser, Gly, Pro, Asp, Asn |
| Evolutionary Conservation | Asp, Glu |
| | His, Lys, Arg |
| | Asn, Gln |
| | Ser, Thr |
| | Leu, Ile, Val |
| | Phe, Tyr, Trp |
| | Ala, Gly |
| | Met, Cys |

"Consists essentially of", and variations such as "consist essentially of" or "consisting essentially of" as used throughout the specification and claims, indicate the inclusion of any recited elements or group of elements, and the optional inclusion of other elements, of similar or different nature than the recited elements, that do not materially change the basic or novel properties of the specified molecule, composition, device, or method. As a non-limiting example, a cell-binding peptide or a GLA protein that consists essentially of a recited amino acid sequence may also include one or more amino acids, including substitutions in the recited amino acid sequence, of one or more amino acid residues, which do not materially affect the relevant biological activity of the cell-binding peptide or the GLA protein, respectively.

"Derived from", as used herein with respect to a cell or cells, refers to cells obtained from tissue, cell lines, or cells, which optionally are then cultured, passaged, immortalized, differentiated and/or induced, etc. to produce the derived cell(s).

"Device", as used herein, refers to any implantable object (e.g., a particle, a hydrogel capsule, an implant, a medical device), which contains live, engineered RPE cells capable of expressing and secreting a GLA protein following implant of the device, and has a configuration that supports the viability of the RPE cells by allowing cell nutrients to enter the device. In some embodiments, the device allows release from the device of metabolic byproducts generated by the live cells.

"Differential volume," as used herein, refers to a volume of one compartment within a device described herein that excludes the space occupied by another compartment(s). For example, the differential volume of the second (e.g., outer) compartment in a 2-compartment device with inner and outer compartments, refers to a volume within the second compartment that excludes space occupied by the first (inner) compartment.

"Effective amount" as used herein refers to an amount of any of the following: engineered RPE cells secreting GLA, a device preparation producing GLA, or a component of a device (e.g., number of engineered RPE cells in the device, amount of a CBS and/or afibrotic compound in the device) that is sufficient to elicit a desired biological response. In some embodiments, the term "effective amount" refers to the amount of a component of the device (e.g., number of cells in the device, the density of an afibrotic compound disposed on the surface and/or in a barrier compartment of the device, the density of a CBS in the cell-containing compartment. In an embodiment, the desired biological response is an increase in GLA levels in a tissue sample removed from a subject treated with (e.g., implanted with) the engineered RPE cells, a device or a device preparation containing such cells. As will be appreciated by those of ordinary skill in this art, the effective amount may vary depending on such factors as the desired biological endpoint, the pharmacokinetics of the secreted GLA, composition or device, the condition being treated, the mode of administration, and the age and health of the subject. An effective amount encompasses therapeutic and prophylactic treatment. In an embodiment, an effective amount of a compound of Formula (I) disposed on or in a device is an amount that reduces the FBR to the implanted device compared to a reference device, e.g., reduces fibrosis or amount of fibrotic tissue on or near the implanted device. In an embodiment, an effective amount of a CBS disposed with engineered RPE cells in a cell-containing compartment is an amount that enhances the viability of the cells (e.g., number of live cells) compared to a reference device and/or increases the production of GLA by the RPE cells (e.g., increased GLA levels in plasma of a subject implanted with the device) compared to a reference device. An effective amount of a device, composition or component (e.g., afibrotic compound, CBS, engineered cells) may be determined by any technique known in the art of described herein.

In an embodiment, the CBS (e.g., an alginate modified with an RGD peptide, e.g. GRGDSP-alginate) in the cell-containing compartment is present in an amount effective to increase viability of the cells and/or increase productivity of the cells at a timepoint after the device is implanted into an immune-compromised or immune-competent animal, e.g., immune-competent mice (e.g., the C57BL/6J mouse strain available from the Jackson Laboratory, Bar Harbor, ME USA) as compared to a CBS-null reference device, as defined below herein. In an embodiment, the increase in cell viability and/or productivity is detectable at a desired time-point after implant, e.g., at one or more of 1 day, 3 days, 5 days, 1 week, 2 weeks, 4 weeks, 8 weeks, 12 weeks, 24 weeks, 36 weeks and 48 weeks. In an embodiment, the effective amount of the CBS results in an increase in one or both of (i) cell viability by at least 10%, 25%, 50% or 100% when measured at 1 week, 2 weeks, 4 weeks or 12 weeks after implant and (ii) increases cell productivity by at least 1.25-fold, 1.5-fold, 2-fold, 5-fold, 8-fold or 10-fold when measured at 1 week, 2 weeks, 4 weeks or 12 weeks after implant. In an embodiment, the effective amount of the CBS in the cell-containing compartment falls within a range between the minimally effective amount and a higher amount at which the cell viability and/or productivity are reduced compared to a CBS-null reference device or compared to the a device containing a maximally-effective amount, e.g., the optimal amount, of the CBS in the cell-containing compartment. In an embodiment, the amount of the CBS in the cell-containing compartment is no more than 50%, 25%, 10% or 5% above or below the optimal amount, e.g., the amount that results in the greatest increase in cell viability and/or productivity as compared to the CBS-null reference device.

The number of viable (and optionally dead) cells in a device described herein may be estimated using any technique known in the art, including an assay that differentially labels live and dead cells with two fluorescent dyes followed by detection, and optionally quantification, of labeled cells using fluorescent microscopy. Cell viability may also be evaluated by assessing other cell viability indicators, including measuring esterase activity, or quantitating the amount of ATP in the cells.

In an embodiment, the post-implant increase in cell productivity is detected by assaying for the level of the GLA protein expressed by the cells in vivo or ex vivo (e.g., cell expression after the device has been retrieved from the animal. GLA expression may be measured extracellularly but inside the device, and/or outside of the device, e.g., in a tissue sample removed from an animal (e.g., a non-human animal) treated with a device or device preparation described herein. In an embodiment, the cell productivity is expressed as the measured amount of the GLA protein or GLA activity divided by the number of administered devices (e.g., number of capsules placed in the animal) and/or by the number of administered engineered RPE cells (e.g., approximate number of cells per capsule in the administered capsule preparation). In an embodiment, the increase in cell productivity is further normalized by dividing the determined amount or activity of GLA by the time between two time points of interest, e.g., between administration and measurement, e.g., number of hours, days or weeks. In an embodiment, the increase in productivity is determined by measuring the amount and/or activity of the GLA protein in a tissue sample removed from the animal (e.g., plasma separated from a blood sample collected from the animal), dividing the measured amount and/or activity by the number of administered devices (e.g, number of implanted 2-compartment capsules), and optionally further dividing the result by the number of days between administration and tissue sample removal.

An "endogenous nucleic acid" as used herein, is a nucleic acid that occurs naturally in a subject cell.

An "endogenous polypeptide," as used herein, is a polypeptide that occurs naturally in a subject cell.

"Engineered RPE cell," as used herein, is an RPE cell having a non-naturally occurring alteration, and typically comprises a nucleic acid sequence (e.g., DNA or RNA) or a polypeptide not present (or present at a different level than) in an otherwise similar RPE cell under similar conditions that is not engineered (an exogenous nucleic acid sequence). In an embodiment, an engineered RPE cell comprises an exogenous nucleic acid (e.g., a vector or an altered chromosomal sequence), encoding a GLA protein. In an embodiment, an engineered RPE cell secretes a GLA protein comprising a human wild-type GLA amino acid sequence or variant thereof. In an embodiment, the exogenous nucleic acid sequence is chromosomal (e.g., the exogenous nucleic acid sequence is an exogenous sequence disposed in endogenous chromosomal sequence) or is extra chromosomal (e.g., a non-integrated expression vector). In an embodiment, the exogenous nucleic acid sequence comprises an RNA sequence, e.g., an mRNA. In an embodiment, the exogenous nucleic acid sequence comprises a chromosomal or extra-chromosomal exogenous nucleic acid sequence that comprises a sequence which is expressed as RNA, e.g., mRNA or a regulatory RNA. In an embodiment, the exogenous nucleic acid sequence comprises a first chromosomal or extra-chromosomal exogenous nucleic acid sequence that modulates the conformation or expression of a second nucleic acid sequence, e.g., a GLA coding sequence, wherein the second amino acid sequence can be exogenous or endogenous. For example, an engineered RPE cell can comprise an exogenous nucleic acid that controls the expression of an endogenous sequence. In an embodiment, the engineered RPE cell comprises an exogenous nucleic acid sequence which comprises a codon optimized sequence that encodes GLA and achieves higher expression of GLA than a naturally-occurring GLA coding sequence. The codon optimized sequence may be generated using a commercially available algorithm, e.g., GeneOptimizer (ThermoFisher Scientific), OptimumGene™ (GenScript, Piscataway, NJ USA), GeneGPS® (ATUM, Newark, CA USA), or Java Codon Adaptation Tool (JCat, www.jcat.de, Grote, A. et al., Nucleic Acids Research, Vol 33, Issue suppl_2, pp. W526-W531 (2005). In an embodiment, an engineered RPE cell (e.g., engineered ARPE-19 cell) is cultured from a population of stably-transfected cells, or from a monoclonal cell line.

"An "exogenous nucleic acid," as used herein, is a nucleic acid that does not occur naturally in a subject cell.

An "exogenous polypeptide," as used herein, is a polypeptide that does not occur naturally in a subject cell, e.g., engineered cell. Reference to an amino acid position of a specific sequence means the position of said amino acid in a reference amino acid sequence, e.g., sequence of a full-length mature (after signal peptide cleavage) wild-type protein (unless otherwise stated), and does not exclude the presence of variations, e.g., deletions, insertions and/or substitutions at other positions in the reference amino acid sequence.

"Fabry disease", "GLA deficiency", "alpha-galactosidase A deficiency", "Fabry's disease", "Anderson-Fabry disease", "angiokeratoma corporis diffusum", "angiokeratoma diffuse", "hereditary dystopic lipidosis" can be used interchangeably and refer to a rare genetic lysosomal storage disease, inherited in an X-linked manner, caused by a deficiency in the lysosomal enzyme galactosidase alpha (GLA). This enzyme cleaves terminal α-D-galactose residues from glycolipids. GLA deficiency results in a systemic and lifetime lysosomal accumulation of glycosphingolipids, primarily globotriaosylceramide (Gb3), in the vascular endothelium and other tissues. This leads to a multi-organ pathology that mostly affects the kidneys, the heart, and the cerebrovascular system. Patients with Fabry disease suffer from a plethora of symptoms including gastro-intestinal diseases, pain, stroke, and cardiac and renal defects, and often die prematurely of complications from strokes, heart disease, or renal failure.

The classic form of Fabry disease, occurring in males with less than 1% α-Gal A enzyme activity, usually has its onset in childhood or adolescence with periodic crises of severe pain in the extremities (acroparesthesia), the appearance of vascular cutaneous lesions (angiokeratomas), sweating abnormalities (anhidrosis, hypohidrosis, and rarely hyperhidrosis), characteristic corneal and lenticular opacities, and proteinuria. Gradual deterioration of renal function to end-stage renal disease (ESRD) usually occurs in men in the third to fifth decade. In middle age, most males successfully treated for ESRD develop cardiac and/or cerebrovascular disease, a major cause of morbidity and mortality. In contrast, males with greater than 1% α-Gal A activity may have: (1) a cardiac variant phenotype that usually presents in the sixth to eighth decade with left ventricular hypertrophy, cardiomyopathy and arrhythmia, and proteinuria, but without ESRD; or (2) a renal variant phenotype, associated with ESRD but without the skin lesions or pain; or (3) cerebrovascular disease presenting as stroke or transient ischemic attack. In an embodiment, patients with the "cardiac variant" Fabry have about 5-15% of normal α-Gal A activity, and present with left ventricular hypertrophy or a cardiomyopathy. Heterozygous females typically have milder symptoms at a later age of onset than males. Rarely, they may be relatively asymptomatic throughout a normal life span or may have symptoms as severe as those observed in males with the classic phenotype.

Signs and symptoms that can provide for a presumptive diagnosis of Fabry disease include angiokeratomas and corneal verticillata. Taking a family history, noting other family members with symptoms such as early renal disease, early stroke, and early cardiac problems, may provide further support. Definitive diagnosis can be made in males by testing for deficient GLA enzyme activity in a biological sample, such as plasma, leukocytes, cultured skin fibroblasts, biopsied tissue, or dried blood. In females, mutation or linkage analysis can identify heterozygous mutation carriers. Many female carriers (with or without symptoms) have below-normal levels of GLA activity and/or characteristic corneal opacities.

"Fabry disease patient" as used herein, refers to an individual who has been diagnosed with or suspected of having Fabry disease. In an embodiment, a Fabry disease patient has a mutated GLA gene. Characteristic markers of Fabry disease can occur in male hemizygotes and female carriers with the same prevalence, although females typically are less severely affected. A female carrier has one X chromosome with a defective α-Gal A gene and one X chromosome with the normal gene and in whom X chromosome inactivation of the normal allele is present in one or more cell types. A carrier is often diagnosed with Fabry disease.

"Polymer composition", as used herein, is a composition (e.g., a solution, mixture) comprising one or more polymers. As a class, "polymers' includes homopolymers, heteropolymers, co-polymers, block polymers, block co-polymers and can be both natural and synthetic. Homopolymers contain one type of building block, or monomer, whereas co-polymers contain more than one type of monomer.

"Polypeptide", as used herein, refers to a polymer comprising amino acid residues linked through peptide bonds and having at least two, and in some embodiments, at least 3, 4, 5, 10, 50, 75, 100, 150 or 200 amino acid residues.

"Prevention," "prevent," and "preventing" as used herein refers to a treatment that comprises administering or applying a GLA replacement therapy, e.g., administering a composition of devices encapsulating engineered RPE cells (e.g., as described herein), prior to the onset of one or more symptoms of Fabry disease to preclude the physical manifestation of the symptom(s). In some embodiments, "prevention," "prevent," and "preventing" require that signs or symptoms of Fabry disease have not yet developed or have not yet been observed. In some embodiments, treatment comprises prevention and in other embodiments it does not.

"Reference device", as used herein with respect to a claimed device (e.g., hydrogel capsule), means a device (e.g., hydrogel capsule) that (i) lacks a particular feature of the claimed device, e.g., a specified exogenous nucleotide sequence, e.g., an element that enhances mRNA or protein expression (e.g., a promoter sequence, a signal peptide sequence), an FBR-mitigating means (e.g., a barrier compartment comprising an afibrotic compound (as defined herein) or a CBS (as defined herein) (e.g., an RGD polymer), (ii) encapsulates in the cell-containing compartment about the same quantity of cells of the same cell type(s) as in the claimed device, and (iii) has a substantially similar polymer composition and structure as in the claimed device other than lacking the particular feature (e.g., the afibrotic compound or CBS). In an embodiment, the number of live, engineered RPE cells in the cell-containing compartment of a reference device is within 80% to 120%, or within 90% to 110%, of the number of live, engineered RPE cells in the cell-containing compartment of the claimed device. In an embodiment, the engineered cells in the reference and claimed devices are obtained from the same cell culture. In an embodiment, a substantially similar polymer composition means all polymers in the reference and claimed device, including the polymer component of any CBP-polymer and afibrotic polymer, as applicable, are of the same chemical and molecular weight class (e.g., an alginate with high G content and the same molecular weight range). For example, in an embodiment, the cell-containing compartment of a CBP-null reference device is formed from the unmodified version of the polymer (e.g., alginate) in the CBP-polymer used to form the cell-containing compartment of the claimed device. In some embodiments in which a claimed two-compartment hydrogel millicapsule has (i) an inner compartment formed from a CBP-polymer encapsulating the plurality of cells and (ii) an outer compartment formed from a mixture of a chemically-modified polymer (e.g., a CM-LMW-alginate as described herein) and an unmodified polymer (e.g., an U-HMW-alginate as described herein), then the outer compartments of the reference and claimed capsules are formed from the same polymer mixture, while the inner compartment of the reference capsule is formed from a suspension of cells in the same polymer mixture used for the outer compartment. In an embodiment, a substantially similar structure means the reference and claimed devices have the same number of compartments (e.g., one, two, three, etc.) and about the same size and shape.

"RPE cell" as used herein refers to a cell having one or more of the following characteristics: a) it comprises a retinal pigment epithelial cell (RPE) (e.g., cultured using the ARPE-19 cell line (ATCC® CRL-2302™)) or a cell derived or engineered therefrom, e.g., by stably transfecting cells cultured from the ARPE-19 cell line with an exogenous sequence that encodes a GLA protein or otherwise engineering such cultured ARPE-19 cells to express a GLA protein a cell derived from a primary cell culture of RPE cells, a cell isolated directly (without long term culturing, e.g., less than 5 or 10 passages or rounds of cell division since isolation) from naturally occurring RPE cells, e.g., from a human or other mammal, a cell derived from a transformed, an immortalized, or a long term (e.g., more than 5 or 10 passages or rounds of cell division) RPE cell culture; b) a cell that has been obtained from a less differentiated cell, e.g., a cell developed, programmed, or reprogramed (e.g., in vitro) into an RPE cell or a cell that is, except for any genetic engineering, substantially similar to one or more of a naturally occurring RPE cell or a cell from a primary or long term culture of RPE cells (e.g., the cell can be derived from an IPS cell); or c) a cell that has one or more of the following properties: i) it expresses one or more of the biomarkers CRALBP, RPE-65, RLBP, BEST1, or αB-crystallin; ii) it does not express one or more of the biomarkers CRALBP, RPE-65, RLBP, BEST1, or αB-crystallin; iii) it is naturally found in the retina and forms a monolayer above the choroidal blood vessels in the Bruch's membrane; or iv) it is responsible for epithelial transport, light absorption, secretion, and immune modulation in the retina; or v) it has been created synthetically, or modified from a naturally occurring cell, to have the same or substantially the same genetic content, and optionally the same or substantially the same epigenetic content, as an immortalized RPE cell line (e.g., the ARPE-19 cell line (ATCC® CRL-2302™)). In an embodiment, an RPE described herein is engineered, e.g., to have a new property, e.g., the cell is engineered to express and secrete GLA. In other embodiments, an RPE cell is not engineered.

"Saline solution" as used herein, means normal saline, i.e., water containing 0.9% NaCl, unless otherwise specified.

"Sequence identity" or "percent identical", when used herein to refer to two nucleotide sequences or two amino acid sequences, means the two sequences are the same within a specified region, or have the same nucleotides or amino acids at a specified percentage of nucleotide or amino acid positions within the specified when the two sequences are compared and aligned for maximum correspondence over a comparison window or designated region. Sequence identity may be determined using standard techniques known in the art including, but not limited to, any of the algorithms described in US Patent Application Publication No. 2017/02334455 A1. In an embodiment, the specified percentage of identical nucleotide or amino acid positions is at least about 80%, 85%, 90%, 91%, 92%, 93%, 94%, 95%, 96%, 97%, 98%, 99% or higher.

"Spherical" as used herein, mean a device (e.g., a hydrogel capsule or other particle) having a curved surface that forms a sphere (e.g., a completely round ball) or sphere-like shape, which may have waves and undulations, e.g., on the surface. Spheres and sphere-like objects can be mathematically defined by rotation of circles, ellipses, or a combination around each of the three perpendicular axes, a, b, and c. For a sphere, the three axes are the same length. Generally, a sphere-like shape is an ellipsoid (for its averaged surface) with semi-principal axes within 10%, or 5%, or 2.5% of each other. The diameter of a sphere or sphere-like shape is the average diameter, such as the average of the semi-principal axes.

"Spheroid", as that term is used herein to refer to a device (e.g., a hydrogel capsule or other particle), means the device has (i) a perfect or classical oblate spheroid or prolate spheroid shape or (ii) has a surface that roughly forms a spheroid, e.g., may have waves and undulations and/or may be an ellipsoid (for its averaged surface) with semi-principal axes within 100% of each other.

"Subject" as used herein refers to a human or non-human animal. In an embodiment, the subject is a human (i.e., a male or female) of any age group, e.g., a pediatric human subject (e.g., infant, child, adolescent) or adult human subject (e.g., young adult, middle-aged adult, or senior adult)). In an embodiment, the subject is a non-human animal, for example, a mammal (e.g., a mouse, a dog, a primate (e.g., a cynomolgus monkey or a rhesus monkey). In an embodiment, the subject is a commercially relevant mammal (e.g., cattle, pig, horse, sheep, goat, cat, or dog) or a bird (e.g., a commercially relevant bird such as a chicken, duck, goose, or turkey). In certain embodiments, the animal is a mammal. The animal may be a male or female and at any stage of development. A non-human animal may be a transgenic animal.

"Total volume," as used herein, refers to a volume within one compartment of a multi-compartment device that includes the space occupied by another compartment. For example, the total volume of the second (e.g., outer) compartment of a two-compartment device refers to a volume within the second compartment that includes space occupied by the first compartment.

"Transcription unit" means a DNA sequence, e.g., present in an exogenous nucleic acid, that comprises at least a promoter sequence operably linked to a coding sequence, and may also comprise one or more additional elements that control or enhance transcription of the coding sequence into RNA molecules or translation of the RNA molecules into polypeptide molecules. In some embodiments, a transcription unit also comprises polyadenylation (polyA) signal sequence and polyA site. In an embodiment, a transcription unit is present in an exogenous, extra-chromosomal expression vector, e.g., as shown in FIG. 8, or is present as an exogenous sequence integrated in a chromosome of an engineered RPE cell described herein.

"Treatment," "treat," and "treating" as used herein refers to one or more of reducing, reversing, alleviating, delaying the onset of, or inhibiting the progress of one or more of a symptom, manifestation, or underlying cause, of Fabry disease. In an embodiment, treating comprises reducing, reversing, alleviating, delaying the onset of, or inhibiting the progress of a symptom or condition associated with Fabry disease. In an embodiment, treating comprises increasing GLA levels in at least one tissue of a subject in need thereof, e.g., in one or more of plasma, liver, kidney and heart. In some embodiments, "treatment," "treat," and "treating" require that signs or symptoms associated with Fabry disease have developed or have been observed. In other embodiments, treatment may be administered in the absence of signs or symptoms of Fabry disease, e.g., in preventive treatment. For example, treatment may be administered to a susceptible individual prior to the onset of symptoms (e.g., in light of a history of symptoms and/or in light of genetic or other susceptibility factors). Treatment may also be continued after symptoms have resolved, for example, to delay or prevent recurrence. In some embodiments, treatment comprises prevention and in other embodiments it does not.

Selected Chemical Definitions

Definitions of specific functional groups and chemical terms are described in more detail below. The chemical elements are identified in accordance with the Periodic Table of the Elements, CAS version, *Handbook of Chemistry and Physics*, $75^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, $5^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, $3^{rd}$ Edition, Cambridge University Press, Cambridge, 1987.

The abbreviations used herein have their conventional meaning within the chemical and biological arts. The chemical structures and formulae set forth herein are constructed according to the standard rules of chemical valency known in the chemical arts.

When a range of values is listed, it is intended to encompass each value and subrange within the range. For example, "$C_1$-$C_6$ alkyl" is intended to encompass, $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$ alkyl.

As used herein, "alkyl" refers to a radical of a straight-chain or branched saturated hydrocarbon group having from 1 to 24 carbon atoms ("$C_1$-$C_{24}$ alkyl"). In some embodiments, an alkyl group has 1 to 12 carbon atoms ("$C_1$-$C_{12}$ alkyl"), 1 to 10 carbon atoms ("$C_1$-$C_{10}$ alkyl"), 1 to 8 carbon atoms ("$C_1$-$C_8$ alkyl"), 1 to 6 carbon atoms ("$C_1$-$C_6$ alkyl"), 1 to 5 carbon atoms ("$C_1$-$C_5$ alkyl"), 1 to 4 carbon atoms ("$C_1$-$C_4$alkyl"), 1 to 3 carbon atoms ("$C_1$-$C_3$ alkyl"), 1 to 2 carbon atoms ("$C_1$-$C_2$ alkyl"), or 1 carbon atom ("$C_1$ alkyl"). In some embodiments, an alkyl group has 2 to 6 carbon atoms ("$C_2$-$C_6$ alkyl"). Examples of $C_1$-$C_6$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_5$) and the like. Each instance of an alkyl group may be independently optionally substituted, i.e., unsubstituted (an "unsubstituted alkyl") or substituted (a "substituted alkyl") with one or more substituents; e.g., for instance from 1 to 5 substituents, 1 to 3 substituents, or 1 substituent.

As used herein, "alkenyl" refers to a radical of a straight-chain or branched hydrocarbon group having from 2 to 24 carbon atoms, one or more carbon-carbon double bonds, and no triple bonds ("$C_2$-$C_{24}$ alkenyl"). In some embodiments, an alkenyl group has 2 to 12 carbon atoms ("$C_2$-$C_{12}$ alkenyl"), 2 to 10 carbon atoms ("$C_2$-$C_{10}$ alkenyl"), 2 to 8 carbon atoms ("$C_2$-$C_8$ alkenyl"), 2 to 6 carbon atoms ("$C_2$-$C_6$ alkenyl"), 2 to 5 carbon atoms ("$C_2$-$C_5$ alkenyl"), 2 to 4 carbon atoms ("$C_2$-$C_4$ alkenyl"), 2 to 3 carbon atoms ("$C_2$-$C_3$ alkenyl"), or 2 carbon atoms ("$C_2$ alkenyl"). The one or more carbon-carbon double bonds can be internal (such as in 2-butenyl) or terminal (such as in 1-butenyl). Examples of $C_2$-$C_4$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_2$-$C_6$ alkenyl groups include the aforementioned $C_{2-4}$ alkenyl groups as well as pentenyl ($C_5$), pentadienyl ($C_5$), hexenyl ($C_6$), and the like. Each instance of an alkenyl group may be independently optionally substituted, i.e., unsubstituted (an "unsubstituted alkenyl") or substituted (a "substituted alkenyl") with one or more substituents e.g., for instance from 1 to 5 substituents, 1 to 3 substituents, or 1 substituent.

As used herein, the term "alkynyl" refers to a radical of a straight-chain or branched hydrocarbon group having from 2 to 24 carbon atoms, one or more carbon-carbon triple bonds ("$C_2$-$C_{24}$ alkenyl"). In some embodiments, an alkynyl group has 2 to 12 carbon atoms ("$C_2$-$C_{12}$ alkynyl"), 2 to 10 carbon atoms ("$C_2$-$C_{10}$ alkynyl"), 2 to 8 carbon atoms ("$C_2$-$C_8$ alkynyl"), 2 to 6 carbon atoms ("$C_2$-$C_6$ alkynyl"), 2 to 5 carbon atoms ("$C_2$-$C_5$ alkynyl"), 2 to 4 carbon atoms ("$C_2$-$C_4$ alkynyl"), 2 to 3 carbon atoms ("$C_2$-$C_3$ alkynyl"), or 2 carbon atoms ("$C_2$ alkynyl"). The one or more carbon-carbon triple bonds can be internal (such as in 2-butynyl) or terminal (such as in 1-butynyl). Examples of $C_2$-$C_4$ alkynyl groups include ethynyl ($C_2$), 1-propynyl ($C_3$), 2-propynyl ($C_3$), 1-butynyl ($C_4$), 2-butynyl ($C_4$), and the like. Each instance of an alkynyl group may be independently optionally substituted, i.e., unsubstituted (an "unsubstituted alkynyl") or substituted (a "substituted alkynyl") with one or more substituents e.g., for instance from 1 to 5 substituents, 1 to 3 substituents, or 1 substituent.

As used herein, the term "heteroalkyl," refers to a non-cyclic stable straight or branched chain, or combinations thereof, including at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) 0, N, P, S, and Si may be placed at any position of the heteroalkyl group. Exemplary heteroalkyl groups include, but are not limited to: $-CH_2-CH_2-O-CH_3$, $-CH_2-CH_2-NH-CH_3$, $-CH_2-CH_2-N(CH_3)-CH_3$, $-CH_2-S-CH_2-CH_3$, $-CH_2-CH_2$, $-S(O)-CH_3$, $-CH_2-CH_2-S(O)_2-CH_3$, $-CH{=}CH-O-CH_3$, $-Si(CH_3)_3$, $-CH_2-CH{=}N-OCH_3$, $-CH{=}CH-N(CH_3)-CH_3$, $-O-CH_3$, and $-O-CH_2-CH_3$. Up to two or three heteroatoms may be consecutive, such as, for example, $-CH_2-NH-OCH_3$ and $-CH_2-O-Si(CH_3)_3$. Where "heteroalkyl" is recited, followed by recitations of specific heteroalkyl groups, such as $-CH_2O$, $-NR^CR^D$, or the like, it will be understood that the terms heteroalkyl and $-CH_2O$ or $-NR^CR^D$ are not redundant or mutually exclusive. Rather, the specific heteroalkyl groups are recited to add clarity. Thus, the term "heteroalkyl" should not be interpreted herein as excluding specific heteroalkyl groups, such as $-CH_2O$, $-NR^CR^D$, or the like. Each instance of a heteroalkyl group may be independently optionally substituted, i.e., unsubstituted (an "unsubstituted heteroalkyl") or substituted (a "substituted heteroalkyl") with one or more substituents e.g., for instance from 1 to 5 substituents, 1 to 3 substituents, or 1 substituent.

The terms "alkylene," "alkenylene," "alkynylene," or "heteroalkylene," alone or as part of another substituent, mean, unless otherwise stated, a divalent radical derived from an alkyl, alkenyl, alkynyl, or heteroalkyl, respectively. An alkylene, alkenylene, alkynylene, or heteroalkylene group may be described as, e.g., a $C_1$-$C_6$-membered alkylene, $C_2$-$C_6$-membered alkenylene, $C_1$-$C_6$-membered alkynylene, or $C_1$-$C_6$-membered heteroalkylene, wherein the term "membered" refers to the non-hydrogen atoms within the moiety. In the case of heteroalkylene groups, heteroatoms can also occupy either or both chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— may represent both —C(O)$_2$R'— and —R'C(O)$_2$—.

As used herein, "aryl" refers to a radical of a monocyclic or polycyclic (e.g., bicyclic or tricyclic) 4n+2 aromatic ring system (e.g., having 6, 10, or 14 $\pi$ electrons shared in a cyclic array) having 6-14 ring carbon atoms and zero heteroatoms provided in the aromatic ring system ("$C_6$-$C_{14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). An aryl group may be described as, e.g., a $C_6$-$C_{10}$-membered aryl, wherein the term "membered" refers to the non-hydrogen ring atoms within the moiety. Aryl groups include phenyl, naphthyl, indenyl, and tetrahydronaphthyl. Each instance of an aryl group may be independently optionally substituted, i.e., unsubstituted (an "unsubstituted aryl") or substituted (a "substituted aryl") with one or more substituents.

As used herein, "heteroaryl" refers to a radical of a 5-10 membered monocyclic or bicyclic 4n+2 aromatic ring system (e.g., having 6 or 10 $\pi$ electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl). A heteroaryl group may be described as, e.g., a 6-10-membered heteroaryl, wherein the term "membered" refers to the non-hydrogen ring atoms within the moiety.

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Each instance of a heteroaryl group may be independently optionally substituted, i.e., unsubstituted (an "unsubstituted heteroaryl") or substituted (a "substituted heteroaryl") with one or more substituents.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Other exemplary heteroaryl groups include heme and heme derivatives.

As used herein, the terms "arylene" and "heteroarylene," alone or as part of another substituent, mean a divalent radical derived from an aryl and heteroaryl, respectively.

As used herein, "cycloalkyl" refers to a radical of a non-aromatic cyclic hydrocarbon group having from 3 to 10 ring carbon atoms ("$C_3$-$C_{10}$ cycloalkyl") and zero heteroatoms in the non-aromatic ring system. In some embodiments, a cycloalkyl group has 3 to 8 ring carbon atoms ("$C_3$-$C_8$ cycloalkyl"), 3 to 6 ring carbon atoms ("$C_3$-$C_6$ cycloalkyl"), or 5 to 10 ring carbon atoms ("$C_5$-$C_{10}$ cycloalkyl"). A cycloalkyl group may be described as, e.g., a $C_4$-$C_7$-membered cycloalkyl, wherein the term "membered" refers to the non-hydrogen ring atoms within the moiety. Exemplary $C_3$-$C_6$ cycloalkyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_3$-$C_8$ cycloalkyl groups include, without limitation, the aforementioned $C_3$-$C_6$ cycloalkyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), cubanyl ($C_8$), bicyclo[1.1.1]pentanyl ($C_5$), bicyclo[2.2.2]octanyl ($C_8$), bicyclo[2.1.1]hexanyl ($C_6$), bicyclo[3.1.1]heptanyl ($C_7$), and the like. Exemplary $C_3$-$C_{10}$ cycloalkyl groups include, without limitation, the aforementioned $C_3$-$C_8$ cycloalkyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro [4.5] decanyl ($C_{10}$), and the like. As the foregoing examples illustrate, in certain embodiments, the cycloalkyl group is either monocyclic ("monocyclic cycloalkyl") or contain a fused, bridged or spiro ring system such as a bicyclic system ("bicyclic cycloalkyl") and can be saturated or can be partially unsaturated. "Cycloalkyl" also includes ring systems wherein the cycloalkyl ring, as defined above, is fused with one or more aryl groups wherein the point of attachment is on the cycloalkyl ring, and in such instances, the number of carbons continue to designate the number of carbons in the cycloalkyl ring system. Each instance of a cycloalkyl group may be independently optionally substituted, i.e., unsubstituted (an "unsubstituted cycloalkyl") or substituted (a "substituted cycloalkyl") with one or more substituents.

"Heterocyclyl" as used herein refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclyl ring, as defined above, is fused with one or more cycloalkyl groups wherein the point of attachment is either on the cycloalkyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. A heterocyclyl group may be described as, e.g., a 3-7-membered heterocyclyl, wherein the term "membered" refers to the non-hydrogen ring atoms, i.e., carbon, nitrogen, oxygen, sulfur, boron, phosphorus, and silicon, within the moiety. Each instance of heterocyclyl may be independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, piperazinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6-membered heterocyclyl groups containing two heteroatoms include, without limitation, triazinanyl or thiomorpholinyl-1,1-dioxide. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Amino" as used herein refers to the radical —$NR^{70}R^{71}$, wherein $R^{70}$ and $R^{71}$ are each independently hydrogen, $C_1$-$C_8$ alkyl, $C_3$-$C_{10}$ cycloalkyl, $C_4$-$C_{10}$ heterocyclyl, $C_6$-$C_{10}$ aryl, and $C_5$-$C_{10}$ heteroaryl. In some embodiments, amino refers to $NH_2$.

As used herein, "cyano" refers to the radical —CN.

As used herein, "halo" or "halogen," independently or as part of another substituent, mean, unless otherwise stated, a fluorine (F), chlorine (Cl), bromine (Br), or iodine (I) atom.

As used herein, "hydroxy" refers to the radical —OH.

Alkyl, alkenyl, alkynyl, heteroalkyl, cycloalkyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" cycloalkyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, such as any of the substituents described herein that result in the formation of a stable compound. The present disclosure contemplates any and all such combinations to arrive at a stable compound. For purposes of this disclosure, heteroatoms such as nitrogen may have hydrogen substituents and/or any suitable substituent as described herein which satisfy the valencies of the heteroatoms and results in the formation of a stable moiety.

Two or more substituents may optionally be joined to form aryl, heteroaryl, cycloalkyl, or heterocyclyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Compounds of Formula (I) described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high-pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, NY, 1962); and Wilen, *Tables of Resolving Agents and Optical Resolutions* p. 268 (E. L. Eliel, Ed., Univ. of Notre Dame Press, Notre Dame, IN 1972). The disclosure additionally encompasses compounds described herein as individual isomers substantially free of other isomers, and alternatively, as mixtures of various isomers.

As used herein, a pure enantiomeric compound is substantially free from other enantiomers or stereoisomers of the compound (i.e., in enantiomeric excess). In other words, an "S" form of the compound is substantially free from the "R" form of the compound and is, thus, in enantiomeric excess of the "R" form. The term "enantiomerically pure" or "pure enantiomer" denotes that the compound comprises more than 75% by weight, more than 80% by weight, more than 85% by weight, more than 90% by weight, more than 91% by weight, more than 92% by weight, more than 93% by weight, more than 94% by weight, more than 95% by weight, more than 96% by weight, more than 97% by weight, more than 98% by weight, more than 99% by weight, more than 99.5% by weight, or more than 99.9% by weight, of the enantiomer. In certain embodiments, the weights are based upon total weight of all enantiomers or stereoisomers of the compound.

Compounds of Formula (I) described herein may also comprise one or more isotopic substitutions. For example, H may be in any isotopic form, including $^1H$, $^2H$ (D or deuterium), and $^3H$ (T or tritium); C may be in any isotopic form, including $^{12}C$, $^{13}C$, and $^{14}C$; O may be in any isotopic form, including $^{16}O$ and $^{18}O$; and the like.

The term "pharmaceutically acceptable salt" is meant to include salts of the active compounds that are prepared with relatively nontoxic acids or bases, depending on the particular substituents found on the compounds described herein. When compounds of Formula (I) used to prepare devices of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds used in the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galacturonic acids and the like (see, e.g., Berge et al, *Journal of Pharmaceutical Science* 66: 1-19 (1977)). Certain specific compounds used in the devices of the present disclosure (e.g., a particle, a hydrogel capsule) contain both basic and acidic functionalities that allow the compounds to be converted into either base or acid addition salts. These salts may be prepared by methods known to those skilled in the art. Other pharmaceutically acceptable carriers known to those of skill in the art are suitable for use in the present disclosure.

Devices of the present disclosure may contain a compound of Formula (I) in a prodrug form. Prodrugs are those compounds that readily undergo chemical changes under physiological conditions to provide the compounds useful to mitigate the FBR to devices of the present disclosure. Additionally, prodrugs can be converted to useful compounds of Formula (I) by chemical or biochemical methods in an ex vivo environment.

Certain compounds of Formula (I) described herein can exist in unsolvated forms as well as solvated forms, including hydrated forms. In general, the solvated forms are equivalent to unsolvated forms and are encompassed within the scope of the present disclosure. Certain compounds of Formula (I) described herein may exist in multiple crystalline or amorphous forms. In general, all physical forms are equivalent for the uses contemplated by the present disclosure and are intended to be within the scope of the present disclosure.

The term "solvate" refers to forms of the compound that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates.

The term "hydrate" refers to a compound which is associated with water. Typically, the number of the water molecules contained in a hydrate of a compound is in a definite ratio to the number of the compound molecules in the hydrate. Therefore, a hydrate of a compound may be represented, for example, by the general formula $R \cdot x\ H_2O$, wherein R is the compound and wherein x is a number greater than 0.

The term "tautomer" as used herein refers to compounds that are interchangeable forms of a compound structure, and that vary in the displacement of hydrogen atoms and electrons. Thus, two structures may be in equilibrium through the movement of 7 electrons and an atom (usually H). For example, enols and ketones are tautomers because they are rapidly interconverted by treatment with either acid or base. Tautomeric forms may be relevant to the attainment of the optimal chemical reactivity and biological activity of a compound of interest.

The symbol "∿∿∿" as used herein refers to a connection to an entity, e.g., a polymer (e.g., hydrogel-forming polymer such as alginate) or surface of an implantable element (e.g., a particle, device (e.g., a hydrogel capsule) or material). The connection represented by "∿∿∿" may refer to direct attachment to the entity, e.g., a polymer or an implantable element (e.g., a device) or may refer to linkage to the entity through an attachment group. An "attachment group," as described herein, refers to a moiety for linkage of a compound of Formula (I) to an entity (e.g., a polymer or an implantable element as described herein), and may comprise any attachment chemistry known in the art. A listing of exemplary attachment groups is outlined in *Bioconjugate Techniques* ($3^{rd}$ ed, Greg T. Hermanson, Waltham, MA: Elsevier, Inc, 2013), which is incorporated herein by reference in its entirety. In some embodiments, an attachment group comprises alkyl, alkenyl, alkynyl, heteroalkyl, cycloalkyl, heterocyclyl, aryl, heteroaryl, —C(O)—, —OC(O)—, —N($R^C$)—, —N($R^C$)C(O)—, —C(O)N($R^C$)—, —N($R^C$)N($R^D$)—, —NCN—, —C(=N($R^C$)($R^D$))O—, —S—, —S(O)—, —OS(O)$_x$—, —N($R^C$)S(O)$_x$—, —S(O)$_x$N($R^C$)—, —P($R^F$)$_y$—, —Si(O$R^A$)$_2$—, —Si($R^G$)(O$R^A$)—, —B(O$R^A$)—, or a metal, wherein each of $R^A$, $R^C$, $R^D$, $R^F$, $R^G$, x and y is independently as described herein. In some embodiments, an attachment group comprises an amine, ketone, ester, amide, alkyl, alkenyl, alkynyl, or thiol. In some embodiments, an attachment group is a cross-linker. In some embodiments, the attachment group is —C(O)($C_1$-$C_6$-alkylene)-, wherein alkylene is substituted with $R^1$, and $R^1$ is as described herein. In some embodiments, the attachment group is —C(O)($C_1$-$C_6$-alkylene)-, wherein alkylene is substituted with 1-2 alkyl groups (e.g., 1-2 methyl groups). In some embodiments, the attachment group is —C(O)C($CH_3$)$_2$—. In some embodiments, the attachment group is —C(O)(methylene)-, wherein alkylene is substituted with 1-2 alkyl groups (e.g., 1-2 methyl groups). In some embodiments, the attachment group is —C(O)CH($CH_3$)—. In some embodiments, the attachment group is —C(O)C($CH_3$)—.

GLA Expression Constructs

The present disclosure provides an isolated polynucleotide comprising a promoter operably linked to a nucleotide sequence encoding a human GLA precursor protein or variant thereof, e.g., a GLA fusion protein.

In an embodiment, the promoter is selected to achieve higher expression of GLA mRNA in RPE cells (e.g., ARPE-19 cells) compared to the same GLA coding sequence operably linked to the promoter in the human GLA gene. In an embodiment, the promoter consists essentially of, or consists of, SEQ ID NO: 18 or a nucleotide sequence that is substantially identical to SEQ ID NO:18, e.g., is at least 95%, 96%, 97%, 98%, 99% or more identical to SEQ ID NO:18. In an embodiment, the promoter consists of SEQ ID NO: 18.

In an embodiment, the GLA precursor protein comprises the mature amino acid sequence from a wild-type human GLA protein, e.g., 32-429 of SEQ ID NO:1 or a conservatively substituted variant thereof. In an embodiment, the conservatively substituted variant has no more than 10, 9, 8, 7, 6, 5, 4, 3, 2 or 1 conservative substitutions. In an embodiment, the GLA precursor protein consists of SEQ ID NO: 1.

In an embodiment, the nucleotide sequence encoding the precursor GLA protein is codon optimized for GLA expression in mammalian cells. In an embodiment, the codon-optimized sequence is SEQ ID NO:3 or a nucleotide sequence that is at least 95%, 96%, 97%, 98%, 99% or more identical to SEQ ID NO:3. In an embodiment, the codon-optimized sequence is SEQ ID NO:4 or a nucleotide sequence that is at least 95%, 96%, 97%, 98%, 99% or more identical to SEQ ID NO:4.

In an embodiment, the nucleotide sequence encodes a (GLA fusion protein.

In an embodiment, the GLA fusion protein comprises a signal peptide from a secretory protein other than GLA operatively linked to an amino acid sequence for mature human GLA or a conservatively substituted variant thereof. In an embodiment, the signal peptide consists of, or consists essentially of, SEQ ID NO:15 or a conservatively substituted variant thereof. In an embodiment, a conservatively substituted variant of SEQ ID NO: 15 has no more than three, two or one conservative substitutions. In an embodiment, the coding sequence for the signal peptide (SEQ ID NO:15) is the wild-type coding sequence for human HSPG2. In an embodiment, the coding sequence for the HSPG2 signal peptide is codon-optimized for expression in mammalian cells, e.g., SEQ ID NO: 16 or a nucleotide sequence that is substantially identical to SEQ ID NO: 16, e.g., is at least 95%, 96%, 97%, 98%, 99% or more identical to SEQ ID NO: 16. In an embodiment, the fusion protein comprises SEQ ID NO:5. In an embodiment, the nucleotide sequence comprises SEQ ID NO:6 or a nucleotide sequence that is substantially identical to SEQ ID NO:6, e.g., is at least 95%, 96%, 97%, 98%, 99% or more identical to SEQ ID NO:6.

In an embodiment, the GLA fusion protein comprises a GLA wild-type or variant amino acid sequence operatively linked to an amino acid sequence encoding a non-GLA polypeptide. The non-GLA polypeptide can be any protein or protein domain that confers a longer half-life or other desired property to the fusion protein, e.g., albumin, an IgG Fc, a constant domain from an IgG light chain, one, two or three constant domains of an IgG heavy chain, a nanobody, transferrin, CTP (28 amino acid C-terminal peptide (CTP) of human chorionic gonadotropin (hCG) with its 4 O-glycans), XTEN, a homo-amino acid polymer (HAP), a proline-alanine-serine (PAS), or any combination thereof. In an embodiment, the GLA fusion protein comprises any of SEQ ID NO:7, SEQ ID NO:11, or SEQ ID NO:13. In an embodiment, the nucleotide sequence encoding the GLA fusion protein comprises any of SEQ ID NOs: 9, 12, or 14.

In an embodiment, the isolated polynucleotide comprises a transcription unit, which further comprises a Kozak translation sequence immediately upstream of the ATG start codon in the polypeptide coding sequence. In an embodiment, the Kozak translation sequence consists essentially of, or consists of, nucleotides 2094-2099 of SEQ ID NO: 17 (referred to herein as SEQ ID NO:19), a nucleotide sequence that is substantially identical to SEQ ID NO: 19, e.g., is at least 95%, 96%, 97%, 98%, 99% or more identical to SEQ ID NO: 19). In an embodiment, the transcription unit further comprises a polyA sequence that consists essentially of, or consists of, nucleotides 2163-2684 of SEQ ID NO:17 (referred to herein as SEQ ID NO:20) or a nucleotide sequence that is substantially identical to SEQ ID NO:20, e.g., is at least 95%, 96%, 97%, 98%, 99% or more identical to SEQ ID NO:20. In an embodiment, the isolated polynucleotide comprises SEQ ID NO: 17 with any of SEQ ID NOs: 3, 4, 6, 9, 12, or 14 inserted between nucleotides 2100 and 2101 of SEQ ID NO:17. In an embodiment, the isolated polynucleotide comprises two, three or more transcription units. In an embodiment, the transcription unit(s) are located between a pair of inverted terminal repeats, e.g. a 5' ITR and a 3' ITR.

Engineered RPE Cells

The isolated polynucleotides described above are useful to generate retinal pigment epithelial (RPE) cells or cells derived from RPE cells that are engineered to express and secrete a GLA protein. In an embodiment, an engineered (e.g., recombinant) RPE cell comprises one or more of SEQ ID NOs 3, 4, 6, 9, 12, and 14, or a nucleotide sequence that is substantially identical to any of these specific sequences, e.g., has at least 95%, 96%, 97%, 98%, 99% or more identity to the specified sequence. In an embodiment, an engineered RPE cell produces a GLA-IgG fusion protein and comprises a first transcription unit comprising SEQ ID NO:9 and a second transcription unit comprising SEQ ID NO:10. In an embodiment, an engineered RPE cell comprises a transcription unit described herein, which may be present in an extra-chromosomal expression vector, or integrated into one or more chromosomal sites in the cell nucleus. In an embodiment, the recombinant cell comprises two, three, four or more copies of the transcription unit that are integrated in tandem in the same genomic site in the cell nucleus.

An engineered RPE cell described herein can be derived from any of a variety of strains. Exemplary strains of RPE cells include ARPE-19 cells, ARPE-19-SEAP-2-neo cells, RPE-J cells, and hTERT RPE-1 cells. In some embodiments, the engineered cell is derived from the ARPE-19 (ATCC© CRL-2302™) cell line. In some embodiments, the engineered RPE (e.g, ARPE-19) cell is propagated from a monoclonal cell line.

In an embodiment, an engineered cell described herein expresses a biomarker, e.g., an antigen, that is characteristic of an RPE cell, e.g., a naturally occurring RPE cell. In some embodiments, the biomarker (e.g., antigen) is a protein. Exemplary biomarkers include CRALBP, RPE-65, RLBP, BEST1, or αB-crystallin. In an embodiment, an engineered cell expresses at least one of CRALBP, RPE-65, RLBP, BEST1, or αB-crystallin. In an embodiment, an engineered cell expresses at least one of CRALBP and RPE-65.

Engineered RPE cells for use in devices, compositions and methods described herein, e.g., as a plurality of engineered cells contained or encapsulated in a hydrogel capsule, may be in various stages of the cell cycle. In some embodiments, at least one engineered cell in the plurality of engineered cells is undergoing cell division. Cell division may be measured using any known method in the art, e.g., as described in DeFazio A et al (1987) *J Histochem Cytochem* 35:571-577 and Dolbeare F et al (1983) *Proc Natl Acad Sci USA* 80:5573-5577, each of which is incorporated by reference in its entirety. In an embodiment at least 1, 2, 3, 4, 5, 10, or 20% of the cells are undergoing cell division, e.g., as determined by 5-ethynyl-2'deoxyuridine (EdU) assay or 5-bromo-2'-deoxyuridine (BrdU) assay. In some embodiments, cell proliferation is visualized or quantified by microscopy (e.g., fluorescence microscopy (e.g., time-lapse or evaluation of spindle formation) or flow cytometry. In some embodiments, none of the engineered cells in the plurality of engineered cells are undergoing cell division and are quiescent. In an embodiment, less than 1, 2, 3, 4, 5, 10, or 20% of the cells are undergoing cell division, 5-ethynyl-2'deoxyuridine (EdU) assay, 5-bromo-2'-deoxyuridine (BrdU) assay, microscopy (e.g., fluorescence microscopy (e.g., time-lapse or evaluation of spindle formation), or flow cytometry.

In an embodiment, at least 1, 2, 3, 4, 5, 10, 20, 40, or 80% of the engineered RPE cells in the plurality are viable. Cell viability may be measured using any known method in the art, e.g., as described in Riss, T. et al (2013) "Cell Viability Assays" in *Assay Guidance Manual* (Sittapalam, G. S. et al, eds). For example, cell viability may be measured or quantified by an ATP assay, 5-ethynyl-2'deoxyuridine (EdU) assay, 5-bromo-2'-deoxyuridine (BrdU) assay. In some embodiments, cell viability is visualized or quantified by microscopy (e.g., fluorescence microscopy (e.g., time-lapse or evaluation of spindle formation) or flow cytometry. In an embodiment, at least 1, 2, 3, 4, 5, 10, 20, 40 or 80% of the RPE cells in the plurality are viable, e.g., as determined by an ATP assay, a 5-ethynyl-2'deoxyuridine (EdU) assay, a 5-bromo-2'-deoxyuridine (BrdU) assay, microscopy (e.g., fluorescence microscopy (e.g., time-lapse or evaluation of spindle formation), or flow cytometry.

Any of the parameters described herein may be assessed using standard techniques known to one of skill in the art, such as histology, microscopy, and various functional assays.

Measuring GLA Activity

The activity of GLA secreted by engineered cells or device described herein may be measured by any direct or indirect GLA activity assay known in the art.

For example, GLA activity can be directly measured in blood leukocytes from a subject, lysing of the cells, and determining the enzymatic activity in the lysate upon addition of an enzyme substrate such as 4-methyl umbelliferal alpha-D-galactoside and/or N-acetylgalactosamine (see U.S. Pat. No. 6,274,597). Immunoassays for measuring GLA activity and protein to determine the concentrations of alpha-galactosidase in blood and plasma are described in Fuller et al., *Clin Chem.* 2004; 50(11):1979-85. In an embodiment, GLA activity is measured in culture media or a tissue sample (e.g., plasma separated from blood, a homogenate of a liver, kidney, or heart tissue sample) using the enzymatic assay described in the Examples below.

Indirect assessments of GLA activity are based on measuring a surrogate biomarker, e.g., levels of Gb3 and/or lysoGb3 (and optionally its 6 related analogues) in blood plasma and/or urine sample collected from the subject or in a biopsy of a tissue of interest, e.g, liver, kidney, heart. Gb3 and lysoGb3 levels can be measured using the assay described in the Examples herein or any assay known in the art. For example, a method for measuring Gb3 levels in plasma and urine of humans affected by Fabry disease is described in, e.g., Boscaro et al., *Rapid Commun Mass Spectrom.* 2002; 16(16):1507-14. In this method, the analyses are performed using flow injection analysis-electrospray ionization-tandem mass spectrometry (FIA-ESI-MS/MS). Gb3 accumulation in skin biopsies obtained using a "punch"

device may be detected using an immunoelectron-microscopic method such as described in Kanekura et al., *Br J Dermatol.* 2005, 153(3):544-8. Various biopsy techniques and assays for detecting Gb3 and other surrogate biomarkers are described in US patent application publication US 2010/0113517. Other plasma surrogate biomarkers of GLA activity and/or Fabry disease progression (e.g., various inflammatory and cardiac remodeling biomarkers) are described in Yogasundaram, H. et al., *J Am Heart Assoc.* 2018; 7:e009098.

Devices

An engineered RPE cell described herein or a plurality of such cells may be incorporated into an implantable device for use in providing GLA protein to a subject, e.g., to a Fabry Disease patient.

Exemplary implantable devices comprise materials such as metals, metallic alloys, ceramics, polymers, fibers, inert materials, and combinations thereof. The device (e.g., particle) can have any configuration and shape appropriate for supporting the viability and productivity of the encapsulated cells after implant into the intended target location. In some embodiments, the device is a hydrogel capsule, e.g., a millicapsule or a microcapsule (e.g., a hydrogel millicapsule or a hydrogel microcapsule). The device (e.g., capsule, particle) may comprise (and optionally is configured to release) one or more exogenous agents that are not expressed by the engineered RPE cells, and may include, e.g., a nucleic acid (e.g., an RNA or DNA molecule), a protein (e.g., a hormone, an enzyme (e.g., glucose oxidase, kinase, phosphatase, oxygenase, hydrogenase, reductase) antibody, antibody fragment, antigen, or epitope)), small molecule, lipid, drug, vaccine, or any derivative thereof, a small-molecule, an active or inactive fragment of a protein or polypeptide. In some embodiments, the device comprises at least one means for mitigating the foreign body response (FBR), for example, mitigate the FBR when the device is implanted into or onto a subject.

A device described herein may be provided as a preparation or composition for implantation or administration to a subject, i.e., a device preparation or device composition. In some embodiments, a device preparation or device composition comprises at least 2, 4, 8, 16, 32, 64 or more devices, and at least 20%, 30%, 35%, 40%, 45%, 50%, 55%, 60%, 65%, 70%, 75%, 80%, 85%, 90%, 95% or 100% of the devices in the preparation or composition have a characteristic as described herein, e.g., mean capsule diameter, or number of cells in the cell-containing compartment.

A device, device preparation or device composition may be configured for implantation, or is implanted or disposed, into or onto any site or part of the body. In some embodiments, the implantable device or device preparation is configured for implantation into the peritoneal cavity (e.g., the lesser sac, also known as the omental bursa or bursalis omentum). A device, device preparation or device composition may be implanted in the peritoneal cavity (e.g., the omentum, e.g., the lesser sac) or disposed on a surface within the peritoneal cavity (e.g., omentum, e.g., lesser sac) via injection or catheter. Additional considerations for implantation or disposition of a device, device preparation or device composition into the omentum (e.g., the lesser sac) are provided in M. Pellicciaro et al. (2017) *CellR4* 5(3): e2410.

In some embodiments, the implantable device comprises at least one cell-containing compartment comprising a plurality of live cells encapsulated by a polymer composition. In an embodiment, the device contains two, three, four or more cell-containing compartments. Each cell-containing compartment comprises a plurality of live cells and the cells in at least one of the compartments are capable of expressing and secreting GLA protein when the device is implanted into a subject.

In some embodiments, the polymer composition in the cell-containing compartment(s) comprises a polysaccharide or other hydrogel-forming polymer (e.g., alginate, hyaluronate or chondroitin). In some embodiments, the polymer is an alginate, which is a polysaccharide made up of β-D-mannuronic acid (M) and α-L-guluronic acid (G). In some embodiments, the alginate has a low molecular weight (e.g., approximate molecular weight of <75 kD) and G:M ratio ≥1.5, (ii) a medium molecular weight alginate, e.g., has approximate molecular weight of 75-150 kDa and G:M ratio ≥1.5, (iii) a high molecular weight alginate, e.g., has an approximate MW of 150 kDa-250 kDa and G:M ratio ≥1.5, (iv) or a blend of two or more of these alginates.

In some embodiments, the cell-containing compartment (s) further comprises at least one cell-binding substance (CBS), e.g., a cell-binding peptide (CBP) or cell-binding polypeptide (CBPP). In an embodiment, the CBS comprises a CBP covalently attached to polymer molecules in the polymer composition via a linker ("CBP-polymer"). In an embodiment, the polymer in the CBP-polymer is a polysaccharide (e.g., an alginate) or other hydrogel-forming polymer. Various cell-binding peptides for use in the devices of the disclosure are described herein. In an embodiment, the cell-binding peptide is 25 amino acids or less (e.g., 20, 15, 10 or less) in length and comprises the cell binding sequence of a ligand for a cell-adhesion molecule (CAM). In an embodiment, the cell-binding peptide consists essentially of a cell binding sequence shown in Table 1 herein. In an embodiment, the cell binding sequence is RGD (SEQ ID NO: 28) or RGDSP (SEQ ID NO: 49). In an embodiment, the amino terminus of the cell-binding peptide is covalently attached to the polymer via an amino acid linker. In an embodiment, the amino acid linker consists essentially of one to three glycine residues. In an embodiment, the cell-binding peptide consists essentially of RGD (SEQ ID NO: 28) or RGDSP (SEQ ID NO: 49) and the linker consists essentially of a single glycine residue.

In an embodiment, each CBP-polymer present in the first compartment has a cell-binding peptide density (% nitrogen as determined by combustion analysis as described in the Examples herein) to be at least 0.05%, 0.1%, 0.2% or 0.3% but less than 4%, 3%, 2% or 1%. In an embodiment, the total density of a linker-CBP in a cell containing compartment is about 0.1 to about 1.0 micromoles of the CBP per g of CBP-polymer (e.g., a MMW-alginate covalently modified with GRGD (SEQ ID NO: 43) or GRGDSP (SEQ ID NO: 44)) in solution as determined by a quantitative peptide conjugation assay, e.g., an assay described herein. In an embodiment, the CBP is RGDSP (SEQ ID NO: 49), the linker is G and the polymer is an alginate with a molecular weight of 75 kDa to 150 kDa and a G:M ratio of greater than or equal to 1.5. In an embodiment, the cell-containing compartment also comprises an unmodified hydrogel-forming polymer which is the same or different than the polymer in the CBP-polymer. In an embodiment, the polymer in the CBP-polymer and the unmodified polymer is an alginate with a molecular weight of 75 kDa to 150 kDa and a G:M ratio of greater than or equal to 1.5.

In an embodiment, the quantitative peptide conjugation assay includes subjecting a sample of a CPB-polymer to acid hydrolysis to generate individual amino acids from the conjugated peptide (and any residual unconjugated peptide in the CBP-polymer), quantitating the individual amino acids, averaging the molar concentration of each amino acid, and calculating the total peptide concentration in the sample. In an embodiment, the quantitative peptide conjugation assay is performed substantially similar to the process described in the Examples herein below. In an embodiment, the quantitative peptide conjugation assay also includes subtracting the concentration of any residual unconjugated peptide in the sample from the total peptide concentration. The concentration of unconjugated peptide in a CBP-polymer composition may be determined using any suitable assay known in the art, e.g., by LC-MS as described herein below. Typically, the quantitative peptide conjugation assay is performed on a sample of a saline solution of the CBP-polymer that is used to prepare the device, but may also be performed on a lyophilized sample of the CBP-polymer.

In some embodiments, the device further comprises at least one means for mitigating the foreign body response (FBR), for example, mitigate the FBR when the device is implanted into or onto a subject. Various means for mitigating the FBR of the devices are described herein, but any biological, chemical or physical element that is capable of reducing the FBR to the device compared to a reference device is contemplated herein.

For example, the means for mitigating the FBR in devices disclosed herein can comprise surrounding the cells with a semi-permeable biocompatible membrane having a pore size that is selected to allow oxygen and other molecules important to cell survival and function to move through the semi-permeable membrane while preventing immune cells from traversing through the pores. In an embodiment, the semi-permeable membrane has a molecular weight cutoff of less than 1000 kD or between 50-700 kD, 70-300 kD, or between 70-150 kD, or between 70 and 130 kD.

Another FBR-mitigating means comprises surrounding the cell-containing compartment with a barrier compartment formed from a cell-free biocompatible material, such as the core-shell microcapsules described in Ma, M et al., *Adv. Healthc Mater.,* 2(5):667-672 (2012). Such a barrier compartment could be used with or without the semi-permeable member means. FBR-mitigating means can comprise disposing on or within the device an anti-inflammatory drug that is released from the implanted device to inhibit FBR, e.g., as described in U.S. Pat. No. 9,867,781. Other FBR-mitigating means employ a CSF-1R inhibitor that is disposed on the device surface or encapsulated within the device, as described in WO 2017/176792 and WO 2017/176804. Other FBR-mitigating means employ configuring the device in a spherical shape with a diameter of greater than 1 mm, as described in Veiseh, O., et al., Nature Materials 14:643-652 (2015). In some embodiments, the means for mitigating the FBR comprises disposing an afibrotic compound on the exterior surface of the device and/or within a barrier compartment surrounding the cell-containing compartment. Exemplary afibrotic compounds include compounds of Formula (I) described herein below. In some embodiments, the device can comprise combinations of two or more of the above FBR-mitigating means.

Figure 9:
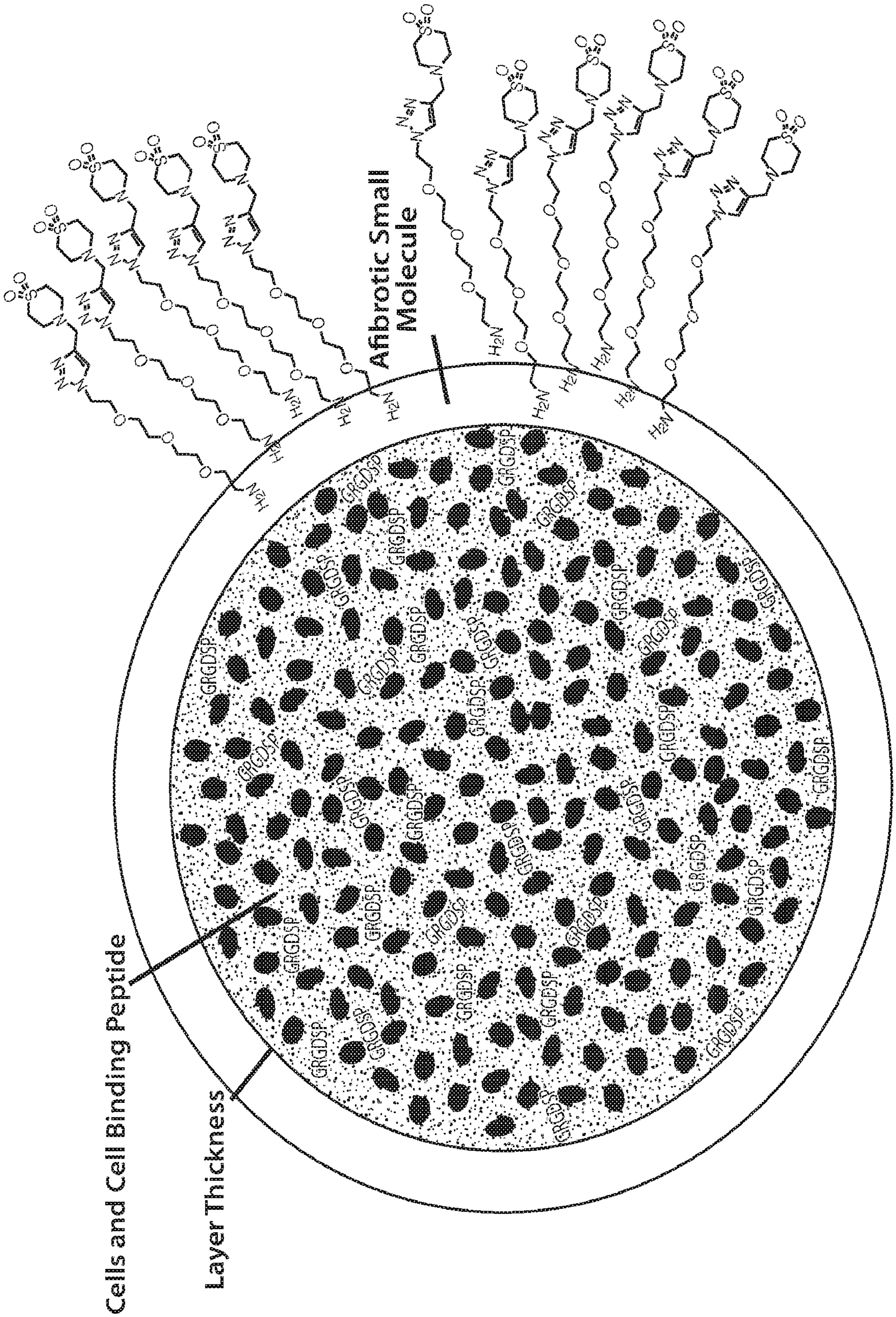
FIG. 9 illustrates an exemplary two-compartment hydrogel capsule of the disclosure, with lines indicating: engineered RPE cells encapsulated in a first, inner compartment formed from a mixture of a hydrogel forming polymer and a hydrogel-forming polymer covalently attached to a cell binding peptide; a second compartment; and an afibrotic compound disposed both within the second compartment and on the surface of the capsule.

In some embodiments, the device has two hydrogel compartments, in which the inner, cell-containing compartment is completely surrounded by the second, outer (e.g., barrier) compartment. In an embodiment, the inner boundary of the second compartment forms an interface with the outer boundary of the first compartment, e.g., as illustrated in FIG. 9. In such embodiments, the thickness of the second (outer) compartment means the average distance between the outer boundary of the second compartment and the interface between the two compartments. In some embodiments, the thickness of the outer compartment is greater than about 10 nanometers (nm), preferably 100 nm or greater and can be as large as 1 millimeter (mm). For example, the thickness of the outer compartment in a hydrogel capsule device described herein may be 10 nm to 1 mm, 100 nm to 1 mm, 500 nm to 1 millimeter, 1 micrometer (μm) to 1 mm, 1 μm to 1 mm, 1 μm to 500 μm, 1 μm to 250 μm, 1 μm to 1 mm, 5 μm to 500 μm, 5 μm to 250 μm, 10 μm to 1 mm, 10 μm to 500 μm, or 10 μm to 250 μm. In some embodiments, the thickness of the outer compartment is 100 nm to 1 mm, between 1 μm and 1 mm, between 1 μm and 500 μm or between 5 μm and 1 mm. In some embodiments, the thickness of the outer compartment is between about 50 μm and about 100 μm.

In some embodiments, one or more compartments in a device comprises an afibrotic polymer, e.g., an afibrotic compound of Formula (I) covalently attached to a polymer that is the same or different than the polymer in the CBP-polymer. In an embodiment, some or all the monomers in the afibrotic polymer are modified with the same compound of Formula (I). In some embodiments, some or all the monomers in the afibrotic polymer are modified with different compounds of Formula (I). In some embodiments in which the device is a two-compartment hydrogel capsule, the afibrotic polymer is present only in the outer, barrier compartment, including its outer surface.

One or more compartments in a device may comprise an unmodified polymer that is the same or different than the polymer in the CBP-polymer and in any afibrotic polymer that is present in the device. In an embodiment, the first compartment, second compartment or all compartments in the device comprises the unmodified polymer. In some embodiments, the unmodified polymer is an unmodified alginate. In an embodiment, the unmodified alginate has a molecular weight of 150 kDa-250 kDa and a G:M ratio of ≥1.5.

In some embodiments, the afibrotic polymer comprises an alginate chemically modified with a Compound of Formula (I). The alginate in the afibrotic polymer may be the same or different than any unmodified alginate that is present in the device. In some embodiments, a compound of Formula (I) (e.g., Compound 101 in Table 3) is covalently attached to an alginate (e.g., an alginate with approximate MW <75 kDa, G:M ratio ≥1.5) at a conjugation density of at least 2.0% and less than 9.0% nitrogen, or 2.0% to 5% nitrogen, 3.0% to 8.0% nitrogen, 5% to 8.0% nitrogen, 4.0% to 7.0% nitrogen, 5.0% to 7.0% nitrogen, or about 6.0% to about 7.0% nitrogen or about 6.8% nitrogen as determined by combustion analysis for percent nitrogen as described in the Examples below. In an embodiment, the amount of Compound 101 produces an increase in % N (as compared with the unmodified alginate) of about 0.5% to 2% 2% to 4% N, about 4% to 6% N, about 6% to 8%, or about 8% to 10% N), where % N is determined by combustion analysis and corresponds to the amount of Compound 101 in the modified alginate.

In other embodiments, the density (e.g., concentration) of the Compound of Formula (I) (e.g., Compound 101) in the afibrotic alginate is defined as the % w/w, e.g., % of weight of amine/weight of afibrotic alginate in solution (e.g., saline) as determined by a suitable quantitative amine conjugation assay (e.g. by an assay described herein), and in certain embodiments, the density of a Compound of Formula (I) (e.g., Compound 101) is between about 1.0% w/w and about 3.0% w/w, between about 1.3% w/w and about 2.5% w/w or between about 1.5% w/w and 2.2% w/w. In an embodiment, the quantitative amine conjugation assay includes subjecting a sample of a chemically-modified polymer (e.g., an alginate modified with a Compound of Formula (I), e.g., CM-LMW-Alg-101) to acid hydrolysis to generate free amine and quantitating the total free amine in the sample. In an embodiment, the quantitative amine conjugation assay also includes subtracting the concentration of unconjugated amine (e.g., Compound of Formula (I)) in an unhydrolyzed sample from the total amine concentration. The quantitative amine conjugation assay is typically performed on a sample of a saline solution of the chemically-modified alginate used to prepare the device, but may also be performed on a lyophilized sample of the chemically-modified alginate. In an embodiment, the quantitative amine conjugation assay is performed substantially similar to the process described in Example 9 herein. In an embodiment, the Compound of Formula (I) is Compound 101 shown in Table 3.

The alginate in an afibrotic polymer can be chemically modified with a compound of Formula (I) using any suitable method known in the art. For example, the alginate carboxylic acid moiety can be activated for coupling to one or more amine-functionalized compounds to achieve an alginate modified with a compound of Formula (I). The alginate polymer may be dissolved in water (30 mL/gram polymer) and treated with 2-chloro-4,6-dimethoxy-1,3,5-triazine (0.5 eq) and N-methylmorpholine (1 eq). To this mixture may be added a solution of the compound of Formula (I) in acetonitrile (0.3M). The reaction may be warmed to 55° C. for 16 h, then cooled to room temperature and gently concentrated via rotary evaporation, then the residue may be dissolved, e.g., in water. The mixture may then be filtered, e.g., through a bed of cyano-modified silica gel (Silicycle) and the filter cake washed with water. The resulting solution may then be dialyzed (10,000 MWCO membrane) against water for 24 hours, e.g., replacing the water twice. The resulting solution can be concentrated, e.g., via lyophilization, to afford the desired chemically modified alginate.

Compounds of Formula (I)

In some embodiments, the devices described herein comprise a compound of Formula (I):

(I)

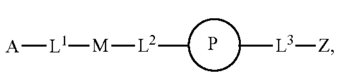

or a pharmaceutically acceptable salt thereof, wherein:

A is alkyl, alkenyl, alkynyl, heteroalkyl, cycloalkyl, heterocyclyl, aryl, heteroaryl, —O—, —C(O)O—, —C(O)—, —OC(O)—, —N($R^C$)—, —N($R^C$)C(O)—, —C(O)N($R^C$)—, —N($R^C$)C(O)($C_1$-$C_6$-alkylene)-, —N($R^C$)C(O)($C_1$-$C_6$-alkenylene)-, —N($R^C$)N($R^D$)—, —NCN—, —C(=N($R^C$)($R^D$))O—, —S—, —S$(O)_x$—, —OS$(O)_x$—, —N($R^C$)S$(O)_x$—, —S$(O)_x$N($R^C$)—, —P$(F)_y$—, —Si$(OR^A)_2$—, —Si($R^G$)($OR^A$)—, —B($OR^A$)—, or a metal, each of which is optionally linked to an attachment group (e.g., an attachment group described herein) and is optionally substituted by one or more $R^1$;

each of $L^1$ and $L^3$ is independently a bond, alkyl, or heteroalkyl, wherein each alkyl and heteroalkyl is optionally substituted by one or more $R^2$;

$L^2$ is a bond;

M is absent, alkyl, heteroalkyl, cycloalkyl, heterocyclyl, aryl, or heteroaryl, each of which is optionally substituted by one or more $R^1$;

P is absent, cycloalkyl, heterocyclyl, or heteroaryl, each of which is optionally substituted by one or more $R^4$;

Z is hydrogen, alkyl, alkenyl, alkynyl, heteroalkyl, —$OR^A$, —C(O)$R^A$, —C(O)$OR^A$, —C(O)N($R^C$)($R^D$), —N($R^C$)C(O)$R^A$, cycloalkyl, heterocyclyl, aryl, or heteroaryl, wherein each alkyl, alkenyl, alkynyl, heteroalkyl, cycloalkyl, heterocyclyl, aryl, and heteroaryl is optionally substituted by one or more $R^5$;

each $R^A$, $R^B$, $R^C$, $R^D$, $R^E$, $R^F$, and $R^G$ is independently hydrogen, alkyl, alkenyl, alkynyl, heteroalkyl, halogen, azido, cycloalkyl, heterocyclyl, aryl, or heteroaryl, wherein each alkyl, alkenyl, alkynyl, heteroalkyl, cycloalkyl, heterocyclyl, aryl, and heteroaryl is optionally substituted with one or more $R^6$;

or $R^C$ and $R^D$, taken together with the nitrogen atom to which they are attached, form a ring (e.g., a 5-7 membered ring), optionally substituted with one or more $R^6$;

each $R^1$, $R^2$, $R^3$, $R^4$, $R^5$, and $R^6$ is independently alkyl, alkenyl, alkynyl, heteroalkyl, halogen, cyano, azido, oxo, —$OR^{A1}$, —C(O)$OR^{A1}$, —C(O)$R^{B1}$, —OC(O)$R^{B1}$, —N($R^{C1}$)($R^{D1}$), —N($R^{C1}$)C(O)$R^{B1}$, —C(O)N($R^{C1}$), $SR^{E1}$, S$(O)_x R^{E1}$, —OS$(O)_x R^{E1}$, —N($R^{C1}$)S$(O)_x R^{E1}$, S$(O)_x$N($R^{C1}$)($R^{D1}$), —P$(R^{F1})_y$, cycloalkyl, heterocyclyl, aryl, heteroaryl, wherein each alkyl, alkenyl, alkynyl, heteroalkyl, cycloalkyl, heterocyclyl, aryl, and heteroaryl is optionally substituted by one or more $R^7$;

each $R^{A1}$, $R^{B1}$, $R^{C1}$, $R^{D1}$, $R^{E1}$, and $R^{F1}$ is independently hydrogen, alkyl, alkenyl, alkynyl, heteroalkyl, cycloalkyl, heterocyclyl, aryl, or heteroaryl, wherein each alkyl, alkenyl, alkynyl, heteroalkyl, cycloalkyl, heterocyclyl, aryl, heteroaryl is optionally substituted by one or more $R^7$;

each $R^7$ is independently alkyl, alkenyl, alkynyl, heteroalkyl, halogen, cyano, oxo, hydroxyl, cycloalkyl, or heterocyclyl;

x is 1 or 2; and y is 2, 3, or 4.

In some embodiments, the compound of Formula (I) is a compound of Formula (I-a):

(I-a)

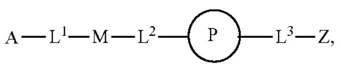

or a salt thereof, wherein:

A is alkyl, alkenyl, alkynyl, heteroalkyl, cycloalkyl, heterocyclyl, aryl, heteroaryl, —O—, —C(O)O—, —C(O)—, —OC(O)—, —N($R^C$)—, —N($R^C$)C(O)—, —C(O)N($R^C$)—, —N($R^C$)N($R^D$)—, —NCN—, —N($R^C$)C(O)($C_1$-$C_6$-alkylene)-, —N($R^C$)C(O)($C_1$-$C_6$-alkenylene)-, —C(=N($R^C$)($R^D$))O—, —S—, —S$(O)_x$, —OS$(O)_x$—, —N($R^C$)S$(O)_x$, —S$(O)_x$N($R^C$)—, —P($R^F$)—, —Si$(OR^A)_2$—, —Si($R^G$)($OR^A$), —B($OR^A$)—, or a metal, each of which is optionally linked to an attachment group (e.g., an attachment group described herein) and optionally substituted by one or more $R^1$;

each of $L^1$ and $L^3$ is independently a bond, alkyl, or heteroalkyl, wherein each alkyl and heteroalkyl is optionally substituted by one or more $R^2$;

$L^2$ is a bond;

M is absent, alkyl, heteroalkyl, cycloalkyl, heterocyclyl, aryl, or heteroaryl, each of which is optionally substituted by one or more $R^3$;

P is heteroaryl optionally substituted by one or more $R^4$;

Z is alkyl, alkenyl, alkynyl, heteroalkyl, cycloalkyl, heterocyclyl, aryl, or heteroaryl, each of which is optionally substituted by one or more $R^5$;

each $R^A$, $R^B$, $R^C$, $R^D$, $R^E$, $R^F$, and $R^G$ is independently hydrogen, alkyl, alkenyl, alkynyl, heteroalkyl, halogen, azido, cycloalkyl, heterocyclyl, aryl, or heteroaryl, wherein each alkyl, alkenyl, alkynyl, heteroalkyl, cycloalkyl, heterocyclyl, aryl, and heteroaryl is optionally substituted with one or more $R^6$, or $R^C$ and $R^D$, taken together with the nitrogen atom to which they are attached, form a ring (e.g., a 5-7 membered ring), optionally substituted with one or more $R^6$, each $R^1$, $R^2$, $R^3$, $R^4$, $R^5$, and $R^6$ is independently alkyl, alkenyl, alkynyl, heteroalkyl, halogen, cyano, azido, oxo, —$OR^A$, —$C(O)OR^{A1}$, —$C(O)R^{B1}$, —$OC(O)R^{B1}$, —$N(R^{C1})(R^{D1})$, —$N(R^{C1})C(O)R^{B1}$, —$C(O)N(R^{C1})$, $SR^{E1}$, $S(O)_xR^{E1}$, —$OS(O)_xR^{E1}$, —$N(R^{C1})S(O)_xR^{E1}$, $S(O)_xN(R^{C1})(R^{D1})$, —$P(R^{F1})_y$, cycloalkyl, heterocyclyl, aryl, heteroaryl, wherein each alkyl, alkenyl, alkynyl, heteroalkyl, cycloalkyl, heterocyclyl, aryl, and heteroaryl is optionally substituted by one or more $R^7$;

each $R^{A1}$, $R^{B1}$, $R^{C1}$, $R^{D1}$, $R^{E1}$, and $R^{F1}$ is independently hydrogen, alkyl, alkenyl, alkynyl, heteroalkyl, cycloalkyl, heterocyclyl, aryl, or heteroaryl, wherein each alkyl, alkenyl, alkynyl, heteroalkyl, cycloalkyl, heterocyclyl, aryl, heteroaryl is optionally substituted by one or more $R^7$;

each $R^7$ is independently alkyl, alkenyl, alkynyl, heteroalkyl, halogen, cyano, oxo, hydroxyl, cycloalkyl, or heterocyclyl;

x is 1 or 2; and y is 2, 3, or 4.

In some embodiments, for Formulas (I) or (I-a), A is alkyl, alkenyl, alkynyl, heteroalkyl, cycloalkyl, heterocyclyl, aryl, heteroaryl, —O—, —C(O)O—, —C(O)—, —OC(O)—, —$N(R^C)C(O)$—, —$N(R^C)C(O)(C_1$-$C_6$-alkylene)-, —$N(R^C)C(O)(C_2$-$C_6$-alkenylene)-, or —$N(R^C)$—. In some embodiments, A is alkyl, alkenyl, alkynyl, heteroalkyl, cycloalkyl, heterocyclyl, aryl, heteroaryl, —O—, —C(O)O—, —C(O)—, —OC(O)—, or —$N(R^C)$—. In some embodiments, A is alkyl, alkenyl, alkynyl, heteroalkyl, —O—, —C(O)O—, —C(O)—, —OC(O)—, or —$N(R^C)$—. In some embodiments, A is alkyl, —O—, —C(O)O—, —C(O)—, —OC(O), or —$N(R^C)$—. In some embodiments, A is —$N(R^C)C(O)$—, —$N(R^C)C(O)(C_1$-$C_6$-alkylene)-, or —$N(R^C)C(O)(C_2$-$C_6$-alkenylene)-. In some embodiments, A is —$N(R^C)$—. In some embodiments, A is —$N(R^C)$—, and $R^C$ an $R^D$ is independently hydrogen or alkyl. In some embodiments, A is —NH—. In some embodiments, A is —$N(R^C)C(O)(C_1$-$C_6$-alkylene)-, wherein alkylene is substituted with $R^1$. In some embodiments, A is —$N(R^C)C(O)(C_1$-$C_6$-alkylene)-, and $R^1$ is alkyl (e.g., methyl). In some embodiments, A is —$NHC(O)C(CH_3)_2$—. In some embodiments, A is —$N(R^C)C(O)$(methylene)-, and $R^1$ is alkyl (e.g., methyl). In some embodiments, A is —$NHC(O)CH(CH_3)$—. In some embodiments, A is —$NHC(O)C(CH_3)$—.

In some embodiments, for Formulas (I) or (I-a), $L^1$ is a bond, alkyl, or heteroalkyl. In some embodiments, $L^1$ is a bond or alkyl. In some embodiments, $L^1$ is a bond. In some embodiments, $L^1$ is alkyl. In some embodiments, $L^1$ is $C_1$-$C_6$ alkyl. In some embodiments, $L^1$ is —$CH_2$—, —$CH(CH_3)$—, —$CH_2CH_2CH_2$, or —$CH_2CH_2$—. In some embodiments, $L^1$ is —$CH_2$— or —$CH_2CH_2$—.

In some embodiments, for Formulas (I) or (I-a), $L^3$ is a bond, alkyl, or heteroalkyl. In some embodiments, $L^3$ is a bond. In some embodiments, $L^3$ is alkyl. In some embodiments, $L^3$ is $C_1$-$C_{12}$alkyl. In some embodiments, $L^3$ is $C_1$-$C_6$ alkyl. In some embodiments, $L^3$ is —$CH_2$—. In some embodiments, $L^3$ is heteroalkyl. In some embodiments, $L^3$ is $C_1$-$C_{12}$ heteroalkyl, optionally substituted with one or more $R^2$ (e.g., oxo). In some embodiments, $L^3$ is $C_1$-$C_6$ heteroalkyl, optionally substituted with one or more $R^2$ (e.g., oxo). In some embodiments, $L^3$ is —$C(O)OCH_2$—, —$CH_2(OCH_2CH_2)_2$—, —$CH_2(OCH_2CH_2)_3$—, $CH_2CH_2O$—, or —$CH_2O$—. In some embodiments, $L^3$ is —$CH_2O$—.

In some embodiments, for Formulas (I) or (I-a), M is absent, alkyl, heteroalkyl, aryl, or heteroaryl. In some embodiments, M is heteroalkyl, aryl, or heteroaryl. In some embodiments, M is absent. In some embodiments, M is alkyl (e.g., $C_1$-$C_6$ alkyl). In some embodiments, M is —$CH_2$—. In some embodiments, M is heteroalkyl (e.g., $C_1$-$C_6$ heteroalkyl). In some embodiments, M is (—$OCH_2CH_2$-)z, wherein z is an integer selected from 1 to 10. In some embodiments, z is an integer selected from 1 to 5. In some embodiments, M is —$OCH_2CH_2$—, (—$OCH_2CH_2$-$)_2$, (—$OCH_2CH_2$-$)_3$, (—$OCH_2CH_2$-$)_4$, or (—$OCH_2CH_2$-$)_5$. In some embodiments, M is —$OCH_2CH_2$—, (—$OCH_2CH_2$-$)_2$, (—$OCH_2CH_2$-$)_3$, or (—$OCH_2CH_2$-$)_4$. In some embodiments, M is (—$OCH_2CH_2$-$)_3$. In some embodiments, M is aryl. In some embodiments, M is phenyl. In some embodiments, M is unsubstituted phenyl. In some embodiments, M is

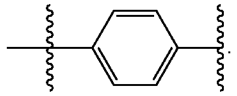 [SMILES: *c1ccc(*)cc1]

n some embodiments, M is phenyl substituted with $R^7$ (e.g., 1 $R^7$). In some embodiments, M is (1-4)

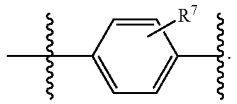

In some embodiments, $R^7$ is $CF_3$.

In some embodiments, for Formulas (I) or (I-a), P is absent, heterocyclyl, or heteroaryl. In some embodiments, P is absent. In some embodiments, for Formulas (I) and (I-a), P is a tricyclic, bicyclic, or monocyclic heteroaryl. In some embodiments, P is a monocyclic heteroaryl. In some embodiments, P is a nitrogen-containing heteroaryl. In some embodiments, P is a monocyclic, nitrogen-containing heteroaryl. In some embodiments, P is a 5-membered heteroaryl. In some embodiments, P is a 5-membered nitrogen-containing heteroaryl. In some embodiments, P is tetrazolyl, imidazolyl, pyrazolyl, or triazolyl, pyrrolyl, oxazolyl, or thiazolyl. In some embodiments, P is tetrazolyl, imidazolyl, pyrazolyl, ortriazolyl, or pyrrolyl. In some embodiments, P is imidazolyl. In some embodiments, P is

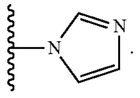

In some embodiments, P is triazolyl. In some embodiments, P is 1,2,3-triazolyl. In some embodiments, P is

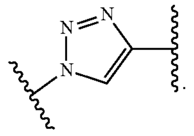 [SMILES: *c1cn(*)nn1]

In some embodiments, P is heterocyclyl. In some embodiments, P is a 5-membered heterocyclyl or a 6-membered heterocyclyl. In some embodiments, P is imidazolidinonyl. In some embodiments, P is

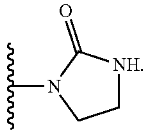 [SMILES: *N1CCNC1=O]

In some embodiments, P is thiomorpholinyl-1,1-dioxidyl.

In some embodiments, P is

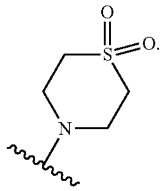 [SMILES: *N1CCS(=O)(=O)CC1]

In some embodiments, for Formulas (I) or (I-a), Z is alkyl, heteroalkyl, cycloalkyl, heterocyclyl, aryl, or heteroaryl. In some embodiments, Z is heterocyclyl. In some embodiments, Z is monocyclic or bicyclic heterocyclyl. In some embodiments, Z is an oxygen-containing heterocyclyl. In some embodiments, Z is a 4-membered heterocyclyl, 5-membered heterocyclyl, or 6-membered heterocyclyl. In some embodiments, Z is a 6-membered heterocyclyl. In some embodiments, Z is a 6-membered oxygen-containing heterocyclyl. In some embodiments, Z is tetrahydropyranyl. In some embodiments, Z is

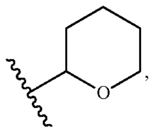, 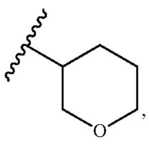, or 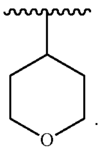.

In some embodiments, Z is a 4-membered oxygen-containing heterocyclyl. In some embodiments, Z is

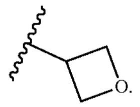 [SMILES: *C1COC1]

In some embodiments, Z is a bicyclic oxygen-containing heterocyclyl. In some embodiments, Z is phthalic anhydridyl. In some embodiments, Z is a sulfur-containing heterocyclyl. In some embodiments, Z is a 6-membered sulfur-containing heterocyclyl. In some embodiments, Z is a 6-membered heterocyclyl containing a nitrogen atom and a sulfur atom. In some embodiments, Z is thiomorpholinyl-1,1-dioxidyl. In some embodiments, Z is

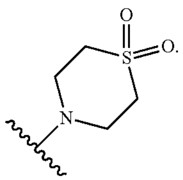 [SMILES: *N1CCS(=O)(=O)CC1]

In some embodiments, Z is a nitrogen-containing heterocyclyl. In some embodiments, Z is a 6-membered nitrogen-containing heterocyclyl. In some embodiments, Z is

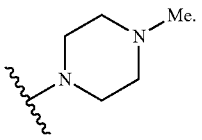 [SMILES: *N1CCN(C)CC1]

In some embodiments, Z is a bicyclic heterocyclyl. In some embodiments, Z is a bicyclic nitrogen-containing heterocyclyl, optionally substituted with one or more $R^5$. In some embodiments, Z is 2-oxa-7-azaspiro[3.5]nonanyl. In some embodiments, Z is

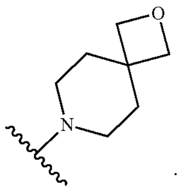 [SMILES: *N1CCC2(CC1)COC2]

In some embodiments, Z is 1-oxa-3,8-diazaspiro[4.5]decan-2-one. In some embodiments, Z is

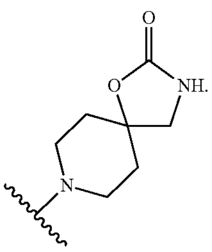 [SMILES: *N1CCC2(CC1)CNC(=O)O2]

In some embodiments, for Formulas (I) or (I-a), Z is aryl. In some embodiments, Z is monocyclic aryl. In some embodiments, Z is phenyl. In some embodiments, Z is monosubstituted phenyl (e.g., with 1 $R^5$). In some embodiments, Z is monosubstituted phenyl, wherein the 1 $R^5$ is a nitrogen-containing group. In some embodiments, Z is monosubstituted phenyl, wherein the 1 $R^5$ is $NH_2$. In some embodiments, Z is monosubstituted phenyl, wherein the 1 $R^5$ is an oxygen-containing group. In some embodiments, Z is monosubstituted phenyl, wherein the 1 $R^5$ is an oxygen-containing heteroalkyl. In some embodiments, Z is monosubstituted phenyl, wherein the 1 $R^5$ is $OCH_3$. In some embodiments, Z is monosubstituted phenyl, wherein the 1 $R^5$ is in the ortho position. In some embodiments, Z is monosubstituted phenyl, wherein the 1 $R^5$ is in the meta position. In some embodiments, Z is monosubstituted phenyl, wherein the 1 $R^5$ is in the para position.

In some embodiments, for Formulas (I) or (I-a), Z is alkyl. In some embodiments, Z is $C_1$-$C_{12}$ alkyl. In some embodiments, Z is $C_1$-$C_{10}$ alkyl. In some embodiments, Z is $C_1$-$C_8$ alkyl. In some embodiments, Z is $C_1$-$C_8$ alkyl substituted with 1-5 $R^5$. In some embodiments, Z is $C_1$-$C_8$ alkyl substituted with 1 $R^5$. In some embodiments, Z is $C_1$-$C_8$ alkyl substituted with 1 $R^5$, wherein $R^5$ is alkyl, heteroalkyl, halogen, oxo, —$OR^{A1}$, —$C(O)OR^{A1}$, —$C(O)R^{B1}$, —$OC(O)R^{B1}$ or —$N(R^{C1})(R^{D1})$. In some embodiments, Z is $C_1$-$C_8$ alkyl substituted with 1 $R^5$, wherein $R^5$ is —$OR^{A1}$ or —$C(O)OR^{A1}$. In some embodiments, Z is $C_1$-$C_8$ alkyl substituted with 1 $R^1$, wherein $R^5$ is —$OR^{A1}$ or —C(O)OH. In some embodiments, Z is —$CH_3$.

In some embodiments, for Formulas (I) or (I-a), Z is heteroalkyl. In some embodiments, Z is $C_1$-$C_{12}$ heteroalkyl. In some embodiments, Z is $C_1$-$C_{10}$ heteroalkyl. In some embodiments, Z is $C_1$-$C_8$ heteroalkyl. In some embodiments, Z is $C_1$-$C_6$ heteroalkyl. In some embodiments, Z is a nitrogen-containing heteroalkyl optionally substituted with one or more $R^5$. In some embodiments, Z is a nitrogen and sulfur-containing heteroalkyl substituted with 1-5 $R^5$. In some embodiments, Z is N-methyl-2-(methylsulfonyl)ethan-1-aminyl.

In some embodiments, Z is —$OR^A$ or —$C(O)OR^A$. In some embodiments, Z is —$OR^A$ (e.g., —OH or —$OCH_3$). In some embodiments, Z is —$OCH_3$. In some embodiments, Z is —$C(O)OR^A$ (e.g., —C(O)OH).

In some embodiments, Z is hydrogen.

In some embodiments, $L^2$ is a bond and P and $L^3$ are independently absent. In some embodiments, $L^2$ is a bond, P is heteroaryl, $L^3$ is a bond, and Z is hydrogen. In some embodiments, P is heteroaryl, $L^3$ is heteroalkyl, and Z is alkyl.

In some embodiments, the compound of Formula (I) is a compound of Formula (I-b):

(I-b)

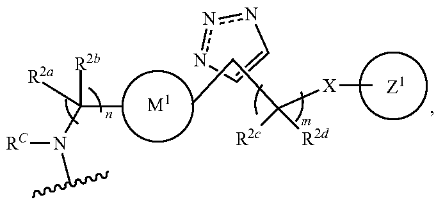

or a salt thereof, wherein Ring $M^1$ is cycloalkyl, heterocyclyl, aryl, or heteroaryl, each of which is optionally substituted with 1-5 $R^3$; Ring $Z^1$ is cycloalkyl, heterocyclyl, aryl or heteroaryl, optionally substituted with 1-5 $R^5$; each of $R^{2a}$, $R^{2b}$, $R^{2c}$, and $R^{2d}$ is independently hydrogen, alkyl, alkenyl, alkynyl, heteroalkyl, halo, cyano, nitro, amino, cycloalkyl, heterocyclyl, aryl, or heteroaryl, or each of $R^{2a}$ and $R^{2b}$ or $R^{2c}$ and $R^{2d}$ is taken together to form an oxo group; X is absent, $N(R^{10})(R^{11})$, O, or S; $R^C$ is hydrogen, alkyl, alkenyl, alkynyl, heteroalkyl, cycloalkyl, heterocyclyl, aryl, or heteroaryl, wherein each of alkyl, alkenyl, alkynyl, heteroalkyl, cycloalkyl, heterocyclyl, aryl, or heteroaryl is optionally substituted with 1-6 $R^6$; each $R^3$, $R^5$, and $R^6$ is independently alkyl, alkenyl, alkynyl, heteroalkyl, halogen, cyano, azido, oxo, —$OR^{A1}$, —$C(O)OR^{A1}$, —$C(O)R^{B1}$, —$OC(O)R^{B1}$, —$N(R^{C1})(R^{D1})$, —$N(R^{C1})C(O)R^{B1}$, —$C(O)N(R^{C1})$, $SR^{E1}$, cycloalkyl, heterocyclyl, aryl, or heteroaryl; each of $R^{10}$ and $R^{11}$ is independently hydrogen, alkyl, alkenyl, alkynyl, heteroalkyl, —$C(O)OR^{A1}$, —$C(O)R^{B1}$, —$OC(O)R^{B1}$, —$C(O)N(R^{C1})$, cycloalkyl, heterocyclyl, aryl, or heteroaryl; each $R^{A1}$, $R^{B1}$, $R^{C1}$, $R^{D1}$, and $R^{E1}$ is independently hydrogen, alkyl, alkenyl, alkynyl, heteroalkyl, cycloalkyl, heterocyclyl, aryl, heteroaryl, wherein each of alkyl, alkenyl, alkynyl, heteroalkyl, cycloalkyl, heterocyclyl, aryl, heteroaryl is optionally substituted with 1-6 $R^7$; each $R^7$ is independently alkyl, alkenyl, alkynyl, heteroalkyl, halogen, cyano, oxo, hydroxyl, cycloalkyl, or heterocyclyl; each m and n is independently 1, 2, 3, 4, 5, or 6; and "∿∿∿" refers to a connection to an attachment group or a polymer described herein. In some embodiments, for each $R^3$ and $R^5$, each alkyl, alkenyl, alkynyl, heteroalkyl, cycloalkyl, heterocyclyl, aryl, or heteroaryl is optionally and independently substituted with halogen, oxo, cyano, cycloalkyl, or heterocyclyl.

In some embodiments, the compound of Formula (I-b) is a compound of Formula (I-b-i):

(I-b-i)

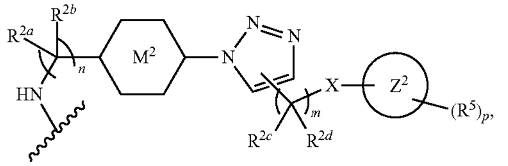

or a pharmaceutically acceptable salt thereof, wherein Ring $M^2$ is aryl or heteroaryl optionally substituted with one or more $R^3$; Ring $Z^2$ is cycloalkyl, heterocyclyl, aryl, or heteroaryl; each of $R^{2a}$, $R^{2b}$, $R^{2c}$, and $R^{2d}$ is independently hydrogen, alkyl, or heteroalkyl, or each of $R^{2a}$ and $R^{2b}$ or $R^{2e}$ and $R^{2d}$ is taken together to form an oxo group; X is absent, O, or S; each $R^3$ and $R^5$ is independently alkyl, heteroalkyl, halogen, oxo, —$OR^{A1}$, —$C(O)OR^{A1}$, or —$C(O)R^{B1}$, wherein each alkyl and heteroalkyl is optionally substituted with halogen; or two $R^5$ are taken together to form a 5-6 membered ring fused to Ring $Z^2$; each $R^{A1}$ and $R^{B1}$ is independently hydrogen, alkyl, or heteroalkyl; m and n are each independently 1, 2, 3, 4, 5, or 6; p is 0, 1, 2, 3, 4, 5, or 6; and "∿∿∿" refers to a connection to an attachment group or a polymer described herein.

In some embodiments, the compound of Formula (I-b-i) is a compound of Formula (I-b-ii):

(I-b-ii)

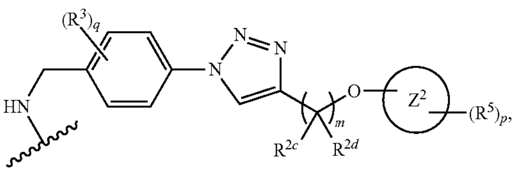

or a pharmaceutically acceptable salt thereof, wherein Ring $Z^2$ is cycloalkyl, heterocyclyl, aryl or heteroaryl; each of $R^{2C}$ and $R^{2d}$ is independently hydrogen, alkyl, or heteroalkyl, or $R^{2C}$ and $R^{2d}$ and taken together to form an oxo group; each $R^3$ and $R^5$ is independently alkyl, heteroalkyl, halogen, oxo, —$OR^{A1}$, —$C(O)OR^{A1}$, or —$C(O)R^{B1}$, wherein each alkyl and heteroalkyl is optionally substituted with halogen; each $R^{A1}$ and $R^{B1}$ is independently hydrogen, alkyl, or heteroalkyl; each of p and q is independently 0, 1, 2, 3, 4, 5, or 6; and “ ” refers to a connection to an attachment group or a polymer described herein.

In some embodiments, the compound of Formula (I) is a compound of Formula (I-c):

(I-c)

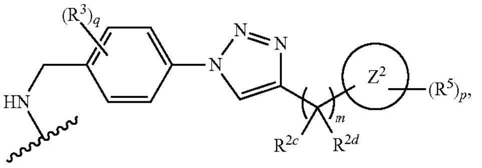

or a pharmaceutically acceptable salt thereof, wherein Ring $Z^2$ is cycloalkyl, heterocyclyl, aryl or heteroaryl; each of $R^{2c}$ and $R^{2d}$ is independently hydrogen, alkyl, or heteroalkyl, or $R^{2c}$ and $R^{2d}$ is taken together to form an oxo group; each $R^3$ and $R^5$ is independently alkyl, heteroalkyl, halogen, oxo, —$OR^{A1}$, —$C(O)OR^{A1}$, or —$C(O)R^{B1}$, wherein each alkyl and heteroalkyl is optionally substituted with halogen; each $R^{A1}$ and $R^{B1}$ is independently hydrogen, alkyl, or heteroalkyl; m is 1, 2, 3, 4, 5, or 6; each of p and q is independently 0, 1, 2, 3, 4, 5, or 6; and “ ” refers to a connection to an attachment group or a polymer described herein.

In some embodiments, the compound of Formula (I) is a compound of Formula (I-d):

(I-d)

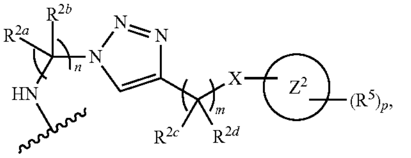

or a pharmaceutically acceptable salt thereof, wherein Ring $Z^2$ is cycloalkyl, heterocyclyl, aryl or heteroaryl; X is absent, O, or S; each of $R^{2a}$, $R^{2b}$, $R^{2c}$, and $R^{2d}$ is independently hydrogen, alkyl, or heteroalkyl, or each of $R^{2a}$ and $R^{2b}$ or $R^{2c}$ and $R^{2d}$ is taken together to form an oxo group; each $R^5$ is independently alkyl, heteroalkyl, halogen, oxo, —$OR^{A1}$, —$C(O)OR^{A1}$, or —$C(O)R^{B1}$, wherein each alkyl and heteroalkyl is optionally substituted with halogen; each $R^{A1}$ and $R^{B1}$ is independently hydrogen, alkyl, or heteroalkyl; each of m and n is independently 1, 2, 3, 4, 5, or 6; p is 0, 1, 2, 3, 4, 5, or 6; and “ ” refers to a connection to an attachment group or a polymer described herein.

In some embodiments, the compound of Formula (I) is a compound of Formula (I-e):

(I-e)

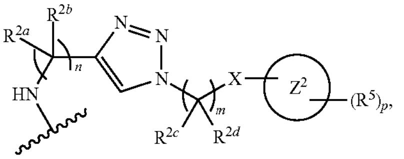

or a pharmaceutically acceptable salt thereof, wherein Ring $Z^2$ is cycloalkyl, heterocyclyl, aryl or heteroaryl; X is absent, O, or S; each of $R^{2a}$, $R^{2b}$, $R^{2c}$, and $R^{2d}$ is independently hydrogen, alkyl, or heteroalkyl, or each of $R^{2a}$ and $R^{2b}$ or $R^{2c}$ and $R^{2d}$ is taken together to form an oxo group; each $R^5$ is independently alkyl, heteroalkyl, halogen, oxo, —$OR^{A1}$, —$C(O)OR^{A1}$, or —$C(O)R^{B1}$; each $R^{A1}$ and $R^{B1}$ is independently hydrogen, alkyl, or heteroalkyl; each of m and n is independently 1, 2, 3, 4, 5, or 6; p is 0, 1, 2, 3, 4, 5, or 6; and “ ” refers to a connection to an attachment group or a polymer described herein.

In some embodiments, the compound of Formula (I) is a compound of Formula (I-f):

(I-f)

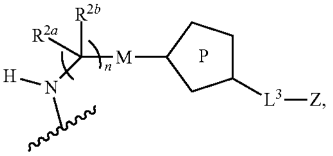

or a pharmaceutically acceptable salt thereof, wherein M is alkyl optionally substituted with one or more $R^3$; Ring P is heteroaryl optionally substituted with one or more $R^4$; $L^3$ is alkyl or heteroalkyl optionally substituted with one or more $R^2$; Z is alkyl, heteroalkyl, cycloalkyl, heterocyclyl, aryl, or heteroaryl, each of which is optionally substituted with one or more $R^5$; each of $R^{2a}$ and $R^{2b}$ is independently hydrogen, alkyl, or heteroalkyl, or $R^{2a}$ and $R^{2b}$ is taken together to form an oxo group; each $R^2$, $R^3$, $R^4$, and $R^5$ is independently alkyl, heteroalkyl, halogen, oxo, —$OR^{A1}$, —$C(O)OR^{A1}$, or —$C(O)R^{B1}$; each $R^{A1}$ and $R^{B1}$ is independently hydrogen, alkyl, or heteroalkyl; n is independently 1, 2, 3, 4, 5, or 6; and “ ” refers to a connection to an attachment group or a polymer described herein.

In some embodiments, the compound of Formula (I) is a compound of Formula (II):

(II)

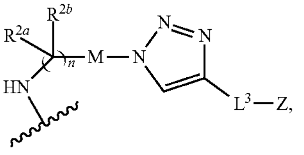

or a pharmaceutically acceptable salt thereof, wherein M is a bond, alkyl or aryl, wherein alkyl and aryl is optionally substituted with one or more $R^3$; $L^3$ is alkyl or heteroalkyl optionally substituted with one or more $R^2$; Z is hydrogen, alkyl, heteroalkyl, cycloalkyl, heterocyclyl, aryl, heteroaryl or —$OR^A$, wherein alkyl, heteroalkyl, cycloalkyl, heterocyclyl, aryl, and heteroaryl is optionally substituted with one or more $R^5$; $R^A$ is hydrogen; each of $R^{2a}$ and $R^{2b}$ is independently hydrogen, alkyl, or heteroalkyl, or $R^{2a}$ and $R^{2b}$ is taken together to form an oxo group; each $R^2$, $R^3$, and $R^5$ is independently alkyl, heteroalkyl, halogen, oxo, —$OR^{A1}$, —$C(O)OR^{A1}$, or —$C(O)R^{B1}$; each $R^{A1}$ and $R^{B1}$ is independently hydrogen, alkyl, or heteroalkyl; n is independently 1, 2, 3, 4, 5, or 6; and "∿∿∿" refers to a connection to an attachment group or a polymer described herein.

In some embodiments, the compound of Formula (II) is a compound of Formula (II-a):

(II-a)

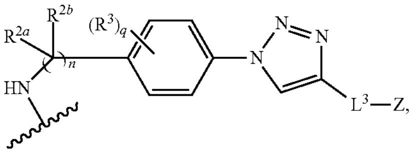

or a pharmaceutically acceptable salt thereof, wherein $L^1$ is alkyl or heteroalkyl, each of which is optionally substituted with one or more $R^2$; Z is hydrogen, alkyl, heteroalkyl, or —$OR^A$, wherein alkyl and heteroalkyl are optionally substituted with one or more $R^5$; each of $R^{2a}$ and $R^{2b}$ is independently hydrogen, alkyl, or heteroalkyl, or $R^{2a}$ and $R^{2b}$ is taken together to form an oxo group; each $R^2$, $R^3$, and $R^5$ is independently alkyl, heteroalkyl, halogen, oxo, —$OR^{A1}$, —$C(O)OR^{A1}$, or —$C(O)R^{B1}$; $R^A$ is hydrogen; each $R^{A1}$ and $R^{B1}$ is independently hydrogen, alkyl, or heteroalkyl; n is independently 1, 2, 3, 4, 5, or 6; and "∿∿∿" refers to a connection to an attachment group or a polymer described herein.

In some embodiments, the compound of Formula (I) is a compound of Formula (III):

(III)

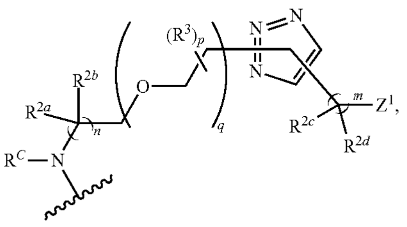

or a pharmaceutically acceptable salt thereof, wherein $Z^1$ is alkyl, alkenyl, alkynyl, heteroalkyl, cycloalkyl, heterocyclyl, aryl, or heteroaryl, each of which is optionally substituted with 1-5 $R^5$; each of $R^{2a}$, $R^{2b}$, $R^{2c}$, and $R^{2d}$ is independently hydrogen, alkyl, alkenyl, alkynyl, heteroalkyl, halo, cyano, nitro, amino, cycloalkyl, heterocyclyl, aryl, or heteroaryl; or $R^{2a}$ and $R^{2b}$ or $R^{2c}$ and $R^{2d}$ are taken together to form an oxo group; $R^C$ is hydrogen, alkyl, alkenyl, alkynyl, or heteroalkyl, wherein each of alkyl, alkenyl, alkynyl, or heteroalkyl is optionally substituted with 1-6 $R^6$; each of $R^3$, $R^5$, and $R^6$ is independently alkyl, heteroalkyl, halogen, oxo, —$OR^{A1}$, —$C(O)OR^{A1}$, or —$C(O)R^{B1}$; each $R^{A1}$ and $R^{B1}$ is independently hydrogen, alkyl, or heteroalkyl; m and n are each independently 1, 2, 3, 4, 5, or 6; q is an integer from 0 to 25; and "∿∿∿" refers to a connection to an attachment group or a polymer described herein.

In some embodiments, the compound of Formula (III) is a compound of Formula (III-a):

(III-a)

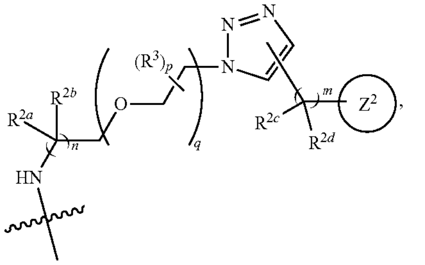

or a pharmaceutically acceptable salt thereof, wherein Ring $Z^2$ is cycloalkyl, heterocyclyl, aryl, or heteroaryl, each of which is optionally substituted with 1-5 $R^5$; each of $R^{2a}$, $R^{2b}$, $R^{2c}$, and $R^{2d}$ is independently hydrogen, alkyl, heteroalkyl, halo; or $R^{2a}$ and $R^{2b}$ or $R^{2c}$ and $R^{2d}$ are taken together to form an oxo group; each of $R^3$ and $R^5$ is independently alkyl, heteroalkyl, halogen, oxo, —$OR^{A1}$, —$C(O)OR^{A1}$, or —$C(O)R^{B1}$; each $R^{A1}$ and $R^{B1}$ is independently hydrogen, alkyl, or heteroalkyl; m and n are each independently 1, 2, 3, 4, 5, or 6; o and p are each independently 0, 1, 2, 3, 4, or 5; q is an integer from 0 to 25; and "∿∿∿" refers to a connection to an attachment group or a polymer described herein.

In some embodiments, the compound of Formula (III-a) is a compound of Formula (III-b):

(III-b)

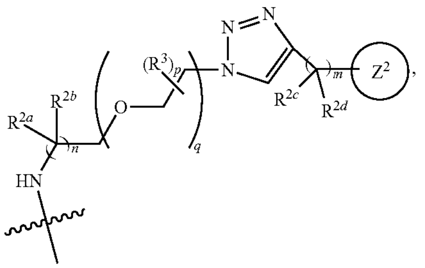

or a pharmaceutically acceptable salt thereof, wherein Ring $Z^2$ is cycloalkyl, heterocyclyl, aryl, or heteroaryl, each of which is optionally substituted with 1-5 $R^5$; each of $R^{2a}$, $R^{2b}$, $R^{2c}$, and $R^{2d}$ is independently hydrogen, alkyl, heteroalkyl, halo; or $R^{2a}$ and $R^{2b}$ or $R^{2c}$ and $R^{2d}$ are taken together to form an oxo group; each of $R^3$ and $R^5$ is independently alkyl, heteroalkyl, halogen, oxo, —$OR^{A1}$, —$C(O)OR^{A1}$, or —$C(O)R^{B1}$; each $R^{A1}$ and $R^{B1}$ is independently hydrogen, alkyl, or heteroalkyl; m and n are each independently 1, 2, 3, 4, 5, or 6; o and p are each independently 0, 1, 2, 3, 4, or 5; q is an integer from 0 to 25; and "∿∿∿" refers to a connection to an attachment group or a polymer described herein.

In some embodiments, the compound of Formula (III-a) is a compound of Formula (III-c):

(III-c)

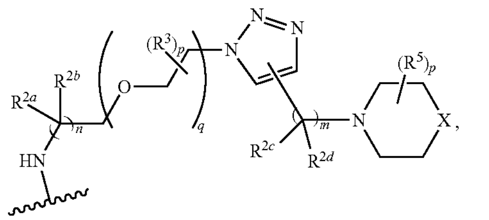

or a pharmaceutically acceptable salt thereof, wherein X is C(R')(R''), N(R'), or $S(O)_x$; each of R' and R'' is independently hydrogen, alkyl, halogen, or cycloalkyl; each of $R^{2a}$, $R^{2b}$, $R^{2c}$, and $R^{2d}$ is independently hydrogen, alkyl, heteroalkyl, or halo; or $R^{2a}$ and $R^{2b}$ or $R^{2c}$ and $R^{2d}$ are taken together to form an oxo group; each of $R^3$ and $R^5$ is independently alkyl, heteroalkyl, halogen, oxo, $—OR^{A1}$, $—C(O)OR^{A1}$, or $—C(O)R^{B1}$; each $R^{A1}$ and $R^{B1}$ is independently hydrogen, alkyl, or heteroalkyl; m and n are each independently 1, 2, 3, 4, 5, or 6; p is 0, 1, 2, 3, 4, or 5; q is an integer from 0 to 25; x is 0, 1, or 2; and " ∿∿∿ " refers to a connection to an attachment group or a polymer described herein.

In some embodiments, the compound of Formula (III-c) is a compound of Formula (III-d):

(III-c)

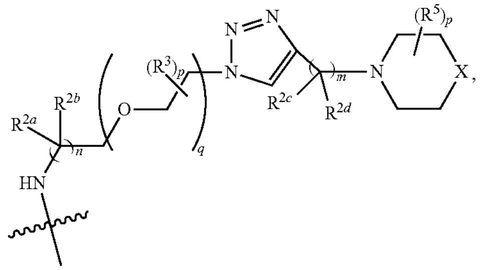

or a pharmaceutically acceptable salt thereof, wherein X is C(R')(R''), N(R'), or $S(O)_x$; each of R' and R'' is independently hydrogen, alkyl, halogen, or cycloalkyl; each of $R^{2a}$, $R^{2b}$, $R^{2c}$, and $R^{2d}$ is independently hydrogen, alkyl, heteroalkyl, or halo; or $R^{2a}$ and $R^{2b}$ or $R^{2e}$ and $R^{2d}$ are taken together to form an oxo group; each of $R^3$ and $R^5$ is independently alkyl, heteroalkyl, halogen, oxo, $—OR^{A1}$, $—C(O)OR^{A1}$, or $—C(O)R^{B1}$; each $R^{A1}$ and $R^{B1}$ is independently hydrogen, alkyl, or heteroalkyl; m and n are each independently 1, 2, 3, 4, 5, or 6; p is 0, 1, 2, 3, 4, or 5; q is an integer from 0 to 25; x is 0, 1, or 2; and " ∿∿∿ " refers to a connection to an attachment group or a polymer described herein ∿∿∿ herein.

In some embodiments, the compound is a compound of Formula (I). In some embodiments, $L^2$ is a bond and P and $L^3$ are independently absent.

In some embodiments, the compound is a compound of Formula (I-a). In some embodiments of Formula (II-a), $L^2$ is a bond, P is heteroaryl, $L^3$ is a bond, and Z is hydrogen. In some embodiments, P is heteroaryl, $L^3$ is heteroalkyl, and Z is alkyl. In some embodiments, $L^2$ is a bond and P and $L^3$ are independently absent. In some embodiments, $L^2$ is a bond, P is heteroaryl, $L^3$ is a bond, and Z is hydrogen. In some embodiments, P is heteroaryl, $L^3$ is heteroalkyl, and Z is alkyl.

In some embodiments, the compound is a compound of Formula (I-b). In some embodiments, P is absent, $L^1$ is $—NHCH_2$, $L^2$ is a bond, M is aryl (e.g., phenyl), $L^3$ is $—CH_2O$, and Z is heterocyclyl (e.g., a nitrogen-containing heterocyclyl, e.g., thiomorpholinyl-1,1-dioxide). In some embodiments, the compound of Formula (I-b) is Compound 116.

In some embodiments of Formula (I-b), P is absent, $L^1$ is $—NHCH_2$, $L^2$ is a bond, M is absent, $L^3$ is a bond, and Z is heterocyclyl (e.g., an oxygen-containing heterocyclyl, e.g., tetrahydropyranyl, tetrahydrofuranyl, oxetanyl, or oxiranyl). In some embodiments, the compound of Formula (I-b) is Compound 105.

In some embodiments, the compound is a compound of Formula (I-b-i). In some embodiments of Formula (I-b-i), each of $R^{2a}$ and $R^{2b}$ is independently hydrogen or $CH_3$, each of $R^{2e}$ and $R^{2d}$ is independently hydrogen, m is 1 or 2, n is 1, X is O, p is 0, $M^2$ is phenyl optionally substituted with one or more $R^3$, $R^3$ is $—CF_3$, and $Z^2$ is heterocyclyl (e.g., an oxygen-containing heterocyclyl, e.g., tetrahydropyranyl, tetrahydrofuranyl, oxetanyl, or oxiranyl). In some embodiments, the compound of Formula (I-b-i) is Compound 100, Compound 106, Compound 107, Compound 108, Compound 109, or Compound 111.

In some embodiments, the compound is a compound of Formula (I-b-ii). In some embodiments of Formula (I-b-ii), each of $R^{2a}$, $R^{2b}$, $R^{2c}$, and $R^{2d}$ is independently hydrogen, q is 0, p is 0, m is 1, and $Z^2$ is heterocyclyl (e.g., an oxygen-containing heterocyclyl, e.g., tetrahydropyranyl). In some embodiments, the compound of Formula (I-b-ii) is Compound 100.

In some embodiments, the compound is a compound of Formula (I-c). In some embodiments of Formula (I-c), each of $R^{2e}$ and $R^{2d}$ is independently hydrogen, m is 1, p is 1, q is 0, $R^5$ is $—CH_3$, and Z is heterocyclyl (e.g., a nitrogen-containing heterocyclyl, e.g., piperazinyl). In some embodiments, the compound of Formula (I-c) is Compound 113.

In some embodiments, the compound is a compound of Formula (I-d). In some embodiments of Formula (I-d), each of $R^{2a}$, $R^{2b}$, $R^{2c}$, and $R^{2d}$ is independently hydrogen, m is 1, n is 3, X is O, p is 0, and Z is heterocyclyl (e.g., an oxygen-containing heterocyclyl, e.g., tetrahydropyranyl, tetrahydrofuranyl, oxetanyl, or oxiranyl). In some embodiments, the compound of Formula (I-d) is Compound 110 or Compound 114.

In some embodiments, the compound is a compound of Formula (I-f). In some embodiments of Formula (I-f), each of $R^{2a}$ and $R^{2b}$ is independently hydrogen, n is 1, M is $—CH_2—$, P is a nitrogen-containing heteroaryl (e.g., imidazolyl), $L^3$ is $—C(O)OCH_2—$, and Z is $CH_3$. In some embodiments, the compound of Formula (I-f) is Compound 115.

In some embodiments, the compound is a compound of Formula (II-a). In some embodiments of Formula (II-a), each of $R^{2a}$ and $R^{2b}$ is independently hydrogen, n is 1, q is 0, $L^3$ is $—CH_2(OCH_2CH_2)_2$, and Z is $—OCH_3$. In some embodiments, the compound of Formula (II-a) is Compound 112.

In some embodiments of Formula (II-a), each of $R^{2a}$ and $R^{2b}$ is independently hydrogen, n is 1, $L^3$ is a bond or $—CH_2$, and Z is hydrogen or —OH. In some embodiments, the compound of Formula (II-a) is Compound 103 or Compound 104.

In some embodiments, the compound is a compound of Formula (III). In some embodiments of Formula (III), each of $R^{2a}$, $R^{2b}$, $R^{2c}$, and $R^{2d}$ is independently hydrogen, m is 1, n is 2, q is 3, p is 0, $R^C$ is hydrogen, and $Z^1$ is heteroalkyl optionally substituted with $R^5$ (e.g., —$N(CH_3)(CH_2CH_2)S(O)_2CH_3$). In some embodiments, the compound of Formula (III) is Compound 120.

In some embodiments, the compound is a compound of Formula (III-b). In some embodiments of Formula (III-b), each of $R^{2a}$, $R^{2b}$, $R^{2c}$, and $R^{2d}$ is independently hydrogen, m is 0, n is 2, q is 3, p is 0, and $Z^2$ is aryl (e.g., phenyl) substituted with 1 $R^5$ (e.g., —$NH_2$). In some embodiments, the compound of Formula (III-b) is Compound 102.

In some embodiments, the compound is a compound of Formula (III-b). In some embodiments of Formula (III-b), each of $R^{2a}$, $R^{2b}$, $R^{2c}$, and $R^{2d}$ is independently hydrogen, m is 1, n is 2, q is 3, p is 0, $R^C$ is hydrogen, and $Z^2$ is heterocyclyl (e.g., an nitrogen-containing heterocyclyl, e.g., a nitrogen-containing spiro heterocyclyl, e.g., 2-oxa-7-azaspiro[3.5]nonanyl). In some embodiments, the compound of Formula (III-a) is Compound 121.

In some embodiments, the compound is a compound of Formula (III-d). In some embodiments of Formula (III-d), each of $R^{2a}$, $R^{2b}$, $R^{2c}$, and $R^{2d}$ is independently hydrogen, m is 1, n is 2, q is 1, 2, 3, or 4, p is 0, and X is $S(O)_2$. In some embodiments of Formula (III-d), each of $R^{2a}$ and $R^{2b}$ is independently hydrogen, m is 1, n is 2, q is 1, 2, 3, or 4, p is 0, and X is $S(O)_2$. In some embodiments, the compound of Formula (III-d) is Compound 101, Compound 117, Compound 118, or Compound 119.

In some embodiments, the compound is a compound of Formula (I-b), (I-d), or (I-e). In some embodiments, the compound is a compound of Formula (I-b), (I-d), or (II). In some embodiments, the compound is a compound of Formula (I-b), (I-d), or (I-f). In some embodiments, the compound is a compound of Formula (I-b), (I-d), or (III).

In some embodiments, the compound of Formula (I) is not a compound disclosed in WO2012/112982, WO2012/167223, WO2014/153126, WO2016/019391, WO 2017/075630, US2012-0213708, US 2016-0030359 or US 2016-0030360.

In some embodiments, the compound of Formula (I) comprises a compound shown in Table 3, or a pharmaceutically acceptable salt thereof. In some embodiments, the exterior surface and/or one or more compartments within a device described herein comprises a compound shown in Table 3, or a pharmaceutically acceptable salt thereof.

TABLE 3

| Exemplary compounds of Formula (I) | |
|---|---|
| Compound No. | Structure |
| 100 | 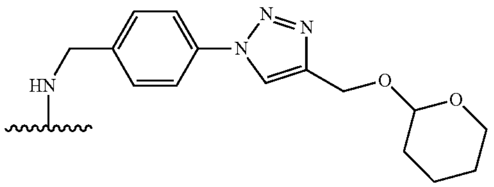 [SMILES: *NCc1ccc(-n2cc(COC3CCCCO3)nn2)cc1] |
| 101 | 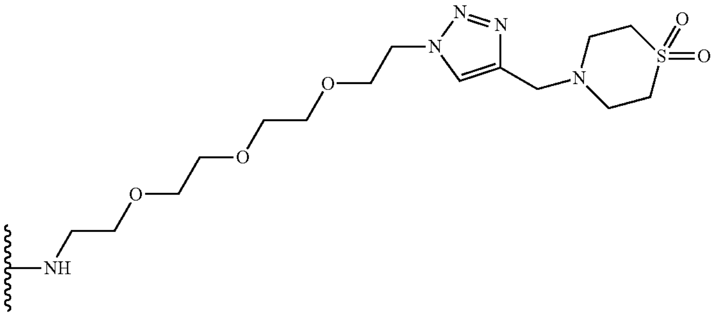 [SMILES: *NCCOCCOCCOCCn1cc(CN2CCS(=O)(=O)CC2)nn1] |
| 102 | 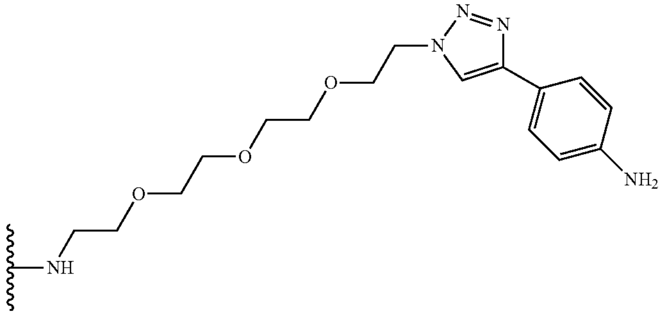 [SMILES: *NCCOCCOCCOCCn1cc(-c2ccc(N)cc2)nn1] |
| 103 | 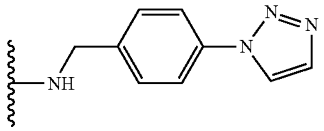 [SMILES: *NCc1ccc(-n2ccnn2)cc1] |

TABLE 3-continued
Exemplary compounds of Formula (I)
| Compound No. | Structure |
|---|---|
| 104 | 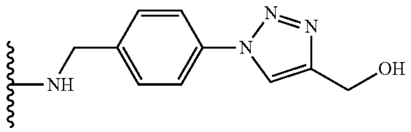 [SMILES: *NCc1ccc(-n2cc(CO)nn2)cc1] |
| 105 | 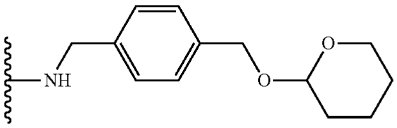 [SMILES: *NCc1ccc(COC2CCCCO2)cc1] |
| 106 | 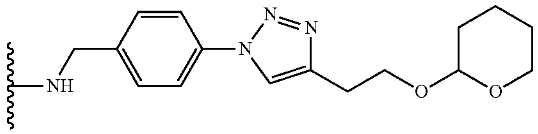 [SMILES: *NCc1ccc(-n2cc(CCOC3CCCCO3)nn2)cc1] |
| 107 | 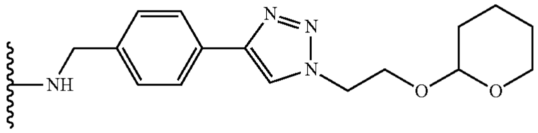 [SMILES: *NCc1ccc(-c2cn(CCOC3CCCCO3)nn2)cc1] |
| 108 | 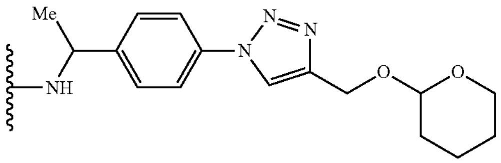 [SMILES: *NC(C)c1ccc(-n2cc(COC3CCCCO3)nn2)cc1] |
| 109 | 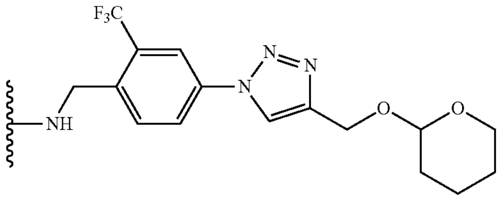 [SMILES: *NCc1ccc(-n2cc(COC3CCCCO3)nn2)cc1C(F)(F)F] |
| 110 | 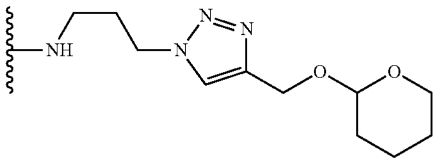 [SMILES: *NCCCn1cc(COC2CCCCO2)nn1] |
| 111 | 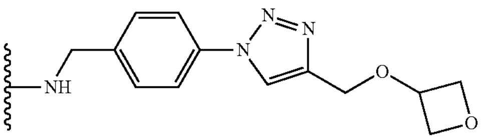 [SMILES: *NCc1ccc(-n2cc(COC3COC3)nn2)cc1] |
| 112 | 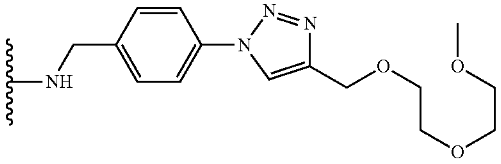 [SMILES: *NCc1ccc(-n2cc(COCCOCCOC)nn2)cc1] |

TABLE 3-continued
Exemplary compounds of Formula (I)
| Compound No. | Structure |
|---|---|
| 113 | 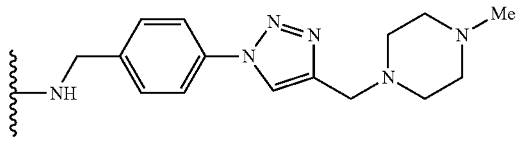 [SMILES: *NCc1ccc(-n2cc(CN3CCN(C)CC3)nn2)cc1] |
| 114 | 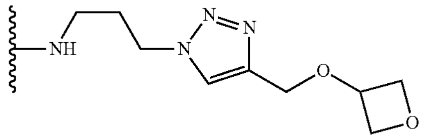 [SMILES: *NCCCn1cc(COC2COC2)nn1] |
| 115 | 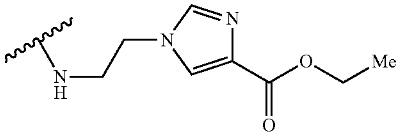 [SMILES: *NCCn1cnc(C(=O)OCC)c1] |
| 116 | 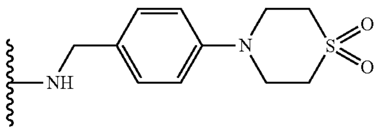 [SMILES: *NCc1ccc(N2CCS(=O)(=O)CC2)cc1] |
| 117 | 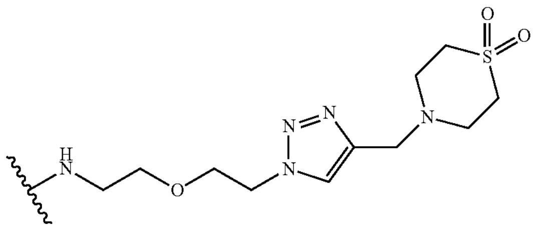 [SMILES: *NCCOCCn1cc(CN2CCS(=O)(=O)CC2)nn1] |
| 118 | 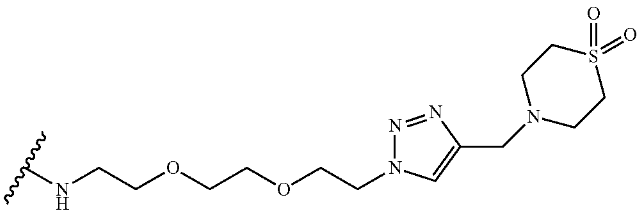 [SMILES: *NCCOCCOCCn1cc(CN2CCS(=O)(=O)CC2)nn1] |
| 119 | 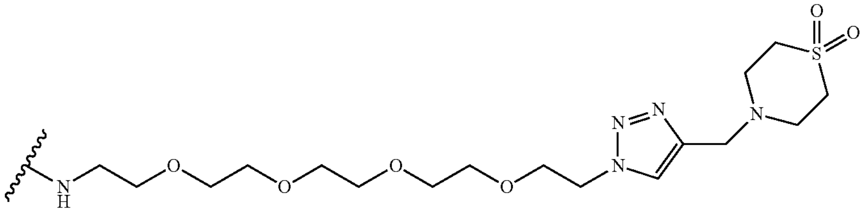 [SMILES: *NCCOCCOCCOCCOCCn1cc(CN2CCS(=O)(=O)CC2)nn1] |
| 120 | 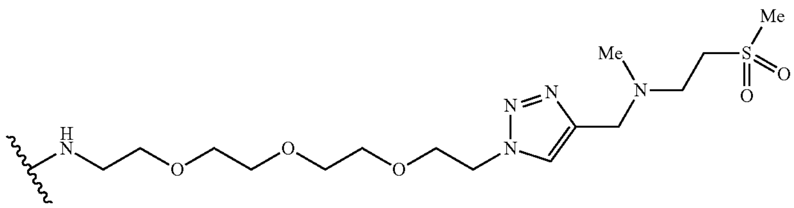 [SMILES: *NCCOCCOCCOCCn1cc(CN(C)CCS(C)(=O)=O)nn1] |

TABLE 3-continued

Exemplary compounds of Formula (I)

| Compound No. | Structure |
|---|---|
| 121 | 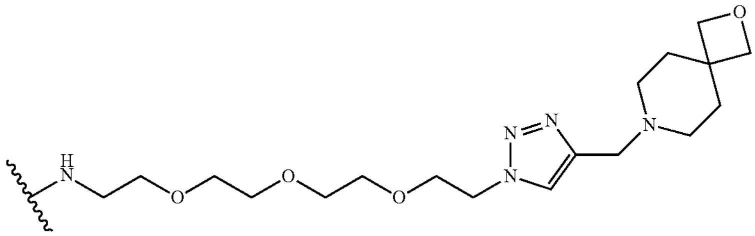 [SMILES: *NCCOCCOCCOCCn1cc(CN2CCC3(CC2)COC3)nn1] |

In some embodiments, the compound is a compound of Formula (I) (e.g., Formulas (I-b), (I-c), (I-d), (I-e), (I-f), (II), (II-a), (III), (III-a), (III-b), (III-c), or (III-d)) or a pharmaceutically acceptable salt thereof, and is selected from:

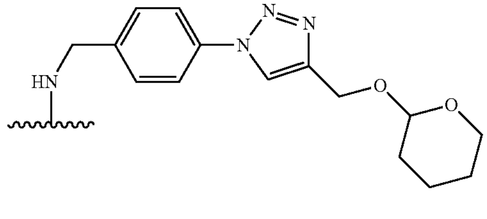
,

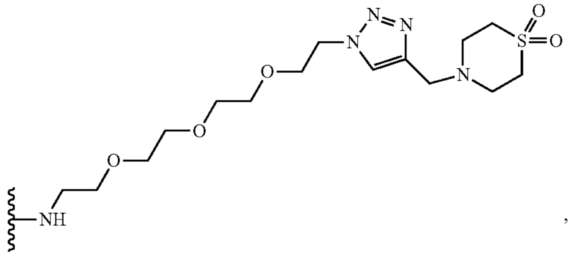
, and

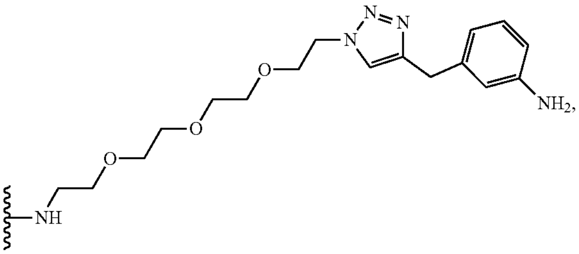

or a pharmaceutically acceptable salt of any of said compounds.

In some embodiments, the device described herein comprises the compound of

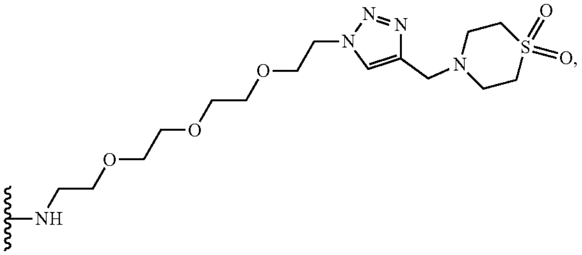

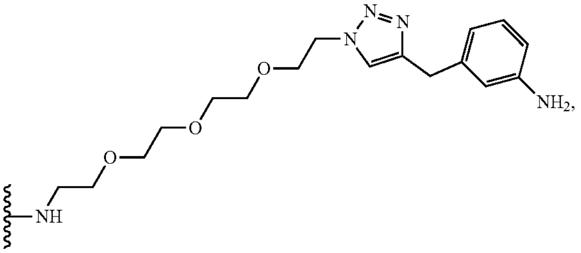

or a pharmaceutically acceptable salt of either compound.

In an embodiment, a device described herein comprises a compound of Formula (I) (e.g., a compound shown in Table 3) covalently bound to an alginate polymer. In an embodiment, a particle described herein comprises a compound of Formula (I) (e.g., a compound shown in Table 3, e.g., Compound 101) covalently bound to one or more guluronic acid and/or mannuronic acid monomers in an alginate polymer, e.g., by an amide bond.

In some embodiments, a compound of Formula (I) (e.g., Compound 101 in Table 3) is covalently attached to an alginate (e.g., an alginate with approximate MW <75 kDa, G:M ratio ≥1.5) at a conjugation density of at least 2.0% and less than 9.0% nitrogen, or 2.0% to 5% nitrogen, 3.0% to 8.0% nitrogen, 5% to 8.0% nitrogen, 4.0% to 7.0% nitrogen, 5.0% to 7.0% nitrogen, or 6.0% to 7.0% nitrogen or about 6.8% nitrogen as determined by combustion analysis for percent nitrogen as described in the Examples below.

Methods of Treatment

Described herein are methods for preventing or treating Fabry Disease in a subject through administration or implantation of a plurality of engineered RPE cells that are capable of expressing and secreting a GLA protein as described herein. In an embodiment, the plurality of RPE cells are contained in an implantable device described herein. In some embodiments, the methods described herein directly or indirectly reduce or alleviate at least one symptom of Fabry Disease, or prevent or slow the onset of Fabry Disease. In an embodiment, the method comprises administering (e.g., implanting) an effective amount of a composition of two-compartment alginate hydrogel capsules which comprise in the inner compartment engineered RPE cells and a cell-binding polymer described herein and comprise a Compound of Formula (I), e.g., Compound 101, on the outer capsule surface and optionally within the outer compartment.

Enumerated Exemplary Embodiments

1. An isolated polynucleotide comprising a promoter operably linked to a precursor GLA coding sequence, wherein the polynucleotide has at least one or more of the following features:
   (a) the promoter consists essentially of a nucleotide sequence that is identical to, or substantially identical to, SEQ ID NO: 18;
   (b) the precursor GLA coding sequence is codon-optimized for expression in mammalian cells;
   (c) the precursor GLA coding sequence encodes a GLA fusion protein, wherein the GLA fusion protein has one or more of the following features:
      (i) the GLA fusion protein comprises a signal peptide from a secretory protein other than GLA (e.g., a mammalian HSPG2 protein, e.g., human HSPG2) operably linked to the N-terminus of a mature human GLA amino acid sequence;
      (ii) the GLA fusion protein comprises a signal peptide (e.g., from human GLA or HSPG2) operably linked to the N-terminus of a mature human GLA amino acid sequence, and an amino acid sequence encoding a non-GLA polypeptide operably linked to the C-terminus of the GLA amino acid sequence.
2. The isolated polynucleotide of embodiment 1, which comprises a combination of features selected from the group consisting of: features (a) and (c)(i); features (a) and (c)(ii); features (b) and (c)(i); features (b) and (c)(ii); features (a), (b) and (c)(i) or and features (a), (b) and (c)(ii).
3. A plurality of engineered RPE cells capable of secreting a GLA protein (e.g., a human GLA protein or variant thereof), wherein each cell in the plurality comprise an exogenous nucleotide sequence, which comprises a promoter operably linked to a precursor GLA coding sequence, wherein the engineered RPE cell has at least one or more of the following features:
   a) the promoter consists essentially of a nucleotide sequence that is identical to, or substantially identical to, SEQ ID NO:18;
   b) the precursor GLA coding sequence is codon-optimized for expression in mammalian cells;
   c) the precursor GLA coding sequence encodes a GLA fusion protein, wherein the GLA fusion protein has one or more of the following features:
      i) the GLA fusion protein comprises a signal peptide from a secretory protein other than GLA (e.g., a mammalian HSPG2 protein, e.g., human HSPG2) operably linked to the N-terminus of a mature human GLA amino acid sequence; and
      ii) the GLA fusion protein comprises a signal peptide (e.g., from human GLA or HSPG2) operably linked to the N-terminus of a mature human GLA amino acid sequence, and an amino acid sequence encoding a non-GLA polypeptide operably linked to the C-terminus of the GLA amino acid sequence.
4. The plurality of engineered RPE cells of embodiment 3, wherein the exogenous nucleotide sequence comprises a combination of features selected from the group consisting of: features (a) and (c)(i); features (a) and (c)(ii); features (b) and (c)(i); features (b) and (c)(ii); features (a), (b) and (c)(i) or and features (a), (b) and (c)(ii).
5. The plurality of engineered RPE cells of embodiment 4, wherein the exogenous nucleotide sequence comprises an extrachromosomal expression vector or is integrated into at least one location in the nuclear genome of the RPE cells.
6. The plurality of engineered RPE cells of any one of embodiments 3 to 5, which are derived from ARPE-19 cells transfected with a transcription unit comprising the exogenous nucleotide sequence.
7. The plurality of engineered RPE cells of embodiment 6, which is provided as a polyclonal cell culture or as a of a monoclonal cell line.
8. The isolated polynucleotide or plurality of engineered RPE cells of any one of embodiments 1 to 7, wherein the precursor GLA codon-optimized coding sequence is SEQ ID NO:3 or SEQ ID NO:4.
9. The isolated polynucleotide or plurality of engineered RPE cells of any one of embodiments 1 to 8, wherein the signal peptide consists essentially of SEQ ID NO: 15.
10. The isolated polynucleotide or plurality of engineered RPE cells of any one of embodiments 1 to 9, wherein the GLA fusion protein comprises SEQ ID NO: 5, SEQ ID NO:7, SEQ ID NO: 11, or SEQ ID NO:13.
11. The isolated polynucleotide or plurality of engineered RPE cells of any one of embodiments 1 to 9, which comprises one or more of SEQ ID NOs 3, 4, 6, 9, 12, and 14.
12. The plurality of engineered RPE cells of any one of embodiments 3 to 11, which exhibits one or more of the following features:
   a) the plurality of engineered RPE cells secrete the GLA protein for at least 5 days, at least 10 days, at least one month, or at least two months, e.g., in an in vitro cell culture or when implanted into a subject (e.g., as evaluated by a reference method described herein); or
   b) the plurality of engineered RPE cells secrete at least a 2-fold, 3-fold, 4-fold, 5-fold or 10-fold higher quantity of the GLA protein than a reference plurality of engineered RPE cells transfected with a wild-type human nucleotide sequence encoding precursor GLA.
13. An implantable device comprising at least one cell-containing compartment which comprises the plurality of engineered RPE cells of any of embodiments 3 to 12 and at least one means for mitigating the foreign body response (FBR) when the device is implanted into the subject.
14. The device of embodiment 13, wherein the at least one cell-containing compartment comprises a polymer composition which encapsulates the plurality of engineered RPE cells, and optionally comprises at least one cell-binding substance (CBS).
15. The device of embodiment 13 or 14, wherein the cell-containing compartment comprises an alginate hydrogel and is surrounded by a barrier compartment, which comprises an alginate hydrogel and optionally comprises a compound of Formula (I), e.g., Compound 101 in Table 3, disposed on the outer surface of the barrier compartment.

16. The device of any embodiment 14 or 15, wherein the polymer composition comprises an alginate covalently modified with a peptide, wherein the peptide consists essentially of or consists of GRGDSP (SEQ ID NO:44), GGRGDSP (SEQ ID NO:45), or GGGRGDSP (SEQ ID NO:46).

17. The device of embodiment 15 or 16, wherein the barrier compartment comprises a mixture of an unmodified alginate and an alginate modified with compound 101, wherein:

(a) the unmodified alginate has a molecular weight of 150 kDa to 250 kDa and a G:M ratio of greater than or equal to 1.5; and (b) the alginate in the modified alginate has a molecular weight of <75 kDa and a G:M ratio of greater than or equal to 1.5.

18. The device of embodiment 17, wherein the conjugation density of Compound 101 in the modified alginate is determined by quantitative free amine analysis, e.g., as described in Example 10 herein below, wherein the determined conjugation density is 1.0% w/w to 3.0% w/w, 1.3% w/w to 2.8% w/w, 1.3% w/w to 2.6% w/w, 1.5% w/w to 2.4% w/w, 1.5% w/w to 2.2% w/w, or 1.7% w/w to 2.2% w/w.

19. A hydrogel capsule comprising:

(a) an inner cell-containing compartment which comprises the plurality of engineered cells of any one of embodiments 3 to 12 encapsulated in a first polymer composition comprising a first RGD-polymer, optionally wherein the concentration of the plurality of cells is 40 million cells per ml of the first polymer composition; is any of 40 million to 100 million cells per ml, 60 million to 100 million cells per ml or 80 million to 100 million cells per ml of the first polymer composition; and (b) a barrier compartment surrounding the cell-containing compartment and comprising a second polymer composition which comprises a mixture of an unmodified alginate and an alginate covalently modified with at least one compound selected from the group consisting of Compound 100, Compound 101, Compound 110, Compound 112, Compound 113 and Compound 114 shown in Table 3, wherein the hydrogel capsule has a spherical shape and has a diameter of 0.5 millimeter to 5 millimeters, and optionally the average thickness of the barrier compartment is about 10 to about 300 microns, about 20 to about 150 microns, or about 40 to about 75 microns.

20. The hydrogel capsule of embodiment 19, which comprises an effective amount of the first RGD-polymer for increased secretion of the GLA protein and wherein the first RGD-polymer consists essentially of an alginate covalently modified with an RGD peptide via a linker, the cell-containing compartment is substantially free of any afibrotic compound and the barrier compartment is substantially free of cells and the RGD peptide, and optionally wherein the effective amount of the RGD-polymer is an optimal amount.

21. The hydrogel capsule of embodiment 19 or 20, wherein the RGD peptide consists essentially of an amino acid sequence of RGD (SEQ ID NO: 28) or RGDSP (SEQ ID NO: 49) and the linker is a single glycine residue or a single beta-alanine residue attached to the N-terminus of the RGD peptide.

22. The hydrogel capsule of any one of embodiments 19 to 21, wherein:

(a) the polymer in the first RGD-polymer is an alginate and has a molecular weight of 150 to 250 kDa and a G:M ratio of greater than or equal to 1.5, and optionally the cell-containing compartment is formed from an alginate solution with a viscosity of between about 90 cP and about 230 cP to about 300, 350 or 400 cP, or between about 80 cP to about 120 cP;

(b) the alginate in the covalently-modified alginate in the barrier compartment has a molecular weight of <75 kDa and a G:M ratio of greater than or equal to 1.5;

(c) the unmodified alginate in the barrier compartment has a molecular weight of 150 kDa to 250 kDa and a G:M ratio of greater than or equal to 1.5; and (d) optionally, the barrier compartment is formed from an alginate solution comprising a mixture of the covalently modified alginate and unmodified alginate and having a viscosity of 250-350 cP.

23. The hydrogel capsule of embodiment 22, wherein:

(a) the capsule has a diameter of between 1.0 millimeters and 2.0 millimeters;

(b) the conjugation density of the RGD peptide on the alginate is the percent nitrogen determined by combustion analysis of the RGD-polymer that has been lyophilized to a constant weight (e.g., as described in Example 1B herein), wherein the determined percent nitrogen is about 0.10% nitrogen (N) to 1.00% N, about 0.20% N to about 0.80% N, about 0.30% N to about 0.60% N, about 0.30% to about 0.50%, or 0.33% N to 0.46% N; and (c) the covalently modified alginate in the barrier compartment is modified only with Compound 101 and the density of Compound 101 in the covalently modified alginate is the percent nitrogen determined by combustion analysis of the covalently modified alginate that has been lyophilized to a constant weight, e.g., as described in Example 1A herein, wherein the determined percent nitrogen is between about nitrogen is at least 2.0% and less than 9.0%, or is 3.0% to 8.0%, 4.0% to 7.0%, 5.0% to 7.0%, or 6.0% to 7.0% or about 6.8%.

24. The hydrogel capsule of embodiment 23, wherein:

(a) the capsule has a diameter of about 1.5 millimeters;

(b) the RGD peptide consists essentially of an amino acid sequence of RGDSP (SEQ ID NO: 49) and the linker is a single glycine residue;

(c) the conjugation density of the RGD peptide on the alginate is selected from the group consisting of (i) an amount effective to increase the viability of the engineered RPE cells, e.g., as determined by an assay described herein, (ii) an amount effective to increase the productivity of the engineered RPE cells, e.g., as determined by an assay described herein, (iii) the percent nitrogen determined by combustion analysis of the RGD-polymer that has been lyophilized to a constant weight (e.g., as described in Example 1B herein), wherein the determined percent nitrogen is about 0.10% nitrogen (N) to 1.00% N, about 0.20% N to about 0.80% N, about 0.30% N to about 0.60% N, about 0.30% to about 0.50%, or 0.33% N to 0.46% N;

(iv) 0.1 to 1.0, 0.2 to 0.8, 0.3 to 0.7 or 0.3 to 0.6 micromoles of GRGDSP (SEQ ID NO: 44) per gram of RGD-polymer in solution, e.g., as described in Example 7 and optionally Example 8 herein; and
(v) any combination of two or more of c(i), c(ii), c(iii) and c(iv); and
(d) the covalently modified alginate in the barrier compartment is modified only with Compound 101 and the density of Compound 101 in the covalently modified alginate is:
(i) the percent nitrogen determined by combustion analysis of the covalently modified alginate that has been lyophilized to a constant weight, e.g., as described in Example 1A herein, wherein the determined percent nitrogen is between about nitrogen is at least 2.0% and less than 9.0%, or is 3.0% to 8.0%, 4.0% to 7.0%, 5.0% to 7.0%, or 6.0% to 7.0% or about 6.8%; or
(ii) the % amine on a weight/weight basis as determined by quantitative free amine analysis, e.g., as described in Example 9 herein, wherein the determined density is 1.0% w/w to 3.0% w/w, 1.3% w/w to 2.8% w/w, 1.3% w/w to 2.6% w/w, 1.5% w/w to 2.4% w/w, 1.5% w/w to 2.2% w/w, or 1.7% w/w to 2.2% w/w.

25. The hydrogel capsule of embodiment 24, wherein the conjugation density of the RGD peptide on the alginate in the RGD-polymer is 0.3 to 0.6 micromoles of GRGDSP (SEQ ID NO: 44) per gram of RGD-polymer in solution.
26. A preparation of devices, wherein each device in the preparation is a device of any one of embodiments 13 to 18.
27. A composition comprising a plurality of hydrogel capsules, wherein each capsule in the composition is a hydrogel capsule of any one of embodiments 19 to 25.
28. The composition of embodiment 27, wherein each capsule is a spherical hydrogel capsule with a diameter selected from the group consisting of 0.5 millimeter to 2 millimeters; 0.7 millimeter to 1.8 millimeters, 1.0 millimeter to 1.8 millimeters; 1.2 millimeters to 1.7 millimeters; 1.3 millimeters to 1.7 millimeters; and 1.4 to 1.6 millimeters.
29. The composition of embodiment 27 or 28, which is a pharmaceutically acceptable composition.
30. A method of treating a patient with Fabry disease, comprising administering to the patient an effective amount of the preparation of devices of embodiment 26 or the composition of any one of embodiments 27 to 29.
31. A method of engineering a plurality of RPE cells to produce a GLA protein (e.g., a human GLA protein or variant thereof) having a property described herein, comprising stably transfecting the RPE cells with a polynucleotide as defined in any one of embodiments 1, 2 or 8 to 11, and optionally isolating a monoclonal cell line expressing the GLA protein.
32. The method of embodiment 31, wherein the plurality of RPE cells are derived from ARPE-19 cells.
33. An engineered mammalian cell capable of expressing and secreting a GLA protein, wherein the cell comprises an exogenous nucleotide sequence comprising a promoter operably linked to a precursor GLA coding sequence having one or more of the following features:
(a) is codon-optimized for expression in the mammalian cell;
(b) encodes a GLA fusion protein, which comprises:
(i) a signal peptide from a secretory protein other than GLA operably linked to the N-terminus of a mature human GLA amino acid sequence; or
(ii) a GLA fusion protein which comprises a signal peptide operably linked to the N-terminus of a mature human GLA amino acid sequence, and an amino acid sequence encoding a non-GLA polypeptide operably linked to the C-terminus of the GLA amino acid sequence.

34. The engineered cell of embodiment 33, wherein the mammalian cell is derived from an RPE cell and optionally wherein the promoter consists essentially of a nucleotide sequence that is identical to, or substantially identical to, SEQ ID NO:18.
35. The engineered cell of embodiment 33 or 34, wherein the precursor GLA coding sequence comprises SEQ ID NO:3 or SEQ ID NO:4.
36. The engineered cell of embodiment 33 or 34, wherein the signal peptide is from a mammalian HSPG2 protein, optionally wherein the signal peptide consists essentially of SEQ ID NO:15.
37. The engineered cell of embodiment 36, wherein the precursor GLA coding sequence comprises SEQ ID NO:16.
38. The engineered cell of embodiment 33 or 34, wherein the GLA fusion protein comprises SEQ ID NO: 5, SEQ ID NO:7, SEQ ID NO: 11, or SEQ ID NO:13.
39. The engineered cell of embodiment 38, wherein the precursor GLA coding sequence comprises SEQ ID NO:6, SEQ ID NO:9, SEQ ID NO:12 or SEQ ID NO:14.
40. The engineered cell of any one of embodiments 33 to 39, wherein the mammalian cell is derived from an ARPE-19 cell transfected with a transcription unit comprising the exogenous nucleotide sequence.
41. The engineered cell of any one of embodiments 33 to 40, wherein the exogenous nucleotide sequence comprises SEQ ID NO:47.
42. The engineered cell of any one of embodiments 33 to 41, wherein the exogenous nucleotide sequence comprises an extrachromosomal vector or is integrated into at least one chromosomal location in the mammalian cell.
43. A composition comprising an engineered mammalian cell of any one of embodiments 33 to 42.
44. The composition of embodiment 43, which is a polyclonal cell culture or a culture of a monoclonal cell line.
45. An isolated double-stranded DNA molecule which comprises a nucleotide sequence selected from the group consisting of SEQ ID NO:3, SEQ ID NO:4, SEQ ID NO:6, SEQ ID NO:9, SEQ ID NO:12, SEQ ID NO:14, SEQ ID NO:47 or SEQ ID NO:48.
46. The isolated DNA molecule of embodiment 45, which consists essentially of SEQ ID NO:48.
47. An implantable device comprising at least one cell-containing compartment which comprises an engineered cell of any one of embodiments 33 to 42 and at least one means for mitigating the foreign body response (FBR) when the device is implanted into the subject.
48. The implantable device of embodiment 47, wherein the at least one cell-containing compartment comprises a polymer composition which encapsulates the engineered cell, and optionally comprises at least one cell-binding substance (CBS).

49. The implantable device of embodiment 47 or 48, wherein the cell-containing compartment is surrounded by a barrier compartment comprising an alginate hydrogel and optionally a compound of Formula (I) disposed on the outer surface of the barrier compartment.

50. The implantable device of embodiment 48 or 49, wherein the polymer composition comprises an alginate covalently modified with a peptide, wherein the peptide consists essentially of or consists of GRGDSP (SEQ ID NO:44) or GGRGDSP (SEQ ID NO:45), and wherein the barrier compartment comprises an alginate modified with

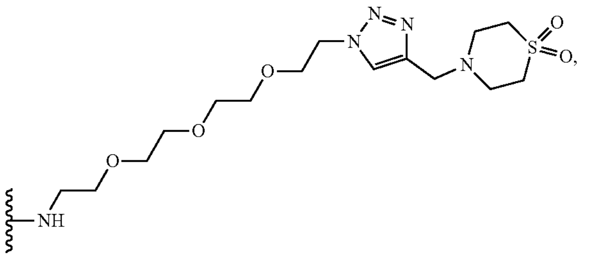 [SMILES: *NCCOCCOCCOCCn1cc(CN2CCS(=O)(=O)CC2)nn1]

or a pharmaceutically acceptable salt thereof.

51. A hydrogel capsule comprising
   (a) an inner compartment which comprises an engineered cell of any one of embodiments 33 to 42 encapsulated in a first polymer composition, wherein the first polymer composition comprises a hydrogel-forming polymer; and
   (b) a barrier compartment surrounding the inner compartment and comprising a second polymer composition, wherein the second polymer composition comprises an alginate covalently modified with at least one compound selected from the group consisting of Compound 100, Compound 101, Compound 110, Compound 112, Compound 113 and Compound 114 as shown in Table 3.

52. The hydrogel capsule of embodiment 51, wherein the selected compound is

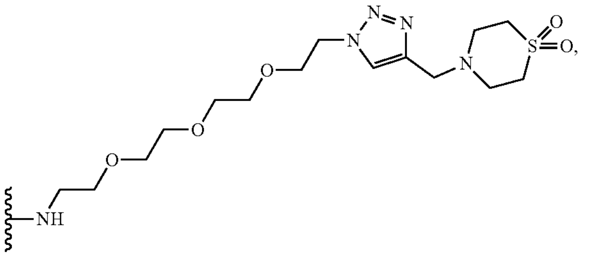 [SMILES: *NCCOCCOCCOCCn1cc(CN2CCS(=O)(=O)CC2)nn1]

53. The hydrogel capsule of embodiment 51 or 52, wherein the inner compartment comprises a plurality of the engineered cell of embodiment 41, optionally wherein the concentration of the engineered cell in the inner compartment is at least 40 million cells per ml of the first polymer composition.

54. A composition comprising a plurality of the hydrogel capsule of any one of embodiments 51 to 53.

55. A method of treating a patient with Fabry disease, comprising administering to the patient an implantable device of any one of embodiments 15 to 18, the hydrogel capsule of any one of embodiments 51 to 53 or the composition of embodiment 54.

EXAMPLES

In order that the disclosure described herein may be more fully understood, the following examples are set forth. The examples described in this application are offered to illustrate the engineered RPE cells, implantable devices, and compositions and methods provided herein and are not to be construed in any way as limiting their scope.

Example 1: Generation and Culturing of Exemplary Engineered ARPE-19 Cells

GLA secreting cells were created using the expression vector shown in FIG. 8, in which an exogenous nucleotide sequence encoding a precursor GLA protein had been inserted using standard cloning methods. To accomplish this, ARPE-19 cells were co-transfected with a PiggyBac containing transposase plasmid along with GLA expression vector and the stably-transfected cells were cultured in complete growth medium containing puromycin.

Stably-transfected ARPE-19 cells were cultured according to the following protocol. Cells were grown in complete growth medium (DMEM:F12 with 10% FBS and 1× Penicillin-Streptomycin-Neomycin antibiotics, Gibco) in 150 $cm^2$ cell culture flasks. To passage cells, the medium in the culture flask was aspirated, and the cell layer was briefly rinsed with phosphate buffered saline (pH 7.4, 137 mM NaCl, 2.7 mM KCl, 8 mM $Na_2HPO_4$, and 2 mM $KH_2PO_4$, Gibco). 5-10 mL of 0.25% (w/v) trypsin/0.53 mM EDTA solution ("TrypsinEDTA") was added to the flask, and the cells were observed under an inverted microscope until the cell layer was dispersed, usually between 3-5 minutes. To avoid clumping, cells were handled with care and hitting or shaking the flask during the dispersion period was minimized. If the cells did not detach, the flasks were placed at 37° C. to facilitate dispersal. Once the cells dispersed, 10 mL complete growth medium was added, and the cells were aspirated by gentle pipetting. The cell suspension was transferred to a centrifuge tube and spun down at approximately 125×g for 5-10 minutes to remove TrypsinEDTA. The supernatant was discarded, and the cells were resuspended in fresh growth medium. Appropriate aliquots of cell suspension were added to new culture vessels, which were incubated at 37° C. The medium was renewed weekly.

Example 2: Secretion of GLA from Exemplary Engineered ARPE-10 Cells

To quantify GLA expression in cells, ARPE-19 cells engineered with various GLA-expression constructs were trypsinized as described above, and 400,000 cells were added to wells of a 6-well plate in duplicate with 2 mL of complete media. The plates were incubated for 16 hours at 37° C. with 5% $CO_2$ and the amount of GLA protein secreted in vitro by the various engineered cell cultures was quantitated by an enzymatic assay using a blue-fluorogenic substrate, 4-methylumbelliferyl-α-D-galactopyranoside. This assay measures the activity of GLA by measuring the formation of free 4-methylumbelliferyl as an increase in fluorescence at 460 nm emission when excited with 360 nm light. This activity in the cell culture media was compared to a standard curve generated with a commercially available recombinant GLA protein, (agalsidase beta, Sanofi Genzyme) to determine the concentration of active GLA.

Figure 10:
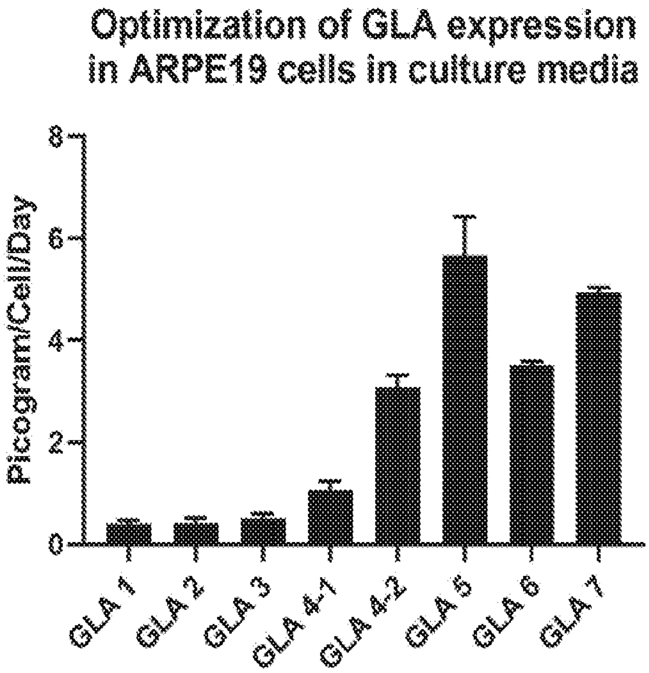
FIG. 10 is a bar graph showing the amount of GLA protein secreted in vitro by RPE cells engineered with various GLA nucleotide sequence constructs shown in FIGS. 1-7: wild-type (GLA 1), codon-optimized (GLA 2, GLA 3), and codon-optimized GLA fusions (GLA4-1, GLA 4-2, GLA 5, GLA 6 and GLA 7).

The results are shown in FIG. 10. GLA 4-1 is a polyclonal culture of cells transfected with a transcription unit comprising SEQ ID NO:6, which is a coding sequence for the human HSPG2 signal peptide fused to a codon-optimized coding sequence for the human wild-type mature GLA amino acid sequence. The codon-optimized sequence in GLA-1 is the same as the corresponding portion of the codon-optimized sequence in the GLA 3 construct. GLA 4-2 is a culture of a clonal cell line isolated using limited dilution cloning from the GLA 4-1 polyclonal culture.

Example 3: Synthesis of Exemplary Compounds of Formula (I)

General Protocols

The procedures below describe methods of preparing exemplary compounds for preparation of implantable devices described herein. The compounds provided herein can be prepared from readily available starting materials using modifications to the specific synthesis protocols set forth below that would be well known to those of skill in the art. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvents used, but such conditions can be determined by those skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in Greene et al., *Protecting Groups in Organic Synthesis*, Second Edition, Wiley, New York, 1991, and references cited therein.

Huisgen Cycloaddition to Afford 1,4-Substituted Triazoles

The copper-catalyzed Huisgen [3+2] cycloaddition was used to prepare triazole-based compounds and compositions, devices, and materials thereof. The scope and typical protocols have been the subject of many reviews (e.g., Meldal, M. and Tornoe, C. W. *Chem. Rev.* (2008) 108:2952-3015; Hein, J. E. and Fokin, V. V. *Chem. Soc. Rev.* (2010) 39(4):1302-1315; both of which are incorporated herein by reference).

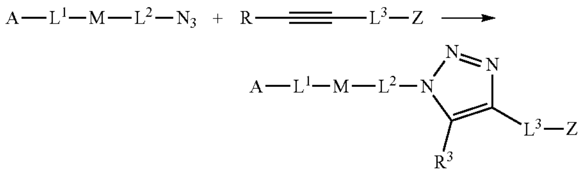

In the example shown above, the azide is the reactive moiety in the fragment containing the connective element A, while the alkyne is the reactive component of the pendant group Z. As depicted below, these functional handles can be exchanged to produce a structurally related triazole product. The preparation of these alternatives is similar, and do not require special considerations.

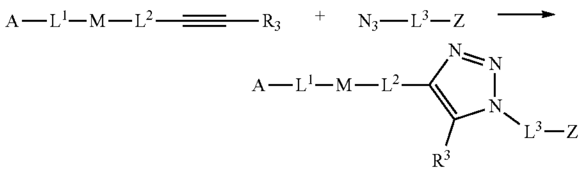

A typical Huisgen cycloaddition procedure starting with an iodide is outlined below. In some instances, iodides are transformed into azides during the course of the reaction for safety.

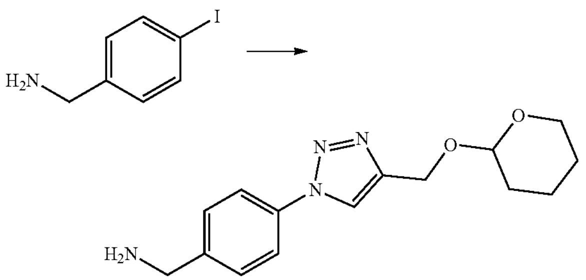

A solution of sodium azide (1.1 eq), sodium ascorbate, (0.1 eq) trans-N,N'-dimethylcyclohexane-1,2-diamine (0.25 eq), copper (I) iodide in methanol (1.0 M, limiting reagent) was degassed with bubbling nitrogen and treated with the acetylene (1 eq) and the aryl iodide (1.2 eq). This mixture was stirred at room temperature for 5 minutes, then warmed to 55° C. for 16 h. The reaction was then cooled to room temperature, filtered through a funnel, and the filter cake washed with methanol. The combined filtrates were concentrated and purified via flash chromatography on silica gel (120 g silica, gradient of 0 to 40% (3% aqueous ammonium hydroxide, 22% methanol, remainder dichloromethane) in dichloromethane to afford the desired target material.

A typical Huisgen cycloaddition procedure starting with an azide is outlined below.

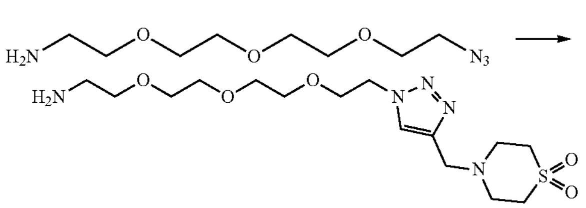

A solution of tris[(1-benzyl-1H-1,2,3-triazol-4-yl)methyl]amine (0.2 eq), triethylamine (0.5 eq), copper (I) iodide (0.06 eq) in methanol (0.4 M, limiting reagent) was treated with the acetylene (1.0 eq) and cooled to 0° C. The reaction was allowed to warm to room temperature over 30 minutes, then heated to 55° C. for 16 h. The reaction was cooled to room temperature, concentrated, and purified with HPLC ($C_{18}$ column, gradient of 0 to 100% (3% aqueous ammonium hydroxide, 22% methanol remainder dichloromethane) in dichloromethane to afford the desired target material.

Huisgen Cycloaddition to Afford 1,5-Substituted Triazoles

The Huisgen [3+2] cycloaddition was also performed with ruthenium catalysts to obtain 1,5-disubstituted products preferentially (e.g., as described in Zhang et al, J. Am. Chem. Soc., 2005, 127, 15998-15999; Boren et al, J. Am.

Chem. Soc., 2008, 130, 8923-8930, each of which is incorporated herein by reference in its entirety).

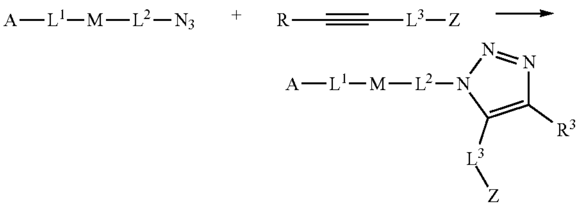

As described previously, the azide and alkyne groups may be exchanged to form similar triazoles as depicted below.

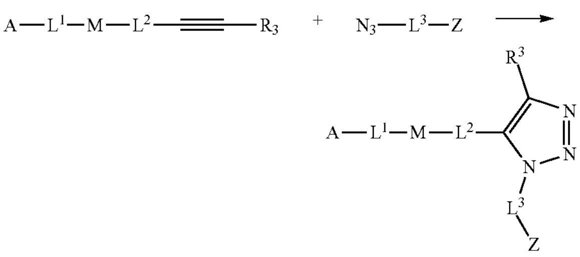

A typical procedure is described as follows: a solution of the alkyne (1 eq) and the azide (1 eq) in dioxane (0.8M) were added dropwise to a solution of pentamethylcyclo-pentadienylbis(triphenylphosphine) ruthenium(II) chloride (0.02 eq) in dioxane (0.16M). The vial was purged with nitrogen, sealed and the mixture heated to 60° C. for 12 h. The resulting mixture was concentrated and purified via flash chromatography on silica gel to afford the requisite compound.

Experimental Procedure for (4-(4-((4-methylpiperazin-1-yl)methyl)-1H-1,2,3-triazol-1-yl)phenyl) methanamine (3)

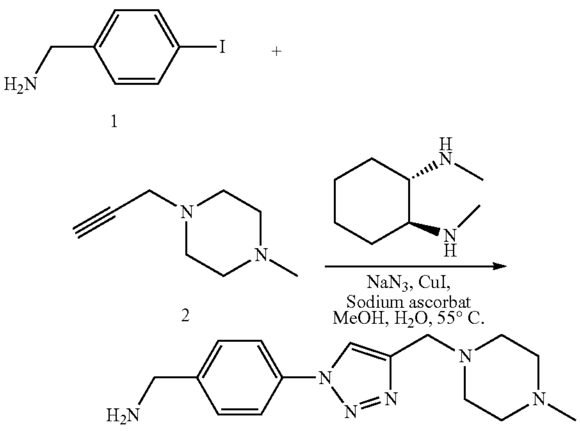

1

2

3

A mixture of (4-iodophenyl)methanamine (1, 843 mg, 3.62 mmol, 1.0 eq), (1S,2S)—N1,N2-dimethylcyclohexane-1,2-diamine (74 µL, 0.47 mmol, 0.13 eq), Sodium ascorbate (72 mg, 0.36 mmol, 0.1 eq), Copper Iodide (69 mg, 0.36 mmol, 0.1 eq), Sodium azide (470 mg, 7.24 mmol, 2.0 eq), and 1-methyl-4-(prop-2-yn-1-yl)piperazine (2, 0.5 g, 3.62 mmol, 1.0 eq) in Methanol (9 mL) and water (1 mL) were purged with nitrogen for 5 minutes and heated to 55° C. for overnight. The reaction mixture was cooled to room temperature, concentrated under reduced pressure, and the brownish slurry was extracted with dichloromethane. Celite was added to the combined dichloromethane phases and the solvent was removed under reduced pressure. The crude product was purified over silica gel (80 g) using dichloromethane/(methanol containing 12% (v/v) aqueous ammonium hydroxide) as mobile phase. The concentration of (methanol containing 12% (v/v) aqueous ammonium hydroxide) was gradually increased from 0% to 7.5% to afford (4-(4-((4-methylpiperazin-1-yl)methyl)-1H-1,2,3-triazol-1-yl)phenyl)methanamine (3, 0.45 g, 43%). LCMS m/z: $[M+H]^+$ Calcd for $C_{15}H_{22}N_6$ 287.2; Found 287.1.

Experimental Procedure for N-(4-(4-((4-methylpiperazin-1-yl)methyl)-1H-1,2,3-triazol-1-yl)benzyl) methacrylamide (4)

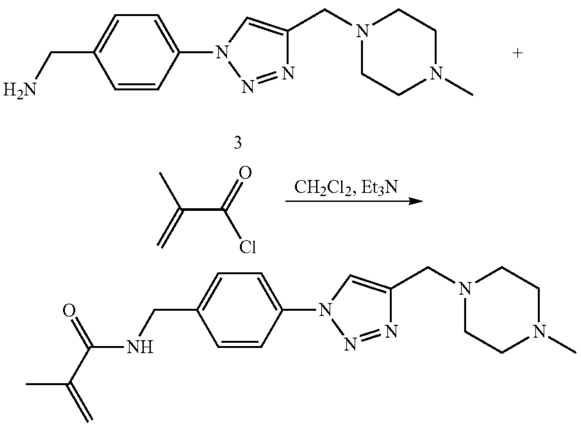

3

4

A solution of (4-(4-((4-methylpiperazin-1-yl)methyl)-1H-1,2,3-triazol-1-yl)phenyl)methanamine (3, 1.2 g, 4.19 mmol, 1.0 eq) and triethylamine (0.70 mL, 5.03 mmol, 1.2 eq) in $CH_2Cl_2$ (50 mL) was cooled to 0° C. with an ice-bath and methacryloyl chloride (0.43 mL, 4.40 mmol, 1.05 eq in 5 mL of $CH_2Cl_2$) was added. The reaction was stirred for a day while cooled with an ice-bath. Ten (10) grams of Celite were added and the solvent was removed under reduced pressure. The residue was purified by silica gel chromatography (80 g) using dichloromethane/(methanol containing 12% (v/v) aqueous ammonium hydroxide) as mobile phase. The concentration of (methanol containing 12% (v/v) aqueous ammonium hydroxide) was gradually increased from 0% to 7.5%. The solvent was removed under reduced pressure and the resulting solid was triturated with diethyl ether, filtered and washed multiple times with diethyl ether to afford N-(4-(4-((4-methylpiperazin-1-yl)methyl)-1H-1,2,3-triazol-1-yl)benzyl)methacrylamide (4, 0.41 g, 28% yield) as a white solid. LCMS m/z: $[M+H]^+$ Calcd for $C_{19}H_{26}N_6O$ 355.2; Found 355.2.

Experimental Procedure for (4-(4-((2-(2-methoxyethoxy)ethoxy)methyl)-1H-1,2,3-triazol-1-yl)phenyl) methanamine (6)

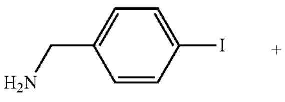

1

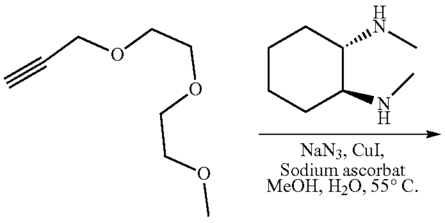

5

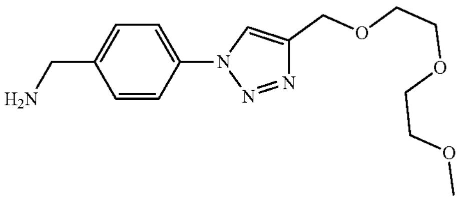

6

A mixture of (4-iodophenyl)methanamine (1, 2.95 g, 12.64 mmol, 1.0 eq), (1S,2S)—N1,N2-dimethylcyclohexane-1,2-diamine (259 μL, 1.64 mmol, 0.13 eq), Sodium ascorbate (250 mg, 1.26 mmol, 0.1 eq), Copper Iodide (241 mg, 1.26 mmol, 0.1 eq), Sodium azide (1.64 g, 25.29 mmol, 2.0 eq), and 1-methyl-4-(prop-2-yn-1-yl)piperazine (5, 2.0 g, 12.64 mmol, 1.0 eq) in Methanol (40 mL) and water (4 mL) were purged with Nitrogen for 5 minutes and heated to 55° C. overnight. The reaction mixture was cooled to room temperature and concentrated under reduced pressure. The residue was dissolved in dichloromethane, filtered, and concentrated with Celite (10 g). The crude product was purified by silica gel chromatography (220 g) using dichloromethane/(methanol containing 12% (v/v) aqueous ammonium hydroxide) as mobile phase. The concentration of (methanol containing 12% (v/v) aqueous ammonium hydroxide) was gradually increased from 0% to 6.25% to afford (4-(4-((2-(2-methoxyethoxy)ethoxy)methyl)-1H-1,2,3-triazol-1-yl)phenyl)methanamine (6, 1.37 g, 35%). LCMS m/z: $[M+H]^+$ Calcd for $C_{15}H_{22}N_4O_3$ 307.2; Found 307.0.

Experimental Procedure for N-(4-(4-((2-(2-methoxyethoxy)ethoxy)methyl)-1H-1,2,3-triazol-1-yl)benzyl)methacrylamide (7)

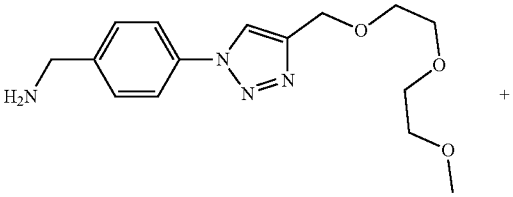

6

-continued

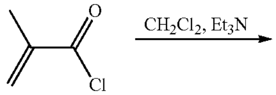

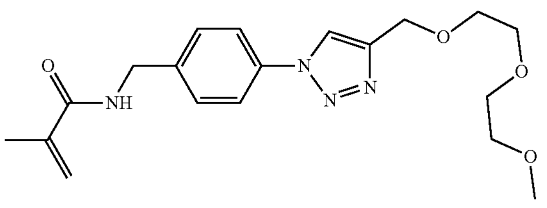

7

A solution of 4-(4-((2-(2-methoxyethoxy)ethoxy)methyl)-1H-1,2,3-triazol-1-yl)phenyl)methanamine (6, 1.69 g, 5.52 mmol, 1.0 eq) and triethylamine (0.92 mL, 6.62 mmol, 1.2 eq) in $CH_2Cl_2$ (50 mL) was cooled to 0° C. with an ice-bath and methacryloyl chloride (0.57 mL, 5.79 mmol, 1.05 eq) was added in a dropwise fashion. The reaction was stirred for 4 h at room temperature. Ten (10) grams of Celite were added and the solvent was removed under reduced pressure. The residue was purified by silica gel (80 g) chromatography using dichloromethane/(methanol containing 12% (v/v) aqueous ammonium hydroxide) as mobile phase. The concentration of (methanol containing 12% (v/v) aqueous ammonium hydroxide) was gradually increased from 0% to 1.25% to afford N-(4-(4-((2-(2-methoxyethoxy)ethoxy)methyl)-1H-1,2,3-triazol-1-yl)benzyl)methacrylamide (7, 1.76 g, 85% yield) as a white solid. LCMS m/z: $[M+H]^+$ Calcd for $C_{19}H_{26}N_4O_4$ 375.2; Found 375.0.

Experimental Procedure for 3-(prop-2-yn-1-yloxy)oxetane (9)

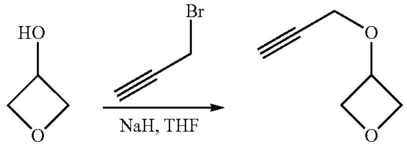

8 9

A suspension of sodium hydride (27.0 g, 675 mmol, 60% purity) in THE (200 mL) was cooled with an ice bath. Oexetan-3-ol (8, 25 g, 337 mmol) was added in a dropwise fashion and stirred for 30 minutes at 0° C. 3-Bromopropl-yne (9, 41.2 mL, 371 mmol, 80% purity) was then added in a dropwise fashion. The mixture was stirred over night while allowed to warm to room temperature. The mixture was filtered over Celite, washed with THF, and concentrated with Celite under reduced pressure. The crude product was purified over silica gel (220 g) and eluted with Hexanes/EtOAc. The concentration of EtOAc in the mobile phase was increased from 0 to 25% to afford a yellow oil of (9, 18.25 g 48%).

Experimental Procedure for 3-(4-((oxetan-3-yloxy) methyl)-1H-1,2,3-triazol-1-yl)propan-J-amine (11)

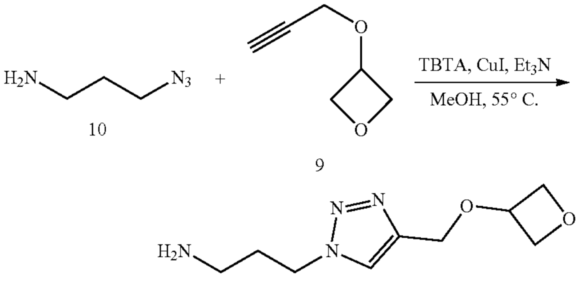

10 9 11

A mixture of 3-(prop-2-yn-1-yloxy)oxetane (9, 7.96 g, 71 mmol, 1.0 eq), 3-azidopropan-1-amine (10, 7.82 g, 78 mmol, 1.1 eq), Tris[(1-benzyl-1H-1,2,3-triazol-4-yl) methyl]-amine (8.29 g, 15.6 mmol, 0.22 eq), Copper Iodide (1.35 g, 7.1 mmol, 0.1 eq), and Triethylamine (2.47 mL, 17.8 mmol, 0.25 eq) in Methanol (80 mL) was warmed to 55° C. and stirred overnight under Nitrogen atmosphere. The reaction mixture was cooled to room temperature, Celite (20 g) was added, and concentrated under reduced pressure. The crude product was purified over silica gel (220 g) using dichloromethane/(methanol containing 12% (v/v) aqueous ammonium hydroxide) as mobile phase. The concentration of (methanol containing 12% (v/v) aqueous ammonium hydroxide) was gradually increased from 0% to 15% to afford 3-(4-((oxetan-3-yloxy)methyl)-1H-1,2,3-triazol-1-yl) propan-1-amine (11, 11.85 g, 79%) as a yellow oil. LCMS m/z: $[M+H]^+$ Calcd for $C_9H_{16}N_4O_2$ 213.1; Found 213.0.

Experimental Procedure for N-(3-(4-((oxetan-3-yloxy)methyl)-1H-1,2,3-triazol-1-yl)propyl)methacrylamide (12)

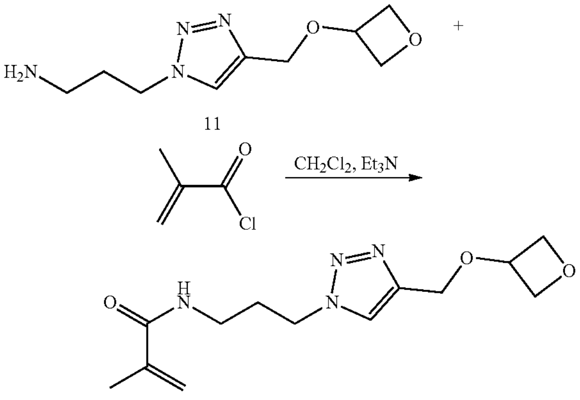

11 12

A solution of 3-(4-((oxetan-3-yloxy)methyl)-1H-1,2,3-triazol-1-yl)propan-1-amine (11, 3.94 g, 18.56 mmol, 1.0 eq) and triethylamine (3.1 mL, 22.28 mmol, 1.2 eq) in $CH_2Cl_2$ (100 mL) was cooled to 0° C. with an ice-bath and methacryloyl chloride (1.99 mL, 20.42 mmol, 1.1 eq) was added in a dropwise fashion. The reaction was stirred over night while allowed to warm to room temperature. 20 grams of Celite were added and the solvent was removed under reduced pressure. The residue was purified by silica gel chromatography (220 g) using dichloromethane/methanol as mobile phase. The concentration of methanol was gradually increased from 0% to 5% to afford N-(3-(4-((oxetan-3-yloxy)methyl)-1H-1,2,3-triazol-1-yl)propyl)methacrylamide (12, 3.22 g, 62% yield) as a solid. LCMS m/z: $[M+H]^+$ Calcd for $C_{13}H_{20}N_4O_3$ 281.2; Found 281.0.

Experimental Procedure for N-(4-(1H-1,2,3-triazol-1-yl)benzyl) methacrylamide (14)

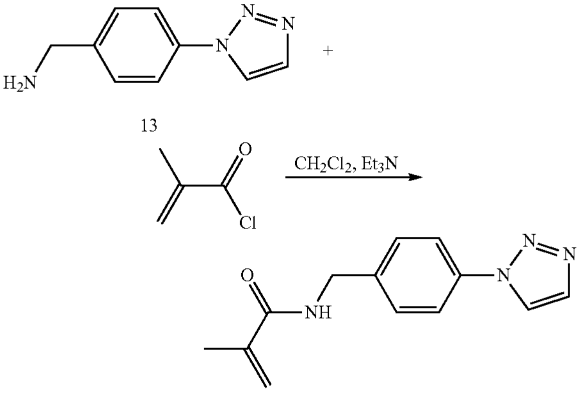

13 14

To a solution of (4-(1H-1,2,3-triazol-1-yl)phenyl)methanamine (13, obtained from WuXi, 1.2 g, 5.70 mmol, 1.0 eq) and triethylamine (15 mL, 107.55 mmol, 18.9 eq) in $CH_2Cl_2$ (100 mL) was slowly added methacryloyl chloride (893 mg, 8.54 mmol, 1.5 eq) in a dropwise fashion. The reaction was stirred overnight. 20 grams of Celite were added and the solvent was removed under reduced pressure. The residue was purified by silica gel chromatography using dichloromethane/(methanol containing 12% (v/v) aqueous ammonium hydroxide) as mobile phase. The concentration of (methanol containing 12% (v/v) aqueous ammonium hydroxide) was gradually increased from 0% to 1.25% to afford N-(4-(1H-1,2,3-triazol-1-yl)benzyl) methacrylamide (14, 1.38 g, 40% yield).

Experimental Procedure for (4-(4-(((tetrahydro-2H-pyran-2-yl)oxy)methyl)-1H-1,2,3-triazol-1-yl)phenyl)methanamine (15)

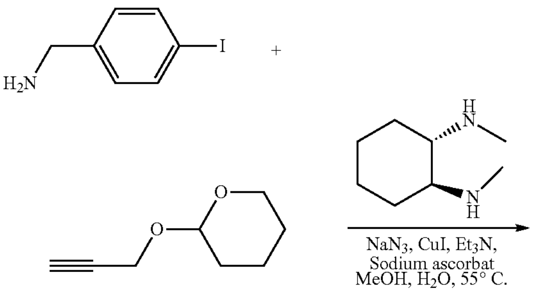

-continued

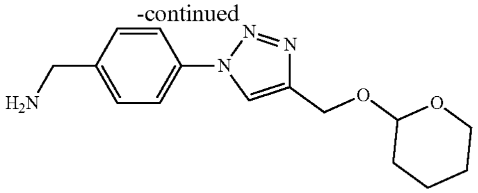

15

A mixture of (4-iodophenyl)methanamine hydrochloride (5.0 g, 18.55 mmol, 1.0 eq), (1S,2S)—N1,N2-dimethylcyclohexane-1,2-diamine (0.59 mL 3.71 mmol, 0.2 eq), Sodium ascorbate (368 mg, 1.86 mmol, 0.1 eq), Copper Iodide (530 mg, 2.78 mmol, 0.15 eq), Sodium azide (2.41 g, 37.1 mmol, 2.0 eq), $Et_3N$ (3.11 mL, 22.26 mmol, 1.2 eq) and 2-(prop-2-yn-1-yloxy)tetrahydro-2H-pyran (2.6 g, 18.55 mmol, 1.0 eq) in Methanol (50 mL) and water (12 mL) were purged with Nitrogen for 5 minutes and heated to 55° C. for overnight. The reaction mixture was cooled to room temperature and filtered through 413 filter paper. Celite was added and the solvent was removed under reduced pressure and the residue was purified over silica gel (120 g) using dichloromethane/(methanol containing 12% (v/v) aqueous ammonium hydroxide) as mobile phase. The concentration of (methanol containing 12% (v/v) aqueous ammonium hydroxide) was gradually increased from 0% to 6.25% to afford (4-(4-(((tetrahydro-2H-pyran-2-yl)oxy)methyl)-1H-1,2,3-triazol-1-yl)phenyl)methanamine (15, 3.54 g, 66%) as a white solid. LCMS m/z: $[M+H]^+$ Calcd for $C_{15}H_{20}N_4O_2$ 289.2; Found 289.2.

Experimental Procedure for N-(4-(4-(((tetrahydro-2H-pyran-2-yl)oxy)methyl)-1H-1,2,3-triazol-1-yl)benzyl)methacrylamide (16)

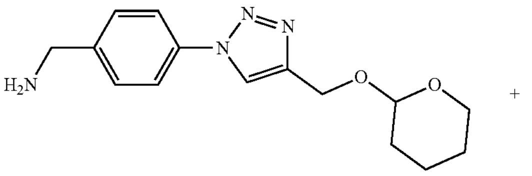

15

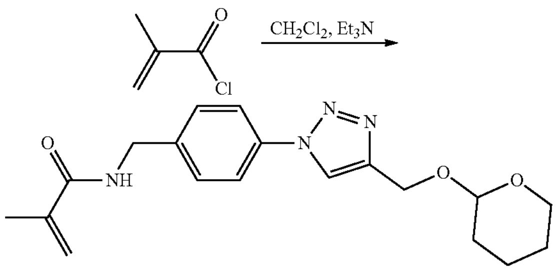

16

A solution of (4-(4-(((tetrahydro-2H-pyran-2-yl)oxy)methyl)-1H-1,2,3-triazol-1-yl)phenyl)methanamin (15, 3.46 g, 12.00 mmol, 1.0 eq) and triethylamine (2.01 mL, 14.40 mmol, 1.2 eq) in $CH_2Cl_2$ (40 mL) was cooled to 0° C. with an ice-bath and methacryloyl chloride (1.23 mL, 12.60 mmol, 1.05 eq, diluted in 5 mL of $CH_2Cl_2$) was added in a dropwise fashion. The cooling bath was removed and the reaction was stirred for 4 h. 20 grams of Celite was added and the solvent was removed under reduced pressure. The residue was purified by silica gel chromatography (80 g) using dichloromethane/(methanol containing 12% (v/v) aqueous ammonium hydroxide) as mobile phase. The concentration of (methanol containing 12% (v/v) aqueous ammonium hydroxide) was gradually increased from 0% to 3.75% to afford N-(4-(4-(((tetrahydro-2H-pyran-2-yl)oxy)methyl)-1H-1,2,3-triazol-1-yl)benzyl)methacrylamide (16, 2.74 g, 64% yield) as a white solid. LCMS m/z: $[M+H]^+$ Calcd for $C_{19}H_{24}N_4O_3$ 357.2; Found 357.3.

Experimental Procedure for N-(4-(4-(hydroxymethyl)-1H-1,2,3-triazol-1-yl)benzyl)methacrylamide (17)

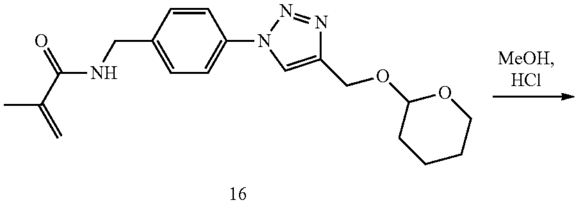

16

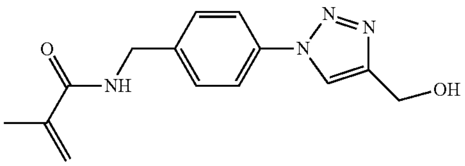

17

A solution of N-(4-(4-(hydroxymethyl)-1H-1,2,3-triazol-1-yl)benzyl)methacrylamide (16, 1.2 g, 3.37 mmol, 1.0 eq) was dissolved in Methanol (6 mL) and HCl (1N, aq., 9 mL) for overnight at room temperature. Celite was added and the solvent was removed under reduced pressure. The crude product was purified over silica gel chromatography (24 g) using dichloromethane/(methanol containing 12% (v/v) aqueous ammonium hydroxide) as mobile phase. The concentration of (methanol containing 12% (v/v) aqueous ammonium hydroxide) was gradually increased from 0% to 12.5% to afford N-(4-(4-(hydroxymethyl)-1H-1,2,3-triazol-1-yl)benzyl)methacrylamide (17, 0.85 g, 92% yield) as a white solid. LCMS m/z: $[M+H]^+$ Calcd for $C_{14}H_{16}N_4O_2$ 273.1; Found 273.1.

Experimental Procedure for (4-(((tetrahydro-2H-pyran-2-yl)oxy)methyl)benzyl)carbamate (19)

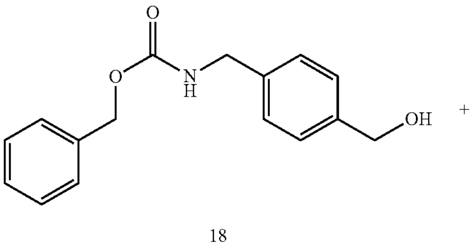

18

-continued

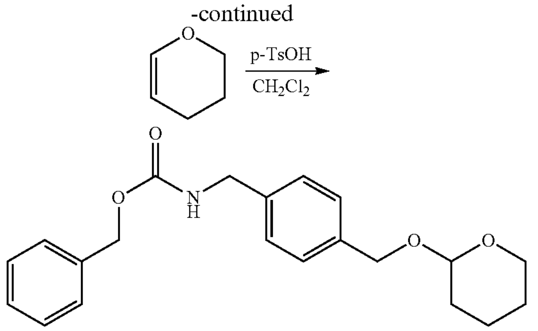

19

Benzyl (4-(hydroxymethyl)benzyl)carbamate (2.71 g, 10 mmol, 1 eq), 3,4-dihydro-2H-pyran (1.81 mL, 20 mmol, 2 eq), p-Toluenesulfonic acid monohydrate (285 mg, 1.5 mmol, 0.15 eq) in dichloromethane (100 mL) were stirred at room temperature overnight. Celite was added and the solvent was removed under reduced pressure. The crude product was purified over silica gel (24 g) using Hexanes/EtOAc as eluent starting at 100% Hexanes and increasing the concentration of EtOAc gradually to 100% to afford benzyl (4-(((tetrahydro-2H-pyran-2-yl)oxy)methyl)benzyl)-carbamate (19, 2.4 g, 68%) as a colorless oil. LCMS m/z: $[M+Na]^+$ Calcd for $C_{21}H_{25}NO_4$ 378.17 Found 378.17.

Experimental Procedure for (4-(((tetrahydro-2H-pyran-2-yl)oxy)methyl)-phenyl)methanamine (20)

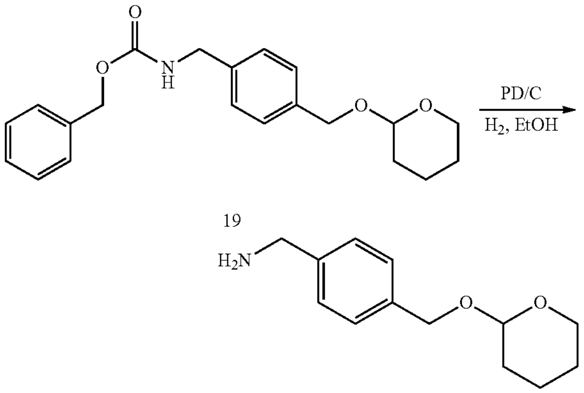

19

20

(4-(((tetrahydro-2H-pyran-2-yl)oxy)methyl)benzyl)carbamate (19, 1.5 g, 4.2 mmol, 1 eq), Palladium on carbon (160 mg, 10 wt. %) in EtOH was briefly evacuated and then Hydrogen was added via a balloon and the mixture was stirred for 1 hour at room temperature. Celite was added and the solvent was removed under reduced pressure. The crude product was purified over silica gel (12 g) using dichloromethane/(methanol containing 12% (v/v) aqueous ammonium hydroxide) as mobile phase. The concentration of (methanol containing 12% (v/v) aqueous ammonium hydroxide) was gradually increased from 0% to 25% to afford (4-(((tetrahydro-2H-pyran-2-yl)oxy)methyl)phenyl) methanamine (20, 890 mg, 95%) as a colorless oil. LCMS m/z: $[M+H]^+$ Calcd for $C_{13}H_{19}NO_2$ 222.15 Found 222.14.

Experimental Procedure for N-(4-(((tetrahydro-2H-pyran-2-yl)oxy)methyl)benzyl)-methacrylamide (21)

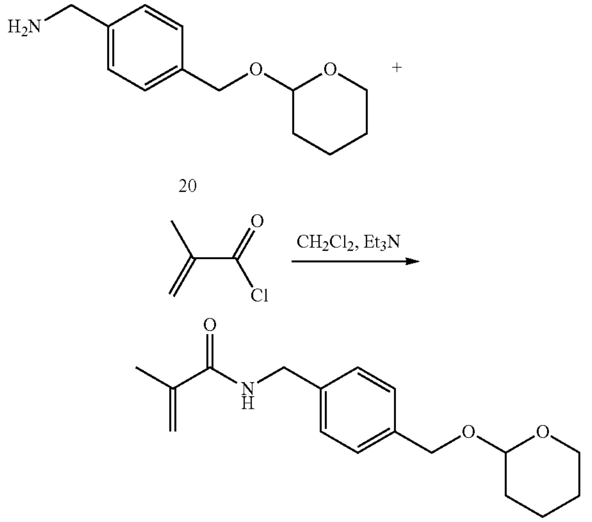

20

21

A solution of (4-(((tetrahydro-2H-pyran-2-yl)oxy)methyl) phenyl)methanamine (20, 0.5 g, 2.26 mmol, 1.0 eq) and triethylamine (0.47 mL, 3.39 mmol, 1.5 eq) in $CH_2Cl_2$ (10 mL) were briefly evacuated and flushed with Nitrogen. Methacryloyl chloride (0.33 mL, 3.39 mmol, 1.5 eq) was added in a dropwise fashion. The reaction mixture was stirred over night at room temperature. Ten (10) grams of Celite was added and the solvent was removed under reduced pressure. The residue was purified by silica gel chromatography (12 g) using Hexanes/EtOAc as eluent starting at 100% Hexanes and increasing the concentration of EtOAc gradually to 100% to afford N-(4-(((tetrahydro-2H-pyran-2-yl)oxy)methyl)benzyl)methacrylamide (21, 0.47 g, 72% yield) as a colorless solid. LCMS m/z: $[M+Na]^+$ Calcd for $C_{17}H_{23}NO_3$ 312.16; Found 312.17.

Experimental Procedure (4-(4-(2-((tetrahydro-2H-pyran-2-yl)oxy)ethyl)-1H-1,2,3-triazol-1-yl)phenyl) methanamine (22)

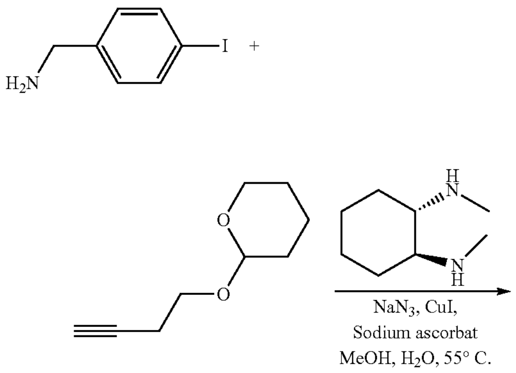

-continued

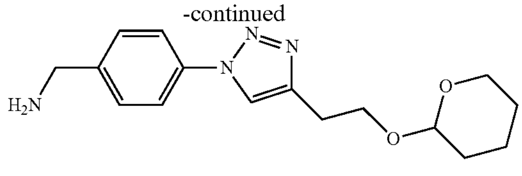

22

A mixture of (4-iodophenyl)methanamine (5.0 g, 21.45 mmol, 1.0 eq), (1S,2S)—N1,N2-dimethylcyclohexane-1,2-diamine (0.44 mL 2.79 mmol, 0.13 eq), Sodium ascorbate (425 mg, 2.15 mmol, 0.1 eq), Copper Iodide (409 mg, 2.15 mmol, 0.1 eq), Sodium azide (2.79 g, 42.91 mmol, 2.0 eq), and 2-(but-3-yn-1-yloxy)tetrahydro-2H-pyran (3.36 mL, 21.45 mmol, 1.0 eq) in Methanol (20 mL) and water (5 mL) were purged with Nitrogen for 5 minutes and heated to 55° C. for overnight. The reaction mixture was cooled to room temperature and filtered through 413 filter paper. Celite (10 g) was added and the solvent was removed under reduced pressure and the residue was purified over silica gel (220 g) using dichloromethane/(methanol containing 12% (v/v) aqueous ammonium hydroxide) as mobile phase. The concentration of (methanol containing 12% (v/v) aqueous ammonium hydroxide) was gradually increased from 0% to 5% to afford (4-(4-(2-((tetrahydro-2H-pyran-2-yl)oxy)ethyl)-1H-1,2,3-triazol-1-yl)phenyl)methanamine (22, 3.15 g, 49%) as a solid. LCMS m/z: $[M+H]^+$ Calcd for $C_{16}H_{22}N_4O_2$ 303.18; Found 303.18.

Experimental Procedure for N-(4-(4-(2-((tetrahydro-2H-pyran-2-yl)oxy)ethyl)-1H-1,2,3-triazol-1-yl)benzyl)methacrylamide (23)

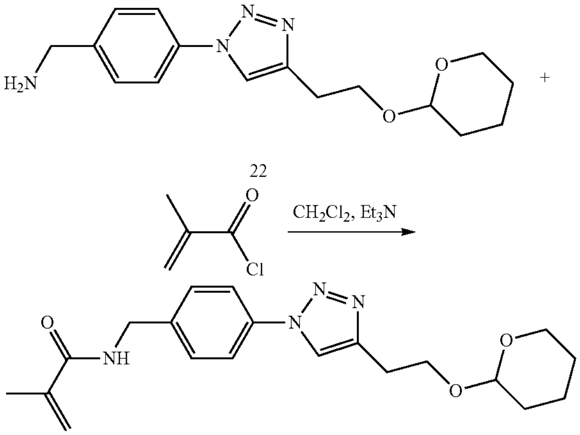

22

23

A solution of (4-(4-(2-((tetrahydro-2H-pyran-2-yl)oxy)ethyl)-1H-1,2,3-triazol-1-yl)phenyl)methanamine (22, 3.10 g, 10.25 mmol, 1.0 eq) and triethylamine (1.71 mL, 12.30 mmol, 1.2 eq) in $CH_2Cl_2$ (55 mL) was cooled to 0° C. with an ice-bath and methacryloyl chloride (1.05 mL, 12.30 mmol, 1.2 eq, diluted in 5 mL of $CH_2Cl_2$) was added in a dropwise fashion. The cooling bath was removed and the reaction was stirred for 4 h. 8 grams of Celite was added and the solvent was removed under reduced pressure. The residue was purified by silica gel chromatography (80 g) using dichloromethane/(methanol containing 12% (v/v) aqueous ammonium hydroxide) as mobile phase. The concentration of (methanol containing 12% (v/v) aqueous ammonium hydroxide) was gradually increased from 0% to 2.5% to afford N-(4-(4-(2-((tetrahydro-2H-pyran-2-yl)oxy)ethyl)-1H-1,2,3-triazol-1-yl)benzyl)methacrylamide (23, 2.06 g, 54% yield) as a white solid. LCMS m/z: $[M+H]^+$ Calcd for $C_{20}H_{26}N_4O_3$ 371.2078; Found 371.2085.

Experimental Procedure (4-(1-(2-((tetrahydro-2H-pyran-2-yl)oxy)ethyl)-1H-1,2,3-triazol-4-yl)phenyl) methanamine (24)

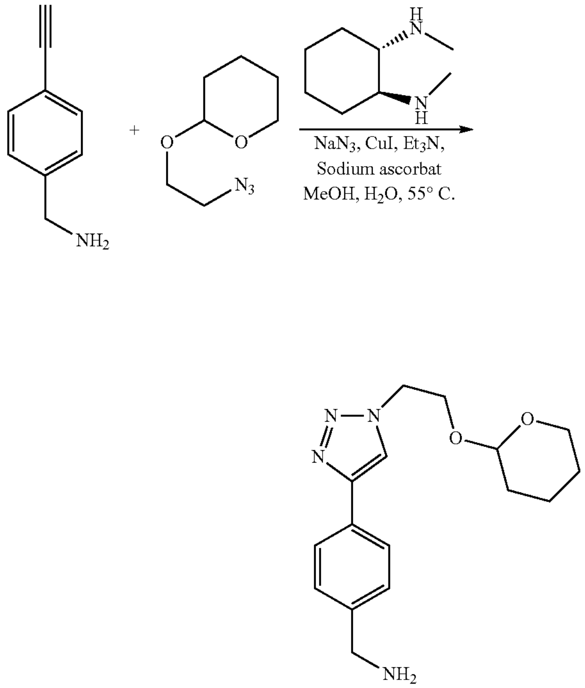

24

A mixture of (4-ethynylphenyl)methanamine (2.36 g, 18.00 mmol, 1.0 eq), (1S,2S)—N1,N2-dimethylcyclohexane-1,2-diamine (0.56 mL, 3.60 mmol, 0.2 eq), Sodium ascorbate (357 mg, 1.80 mmol, 0.1 eq), Copper Iodide (514 mg, 2.70 mmol, 0.15 eq), and 2-(2-azidoethoxy)tetrahydro-2H-pyran (3.08, 18.00 mmol, 1.0 eq) in Methanol (24 mL) and water (6 mL) were purged with Nitrogen for 5 minutes and heated to 55° C. for overnight. The reaction mixture was cooled to room temperature and filtered over Celite and rinsed with MeOH (3×50 mL). The solvent was removed under reduced pressure and the residue was redissolved in dichloromethane, Celite (20 g) was added and the solvent was removed under reduced pressure and the residue was purified over silica gel (120 g) using dichloromethane/(methanol containing 12% (v/v) aqueous ammonium hydroxide) as mobile phase. The concentration of (methanol containing 12% (v/v) aqueous ammonium hydroxide) was gradually increased from 0% to 25% to afford (4-(1-(2-((tetrahydro-2H-pyran-2-yl)oxy)ethyl)-1H-1,2,3-triazol-4-yl)phenyl)methanamine (24, 3.51 g, 64%) as a yellowish oil. LCMS m/z: $[M+H]^+$ Calcd for $C_{16}H_{22}N_4O_2$ 303.1816; Found 303.1814.

Experimental Procedure for N-(4-(1-(2-((tetrahydro-2H-pyran-2-yl)oxy)ethyl)-1H-1,2,3-triazol-4-yl)benzyl)methacrylamide (25)

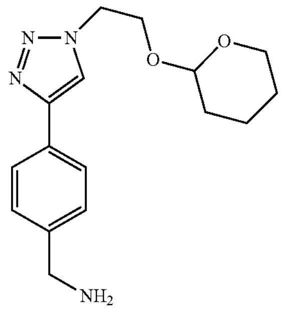

24

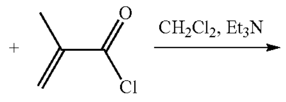

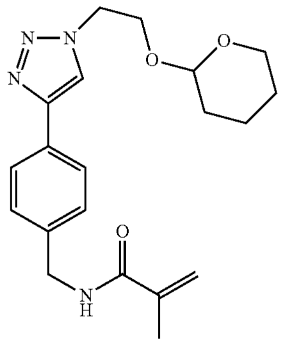

25

A solution of (4-(1-(2-((tetrahydro-2H-pyran-2-yl)oxy)ethyl)-1H-1,2,3-triazol-4-yl)phenyl)methanamine (24, 1.5 g, 4.96 mmol, 1.0 eq) and triethylamine (1.04 mL, 7.44 mmol, 1.5 eq) in $CH_2Cl_2$ (30 mL) were briefly evacuated and flushed with Nitrogen. Methacryloyl chloride (0.72 mL, 7.44 mmol, 1.5 eq) was added in a dropwise fashion. The reaction mixture was stirred for 2 h at room temperature. Ten (10) grams of Celite was added and the solvent was removed under reduced pressure. The residue was purified by silica gel chromatography (40 g) using Hexanes/EtOAc as eluent starting at 100% Hexanes and increasing the concentration of EtOAc gradually to 100% to afford N-(4-(1-(2-((tetrahydro-2H-pyran-2-yl)oxy)ethyl)-1H-1,2,3-triazol-4-yl)benzyl)methacrylamide (25, 0.9 g, 49% yield) as a colorless solid. LCMS m/z: $[M+Na]^+$ Calcd for $C_{20}H_{26}N_4O_3$ 371.2078; Found 371.2076.

Experimental Procedure for 1-(4-(4-(((tetrahydro-2H-pyran-2-yl)oxy)methyl)-1H-1, 2, 3-triazol-1-yl) phenyl)ethan-1-amine (26)

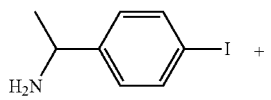

-continued

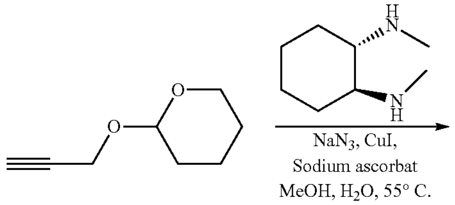

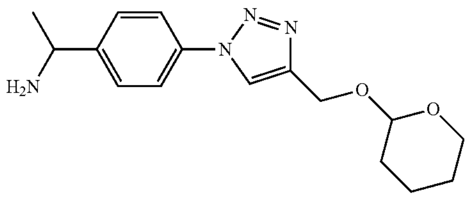

26

A mixture of 1-(4-iodophenyl)ethan-1-amine hydrochloride (1.0 g, 4.05 mmol, 1.0 eq), (1S,2S)—N1,N2-dimethylcyclohexane-1,2-diamine (0.08 mL 0.53 mmol, 0.13 eq), Sodium ascorbate (80 mg, 0.40 mmol, 0.1 eq), Copper Iodide (77 mg, 0.40 mmol, 0.1 eq), Sodium azide (526 g, 8.09 mmol, 2.0 eq), and 2-(prop-2-yn-1-yloxy)tetrahydro-2H-pyran (0.57 g, 4.05 mmol, 1.0 eq) in Methanol (9 mL) and water (1 mL) were purged with Nitrogen for 5 minutes and heated to 55° C. for overnight. The reaction mixture was cooled to room temperature and the solvent was removed under reduced pressure. The residue was redissolved in dichloromethane and filtered over a plug of Celite. Celite was added to the filtrate and the solvent was removed under reduced pressure. The residue was purified over silica gel (40 g) using dichloromethane/(methanol containing 12% (v/v) aqueous ammonium hydroxide) as mobile phase. The concentration of (methanol containing 12% (v/v) aqueous ammonium hydroxide) was gradually increased from 0% to 5% to afford 1-(4-(4-(((tetrahydro-2H-pyran-2-yl)oxy)methyl)-1H-1,2,3-triazol-1-yl)phenyl)ethan-1-amine (26, 0.62 g, 51%) as a yellowish solid. LCMS m/z: $[M+H]^+$ Calcd for $C_{16}H_{22}N_4O_2$ 303.2; Found 303.2.

Experimental Procedure for N-(1-(4-(4-(((tetrahydro-2H-pyran-2-yl)oxy) methyl)-1H-1,2,3-triazol-1-yl)phenyl)ethyl)methacrylamide (27)

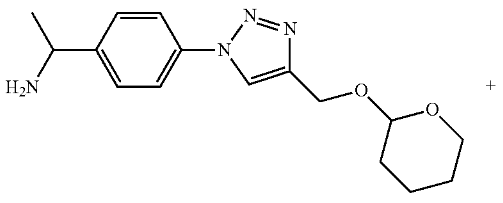

26

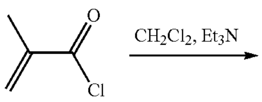

-continued

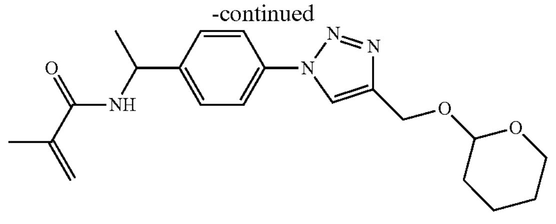

27

A solution of 1-(4-(4-(((tetrahydro-2H-pyran-2-yl)oxy)methyl)-1H-1,2,3-triazol-1-yl)phenyl)ethan-1-amine (26, 0.52 g, 1.7 mmol, 1.0 eq) and triethylamine (0.29 mL, 2.1 mmol, 1.2 eq) in $CH_2Cl_2$ (11 mL) was cooled to 0° C. with an ice-bath and methacryloyl chloride (0.18 mL, 1.8 mmol, 1.05 eq, diluted in 11 mL of $CH_2Cl_2$) was added in a dropwise fashion. The cooling bath was removed and the reaction was stirred for 4 h. Five (5) grams of Celite was added and the solvent was removed under reduced pressure. The residue was purified by silica gel chromatography (40 g) using dichloromethane/(methanol containing 12% (v/v) aqueous ammonium hydroxide) as mobile phase. The concentration of (methanol containing 12% (v/v) aqueous ammonium hydroxide) was gradually increased from 0% to 2.5% to afford N-(1-(4-(4-(((tetrahydro-2H-pyran-2-yl)oxy)methyl)-1H-1,2,3-triazol-1-yl)phenyl)ethyl)methacrylamide (27, 0.49 g, 76% yield) as a white solid. LCMS m/z: $[M+H]^+$ Calcd for $C_{20}H_{26}N_4O_3$ 371.2078; Found 371.2087.

Experimental Procedure for (4-(4-(((tetrahydro-2H-pyran-2-yl)oxy)methyl)-1H-1,2,3-triazol-1-yl)-2-(trifluoromethyl)phenyl)methanamine (28)

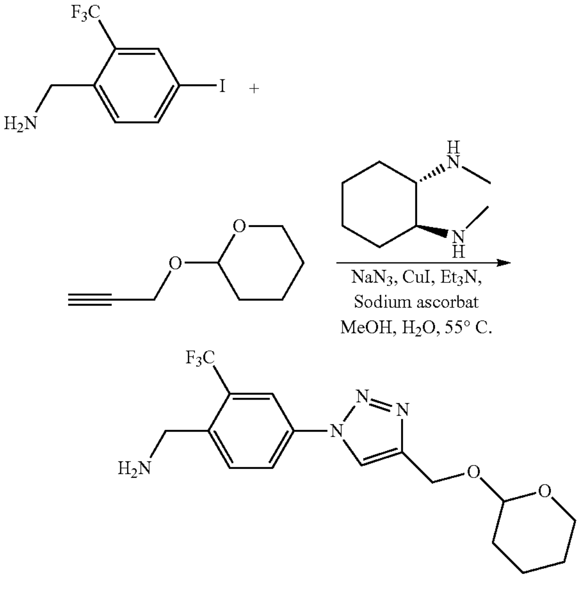

28

A mixture of (4-iodo-2-(trifluoromethyl)phenyl)methanamine (3.0 g, 9.97 mmol, 1.0 eq), (1S,2S)—N1,N2-dimethylcyclohexane-1,2-diamine (0.31 mL 1.99 mmol, 0.2 eq), Sodium ascorbate (197 mg, 1.00 mmol, 0.1 eq), Copper Iodide (285 mg, 1.49 mmol, 0.15 eq), Sodium azide (1.30 g, 19.93 mmol, 2.0 eq), $Et_3N$ (1.67 mL, 11.96 mmol, 1.2 eq) and 2-(prop-2-yn-1-yloxy)tetrahydro-2H-pyran (1.40 g, 9.97 mmol, 1.0 eq) in Methanol (24 mL) and water (6 mL) were purged with Nitrogen for 5 minutes and heated to 55° C. for overnight. The reaction mixture was cooled to room temperature and filtered through a plug of Celite and rinsed with Methanol (3×50 mL). Celite was added to the filtrate and the solvent was removed under reduced pressure. The residue was purified over silica gel (120 g) using dichloromethane/(methanol containing 12% (v/v) aqueous ammonium hydroxide) as mobile phase. The concentration of (methanol containing 12% (v/v) aqueous ammonium hydroxide) was gradually increased from 0% to 25% to afford (4-(4-(((tetrahydro-2H-pyran-2-yl)oxy)methyl)-1H-1,2,3-triazol-1-yl)-2-(trifluoromethyl)phenyl)methanamine (28, 2.53 g, 71%) as a green oil. LCMS m/z: $[M+H]^+$ Calcd for $C_{16}H_{19}N_4O_2F_3$ 357.2; Found 357.1.

Experimental Procedure for N-(4-(4-(((tetrahydro-2H-pyran-2-yl)oxy)methyl)-1H-1,2,3-triazol-1-yl)-2 (trifluoromethyl)benzyl) methacrylamide (29)

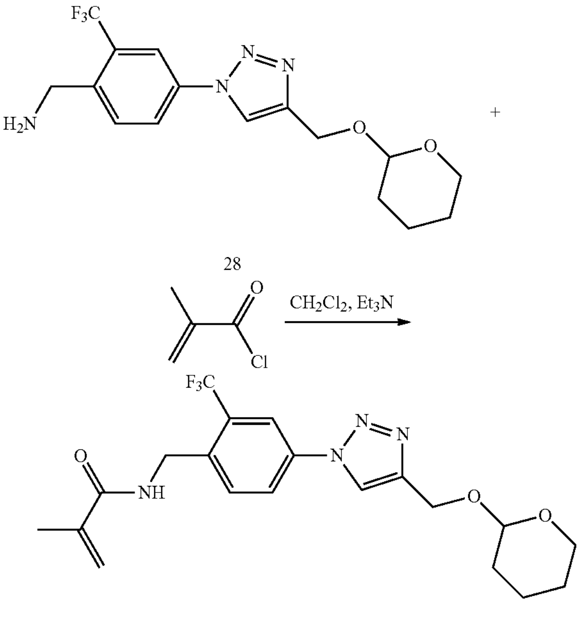

29

A solution of (4-(4-(((tetrahydro-2H-pyran-2-yl)oxy)methyl)-1H-1,2,3-triazol-1-yl)-2-(trifluoromethyl)phenyl)methanamine (28, 1.0 g, 2.81 mmol, 1.0 eq) and triethylamine (0.59 mL, 4.21 mmol, 1.5 eq) in $CH_2Cl_2$ (25 mL) were briefly evacuated and flushed with Nitrogen. Methacryloyl chloride (0.41 mL, 4.21 mmol, 1.5 eq) was added in a dropwise fashion. The reaction mixture was stirred for 6 h at room temperature. Ten (10) grams of Celite was added and the solvent was removed under reduced pressure. The residue was purified by silica gel chromatography (40 g) using Hexanes/EtOAc as eluent starting at 100% Hexanes and increasing the concentration of EtOAc gradually to 100% to afford N-(4-(4-(((tetrahydro-2H-pyran-2-yl)oxy)methyl)-1H-1,2,3-triazol-1-yl)-2(trifluoromethyl)benzyl) methacrylamide (29, 0.65 g, 55% yield) as a colorless solid. LCMS m/z: $[M+H]^+$ Calcd for $C_{20}H_{23}N_4O_3F_3$ 425.2; Found 425.1.

Experimental Procedure for 3-(4-(((tetrahydro-2H-pyran-2-yl)oxy)methyl)-1H-1,2,3-triazol-1-yl)propan-1-amine (30)

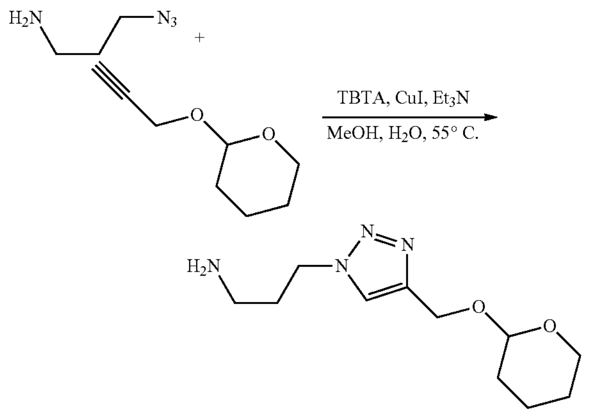

30

A mixture of 3-azidopropan-1-amine hydrochloride (1.5 g, 14.98 mmol, 1.0 eq), Tris[(1-benzyl-1H-1,2,3-triazol-4-yl)methyl]-amine (1.99 g, 3.75 mmol, 0.25 eq), Copper Iodide (0.29 g, 1.50 mmol, 0.1 eq), and Triethylamine (0.52 mL, 3.75 mmol, 0.25 eq) in Methanol (50 mL) and water (6 mL) were purged with Nitrogen for 5 minutes and cooled to 0° C. 2-(prop-2-yn-1-yloxy)tetrahydro-2H-pyran (2.10 g, 14.98 mmol, 1.0 eq) was added and the reaction mixture was warmed to 55° C. and stirred overnight under Nitrogen atmosphere. The reaction mixture was cooled to room temperature, filtered over a plug of Celite and rinsed with Methanol (3×50 mL). Celite (20 g) was added to the filtrate the solvent was removed under reduced pressure. The residue was purified over silica gel (120 g) using dichloromethane/(methanol containing 12% (v/v) aqueous ammonium hydroxide) as mobile phase. The concentration of (methanol containing 12% (v/v) aqueous ammonium hydroxide) was gradually increased from 0% to 20% to afford 3-(4-(((tetrahydro-2H-pyran-2-yl)oxy)methyl)-1H-1,2,3-triazol-1-yl)propan-1-amine (30, 2.36 g, 66%). LCMS m/z: $[M+H]^+$ Calcd for $C_{11}H_{20}N_4O_2$ 241.2; Found 241.2.

Experimental Procedure for N-(3-(4-(((tetrahydro-2H-pyran-2-yl)oxy)methyl)-1H-1,2,3-triazol-1-yl)propyl)methacrylamide (31)

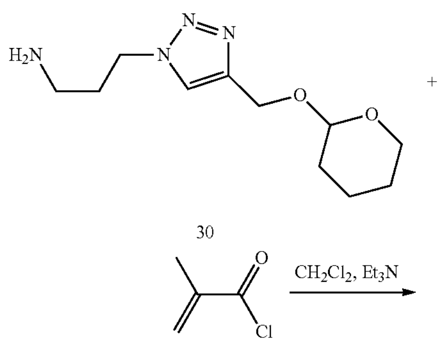

-continued

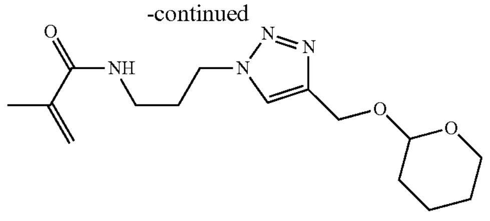

31

A solution of 3-(4-(((tetrahydro-2H-pyran-2-yl)oxy)methyl)-1H-1,2,3-triazol-1-yl)propan-1-amine (30, 1.0 g, 4.16 mmol, 1.0 eq) and triethylamine (0.58 mL, 4.16 mmol, 1.0 eq) in $CH_2Cl_2$ (20 mL) were briefly evacuated and flushed with Nitrogen. Methacryloyl chloride (0.40 mL, 4.16 mmol, 1.0 eq) was added in a dropwise fashion. The reaction mixture was stirred at room temperature overnight. Ten (10) grams of Celite was added and the solvent was removed under reduced pressure. The residue was purified by silica gel chromatography (40 g) using dichloromethane/(methanol containing 12% (v/v) aqueous ammonium hydroxide) as mobile phase. The concentration of (methanol containing 12% (v/v) aqueous ammonium hydroxide) was gradually increased from 0% to 20% to afford N-(3-(4-(((tetrahydro-2H-pyran-2-yl)oxy)methyl)-1H-1,2,3-triazol-1-yl)propyl)methacrylamide (31, 0.96 g, 75% yield) as a colorless oil. LCMS m/z: $[M+H]^+$ Calcd for $C_{15}H_{24}N_4O_3$ 309.2; Found 309.4.

Experimental Procedure for (4-(4-((oxetan-3-yloxy)methyl)-1H-1,2,3-triazol-1-yl)phenyl)methanamine (32)

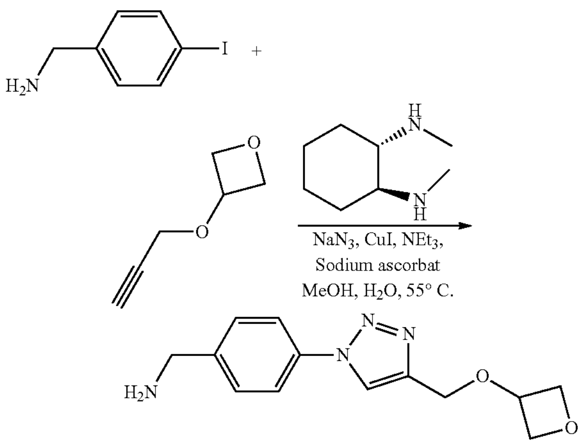

32

A mixture of (4-iodophenyl)methanamine hydrochloride (2.64 g, 9.80 mmol, 1.0 eq), (1S,2S)—N1,N2-dimethylcyclohexane-1,2-diamine (0.31 mL 1.96 mmol, 0.2 eq), Sodium ascorbate (198 mg, 0.98 mmol, 0.1 eq), Copper Iodide (279 mg, 1.47 mmol, 0.15 eq), Sodium azide (1.27 g, 19.59 mmol, 2.0 eq), $Et_3N$ (1.64 mL, 11.75 mmol, 1.2 eq) and 3-(prop-2-yn-1-yloxy)oxetane (9, 1.10 g, 9.80 mmol, 1.0 eq) in Methanol (24 mL) and water (6 mL) were purged with Nitrogen for 5 minutes and heated to 55° C. for overnight. The reaction mixture was cooled to room temperature and filtered through a plug of Celite and rinsed with Methanol (3×50 mL). Celite was added to the filtrate and the solvent was removed under reduced pressure. The residue was purified over silica gel (120 g) using dichloromethane/(methanol containing 12% (v/v) aqueous ammonium hydroxide) as mobile phase. The concentration of (methanol containing 12% (v/v) aqueous ammonium hydroxide) was gradually increased from 0% to 25% to afford (4-(4-((oxetan-3-yloxy)methyl)-1H-1,2,3-triazol-1-yl)phenyl) methanamine (32, 1.43 g, 56%) as an oil. LCMS m/z: $[M+H]^+$ Calcd for $C_{13}H_{16}N_4O_2$ 261.1346; Found 261.1342.

Experimental Procedure for N-(4-(4-((oxetan-3-yloxy)methyl)-1H-1,2,3-triazol-1-yl)benzyl)methacrylamide (33)

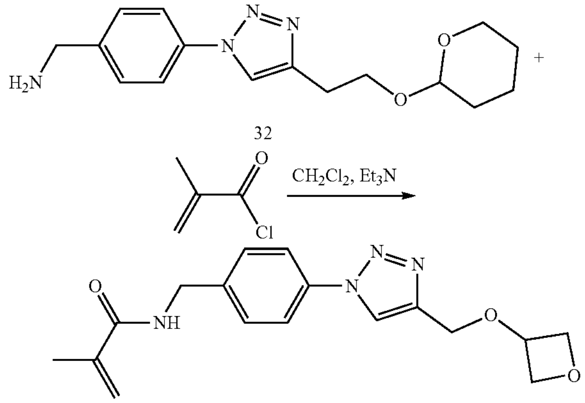

32

33

A solution of (4-(4-((oxetan-3-yloxy)methyl)-1H-1,2,3-triazol-1-yl)phenyl)methanamine (32, 0.58 g, 2.23 mmol, 1.0 eq) and triethylamine (0.47 mL, 3.34 mmol, 1.5 eq) in $CH_2Cl_2$ (20 mL) were briefly evacuated and flushed with Nitrogen. Methacryloyl chloride (0.32 mL, 3.34 mmol, 1.5 eq) was added in a dropwise fashion. The reaction mixture was stirred for 6 h at room temperature. Ten (10) grams of Celite was added and the solvent was removed under reduced pressure. The residue was purified by silica gel chromatography (24 g) using Hexanes/EtOAc as eluent starting at 100% Hexanes and increasing the concentration of EtOAc gradually to 100% to afford N-(4-(4-((oxetan-3-yloxy)methyl)-1H-1,2,3-triazol-1-yl)benzyl)methacrylamide (33, 0.48 g, 66% yield) as a colorless solid. LCMS m/z: $[M+H]^+$ Calcd for $C_{17}H_{20}N_4O_3$ 329.1608; Found 329.1611.

Experimental Procedure for ethyl 1-(2-methacrylamidoethyl)-1H-imidazole-4-carboxylate (35)

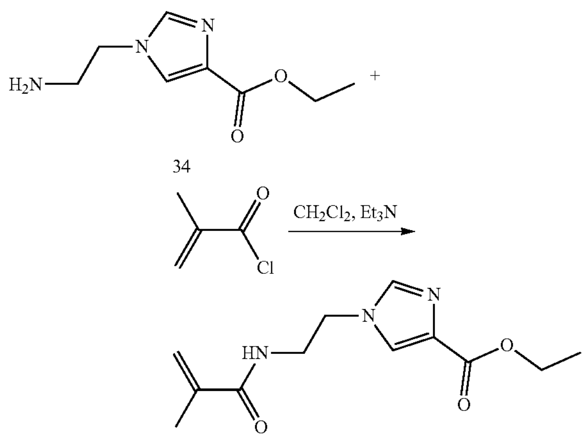

34

35

A solution of ethyl 1-(2-aminoethyl)-1H-imidazole-4-carboxylate (34, 2.0 g, 10.91 mmol, 1.0 eq) and triethylamine (3.80 mL, 27.29 mmol, 2.5 eq) in $CH_2Cl_2$ (20 mL) were briefly evacuated and flushed with Nitrogen. Methacryloyl chloride (1.60 mL, 16.37 mmol, 1.5 eq) was added in a dropwise fashion. The reaction mixture was stirred for 3 h at room temperature. Fifteen (15) grams of Celite was added and the solvent was removed under reduced pressure. The residue was purified by silica gel chromatography (40 g) using dichloromethane/(methanol containing 12% (v/v) aqueous ammonium hydroxide) as mobile phase. The concentration of (methanol containing 12% (v/v) aqueous ammonium hydroxide) was gradually increased from 0% to 25% to afford ethyl 1-(2-methacrylamidoethyl)-1H-imidazole-4-carboxylate (35, 1.28 g, 47% yield) as a colorless solid. LCMS m/z: $[M+H]^+$ Calcd for $C_{12}H_{17}N_3O_3$ 252.1; Found 252.1.

Experimental Procedure for N-(4-(1,1-dioxidothiomorpholino)benzyl) methacrylamide (37)

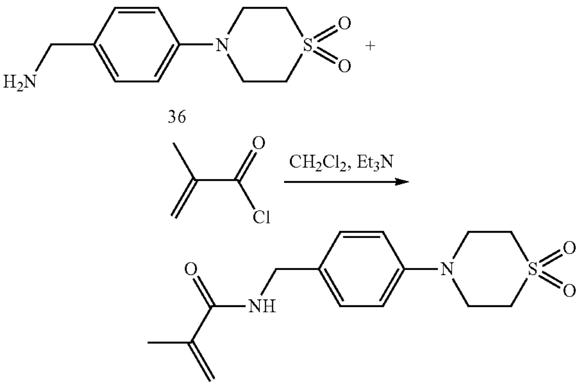

36

37

To a solution of 4-(4-(aminomethyl)phenyl)thiomorpholine 1,1-dioxide hydrochloride (36, 1.15 g, 4.15 mmol, 1.0 eq) and triethylamine (1.39 mL, 9.97 mmol, 2.4 eq) in $CH_2Cl_2$ (80 mL) was added a solution of methacryloyl chloride (0.43 mL, 4.36 mmol, 1.05 eq, in $CH_2Cl_2$, 5 mL) in a dropwise fashion. The reaction mixture was stirred for 22 h at room temperature. Eight (8) grams of Celite was added and the solvent was removed under reduced pressure. The residue was purified by silica gel chromatography (80 g) using dichloromethane/(methanol containing 12% (v/v) aqueous ammonium hydroxide) as mobile phase. The concentration of (methanol containing 12% (v/v) aqueous ammonium hydroxide) was gradually increased from 0% to 3.75% to afford N-(4-(1,1-dioxidothiomorpholino)benzyl) methacrylamide (37, 0.32 g, 25% yield) as a solid.

Experimental Procedure for N-methyl-N-(2-(methylsulfonyl)ethyl)prop-2-yn-1-amine (38)

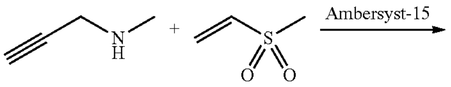

-continued

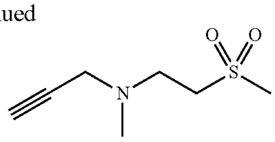

38

To a mixture of 1-methylsulfonylethylene (4.99 g, 47.03 mmol, 4.13 mL) and Amberlyst-15 ((30% w/w)), N-methylprop-2-yn-1-amine (2.6 g, 37.62 mmol) was added in a dropwise fashion. The mixture was stirred at room temperature for 12 hours. The catalyst was removed by filtration and the filtrate was concentrated under reduced pressure to afford: N-methyl-N-(2-(methylsulfonyl)ethyl)prop-2-yn-1-amine (38, 6.43 g, 98%) as an oil. LCMS m/z: $[M+H]^+$ Calcd for $C_7H_{13}NSO_2$ 176.11; Found 176.1.

Experimental Procedure for N-((1-(2-(2-(2-(2-aminoethoxy)ethoxy)ethoxy) ethyl)-1H-1,2,3-triazol-4-yl)methyl)-N-methyl-2-(methylsulfonyl)ethan-1-amine (40)

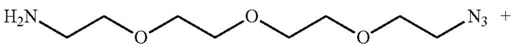

39

A mixture of N-methyl-N-(2-(methylsulfonyl)ethyl)prop-2-yn-1-amine (38, 5.02 g, 28.64 mmol, 1.25 eq), Tris[(1-benzyl-1H-1,2,3-triazol-4-yl)methyl]-amine (3.04 g, 5.73 mmol, 0.25 eq), Copper Iodide (436 mg, 2.29 mmol, 0.1 eq), and Triethylamine (0.8 mL, 5.7 mmol, 0.25 eq) in Methanol (50 mL) and water (6 ml) was evacuated and flushed with Nitrogen (3 times) and cooled with an ice bath. 2-(2-(2-(2-azidoethoxy)ethoxy)ethoxy)ethan-1-amine (39, 5.02 g, 22.91 mmol, 1.0 eq) was added in a dropwise fashion, the cooling bath was removed and the mixture was stirred for 5 minutes. The reaction was warmed to 55° C. and stirred overnight under Nitrogen atmosphere. The reaction mixture was cooled to room temperature, Celite (20 g) was added, and concentrated under reduced pressure. The crude product was purified over silica gel (220 g) using dichloromethane/(methanol containing 12% (v/v) aqueous ammonium hydroxide) as mobile phase. The concentration of (methanol containing 12% (v/v) aqueous ammonium hydroxide) was gradually increased from 0% to 25% to afford N-((1-(2-(2-(2-(2-aminoethoxy)ethoxy)ethoxy)ethyl)-1H-1,2,3-triazol-4-yl)methyl)-N-methyl-2-(methylsulfonyl)ethan-1-amine (40, 4.98 g, 55%) as an oil. LCMS m/z: $[M+H]^+$ Calcd for $C_{15}H_{31}N_5O_5S$ 394.2; Found 394.2.

Experimental Procedure N-(2-(2-(2-(2-(4-((methyl (2-(methylsulfonyl)ethyl) amino)methyl)-1H-1,2,3-triazol-1-yl)ethoxy)ethoxy)ethoxy) ethyl)methacrylamide (41)

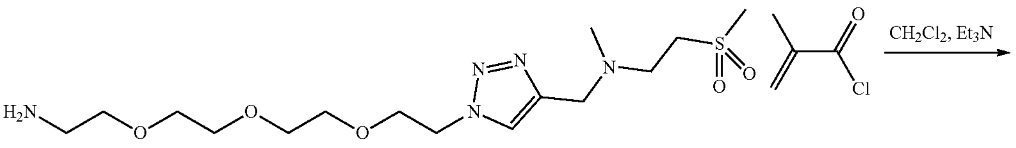

40

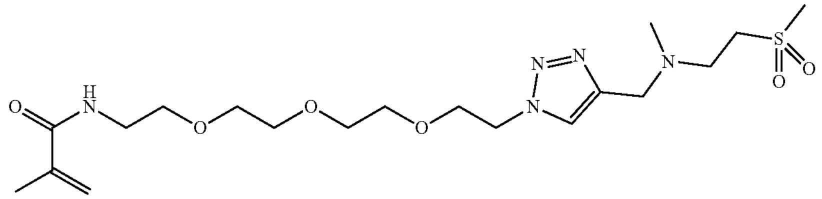

41

-continued

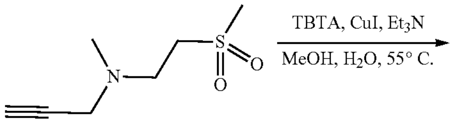

38

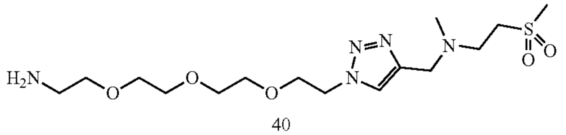

40

To a solution of N-((1-(2-(2-(2-(2-aminoethoxy)ethoxy) ethoxy)ethyl)-1H-1,2,3-triazol-4-yl)methyl)-N-methyl-2-(methylsulfonyl)ethan-1-amine (40, 1.0 g, 2.54 mmol, 1.0 eq) and triethylamine (0.43 mL, 3.05 mmol, 1.2 eq) in $CH_2Cl_2$ (15 mL) was added a solution of methacryloyl chloride (0.30 mL, 3.05 mmol, 1.5 eq) in a dropwise fashion. The reaction mixture was stirred for 5 h at room temperature. Celite was added and the solvent was removed under reduced pressure. The residue was purified by silica gel chromatography (40 g) using dichloromethane/(methanol containing 12% (v/v) aqueous ammonium hydroxide) as mobile phase. The concentration of (methanol containing 12% (v/v) aqueous ammonium hydroxide) was gradually increased from 0% to 12.5% to afford N-(2-(2-(2-(2-(4-((methyl(2-(methylsulfonyl)ethyl) amino)methyl)-1H-1,2, 3-triazol-1-yl)ethoxy)ethoxy)ethoxy) ethyl)methacrylamide (41, 0.86 g, 73% yield) as an oil. LCMS m/z: $[M+H]^+$ Calcd for $C_{19}H_{35}N_5O_6S$ 462.2; Found 462.2.

Experimental Procedure for 7-(prop-2-yn-1-yl)-2-oxa-7-azaspiro[3.5]nonane (42)

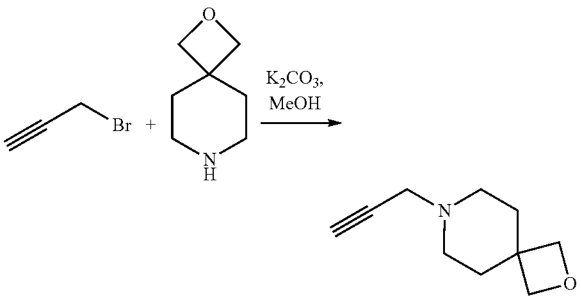

42

3-Bromoprop-1-yne (4.4 mL, 39.32 mmol 1.0 eq) was added to a mixture of 2-oxa-7-azaspiro[3.5]nonane (8.54 g, 39.32 mmol, 1.0 eq), potassium carbonate (17.9 g, 129.7 mmol, 3.3 eq) in Methanol (200 mL) and stirred over night at room temperature. The mixture was filtered, Celite was added and the solvent was removed under reduced pressure. The residue was purified by silica gel chromatography (220 g) using dichloromethane/methanol as mobile phase. The concentration of methanol was gradually increased from 0% to 5% to afford 7-(prop-2-yn-1-yl)-2-oxa-7-azaspiro[3.5] nonane (42, 4.44 g, 68%) as an oil.

Experimental Procedure for 2-(2-(2-(2-(4-((2-oxa-7-azaspiro[3.5]nonan-7-yl) methyl)-1H-1, 2, 3-triazol-1-yl)ethoxy)ethoxy)ethoxy)ethan-1-amine (43)

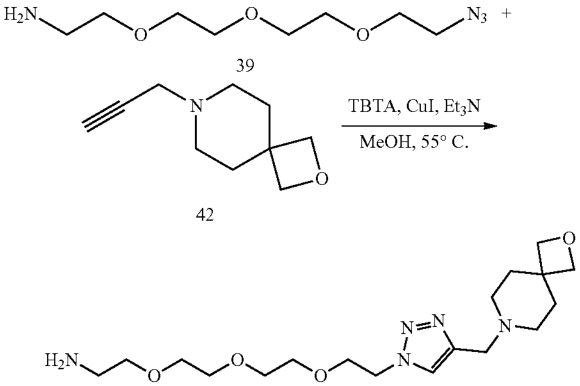

43

A mixture of 7-(prop-2-yn-1-yl)-2-oxa-7-azaspiro[3.5] nonane (42, 2.5 g, 15.13 mmol, 1.0 eq), Tris[(1-benzyl-1H-1,2,3-triazol-4-yl)methyl]-amine (1.77 g, 3.33 mmol, 0.22 eq), Copper Iodide (288 mg, 1.51 mmol, 0.1 eq), and Triethylamine (0.53 mL, 3.8 mmol, 0.25 eq) in Methanol (50 mL) was cooled with an ice bath. 2-(2-(2-(2-azidoethoxy) ethoxy)ethoxy)ethan-1-amine (39, 3.86 g, 17.70 mmol, 1.17 eq) was added in a dropwise fashion, the cooling bath was removed and the mixture was stirred for 5 minutes. The reaction was warmed to 55° C. and stirred overnight under Nitrogen atmosphere. The reaction mixture was cooled to room temperature, Celite (10 g) was added, and concentrated under reduced pressure. The crude product was purified over silica gel (220 g) using dichloromethane/(methanol containing 12% (v/v) aqueous ammonium hydroxide) as mobile phase. The concentration of (methanol containing 12% (v/v) aqueous ammonium hydroxide) was gradually increased from 0% to 10% to afford for 2-(2-(2-(2-(4-((2-oxa-7-azaspiro[3.5]nonan-7-yl) methyl)-1H-1,2,3-triazol-1-yl)ethoxy)ethoxy)ethoxy)ethan-1-amine (43, 4.76 g, 82%) as an oil. LCMS m/z. $[M+H]^+$ Calcd for $C_{18}H_{33}N_5O_4$ 384.3; Found 384.2.

Experimental Procedure for N-(2-(2-(2-(2-(4-((2-oxa-7-azaspiro[3.5]nonan-7-yl)methyl)-1H-1,2,3-triazol-J-yl)ethoxy)ethoxy)ethoxy)ethyl)methacrylamide (44)

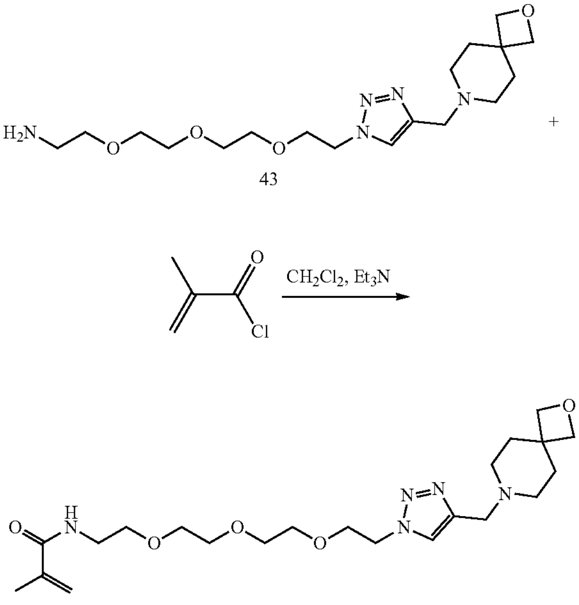

44

A solution of 2-(2-(2-(2-(4-((2-oxa-7-azaspiro[3.5]nonan-7-yl) methyl)-1H-1,2,3-triazol-1-yl)ethoxy)ethoxy)ethoxy) ethan-1-amine (43, 2.65 g, 6.91 mmol, 1.0 eq) and triethylamine (1.16 mL, 8.29 mmol, 1.2 eq) in $CH_2Cl_2$ (100 mL) was cooled with an ice-bath under Nitrogen atmosphere. Methacryloyl chloride (0.74 mL, 7.6 mmol, 1.1 eq) was added in a dropwise fashion. The cooling bath was removed and the reaction mixture was stirred for 4 h at room temperature. Ten (10) grams of Celite was added and the solvent was removed under reduced pressure. The residue was purified by silica gel chromatography (120 g) using dichloromethane/methanol as mobile phase. The concentration of methanol was gradually increased from 0% to 10% to afford N-(2-(2-(2-(2-(4-((2-oxa-7-azaspiro[3.5]nonan-7-yl)methyl)-1H-1,2,3-triazol-1-yl)ethoxy)ethoxy)ethoxy) ethyl)methacrylamide (44, 1.50 g, 48% yield) as a colorless oil. LCMS m/z: $[M+H]^+$ Calcd for $C_{22}H_{37}N_5O_5$ 452.29; Found 452.25.

Experimental Procedure for 4-((1-(2-(2-aminoethoxy)ethyl)-1H-1,2,3-triazol-4-yl)methyl)thiomorpholine 1,1-dioxide (45)

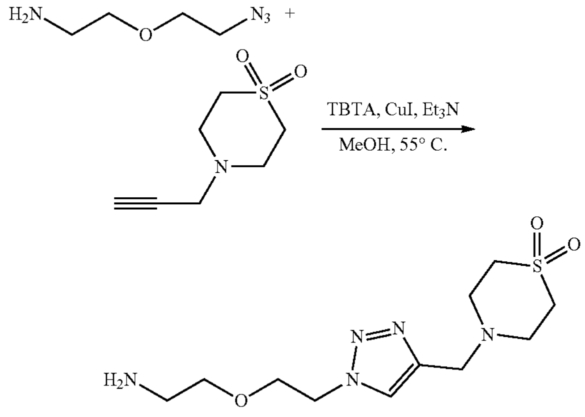

45

A mixture of 4-(prop-2-yn-1-yl)thiomorpholine 1,1-dioxide (1.14 g, 6.58 mmol, 1.0 eq), Tris[(1-benzyl-1H-1,2,3-triazol-4-yl)methyl]-amine (768 mg, 1.45 mmol, 0.22 eq), Copper Iodide (125 mg, 0.66 mmol, 0.1 eq), and Triethylamine (0.23 mL, 1.65 mmol, 0.25 eq) in Methanol (20 mL) was cooled with an ice bath. 2-(2-azidoethoxy)ethan-1-amine (1.00 g, 7.70 mmol, 1.17 eq) was added in a dropwise fashion, the cooling bath was removed and the mixture was stirred for 5 minutes. The reaction was warmed to 55° C. and stirred overnight under Nitrogen atmosphere. The reaction mixture was cooled to room temperature, Celite (10 g) was added, and concentrated under reduced pressure. The crude product was purified over silica gel (40 g) using dichloromethane/(methanol containing 12% (v/v) aqueous ammonium hydroxide) as mobile phase. The concentration of (methanol containing 12% (v/v) aqueous ammonium hydroxide) was gradually increased from 0% to 9.5% to afford for 4-((1-(2-(2-aminoethoxy)ethyl)-1H-1,2,3-triazol-4-yl)methyl)thiomorpholine 1,1-dioxide (45, 1.86 g, 93%) as a white solid. LCMS m/z: $[M+H]^+$ Calcd for $C_{11}H_{21}N_5O_4S$ 304.1438; Found 304.1445.

Experimental Procedure for N-(2-(2-(4-((1,1-dioxidothiomorpholino)methyl)-1H-1,2,3-triazol-1-yl)ethoxy)ethyl)methacrylamide (46)

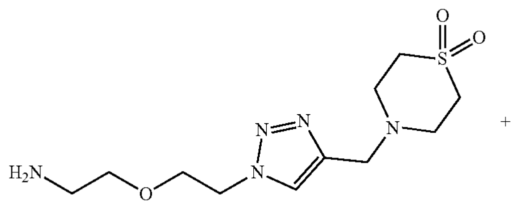

45

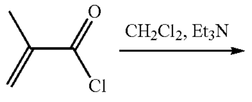

-continued

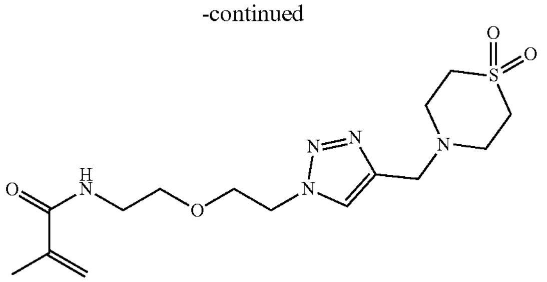

46

A solution of 4-((1-(2-(2-aminoethoxy)ethyl)-1H-1,2,3-triazol-4-yl)methyl)thiomorpholine 1,1-dioxide (45, 1.32 g, 4.35 mmol, 1.0 eq) and triethylamine (0.73 mL, 5.22 mmol, 1.2 eq) in $CH_2Cl_2$ (100 mL) was cooled with an ice-bath under Nitrogen atmosphere. Methacryloyl chloride (0.47 mL, 4.8 mmol, 1.1 eq) was added in a dropwise fashion. The cooling bath was removed and the reaction mixture was stirred for 4 h at room temperature. Ten (10) grams of Celite was added and the solvent was removed under reduced pressure. The residue was purified by silica gel chromatography (120 g) using dichloromethane/(methanol containing 12% (v/v) aqueous ammonium hydroxide) as mobile phase. The concentration of (methanol containing 12% (v/v) aqueous ammonium hydroxide) was gradually increased from 0% to 1.25% to afford N-(2-(2-(4-((1,1-dioxidothiomorpholino)methyl)-1H-1,2,3-triazol-1-yl)ethoxy)ethyl)-methacrylamide (46, 0.90 g, 56% yield) as a colorless oil. LCMS m/z: $[M+H]^+$ Calcd for $C_{15}H_{25}N_5O_4S$ 372.17; Found 372.15.

Experimental Procedure for 4-((I-(2-(2-(2-aminoethoxy)ethoxy)ethyl)-1H-1,2,3-triazol-4-yl)methyl) thiomorpholine 1,1-dioxide (47)

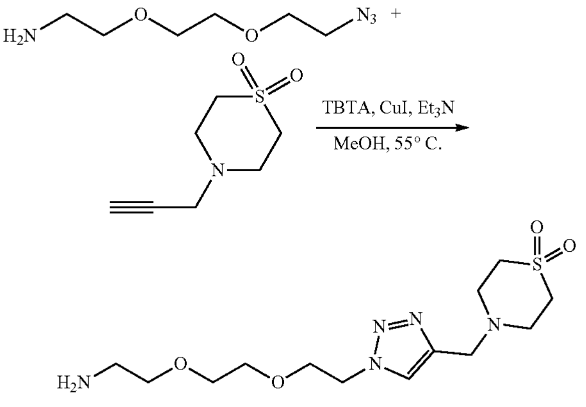

47

A mixture of 4-(prop-2-yn-1-yl)thiomorpholine 1,1-dioxide (4.6 g, 26.55 mmol, 1.0 eq), Tris[(1-benzyl-1H-1,2,3-triazol-4-yl)methyl]-amine (3.1 g, 5.84 mmol, 0.22 eq), Copper Iodide (506 mg, 2.66 mmol, 0.1 eq), and Triethylamine (0.93 mL, 6.64 mmol, 0.25 eq) in Methanol (80 mL) was cooled with an ice bath. 2-(2-(2-azidoethoxy)ethoxy)ethan-1-amine (5.00 g, 28.68 mmol, 1.08 eq) was added in a dropwise fashion, the cooling bath was removed and the mixture was stirred for 5 minutes. The reaction was warmed to 55° C. and stirred overnight under Nitrogen atmosphere.

The reaction mixture was cooled to room temperature, Celite was added, and concentrated under reduced pressure. The crude product was purified over silica gel (220 g) using dichloromethane/(methanol containing 12% (v/v) aqueous ammonium hydroxide) as mobile phase. The concentration of (methanol containing 12% (v/v) aqueous ammonium hydroxide) was gradually increased from 0% to 10% to afford for 4-((1-(2-(2-(2-aminoethoxy)ethoxy)ethyl)-1H-1,2,3-triazol-4-yl)methyl)thiomorpholine 1,1-dioxide (47, 5.26 g, 57%) as a yellowish oil. LCMS m/z: $[M+H]^+$ Calcd for $C_{13}H_{25}N_5O_4S$ 348.1700; Found 348.1700.

Experimental Procedure N-(2-(2-(2-(4-((1,1-dioxidothiomorpholino)methyl)-1H-1,2,3-triazol-1-yl)ethoxy)ethoxy)ethyl)methacrylamide (48)

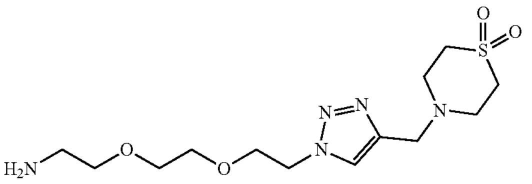

+

47

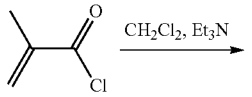

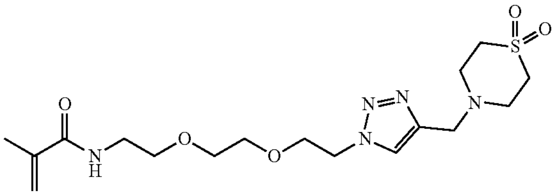

48

A solution of 4-((1-(2-(2-(2-aminoethoxy)ethoxy)ethyl)-1H-1,2,3-triazol-4-yl)methyl)thiomorpholine 1,1-dioxide (47, 1.49 g, 4.29 mmol, 1.0 eq) and triethylamine (0.72 mL, 5.15 mmol, 1.2 eq) in $CH_2Cl_2$ (50 mL) was cooled with an ice-bath under Nitrogen atmosphere. Methacryloyl chloride (0.46 mL, 4.7 mmol, 1.1 eq) was added in a dropwise fashion. The cooling bath was removed and the reaction mixture was stirred for 4 h at room temperature. Ten (10) grams of Celite was added and the solvent was removed under reduced pressure. The residue was purified by silica gel chromatography (80 g) using dichloromethane/methanol as mobile phase. The concentration of methanol was gradually increased from 0% to 5% to afford N-(2-(2-(2-(4-((1,1-dioxidothiomorpholino)methyl)-1H-1,2,3-triazol-1-yl)ethoxy)ethoxy)ethyl)-methacrylamide (48, 0.67 g, 38% yield) as a colorless oil. LCMS m/z: $[M+H]^+$ Calcd for $C_{17}H_{29}N_5O_5S$ 416.20; Found 416.20.

Experimental Procedure for 4-((1-(14-amino-3,6,9,12-tetraoxatetradecyl)-1H-1,2,3-triazol-4-yl)methyl) thiomorpholine 1,1-dioxide (49)

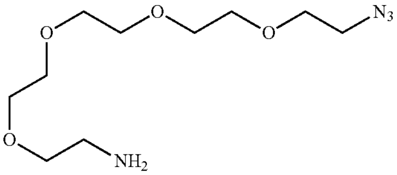

+

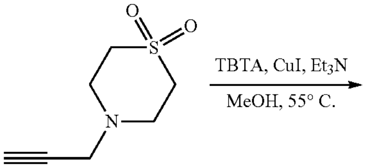

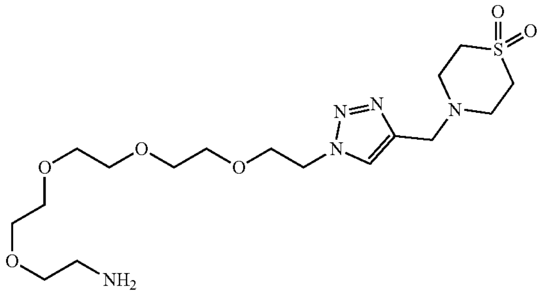

49

A mixture of 4-(prop-2-yn-1-yl)thiomorpholine 1,1-dioxide (5.0 g, 28.86 mmol, 1.0 eq), Tris[(1-benzyl-1H-1,2,3-triazol-4-yl)methyl]-amine (3.37 g, 6.35 mmol, 0.22 eq), Copper Iodide (550 mg, 2.89 mmol, 0.1 eq), and Triethylamine (1.01 mL, 7.22 mmol, 0.25 eq) in Methanol (90 mL) was cooled with an ice bath. 14-azido-3,6,9,12-tetraoxatetradecan-1-amine (8.86 g, 33.77 mmol, 1.17 eq) was added in a dropwise fashion, the cooling bath was removed and the mixture was stirred for 5 minutes. The reaction was warmed to 55° C. and stirred overnight under Nitrogen atmosphere. The reaction mixture was cooled to room temperature, Celite (15 g) was added, and concentrated under reduced pressure. The crude product was purified over silica gel (220 g) using dichloromethane/(methanol containing 12% (v/v) aqueous ammonium hydroxide) as mobile phase. The concentration of (methanol containing 12% (v/v) aqueous ammonium hydroxide) was gradually increased from 0% to 10% to afford for 4-((1-(14-amino-3,6,9,12-tetraoxatetradecyl)-1H-1,2,3-triazol-4-yl)methyl)thiomorpholine 1,1-dioxide (49, 7.56 g, 60%) as an oil. LCMS m/z: $[M+H]^+$ Calcd for $C_{17}H_{33}N_5O_6S$ 436.2224; Found 436.2228.

Experimental Procedure N-(14-(4-((1,1-dioxidothiomorpholino)methyl)-1H-1,2,3-triazol-1-yl)-3,6,9,12-tetraoxatetradecyl)methacrylamide (50)

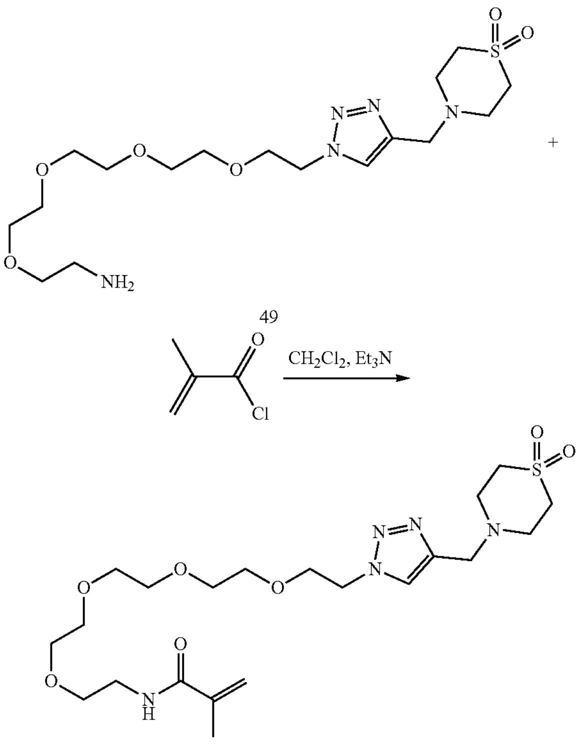

49

50

A solution of 4-((1-(14-amino-3,6,9,12-tetraoxatetradecyl)-1H-1,2,3-triazol-4-yl)methyl)thiomorpholine 1,1-dioxide (49, 1.95 g, 4.79 mmol, 1.0 eq) and triethylamine (0.80 mL, 5.74 mmol, 1.2 eq) in $CH_2Cl_2$ (50 mL) was cooled with an ice-bath under Nitrogen atmosphere. Methacryloyl chloride (0.51 mL, 5.26 mmol, 1.1 eq) was added in a dropwise fashion. The cooling bath was removed and the reaction mixture was stirred for 4 h at room temperature. Ten (10) grams of Celite was added and the solvent was removed under reduced pressure. The residue was purified by silica gel chromatography (80 g) using dichloromethane/methanol as mobile phase. The concentration of methanol was gradually increased from 0% to 5% to afford N-(14-(4-((1,1-dioxidothiomorpholino)methyl)-1H-1,2,3-triazol-1-yl)-3,6,9,12-tetraoxatetradecyl)methacrylamide (50, 0.76 g, 32% yield) as a colorless oil. LCMS m/z: $[M+H]^+$ Calcd for $C_{21}H_{37}N_5O_7S$ 504.25; Found 504.20.

Example 4A: Preparation of Exemplary Modified Polymers

1A. Chemically-modified Polymer. A polymeric material may be chemically modified with a compound of Formula (I) (or pharmaceutically acceptable salt thereof) prior to formation of a device described herein (e.g., a hydrogel capsule). Synthetic protocols of exemplary compounds for modification of polymeric materials are outlined above in Example 3. These compounds, or others, may be used to chemically modify any polymeric material.

For example, in the case of alginate, the alginate carboxylic acid is activated for coupling to one or more amine-functionalized compounds to achieve an alginate modified with an afibrotic compound, e.g., a compound of Formula (I). The alginate polymer is dissolved in water (30 mL/gram polymer) and treated with 2-chloro-4,6-dimethoxy-1,3,5-triazine (0.5 eq) and N-methylmorpholine (1 eq). To this mixture is added a solution of the compound of interest (e.g., Compound 101 shown in Table 3) in acetonitrile (0.3M).

The amounts of the compound and coupling reagent added depends on the desired concentration of the compound bound to the alginate, e.g., conjugation density. A medium conjugation density of Compound 101 typically ranges from 2% to 5% N, while a high conjugation density of Compound 101 typically ranges from 5.1% to 8% N. To prepare a CM-LMW-Alg-101-Medium polymer solution, the dissolved unmodified low molecular weight alginate (approximate MW <75 kDa, G:M ratio ≥1.5) is treated with 2-chloro-4,6-dimethoxy-1,3,5-triazine (5.1 mmol/g alginate) and N-methylmorpholine (10.2 mmol/g alginate) and Compound 101 (5.4 mmol/g alginate). To prepare a CM-LMW-Alg-101-High polymer solution, the dissolved unmodified low-molecular weight alginate (approximate MW <75 kDa, G:M ratio ≥1.5) is treated with 2-chloro-4,6-dimethoxy-1,3,5-triazine (5.1 mmol/g alginate) and N-methylmorpholine (10.2 mmol/g alginate) and Compound 101 (10.5 mmol/g alginate).

The reaction is warmed to 55° C. for 16 h, then cooled to room temperature and gently concentrated via rotary evaporation, then the residue is dissolved in water. The mixture is filtered through a bed of cyano-modified silica gel (Silicycle) and the filter cake is washed with water. The resulting solution is then extensively dialyzed (10,000 MWCO membrane) and the alginate solution is concentrated via lyophilization to provide the desired chemically-modified alginate as a solid or is concentrated using any technique suitable to produce a chemically modified alginate solution with a viscosity of 25 cP to 35 cP.

The conjugation density of a chemically modified alginate is measured by combustion analysis for percent nitrogen. The sample is prepared by dialyzing a solution of the chemically modified alginate against water (10,000 MWCO membrane) for 24 hours, replacing the water twice followed by lyophilization to a constant weight.

For use in generating the hydrogel capsules described in the Examples below, chemically modified alginate polymers were prepared with Compound 101 (shown in Table 3) conjugated to a low molecular weight alginate (approximate MW <75 kDa, G:M ratio ≥1.5) at medium (2% to 5% N) or high (5.1% to 8% N) densities, as determined by combustion analysis for percent nitrogen, and are referred to herein as CM-LMW-Alg-101-Medium and CM-LMW-Alg-101-High.

1B. CBP-Alginates. A polymeric material may be covalently modified with a cell-binding peptide prior to formation of a device described herein (e.g., a hydrogel capsule described herein) using methods known in the art, see, e.g., Jeon 0, et al., *Tissue Eng Part A.* 16:2915-2925 (2010) and Rowley, J. A. et al., *Biomaterials* 20:45-53 (1999).

For example, in the case of alginate, an alginate solution (1%, w/v) is prepared with 50 mM of 2-(N-morpholino)-ethanesulfonic acid hydrate buffer solution containing 0.5M NaCl at pH 6.5, and sequentially mixed with N-hydroxysuccinimide and 1-ethyl-3-[3-(dimethylamino)propyl]carbodiimide (EDC). The molar ratio of N-hydroxysuccinimide to EDC is 0.5:1.0. The peptide of interest is added to the alginate solution. The amounts of peptide and coupling reagent added depends on the desired concentration of the peptide bound to the alginate, e.g., peptide conjugation density. By increasing the amount of peptide and coupling reagent, higher conjugation density can be obtained. After reacting for 24 h, the reaction is purified by dialysis against ultrapure deionized water (diH2O) (MWCO 3500) for 3 days, treated with activated charcoal for 30 min, filtered (0.22 mm filter), and concentrated to the desired viscosity.

The conjugation density of a peptide-modified alginate is measured by combustion analysis for percent nitrogen. The sample is prepared by dialyzing a solution of the chemically modified alginate against water (10,000 MWCO membrane) for 24 hours, replacing the water twice followed by lyophilization to a constant weight.

In another embodiment, the conjugation density of a peptide-modified alginate is measured using a quantitative peptide-conjugation assay as described in Example 7 and optionally Example 8.

Example 4B: Preparation of Exemplary Alginate Solutions for Making Hydrogel Capsules 70:30 mixture of chemically-modified and unmodified alginate. A low molecular weight alginate (PRONOVA™ VLVG alginate, NovaMatrix, Sandvika, Norway, cat. #4200506, approximate molecular weight <75 kDa; G:M ratio ≥1.5) was chemically modified with Compound 101 in Table 3 to produce chemically modified low molecular weight alginate (CM-LMW-Alg-101) solution with a viscosity of 25 cp to 35 cP and a conjugation density of 5.1% to 8% N, as determined by combustion analysis for percent nitrogen. A solution of high molecular weight unmodified alginate (U-HMW-Alg) was prepared by dissolving unmodified alginate (PRONOVA™ SLG100, NovaMatrix, Sandvika, Norway, cat. #4202106, approximate molecular weight of 150 kDa-250 kDa) at 3% weight to volume in 0.9% saline. The CM-LMW-Alg solution was blended with the U-HMW-Alg solution at a volume ratio of 70% CM-LMW-Alg to 30% U-HMW-Alg (referred to herein as a 70:30 CM-Alg:UM-Alg solution).

Unmodified alginate solution. An unmodified medium molecular weight alginate (SLG20, NovaMatrix, Sandvika, Norway, cat. #4202006, approximate molecular weight of 75-150 kDa), was dissolved at 1.4% weight to volume in 0.9% saline to prepare a U-MMLW-Alg solution.

Alginate Solution Comprising Cell Binding Sites. A solution of SLG20 alginate was modified with a peptide consisting of GRGDSP (SEQ ID NO: 44) and concentrated to a viscosity of about 100 cP as described in Example 4A above. In an embodiment, the amount of the GRGDSP peptide (SEQ ID NO: 44) and coupling reagent used were selected to achieve a target peptide conjugation density of about 0.2 to 0.3, as measured by combustion analysis as described in Example 4A above. In another embodiment, the amounts of a medium molecular weight alginate (approximate molecular weight of 75-150 kDa, G:M ratio of greater than or equal to 1.5), GRGDSP peptide and coupling reagent used are selected to prepare a GRGDSP-MMW-Alg solution ("GRGDSP" disclosed as SEQ ID NO: 44) with a target peptide conjugation density of 0.3 to 0.6 micromoles of GRGDSP (SEQ ID NO: 44) per gram of the GRGDSP-MMW-Alg ("GRGDSP" disclosed as SEQ ID NO: 44) in saline with a viscosity of 80-120 cP.

Example 5: Formation of Two-Compartment Hydrogel Capsules

A suspension of engineered ARPE-19 cells (i.e., GLA 4-2 cells) were encapsulated as single cells in two-compartment hydrogel capsules according to the protocols described below.

Immediately before encapsulation, engineered ARPE-19 cells were centrifuged at 1,400 r.p.m. for 1 min and washed with calcium-free Krebs-Henseleit (KH) Buffer (4.7 mM KCl, 25 mM HEPES, 1.2 mM $KH_2PO_4$, 1.2 mM $MgSO_4 \times 7H_2O$, 135 mM NaCl, pH ≈7.4, ≈290 mOsm). After washing, the cells were centrifuged again and all of the supernatant was aspirated. The cell pellet was then resuspended in the GRGDSP-modified alginate solution described in Example 4B at a density of about 100 million suspended single cells per ml alginate solution.

Prior to fabrication of hydrogel capsules, buffers and alginate solutions were sterilized by filtration through a 0.2-μm filter using aseptic processes.

To prepare particles configured as two-compartment hydrogel millicapsules of about 1.5 mm diameter, an electrostatic droplet generator was set up as follows: an ES series 0-100-kV, 20-watt high-voltage power generator (EQ series, Matsusada, NC, USA) was connected to the top and bottom of a coaxial needle (inner lumen of 22G, outer lumen of 18G, Ramé-Hart Instrument Co., Succasunna, NJ, USA). The inner lumen was attached to a first 5-ml Luer-lock syringe (BD, NJ, USA), which was connected to a syringe pump (Pump 11 Pico Plus, Harvard Apparatus, Holliston, MA, USA) that was oriented vertically. The outer lumen was connected via a luer coupling to a second 5-ml Luer-lock syringe which was connected to a second syringe pump (Pump 11 Pico Plus) that was oriented horizontally. A first alginate solution containing the engineered GLA-ARPE-19 cells (as single cells) suspended in a GRGDSP-modified alginate solution ("GRGDSP" disclosed as SEQ ID NO: 44) was placed in the first syringe and a cell-free alginate solution comprising a mixture of a chemically-modified alginate and unmodified alginate was placed in the second syringe. The two syringe pumps move the first and second alginate solutions from the syringes through both lumens of the coaxial needle and single droplets containing both alginate solutions are extruded from the needle into a glass dish containing a cross-linking solution. The settings of each Pico Plus syringe pump were 12.06 mm diameter and the flow rates of each pump were adjusted to achieve a flow rate ratio of 1:1 for the two alginate solutions. Thus, with the total flow rate set at 10 ml/h, the flow rate for each alginate solution was about 5 mL/h. Control (empty) capsules were prepared in the same manner except that the alginate solution used for the inner compartment was a cell-free solution.

After extrusion of the desired volumes of alginate solutions, the alginate droplets were crosslinked for five minutes in a cross-linking solution which contained 25 mM HEPES buffer, 20 mM $BaCl_2$, 0.2M mannitol and 0.01% of poloxamer 188. Capsules that had fallen to the bottom of the crosslinking vessel were collected by pipetting into a conical tube. After the capsules settled in the tube, the crosslinking buffer was removed, and capsules were washed. Capsules without cells were washed four times with HEPES buffer (NaCl 15.428 g, KCl 0.70 g, $MgCl_2.6H_2O$ 0.488 g, 0 ml of HEPES (1 M) buffer solution (Gibco, Life Technologies, California, USA) in 2 liters of deionized water) and stored at 4° C. until use. Capsules encapsulating cells were washed four times in HEPES buffer, two times in 0.9% saline, and two times in culture media and stored in an incubator at 37° C.

The quality of capsules in a composition of two-compartment can be examined. For example, an aliquot containing at least 200 capsules is taken from the composition and transferred to a well plate and the entire aliquot examined by optical microscopy for quality by counting the number of spherical capsules out of the total.

Example 6: Evaluation of a Device Containing GLA-Engineered RPE Cells in an Animal Model of Fabry Disease The biological activity of an exemplary GLA-producing implanted device to treat Fabry mice was evaluated in the single dose and dose-response experiments described below.

The Fabry mice used in each experiment were 8 to 11 weeks old male mice purchased from Jackson Labs (https://www.jax.org/strain/003535). This mice strain contains a neo cassette replacing exon 3 and intron 3 of the galactosidase, alpha (Gla) gene, and thereby abolishing gene expression. All mice were housed under pathogen-free conditions in an animal facility according to IACUC approved protocols. Procedures involving mice were followed the guidelines established by the Association for Assessment of Accreditation of Laboratory Animal Care (AAALAC).

Two-compartment GLA-producing or control hydrogel capsules were prepared as described in Example 5 above. The GLA-producing capsules were prepared by encapsulating cells from the GLA 4-2 clone (e.g., ARPE-19 cells engineered with the GLA 4 expression construct). In the single dose experiment, two groups of three Fabry mice were implanted intraperitoneal with about 140 of either the GLA-producing capsules or control capsules. In the dose-response experiment, four groups of five Fabry mice were implanted with about 40, 70 or 140 of the GLA-producing capsules or about 140 control capsules.

Either fourteen days (single dose) or ten days (dose-response) after implantation, mice were sacrificed and blood, liver, kidney and heart samples were collected from the sacrificed mice. Human GLA activity and Gb3 and Lyso-Gb3 levels were measured in the samples using the following assays.

Enzymatic Assay for GLA Activity

Blood samples were collected in EDTA solution and plasma separated according to a standard protocol.

Liver, kidney and heart tissue samples were homogenized in 50 mM citric acid, 176 mM $K_2PO_4$, pH 5.0 using a MP Bio FastPrep-24 tissue homogenizer with matrix D. Samples were centrifuged for 12,000×g at 4° C. for 10 minutes. The supernatant was diluted 5-fold into assay buffer (50 mM citric acid, 176 mM $K_2PO_4$, 0.01% Tween-20, pH 5.0). Forty μl of diluted homogenate or plasma was added to a Greiner black 96 well plate containing 40 μL of 1 mM 4-Methylumbelliferyl β-D-galactopyranoside substrate and incubated for 60 minutes at 37° C. The reaction was stopped with 200 μL of 0.5 M sodium hydroxide and 0.5 M glycine at pH 11.6. Fluorescence intensity was measured on a Biotek Synergy LX (Excitation: 360/40, Emission: 460/40). Data was normalized to total protein concentration of the homogenate. Enzyme activity levels were compared to a standard curve generated with agalsidase beta and 4-methylumbelliferone.

Lyso Gb3 and Gb3 Detection

The liver, kidney and heart tissue samples were homogenized using an MP Biomedicals FastPrep-25 5G Grinder, utilizing the 2 mL matrix D homogenization tubes provided by MP Biomedicals. The homogenate was then centrifuged at 14,000 g for 10 minutes, and the supernatant transferred directly to HPLC vials for LCMS/MS analysis.

For plasma analysis, the plasma was diluted 20× methanol and the diluted plasma was vortexed and sonicated vigorously. The plasma extract was centrifuged at 14,000 g for 10 minutes and the supernatant was removed and dried under a gentle stream of nitrogen. The dried extracts were reconstituted in 100 uL of methanol and transferred to HPLC vials for LCMS/MS analysis.

LCMS Analysis

For measurement for Lyso GB3 and GB3 isoforms, a Thermo Vanquish UHPLC and Thermo Q-Exactive mass spectrometer was used. The chromatographic separations were performed using a Waters 2.1×100 mm BEH amide column packed with 1.7 um particles. The column was held at a temperature of 60° C. and a flow rate of 0.3 mL/min. All separations were performed in gradient mode with mobile phase A consisting of 95:5 Acetonitrile:$H_2O$ and Mobile Phase B being aqueous, both mobile phases containing 10 mM ammonium formate. The mass spectral measures were performed using full scan mode from 750-1200 m/z at a resolution of 70,000. Exact masses were used for quantification of 13 GB3 isoforms and Lyso GB3. For identity confirmation of each analyte, data dependent MS2 scans were acquired and inspected for indicative fragment ions for each species. Quantification of GB3 isoforms and Lyso GB3 was performed by spiking C17 GB3 and Lyso GB3 into each tissue type to generate standard curves.

Figure 11A:
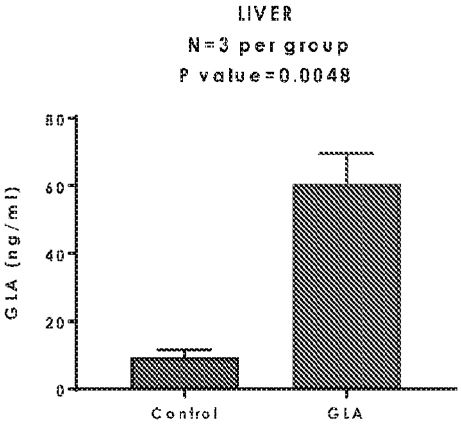
FIG. 11 shows human GLA activity in tissue samples (liver (FIG. 11A) and plasma (FIG. 11B)) obtained from Fabry mice at 14 days after implantation with two-compartment alginate hydrogel capsules in which the outer compartment was formed from a chemically-modified alginate solution and the inner compartment was formed from an alginate solution comprising a blend of GRGDSP-modified alginate ("GRGDSP" disclosed as SEQ ID NO: 44) and unmodified alginate that lacked (Control) or contained a suspension of a clonal cell line transfected with the GLA 4 construct (GLA).
Figure 11B:
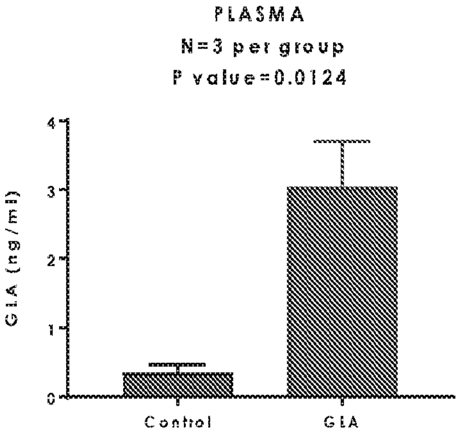
Figure 12A:
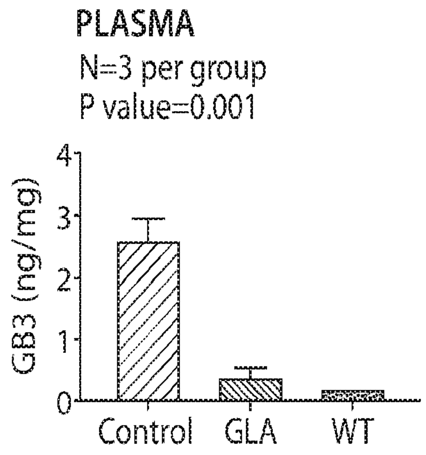
FIG. 12 shows Gb3 levels in various tissue samples (plasma (FIG. 12A), liver (FIG. 12B), kidney (FIG. 12C) and heart (FIG. 12D)) obtained from (i) the same Fabry mice described in FIG. 11 at 14 days after implantation with control capsules or GLA-producing capsules or (ii) wild-type mice that were not implanted (WT).
Figure 12B:
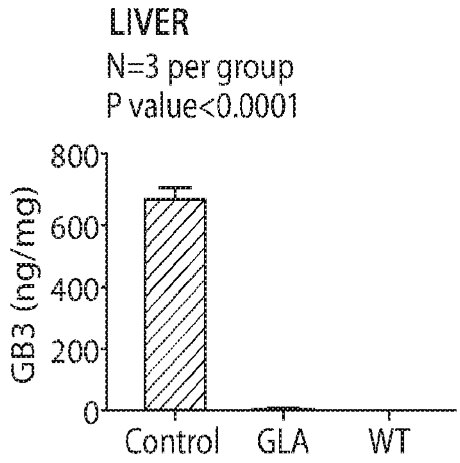
Figure 12C:
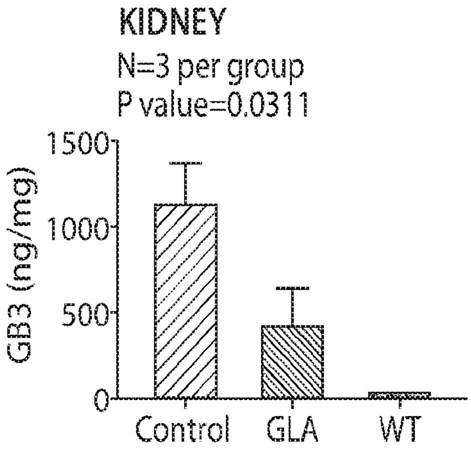
Figure 12D:
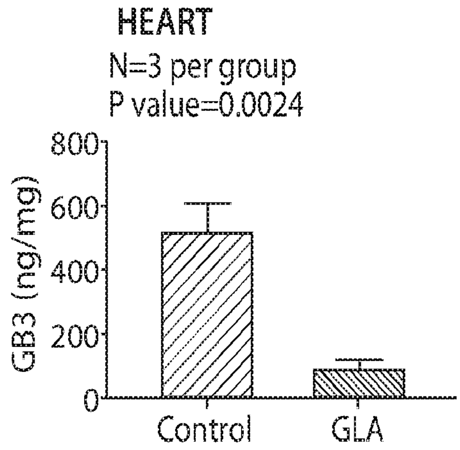
Figure 13A:
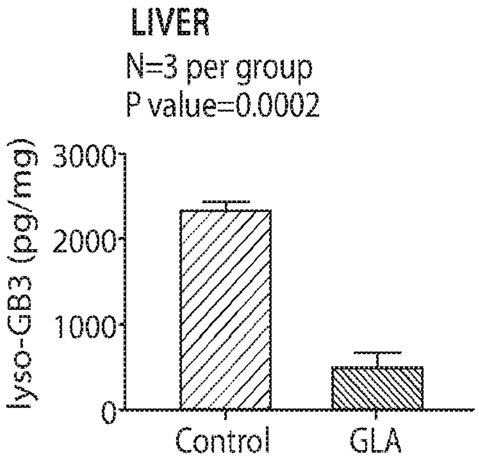
FIG. 13 illustrates the amount of Lyso-Gb3 reduction in the same tissue samples described in FIG. 12, with FIGS. 13A, 13B, 13C and 13D showing Lyso-Gb3 levels in liver kidney, heart and plasma, respectively.
Figure 13B:
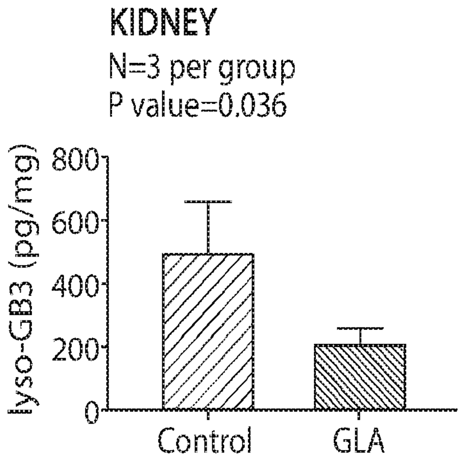
Figure 13C:
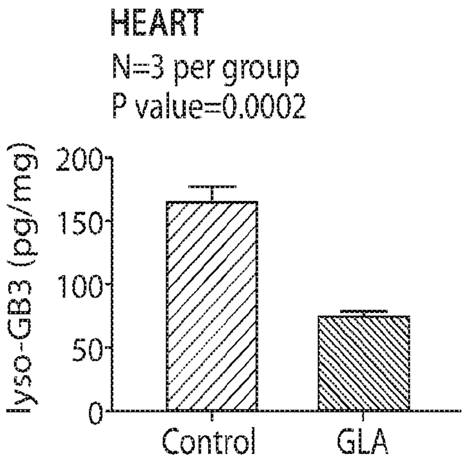
Figure 13D:
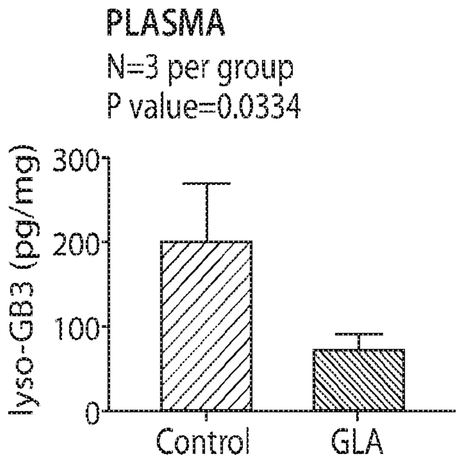
Figure 14A:
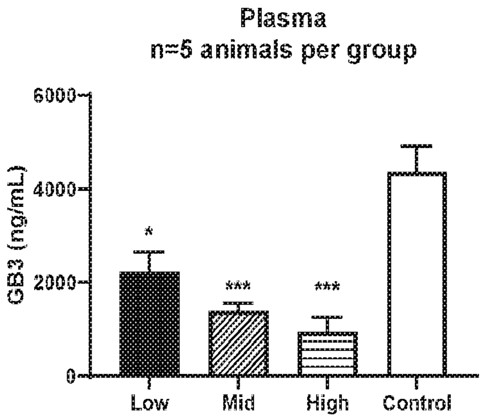
FIG. 14 illustrates the amount of Gb3 reduction in various tissue samples (plasma, (FIG. 14A), liver (FIG. 14B), kidney (FIG. 14C) and heart (FIG. 14D)) obtained from Fabry mice at 10 days after implantation with a low, medium or high dose of the GLA-producing capsules described in FIG. 11 or with a high dose of control capsules.
Figure 14B:
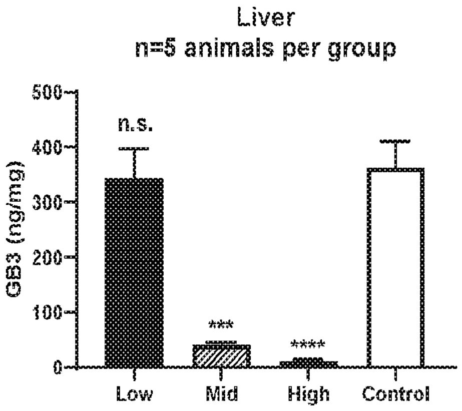
Figure 14C:
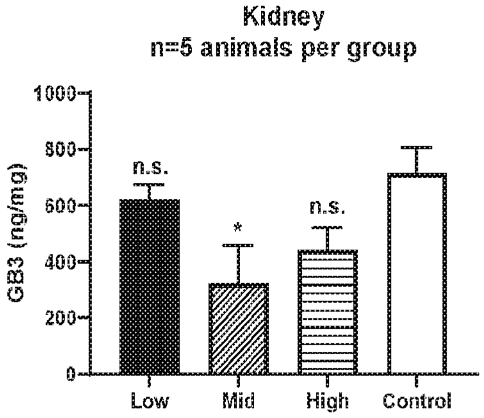
Figure 14D:
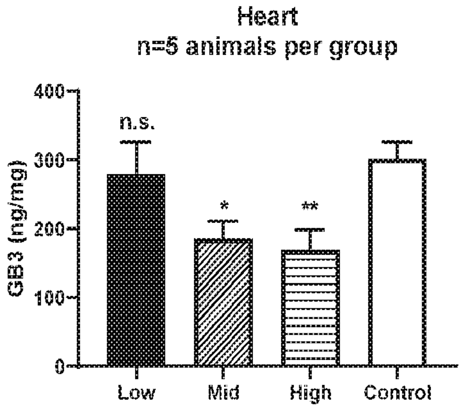
Figure 15A:
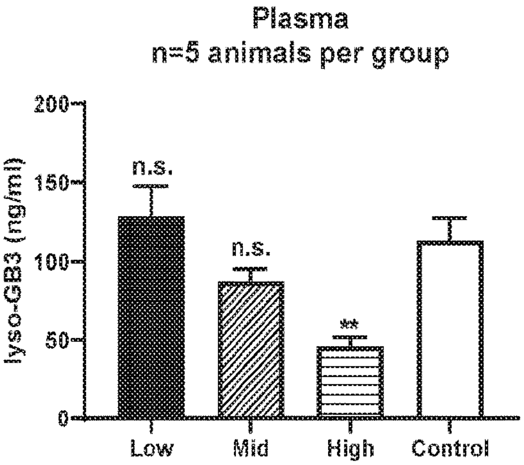
FIG. 15 illustrates the amount of Lyso-Gb3 reduction in the same tissue samples described in FIG. 14, with FIGS. 15A, 15B, 15C and 15D showing the Lyso-GB3 levels in liver kidney, heart and plasma, respectively.
Figure 15B:
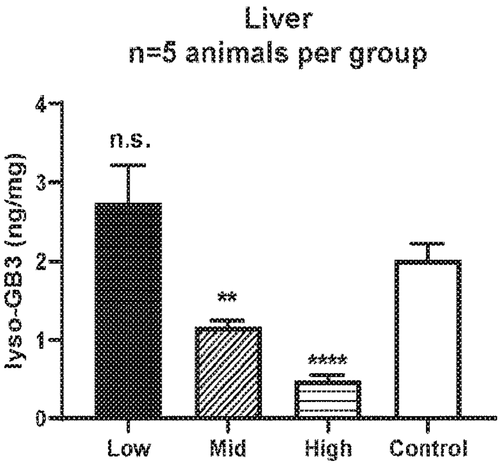
Figure 15C:
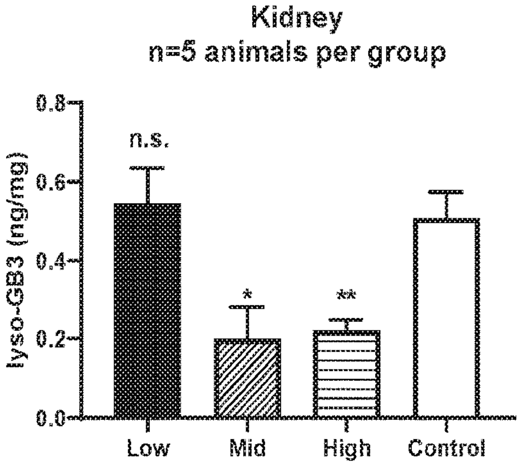
Figure 15D:
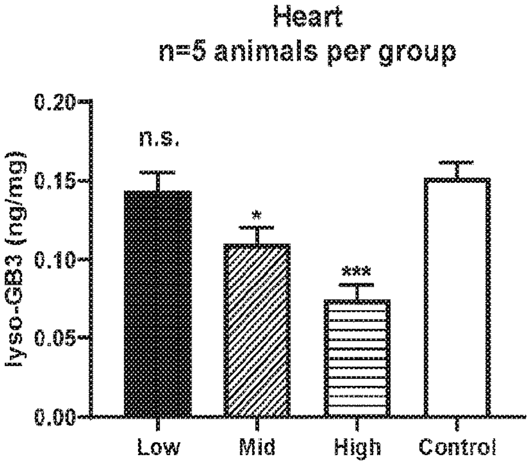

The results of these direct and indirect GLA activity assays for the single dose experiment are shown in FIGS. 11-13, and the results of the indirect GLA activity assays for the dose-response experiment are shown in FIGS. 14-15. Human GLA activity was detected in both liver and plasma samples (FIG. 11A and FIG. 11B). Gb3 was readily detectable in the plasma, liver, kidney and heart tissues obtained at 14 days (FIG. 12) or 10 days (FIG. 14) from the control Fabry mice, with the higher Gb3 levels observed in the kidney than the liver and heart being consistent with the original description of this Fabry disease model. In Fabry mice implanted with a single dose of GLA-producing hydrogel capsules, significant and comparable reductions of accumulated Gb3 and Lyso-Gb3 levels in the plasma, liver, kidney and heart samples were observed at 14 days after implant (FIGS. 12 and 13). Also, the amount of reduction in Gb3 and Lyso-Gb3 levels in plasma, liver and heart tissues at 10 days increased with increasing dose of GLA-producing capsules (FIGS. 14 and 15. These results indicate that a device preparation described herein can produce biologically active and therapeutically-effective levels of human GLA when implanted in Fabry mice.

Example 7: Exemplary Quantitative Peptide Conjugation Assay

This assay determines the amount of peptide in a CBP-polymer by subjecting a sample of the CBP-polymer to acid hydrolysis, which cleaves off the CBP as individual amino acids. The individual amino acids in the hydrolyzed sample are separated and quantitated using amino acid references by pre-column on-line derivatization and reverse-phase liquid chromatography-Ultra-Violet-Fluoscense (LC-UV-FLR) (adapted from Agilent Biocolumns Amino Acid Analysis "How-To" Guide, Agilent Technologies, Inc., 5991-7694EN, published Mar. 1, 2018). Primary AAs (e.g., all but proline of the 20 standard L-alpha amino acids) are derivatized with Ortho-phthaladehyde (OPA) and secondary AAs (e.g., proline) are derivatized with 9-Fluorenylmethyl chloroformate (FMOC). The molar concentration of each amino acid is then averaged to calculate the concentration of the total peptide in the sample. This concentration can be corrected for the presence of any residual unconjugated CBP in the CBP-polymer by determining the amount of peptide in an unhydrolyzed sample of the CBP-polymer using any suitable analytical technique, e.g., as described in Example 8, and subtracting that amount from the total peptide amount.

The assay is further described below as applied to determining peptide conjugation density in a GRGDSP-alginate (SEQ ID NO: 44); however, the skilled artisan can readily modify the assay to determine peptide concentration in a GRGDSP-alginate (SEQ ID NO: 44) or other peptide-modified polymers, provided the unmodified polymer does not contain any amino acids. Also, the skilled person can readily substitute any equipment, material or chemical specified below with a different equipment, material or chemical that can perform or provide substantially the same function or role in the assay.

DEFINITIONS

| Abbreviation | Definition |
|---|---|
| LC-UV-FLR | Liquid Chromatography-Ultra-Violet-Fluorescence |
| LCMS | Liquid Chromatography-Mass Spectroscopy |
| SLG20 | Pronova Ultrapure SLG20 sterile sodium alginate |
| RT | Retention Time |
| ACN | Acetonitrile |
| MeOH | Methanol |
| SST | System Suitability |
| RSD | Relative Standard Deviation |
| TBD | To Be Determined |
| NMT | No More Than |
| NLT | No Less Than |
| RSQ | Coefficient of Determination |
| AA | Amino acid |
| OPA | Ortho-phthaladehyde |
| FMOC | 9-Fluorenylmethyl chloroformate |
| G | Glycine |
| R | Arginine |
| D | Aspartic acid |
| S | Serine |
| P | Proline |
| iSTD | Internal standard |
| PPE | Personal Protective Equipment |
| SDS | Safety Data Sheet |
| MW | Molecular Weight |
| PTFE | Polytetrafluoroethylene |
| RPM | Revolutions per Minute |
| Min | Minutes |
| S | Seconds |
| mL | Millilitre |
| μL | Microlitre |
| nm | Nanometre |

Equipment, Materials and Chemicals

Equipment

- Agilent 1260 LC system
- Agilent diode array detector (G1315D): 13 μL/10 mm flow cell
- Agilent Fluorescence detector (G1321B)
- AdvanceBio AA LC column, 2.7 m, 4.6×100 mm, Agilent 655950-80
- AdvanceBio AAA guard column, 2.7 μm, 4.6×5 mm, Agilent 820750-931

| | | | |
|---|---|---|---|
| AA standard (17 AA): 25 pmol/μL | n/a | Agilent 5061-3333 | 2-8° C. |
| AA standard (17 AA): 100 pmol/μL | n/a | Agilent 5061-3332 | 2-8° C. |
| AA standard (17 AA): 250 pmol/μL | n/a | Agilent 5061-3331 | 2-8° C. |

Procedure

Prepare a 10 mM $Na_2HPO_4/Na_2B_4O_7$/pH 8.2 (aqueous mobile phase) and 45/45/10 ACN/MeOH/water (organic mobile phase) for use in the LC/MS procedure.

Acid Hydrolysis of a Sample of an Exemplary Peptide-Alginate Conjugate

- Weigh 12-16 mg of the lyophilized peptide-alginate conjugate into a microwave reaction vial, ensuring that the sample is not agitated.
- Hydrolyze according to steps 3.3.2-3.3.19 below Acid Hydrolysis of a Sample of an Exemplary Peptide-Alginate Conjugate in Saline Solution

- Weigh 1000±50 mg of the peptide-alginate conjugate solution in saline into a microwave reaction vial
- Add 10.0 mL of 6N HCl to the sample using a 10-mL transfer pipet or volumetric pipet and a stir bar, and seal the PTFE-lined cap with a crimper.
- Place each sample vial in the matching heat block on a hot/stir plate and heat at 120° C., stirring at 400 rpm, for 6 hours
- Remove from heat and let cool to ambient temperature
- Remove cap and transfer the entire solution from the reaction vial to a 20-mL volumetric flask with a disposable transfer pipet
- Pipet 2 mL of LCMS grade water into the empty reaction vial, rinse the inner wall thoroughly with the same disposable transfer pipet, and transfer the rinseate completely to the same 20-mL volumetric flask
- Repeat the above step twice
- Bring to mark of the volumetric flask with LCMS grade water
- Cap and invert the flask multiple times to mix well
- Transfer completely to a 50-mL centrifuge tube
- Centrifuge at 5000 rpm for 10 minutes
- Pipet accurately 1 mL of the supernatant to an LC vial and store at 2-8° C. until drying (e.g., the next day) (store the remaining supernatant at 2-8° C. for any repeat testing if needed)
- Dry the 1 mL supernatant completely under nitrogen at 60° C., make sure the needle does not touch the sample but is low enough for fast drying of the sample
- Into the vial with the dried sample, pipet 0.25 mL of 0.1 μmol/mL internal standard mixture
- Vortex thoroughly
- Transfer with a pipet to an LC vial with a LC vial insert
- Store at 2-8° C. until HPLC analysis (step 3.6)

Standard Preparation

AA Standard Stock Solutions: 10 μmol/mL

- For each AA, calculate the weight needed to prepare a 10 μmol/mL stock solution based on the MW
- See an example below:

| Letter name | Full name | MW (g/mol) | Actual weight (mg) | Volume (mL) | Purity (%) | Actual Concentration (μmol/mL) |
|---|---|---|---|---|---|---|
| D | Aspartic acid | 133.10 | 66.38 | 50 | 100 | 9.97 |
| S | Serine | 105.09 | 52.55 | 50 | 100 | 10.00 |
| G | Glycine | 75.07 | 38.56 | 50 | 100 | 10.27 |
| R | Arginine HCl | 210.66 | 102.67 | 50 | 100 | 9.75 |
| N-iSTD | Norvaline | 117.15 | 58.76 | 50 | 100 | 10.03 |
| S-iSTD | Sarcosine | 89.09 | 44.00 | 50 | 98.4 | 9.72 |
| P | Proline | 115.13 | 57.74 | 50 | 100 | 10.03 |

Weigh the calculated weight into a 50-mL volumetric flask
Dissolve and bring to mark with 0.1N HCl
Mix well by capping and inverting or vortexing
Store at 2-8° C. until HPLC analysis (step 3.6)

Internal Standard Mixture: 1 µmol/mL
Into the same 10-mL volumetric flask, pipet accurately 1.0 mL of Norvaline stock (10 µmol/mL) and 1.0 mL of Sarcosine stock (10 µmol/mL) solutions
Bring to mark with 0.1N HCl
Mix well by capping and inverting or vortexing
Store at 2-8° C. until HPLC analysis (step 3.6)

Internal Standard Mixture: 0.1 µmol/mL

NOTE: this solution is for reconstituting samples after drying
Into a 10-mL volumetric flask, pipet accurately 1.0 mL of the internal standard mixture (1 µmol/mL)
Bring to mark with 0.1N HCl
Mix well by capping and inverting or vortexing
Store at 2-8° C. until HPLC analysis (step 3.6)

5 AA Mixture (+iSTD 0.1): 0.025/0.1/0.25 µmol/mL
(Into the same 10-mL volumetric flask, pipet accurately xx µL (see table below, "AA Std") of D, 1, G, R, N-iSTD, S-iSTD, and P (10 µmol/mL) solutions
Bring to mark with 0.1N HCl
Mix well by capping and inverting or vortexing
Store at 2-8° C. until HPLC analysis (step 3.6)

| D/S/G/R/P STD (µmol/mL) | AA STD (xx µL) | N-iSTD or S-iSTD (µmol/mL) | N-iSTD or S-iSTD (xx µL) | Total (mL) | Final µmol/mL (D/S/G/R/P) | Final µmol/mL (iSTD) |
|---|---|---|---|---|---|---|
| 10 | 25 | 10 | 100 | 10 | 0.025 | 0.1 |
| 10 | 100 | 10 | 100 | 10 | 0.1 | 0.1 |
| 10 | 250 | 10 | 100 | 10 | 0.25 | 0.1 |

17 AA Standard (+iSTD 0.1) Mixture: 0.1 µMol/mL
Break open an ampoule of the 0.1 µmol/mL 17 AA standard solution
Accurately pipet 0.9 mL of the AA standard mixture into an LC vial
Into the same LC vial, pipet accurately 100 mL of the iSTD mixture (1 µmol/mL)
Mix well by vortexing
Aliquot NLT 100 µL into an LC vial with an LC vial insert
Store at 2-8° C. until HPLC analysis (step 3.6)

| HPLC conditions | | | |
|---|---|---|---|
| Instrument | Agilent 1260 LC with UV and Fluorescence detector | | |
| Column | AdvanceBio AAA LC, 2.7 µm, 4.6 × 100 mm<br>Agilent 655950-802 | | |
| Gulard column | AdvanceBio AAA guard column, 2.7 µm, 4.6 × 5 mm<br>Agilent 820750-931 | | |
| Mobile phase aqueous | 10 mM $Na_2HPO_4$ 10 mM $Na_2B_4O_7$ (pH 8.2) | | |
| Mobile phase organic | 45/45/10 ACN/MeOH/water | | |
| Flow rate | 1.5 mL/min | | |
| **Gradient** | **Minute** | **% Aqueous** | **% Organic** |
| | 0.0 | 98 | 2 |
| | 0.35 | 98 | 2 |
| | 13.4 | 43 | 57 |
| | 13.5 | 0 | 100 |
| | 15.7 | 0 | 100 |
| | 15.8 | 98 | 2 |
| | 18 | 98 | 2 |
| Column temperature | 40° C. | | |
| Injection | 1 µL | | |
| Needle wash | Flush port for 7 s | | |
| **Online derivatization** | **Function** | **Parameter** | |
| (Use Injector Program) | Draw | Draw 2.5 µL from location "1" with default speed using default offset (borate buffer) | |
| | Draw | Draw 1 µL from sample with default speed using default offset | |
| | Mix | Mix 3.5 µL from seat with default speed for 5 times | |
| | Wait | Wait 0.2 min | |
| | Draw | Draw 0.5 µL from location "2" with default speed using default offset (OPA) | |
| | Mix | Mix 4 µL from seat with default speed for 10 times | |
| | Draw | Draw 0.4 µL from location "3" with default speed using default offset (FMOC) | |
| | Mix | Mix 4.4 µL from seat with default speed for 10 times | |
| | Draw | Draw 32 µL from location "4" with default speed using default offset (Injection diluent) | |
| | Mix | Mix 20 µL from seat with default speed for 8 times | |
| | Inject | Inject | |
| | Wait | Wait 0.1 min | |
| | Valve | Switch valve to "Bypass" | |
| UV | Response time: 1 s<br>Autobalance: prerun<br>Slit: 4 nm | | |

-continued

| HPLC conditions | | | | |
|---|---|---|---|---|
| | Wavelength | Bandwidth | Reference | Bandwith |
| | 338 nm | 10 nm | 390 nm | 20 nm |
| | Switch between the last eluting OPA-derivatized AA (Lysine) and before the 1st eluting FMOC-derivatized AA (Hydroxyproline): ~11 min | | | |
| | 262 nm | 16 nm | 324 nm | 8 nm |
| FLR | Response time: 1 s<br>PMT gain: 10 (adjust if needed) | | | |
| | Excitation | | Emission | |
| | 340 nm | | 450 nm | |
| | Switch between the last eluting OPA-derivatized AA (Lysine) and before the 1st eluting FMOC-derivatized AA (Hydroxyproline): ~11 min | | | |
| | 260 nm | | 325 | |

System Suitability Criteria

Analyze retention time and peak area for each AA of interest used in quantitation (D/S/G/R) and internal standards (Norvaline and Sarcosine) in standard injections (both UV and FLR).

| Parameter | Criteria |
|---|---|
| Blanks | No significant interference in UV and FLR |
| % RSD (Retention time), initial 3 | NMT 5% |
| % RSD (Area), initial 3 | NMT 20% |
| % RSD (Relative Area), initial 3 | NMT 20% |
| % RSD (Retention time), all | NMT 5% |
| % RSD (Area), all | NMT 20% |
| % RSD (Relative Area), all | NMT 20% |
| Resolution:<br>Glycine from other AAs<br>Norvaline (iSTD) from other AAs<br>Sarcosine (iSTD) vs. Proline | Baseline separation |
| Linearity | RSQ NLT 0.99 |
| Check standard | Quantitated result: within 80%~120% of theoretical |

Data Analysis—Analyze Samples Only when System Suitability Passes

Identification of AA of Interest

- RT of AA of interest and internal standards in the 17AA (+iSTD) standard mixture should match the RT of the 5AA (+iSTD) standard mixture
- RT of the AA in each sample should match the RT of the standard (UV/FLR)

Relative area (D, S, G, R)=Area (D, S, G, R)/Area (Norvaline)

Relative area (P)=Area (P)/Area (Sarcosine)

Standard Calibration Curve

- Calculate concentrations of standard solutions using the reported value on certificate of analysis or actual weights adjusted by dilution factor during the standard preparation.
- Plot the average area or average relative area vs. concentration for each AA of interest from the standard injections: 0.025, 0.1, and 0.25 μmol/mL. Perform linear regression.
- Conc=m*Area or Relative Area+b
- Where, m is the slope of the linear fitted curve and b is the Y-intercept of the linear fitted curve.
- The RSQ should be no less than 0.99.
- If the linearity fails, prepare fresh derivatization reagents/standard solutions, and troubleshoot system malfunction and repeat the test.

Sample Analysis

- Quantitation can be done by both UV and FLR
- Quantitation is done using relative area (area ratio relative to the internal standard)
- Calculate concentration of AA: G, R, D, S in each sample using the linear fitted standard curve:
- Conc, AA (μmol/mL)=(m*Area or Relative Area+b)
- Calculate concentration of the total GRGDSP (SEQ ID NO: 44) by averaging the concentration of each AA:
- Concentration, total GRGDSP (SEQ ID NO: 44) (μmol/mL)=(Conc, G/2+Conc, R+Conc, D+Conc, S+Conc, P)/5
- μmol (Total GRGDSP (SEQ ID NO: 44))/g (conjugate)=Conc, total GRGDSP (μmol/mL)×0.25 mL/1.0 mL×20 mL/Weight (g)
- μmol (conjugated GRGDSP (SEQ ID NO: 44))/g (conjugate)=μmol (Total GRGDSP (SEQ ID NO: 44))/g (conjugate)−μmol (Residual free GRGDSP (SEQ ID NO: 44))/g (conjugate)

Example 8: Exemplary Assay to Determine Residual Free Peptide in a CBP-Polymer Composition This assay uses liquid chromatography-mass spectroscopy (LC-MS) to determine the amount of residual, unconjugated peptide in a composition containing a peptide-polymer conjugate, e.g., typically after one or more purification steps have been performed to remove a substantial portion, e.g., greater than 95%, 98%, 99% or more, of unconjugated peptide. In brief, a sample of the conjugate in saline solution is added to a molecular weight cut-off (MWCO) tube that has a MWCO higher than the molecular weight of the peptide, the tube is centrifuged to separate the residual peptide from the conjugate, and the amount of peptide is quantitated by LC-MS using as a standard a reference composition containing a known concentration of the same peptide.

Example 9: Exemplary Quantitative Amine Assay to Determine Amine-Conjugation Density in an Afibrotic Polymer Modified with a Compound of Formula (I)

This assay determines the amount of an amine-containing compound (e.g., a compound of Formula I, e.g., Compound 101 in Table 3) in a polymer chemically modified with the amine compound. A sample of the chemically-modified polymer is subjected to acid hydrolysis, which cleaves off the conjugated amine and the weight % of total amine in the hydrolyzed sample is quantitated by reverse-phase, liquid chromatography with ultraviolet detection (LC-UV) using the unconjugated amine compound as a standard. The identity of the LC peak can be further confirmed by mass spectrometry. The weight % of total amine can be used as the % conjugation of the amine-compound in the chemically-modified polymer. A more precise result can be obtained by determining the amount of any residual unconjugated amine compound in an unhydrolyzed sample of the chemically-modified polymer using any suitable method (e.g., as described below) and subtracting that amount from the total peptide amount.

The assay is further described below as applied to determining % conjugation density in an alginate chemically modified with Compound 101 (i.e., CM-LMW-Alg-101); however, the skilled artisan can readily modify the assay to determine the conjugation density of any Formula I compound used to chemically-modify a polysaccharide (e.g., an alginate) or another polymer that does not contain amines. Also, the skilled person can readily substitute any equipment, material or chemical specified below with a different equipment, material or chemical that can perform or provide substantially the same function or role in the assay.

DEFINITIONS

| Abbreviation | Definition |
|---|---|
| LC-UV-MS | Liquid Chromatography-Ultra-Violet-Mass Spectrometry |
| VLVG | Pronova Ultrapure VLVG sodium alginate |
| SLG100 | Pronova Ultrapure Sterile Alginate |
| TIC | Total Ion Chromatogram |
| SST | System Suitability |
| RSD | Relative Standard Deviation |
| m/z | Mass charge ratio |

Equipment

- Agilent 1260 LC system (DAD: 13 μL/10 mm flow cell)
- Agilent SQ MS detector (G1956B)
- XBridge C18, 2.5 μm, 4.6×50 mm, Waters 186006037
- Small molecule reference material (unconjugated, free amine version of Compound 101 in Table 3; >98.0% purity)

Procedure

Prepare a 0.1% ammonia in water solution (aqueous mobile phase) and a 0.1% ammonia in ACN solution (organic mobile phase) for use in the LC procedure.

Acid Hydrolysis of an Exemplary Solid Alginate-Small Molecule Conjugate Sample

- Weigh 50±5 mg of the lyophilized small molecule-alginate conjugate solid, into a microwave reaction vial, ensuring that the sample is not agitated.
- Add 10.0 mL of 2N HCl using a 10-mL transfer pipet or volumetric pipet and a stir bar, and seal the PTFE-lined cap with a crimper.
- Place each sample vial in the matching heat block on a hot/stir plate and heat at 120° C., stirring at 400 rpm for 120 minutes.
- Remove from heat and let cool to ambient temperature
- Transfer the entire solution from the reaction vial to a 25-mL volumetric flask with a disposable transfer pipet
- Pipet 5 mL of LCMS grade water into the empty reaction vial, rinse the inner wall thoroughly with the same disposable transfer pipet, and transfer the rinseate completely to the same 25-mL volumetric flask
- Repeat the above step twice
- Bring to mark of the volumetric flask with LCMS grade water
- Transfer completely to a 50-mL centrifuge tube
- Centrifuge at 3000 rpm for 10 minutes
- Take supernatant for HPLC analysis
- Store at 2-8° C.

Acid Hydrolysis of an Exemplary Small Molecule-Alginate Conjugate in Saline Sample

- Weigh 1000±50 mg of the small molecule-alginate conjugate solution in saline into a microwave reaction vial
- Add 10.0 mL of 2N HCl using a 10-mL transfer pipet or volumetric pipet and a stir bar, and seal the PTFE-lined cap with a crimper.
- Place each sample vial in the matching heat block on a hot/stir plate
- Heat at 120° C., stir at 400 rpm, for 120 minutes
- Remove from heat and let cool to ambient temperature
- Transfer the entire solution from the reaction vial to a 25-mL volumetric flask with a disposable transfer pipet
- Pipet 5 mL of LCMS grade water into the empty reaction vial, rinse the inner wall thoroughly with the same disposable transfer pipet, and transfer the rinseate completely to the same 25-mL volumetric flask
- Repeat the above step twice
- Bring to mark of the volumetric flask with LCMS grade water
- Transfer completely to a 50-mL centrifuge tube
- Centrifuge at 3000 rpm for 10 minutes
- Take supernatant for HPLC analysis
- Store at 2-8° C.

Sample Preparation for Residual Free Amine in Solid Small Molecule-Alginate Conjugate

- Weigh 50±5 mg of the lyophilized small molecule-alginate conjugate solid, into a scintillation vial
- Pipet 5.0 mL of saline into the scintillation vial
- Dissolve completely by shaking and vortexing for 10 minutes
- Transfer completely to a MWCO tube
- Centrifuge at 5000 rpm for 60 minutes
- Remove the top portion of the MWCO tube and discard
- Transfer the sample in the bottom portion completely to a 5 mL volumetric flask
- Bring to mark with water or saline and invert to mix well
- Transfer to a scintillation vial for storage at 2-8° C.
- Transfer an aliquot for HPLC analysis Sample Preparation for Residual Free Amine in Small Molecule-Alginate Conjugate in Saline

- Weigh 1000±50 mg of the small molecule-alginate conjugate (or blend with unmodified alginate) in saline, into a MWCO tube
- Pipet 4.0 mL of saline into the MWCO tube
- Invert and vortex the tube 5 times or until the solution is mixed well to fully extract free amine
- Centrifuge at 5000 rpm for 90 minutes
- Remove the top portion of the MWCO tube and discard
- Transfer the sample in the bottom portion completely to a 5 mL volumetric flask
- Bring to mark with water and invert to mix well
- Transfer to a scintillation vial for storage at 2-8° C.
- Transfer an aliquot for HPLC analysis Standard Preparation Standard Solution: 1 mg/mL

- Weigh 50.00±5.00 mg of small molecule reference material standard into a scintillation vial
- Add ~10 mL of LCMS-grade water, dissolve the solid completely by shaking and vortexing

- Transfer completely to a 50-mL volumetric flask by rinsing the scintillation vial twice with LCMS-grade water, using a disposable transfer pipet
- Bring to volume with LCMS-grade water, mix well
- Store at 2-8° C.

Standard Solution: 0.01 mg/mL

- Pipet 100 μL of the 1 mg/mL solution to a 10-mL volumetric flask
- Bring to volume with LCMS-grade water
- Mix well by inverting
- Store at 2-8° C.

| HPLC conditions | | | |
|---|---|---|---|
| Instrument | Agilent 1260 LC with DAD and SQ MS (optional) | | |
| Column | XBridge C18, 2.5 μm, 4.6 × 50 mm | | |
| Mobile phase aqueous | 0.1% ammonia | | |
| Mobile phase organic | 0.1% ammonia in ACN | | |
| Flow rate | 1.0 mL/min | | |
| Gradient | Minute | % Aqueous | % Organic |
| | 0.0 | 98 | 2 |
| | 6.0 | 86 | 14 |
| | 12.0 | 20 | 80 |
| | 12.1 | 98 | 2 |
| | 15.0 | 98 | 2 |
| Column temperature | 30° C. | | |
| Injection | 10 μL | | |
| UV | Detection: 220 nm, bw 10 nm;<br>Reference: 360 nm, bw 100 nm;<br>Response time: 1 s<br>Autobalance: prerun<br>Slit: 4 nm | | |
| MS (optional) | API-ES (scan: positive and negative)<br>Drying gas: 12 L/min; Nebulizer pressure: 55 psig; Drying gas temperature: 350° C.; Capillary Voltage: 3000 V; Scan range 90-1000; Fragmentor 70V; Gain 1.00; Threshold 150; Step size 0.10 | | |

| System suitability criteria | |
|---|---|
| Parameter | Criteria |
| Blanks | No significant interference in UV and TIC (optional) |
| % RSD (Retention time), initial 5<br>Small molecule reference material | NMT 2% |
| % RSD (area), initial 5<br>Small molecule reference material | NMT 10% |
| % RSD (Retention time), initial 5 and all bracketing<br>Small molecule reference material | NMT 2% |
| % RSD (area), initial 5 and all bracketing<br>Small molecule reference material | NMT 10% |
| m/z: amine peak (optional) | 392.1 ± 0.5 |

Data Analysis—Analyze Samples Only when System Suitability Passes

Identification of Free Amine

- (optional) m/z of the free amine peak in each sample should be within 392.1±0.5.
- RT of the amine peak in UV in each sample matches the RT of the standard.

Concentration, Standard (Mg/mL)=

- Weight (mg)/50 mL/dilution factor,
- Where dilution factor=1 for 1.0 mg/mL standard;
- Where dilution factor=100 for 0.01 mg/mL standard Concentration, Free Amine (Mg/mL)=

- Area, non-hydrolyzed sample/Area, 0.01 standard×Concentration, 0.01 standard

% Residual Free Amine=

- Concentration, free amine (mg/mL)×5 mL/weight, non-hydrolyzed conjugate (mg)×100

Concentration, Total Amine (Mg/mL)=

- Area, hydrolyzed sample/Area, 1.0 standard×Concentration, 1.0 standard

% Total Amine=

- Concentration, total amine (mg/mL)×25 mL/weight, hydrolyzed conjugate (mg)×100.

EQUIVALENTS AND SCOPE

This application refers to various issued patents, published patent applications, journal articles, and other publications, all of which are incorporated herein by reference. If there is a conflict between any of the incorporated references and the instant specification, the specification shall control. In addition, any particular embodiment of the present disclosure that falls within the prior art may be explicitly excluded from any one or more of the claims. Because such embodiments are deemed to be known to one of ordinary skill in the art, they may be excluded even if the exclusion is not set forth explicitly herein. Any particular embodiment of the disclosure can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, Figures, or Examples but rather is as set forth in the appended claims. Those of ordinary skill in the art will appreciate that various changes and modifications to this description may be made without departing from the spirit or scope of the present disclosure, as defined in the following claims.

The invention claimed is:

1. An isolated double-stranded DNA molecule which comprises a nucleotide sequence selected from the group consisting of: SEQ ID NO:3, SEQ ID NO:4, SEQ ID NO:6, SEQ ID NO:9, SEQ ID NO:12, SEQ ID NO:14, SEQ ID NO:47 or SEQ ID NO:48.

2. The isolated DNA molecule of claim 1, which consists essentially of SEQ ID NO: 48.

3. An isolated double-stranded DNA molecule comprising a nucleotide sequence comprising a promoter operably linked to a precursor alpha-galactosidase A (GLA) coding sequence, wherein the precursor GLA coding sequence comprises the nucleotide sequence of SEQ ID NO:3 or SEQ ID NO:4.

4. The isolated double-stranded DNA molecule of claim 3, wherein the precursor GLA coding sequence comprises the nucleotide sequence of SEQ ID NO:3.

5. The isolated double-stranded DNA molecule of claim 3, wherein the precursor GLA coding sequence comprises the nucleotide sequence of SEQ ID NO:4.

6. The isolated double-stranded DNA molecule of claim 3, wherein the promoter comprises SEQ ID NO: 18.

7. The isolated double-stranded DNA molecule of claim 1, wherein the nucleotide sequence encodes a protein comprising SEQ ID NO: 5, SEQ ID NO:7, SEQ ID NO:11, or SEQ ID NO:13.

8. The isolated double-stranded DNA molecule of claim 1, wherein the nucleotide sequence is SEQ ID NO:3.

9. The isolated double-stranded DNA molecule of claim 1, wherein the nucleotide sequence is SEQ ID NO:4.

10. The isolated double-stranded DNA molecule of claim 1, wherein the nucleotide sequence is SEQ ID NO:6.

11. The isolated double-stranded DNA molecule of claim 1, wherein the nucleotide sequence is SEQ ID NO:9.

12. The isolated double-stranded DNA molecule of claim 1, wherein the nucleotide sequence is SEQ ID NO:12.

13. The isolated double-stranded DNA molecule of claim 1, wherein the nucleotide sequence is SEQ ID NO:14.

14. The isolated double-stranded DNA molecule of claim 1, wherein the nucleotide sequence is SEQ ID NO:47.

15. The isolated double-stranded DNA molecule of claim 1, wherein the nucleotide sequence is SEQ ID NO:48.

16. An isolated double-stranded DNA molecule comprising a nucleotide sequence comprising a promoter operably linked to a precursor alpha-galactosidase A (GLA) coding sequence, wherein the precursor GLA coding sequence encodes a GLA fusion protein comprising a signal peptide comprising:

(a) SEQ ID NO: 15 or a conservatively substituted variant thereof that is at least 95% identical to SEQ ID NO: 15, or (b) the signal peptide of SEQ ID NO: 1, or a conservatively substituted variant thereof that is at least 95% identical to SEQ ID NO: 1.

17. The isolated double-stranded DNA molecule of claim 16, wherein the signal peptide comprises SEQ ID NO: 15 or a conservatively substituted variant thereof that is at least 95% identical to SEQ ID NO: 15.

18. The isolated double-stranded DNA molecule of claim 16, wherein the signal peptide comprises the signal peptide encoded in any of SEQ ID NO: 1, SEQ ID NO: 3, or SEQ ID NO: 4, or a conservatively substituted variant thereof that is at least 95% identical to SEQ ID NO: 1, SEQ ID NO: 3, or SEQ ID NO: 4.

* * * * *